(12) United States Patent
Chappie et al.

(10) Patent No.: US 8,933,224 B2
(45) Date of Patent: Jan. 13, 2015

(54) TRIAZINE DERIVATIVES

(71) Applicant: Pfizer Inc., New York, NY (US)

(72) Inventors: Thomas Allen Chappie, Carlisle, MA (US); Christopher John Helal, Mystic, CT (US); Bethany Lyn Kormos, Somerville, MA (US); Jamison Bryce Tuttle, Marblehead, MA (US); Patrick Robert Verhoest, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/265,458

(22) Filed: Apr. 30, 2014

(65) Prior Publication Data

US 2014/0329820 A1    Nov. 6, 2014

Related U.S. Application Data

(60) Provisional application No. 61/818,650, filed on May 2, 2013.

(51) Int. Cl.

| | | |
|---|---|---|
| *C07D 487/04* | (2006.01) | |
| *C07D 471/04* | (2006.01) | |
| *C07D 498/04* | (2006.01) | |
| *C07D 513/04* | (2006.01) | |
| *A61K 31/53* | (2006.01) | |
| *A61K 31/4353* | (2006.01) | |
| *A61P 25/14* | (2006.01) | |

(52) U.S. Cl.
CPC ............ *C07D 487/04* (2013.01); *C07D 471/04* (2013.01); *C07D 498/04* (2013.01); *C07D 513/04* (2013.01)
USPC .......................................... 544/184; 514/243

(58) Field of Classification Search
CPC .... C07D 487/04; C07D 471/04; A61K 31/53; A61K 31/4353
USPC .......................................... 544/184; 514/243
See application file for complete search history.

(56) References Cited

U.S. PATENT DOCUMENTS

| | | | |
|---|---|---|---|
| 6,900,217 B2 | 5/2005 | Chen | |
| 6,936,609 B2 | 8/2005 | Erguden et al. | |
| 8,404,694 B2 | 3/2013 | White et al. | |
| 8,569,300 B2 | 10/2013 | Borchardt et al. | |
| 8,598,155 B2 | 12/2013 | Helal et al. | |
| 8,716,282 B2 | 5/2014 | Pastor-Fernandez et al. | |
| 2006/0166992 A1 | 7/2006 | Hendrix et al. | |
| 2008/0051419 A1 | 2/2008 | Corbett et al. | |
| 2012/0004222 A1 | 1/2012 | Wu et al. | |
| 2012/0329792 A1 | 12/2012 | Bartolome-Nebreda et al. | |
| 2013/0053371 A1 | 2/2013 | Pastor Fernandez et al. | |
| 2013/0071415 A1 | 3/2013 | Babu et al. | |
| 2013/0131057 A1 | 5/2013 | Pastor Fernandez et al. | |

FOREIGN PATENT DOCUMENTS

WO    2008057402 A2    5/2008

OTHER PUBLICATIONS

Giralt et al. Hippocampus. Aug. 2013;23(8):684-95.*
Freshney et al.,Culture of Animal Cells, A Manual of Basic Technique, Alan R. Liss, Inc., 1983, New York, p. 4.*
Dermer et al., Bio/Technology, 1994, 12:320.*
International application No. PCT/IB2014/060945, filed Apr. 23, 2014, Written Opinion of International Searching Authority, mailed Jul. 11, 2014, 8 pages.

* cited by examiner

*Primary Examiner* — Venkataraman Balasubramanian
(74) *Attorney, Agent, or Firm* — J. Michael Dixon

(57) ABSTRACT

The present invention is directed to a new class of triazine derivatives as described by formula I below in which A, X, $R^1$, $R^2$, $R^3$, and $R^4$ are as defined herein and to the use of the compounds as PDE10 inhibitors.

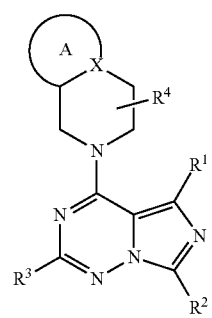

24 Claims, No Drawings

TRIAZINE DERIVATIVES

CROSS REFERENCE

This applications claims priority from of U.S. Provisional Patent Application Ser. No. 61/818,650, filed May 2, 2013, the contents of which are incorporated by reference.

FIELD OF THE INVENTION

The present invention pertains to a new class of triazine derivatives, their use as PDE10 inhibitors, and to pharmaceutical compositions containing these compounds.

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphate (cGMP) into their respective nucleotide monophosphates. The cyclic nucleotides cAMP and cGMP are synthesized by adenylyl and guanylyl cyclase, respectively, and serve as secondary messengers in several cellular pathways.

The cAMP and cGMP function as intracellular secondary messengers regulating a vast array of intracellular processes, particularly in neurons of the central nervous system. In neurons, this includes the activation of cAMP- and cGMP-dependent kinases and subsequent phosphorylation of proteins involved in acute regulation of synaptic transmission, as well as in neuronal differentiation and survival. The complexity of cyclic nucleotide signaling is indicated by the molecular diversity of the enzymes involved in the synthesis and degradation of cAMP and cGMP. There are at least ten families of adenylyl cyclase, two of guanylyl cyclase, and eleven of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is by phosphodiesterase-catalyzed cyclic nucleotide catabolism. There are 11 known families of PDEs, encoded by 21 different genes. Each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE families or isozymes may offer particular therapeutic effects, fewer side effects or both. PDE10 sequences were identified by using bioinformatics and sequence information from other PDE gene families (Fujishige et al., J. Biol. Chem. 274:18438-18445, 1999; Loughney et al., Gene 234: 109-117, 1999; Soderling et al., Proc. Natl. Acad. Sci. USA 96:7071-7076, 1999). The PDE10 gene family is distinguished based on its amino acid sequence, functional properties and tissue distribution. The human PDE10 gene is large, over 200 kb, with up to 24 exons coding for each of the splice variants. The amino acid sequence is characterized by two GAP domains (which bind cGMP), a catalytic region, and alternatively spliced N and C termini. Numerous splice variants are possible because at least three alternative exons encode N-termini and two exons encode C-termini. PDE10 is a 779-amino acid protein that hydrolyzes both cAMP and cGMP; the $K_m$ values for cAMP and cGMP are 0.05 and 3.0 micromolar, respectively. In addition to human variants, several variants with high homology have been isolated from both rat and mouse tissues.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. The tissue distribution of PDE10 indicates that PDE10 inhibitors can be used to raise levels of cAMP and/or cGMP within cells that express the PDE10 enzyme, for example, in neurons that comprise the basal ganglia, and therefore would be useful in treating a variety of neuropsychiatric conditions involving the basal ganglia such as Huntington's disease, schizophrenia, bipolar disorder, obsessive compulsive disorder, and the like.

SUMMARY OF THE INVENTION

In accordance with the present invention, a new class of PDE10 inhibitors has been discovered. These compounds, or their pharmaceutically acceptable salts, may be described by Formula I below:

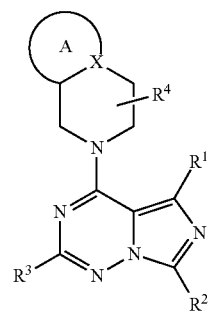

in which:

A, along with X and the carbon atom to which it is attached, forms a ($C_6$-$C_{10}$)aryl or a 5- to 10-membered heteroaryl moiety, in which said aryl or heteroaryl moiety is optionally substituted with up to 4 substituents, each independently selected from the group consisting of $C_3$-$C_6$ cycloalkyl, oxo, optionally substituted $C_1$-$C_6$ alkyl, optionally substituted $C_1$-$C_6$ alkoxy, hydroxy, cyano, halo, —$NR^5R^6$, —C(O)—$NR^5R^6$, —NH—C(O)$R^5$, —C(O)—$OR^5$, —($C_1$-$C_6$)alkyl-($C_3$-$C_6$)cycloalkyl, a 4- to 6-membered heterocyclic moiety, phenyl, and benzyl;

X is represented by N or C;

$R^1$ is represented by $C_1$-$C_6$ alkyl, ($C_6$-$C_{10}$)aryl or a 5- to 6-membered heterocyclic moiety, in which said alkyl, aryl or heterocyclic moiety is optionally substituted with up to 4 substituents selected from the group consisting of halogen, optionally substituted $C_1$-$C_6$ alkyl, optionally substituted $C_1$-$C_6$ alkoxy, hydroxy, cyano, —$NR^5R^6$, —C(O)—$NR^5R^6$, —NH—C(O)$R^5$, and —C(O)—$OR^5$;

$R^2$ and $R^3$ are each independently represented by hydrogen, optionally substituted $C_1$-$C_6$ alkyl, or optionally substituted $C_1$-$C_6$ alkoxy;

$R^4$, if present, is optionally represented by up to 2 substituents, each independently selected from the group consisting of fluoro, hydroxy, optionally substituted $C_1$-$C_6$ alkyl, or optionally substituted $C_1$-$C_6$ alkoxy, and;

$R^5$ and $R^6$ are each optionally and independently represented by hydrogen or $C_1$-$C_6$ alkyl.

The compounds of Formula I are PDE10 inhibitors and thus may be used in the treatment of any disease or disorder in which PDE10 inhibition provides a beneficial effect. Due to the high level of PDE10 expression within the brain, the compounds may be used in the treatment of a variety of neurological disorders such as, for example, schizophrenia, Huntington's disease, cognitive impairment associated with schizophrenia, Parkinson's disease, Alzheimer's disease, dementia, mania, substance abuse, etc.

In order to simplify administration, the compounds will typically be admixed with at least one pharmaceutically acceptable excipient and formulated into a pharmaceutical dosage form. Examples of such dosage forms include tablets, capsules, and solutions/suspensions for oral ingestion. Other examples include solutions/suspensions for injection, aerosols for inhalation, patches for topical administration, etc.

DETAILED DESCRIPTION OF THE INVENTION

The headings within this document are being utilized only to expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine, iodine, or bromine atom.

b. "$C_1$-$C_6$ alkyl" refers to a branched- or straight-chain alkyl group containing from 1 to 6 carbon atoms, such as methyl, ethyl, n-propyl, isopropyl, n-butyl, isobutyl, pentyl, etc.

c. "$C_1$-$C_6$ alkyl, optionally substituted" refers to a branched- or straight-chain alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are independently replaced by a substituent selected from the group consisting of halogen, cyano, —$OR^a$, —$SR^a$, and —$NR^aR^b$, in which $R^a$ and $R^b$ are each independently represented by hydrogen or $C_1$-$C_6$ alkyl.

d. "$C_1$-$C_6$ alkoxy" refers to a straight- or branched-chain alkoxy group containing from 1 to 6 carbon atoms, such as methoxy, ethoxy, n-propoxy, isopropoxy, n-butoxy, isobutoxy, pentoxy, etc.

e. "$C_1$-$C_6$ alkoxy, optionally substituted" refers to a straight- or branched-chain alkoxy group containing from 1 to 6 carbon atoms, such as methoxy, ethoxy, n-propoxy, isopropoxy, n-butoxy, isobutoxy, pentoxy, etc. Such an alkoxy group may be optionally substituted, in which up to 6 hydrogen atoms are independently replaced by a substituent selected from the group consisting of halogen, cyano, —$OR^a$, —$SR^a$, and —$NR^aR^b$, in which $R^a$ and $R^b$ are each as defined above.

f. "($C_6$-$C_{10}$)aryl" means an aromatic hydrocarbon containing from 6 to 10 carbon atoms. Examples of such aryl groups include phenyl, naphthyl, etc.

g. "5- to 10-membered heteroaryl moiety" refers to a monocyclic or fused-ring polycyclic aromatic moiety containing one or more heteroatom ring members (ring-forming atoms), each independently selected from O, S and N, in at least one ring. The heteroaryl group has 5 to 10 ring-forming atoms, including 1 to 9 carbon atoms, and 1 to 4 heteroatoms selected from O, S, and N. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms. Examples of heteroaryl groups include, but are not limited to, pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), benzothienyl, benzofuryl, indolyl, etc.

h. "5- to 6-membered heteroaryl moiety" refers to a monocyclic aromatic moiety having one, or more, heteroatoms selected from oxygen, sulfur, or nitrogen. In a more specific embodiment, 5- to 6-membered heteroaryl refers to a 5- or 6-membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. Examples of such heteroaryl moieties include, but are not limited to, pyridinyl, pyrazinyl, pyrimidinyl, pyridazinyl, thiazolyl (e.g., 1,2-thiazolyl, 1,3-thiazolyl), furyl, thienyl, oxazolyl (e.g., 1,3-oxazolyl, 1,2-oxazolyl), imidazolyl, pyrrolyl, oxazolyl, pyrazolyl, triazolyl (e.g., 1,2,3-triazolyl, 1,2,4-triazolyl), oxadiazolyl (e.g., 1,2,3-oxadiazolyl), and thiadiazolyl (e.g., 1,3,4-thiadiazolyl).

i. "$C_3$-$C_6$ cycloalkyl" refers to refers to a cyclopropyl, cyclobutyl, cyclopentyl or cyclohexyl moiety.

j. "4- to 6-membered heterocyclic moiety" refers to any 4-membered ring containing a heteroatom selected from oxygen, nitrogen and sulfur; or a 5- or 6-membered non-aromatic ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, and the 6-membered ring has 0 to 2 double bonds. The term "heterocyclic" also includes bicyclic groups in which any of the above heterocyclic rings is fused to a benzene ring, a cyclohexane or cyclopentane ring or another heterocyclic ring (for example, tetrahydroquinolyl or dihydrobenzofuryl and the like). Heterocyclics include: pyrrolidinyl, tetrahydrofuranyl, tetrahydrothiophenyl, piperidinyl, piperazinyl, morpholinyl, tetrahydrotriazinyl, tetrahydropyrazolyl, tetrahydro-oxazolyl, tetrahydro-oxazinyl, thiomorpholinyl, tetrahydropyrimidinyl, etc.

k. "5- to 6-membered heterocyclic moiety" refers to refers to a 5- or 6-membered non-aromatic ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, and the 6-membered ring has 0 to 2 double bonds. The term "heterocyclic" also includes bicyclic groups in which any of the above heterocyclic rings is fused to a benzene ring, a cyclohexane or cyclopentane ring or another heterocyclic ring (for example, tetrahydroquinolyl or dihydrobenzofuryl and the like). Heterocyclics include: pyrrolidinyl, tetrahydrofuranyl, tetrahydrothiophenyl, piperidinyl, piperazinyl, morpholinyl, tetrahydrotriazinyl, tetrahydropyrazolyl, tetrahydro-oxazolyl, tetrahydro-oxazinyl, thiomorpholinyl, tetrahydropyrimidinyl, etc.

l. "therapeutically effective amount" refers to an amount of a compound of Formula I that, when administered to a patient, provides the desired effect; i.e., inhibiting a PDE10 enzyme, decreasing the symptoms of the patient's disease or disorder, decreasing the rate at which the disease or disorder progresses, preventing the occurrence of the disease or disorder, etc.

m. "patient" refers to warm-blooded animals such as, for example, guinea pigs, mice, rats, gerbils, cats, rabbits, dogs, monkeys, chimpanzees, and humans.

n. "treat" refers to the ability of the compounds to relieve, alleviate or slow the progression of the patient's disease (or disorder) or any tissue damage associated with the disease or disorder.

o. "pharmaceutically acceptable" indicates that the substance or composition must be compatible, chemically and/or toxicologically, with the other ingredients comprising a formulation, and/or the mammal being treated therewith.

p. "compounds of Formula I", "formula I", "compounds of the invention", etc, are being used interchangeably throughout the application and should be treated as synonyms.

The compounds of Formula I may have optical centers and therefore may occur in different enantiomeric and diastereomeric configurations. The present invention includes all enantiomers, diastereomers, and other stereoisomers of such compounds, as well as racemic compounds and racemic mixtures and other mixtures of stereoisomers thereof.

Pharmaceutically acceptable salts of the compounds of Formula I include the acid addition and basic addition salts thereof. Suitable acid addition salts are formed from acids which form non-toxic salts. Examples include, but are not limited to, the acetate, adipate, aspartate, benzoate, besylate, bicarbonate/carbonate, bisulfate/sulfate, borate, camsylate, citrate, cyclamate, formate, fumarate, gluconate, glucuronate, hexafluorophosphate, hydrochloride/chloride, hydrobromide/bromide, hydroiodide/iodide, isothionate, lactate, malate, maleate, malonate, mandelates, methanesulfonate, methylsulfate, naphthalate, nicotinate, nitrate, oxalate, palmitate, pamoate, phosphate/hydrogen phosphate/dihydrogen phosphate, pyroglutamate, salicylate, saccharate, stearate, succinate, sulfonate, tartrate, p-toluenesulfonate, trifluoroacetate salts, etc.

Suitable basic addition salts are formed from bases which form non-toxic salts. Examples include, but are not limited to, aluminum, arginine, benzathine, calcium, choline, diethylamine, diolamine, glycine, lysine, magnesium, meglumine, olamine, potassium, sodium, tin tromethamine, zinc salts, etc. Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002).

Pharmaceutically acceptable salts of compounds of Formula I may be prepared by one or more of three methods:

(i) by reacting the compound of Formula I with the desired acid or base;
(ii) by removing an acid- or base-labile protecting group from a suitable precursor of the compound of Formula I, or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs that is characterized by a change of state, typically second-order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first-order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO—Na+, —COO—K+, or —SO3-Na+) or non-ionic [such as —N—N+(CH3)3] polar head group. For more information, see Crystals and the Polarizing Microscope by N. H. Hartshorne and A. Stuart, 4th Edition (Edward Arnold, 1970).

Hereinafter all references to compounds of Formula I include references to salts, solvates, multi-component complexes and liquid crystals thereof and to solvates, multi-component complexes and liquid crystals of salts thereof.

As indicated, so-called 'prodrugs' of the compounds of Formula I are also within the scope of the invention. Thus certain derivatives of compounds of Formula I that may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and V. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985). Some examples of prodrugs in accordance with the invention include, but are not limited to:

(i) where the compound of Formula I contains a carboxylic acid functionality (—COOH), an ester thereof, for example, a compound wherein the hydrogen of the carboxylic acid functionality of the compound of Formula (I) is replaced by $(C_1-C_6)$alkyl;

(ii) where the compound of Formula I contains an alcohol functionality (—OH), an ether thereof, for example, a compound wherein the hydrogen of the alcohol functionality of the compound of Formula I is replaced by $(C_1-C_6)$alkanoyloxymethyl; and (iii) where the compound of Formula I contains a primary or secondary amino functionality (—NH$_2$ or —NHR where R≠H), an amide thereof, for example, a compound wherein, as the case may be, one or both hydrogens of the amino functionality of the compound of Formula I is/are replaced by $(C_1-C_6)$alkanoyl.

Also included within the scope of the invention are metabolites of compounds of Formula I, that is, compounds formed in vivo upon administration of the drug. Some examples of metabolites in accordance with the invention include, but are not limited to:

(i) where the compound of Formula I contains a methyl group, a hydroxymethyl derivative thereof (—CH$_3$→—CH$_2$OH):

(ii) where the compound of Formula I contains an alkoxy group, a hydroxy derivative thereof (—OR→—OH);

(iii) where the compound of Formula I contains a tertiary amino group, a secondary amino derivative thereof (—NR$^5$R$^6$→—NHR$^5$ or —NHR$^6$);

(iv) where the compound of Formula I contains a secondary amino group, a primary derivative thereof (—NHR$^5$→—NH$_2$);

(v) where the compound of Formula I contains a phenyl moiety, a phenol derivative thereof (-Ph→PhOH);

(vi) where the compound of Formula I contains an amide group, a carboxylic acid derivative thereof (—CONH$_2$→COOH), and;

(vii) where the compound contains an aromatic nitrogen atom or a tertiary aliphatic amine function, an N-oxide derivative thereof.

Compounds of Formula I having a nitrogen atom in a tertiary amine functional group may be further substituted with oxygen (i.e., an N-oxide).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds that contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically labeled compounds of Formula I wherein one or more atoms are replaced by atoms having the same atomic number, but an atomic mass or mass number different from the atomic mass or mass number which predominates in nature. Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically labeled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances. Substitution with positron-emitting isotopes, such as $^{11}$C, $^{18}$F, $^{15}$O and $^{13}$N, can be useful in Positron Emission Tomagraphy (PET) studies for examining substrate receptor occupancy. Pharmaceutically acceptable solvates in accordance with the invention include those wherein the solvent of crystallization may be isotopically substituted, e.g., D$_2$O, acetone-d$_6$, DMSO-d$_6$. Isotopically labeled compounds of Formula I can generally be prepared by conventional techniques known to those skilled in the art or by processes analogous to those described in the accompanying Examples and Preparations, by using an appropriate isotopically labeled reagent in place of the non-labeled reagent previously employed.

Any reference to the compounds of the invention should be construed as including the compounds, their salts, polymorphs, solvates, hydrates, stereoisomers, metabolites, prodrugs, isotopically labeled versions of the compounds, deuterated forms of the compounds, PET forms of the compounds, etc.

As noted above, all of the compounds of Formula I contain a triazine moiety in which the 4-position is substituted with a piperidine or piperazine moiety fused to a ring A. As described above, A, along with X and the carbon atom to which it is attached, can form either a 5- to 10-membered heteroaryl or a 6- to 10-membered aryl moiety. For the sake of clarity, both X and the carbon atom to which A is attached should be included in that numerical total. For example, if X is C, and A forms a 6-membered aryl moiety (i.e., phenyl) then it will be represented by structure Ia below.

Ia

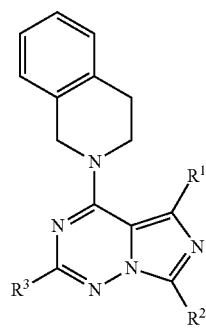

In a more specific embodiment of the invention, as depicted in formula Ib below, R$^2$ is represented by methyl, R$^3$ is represented by hydrogen, and R$^4$ is absent. A, X and R$^1$ are as defined above in Formula I.

Ib

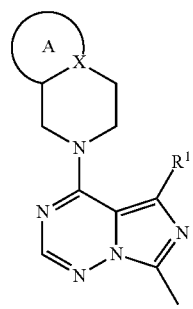

In a further embodiment of the invention, as depicted in formula Ic and Ic' immediately below:

Ic

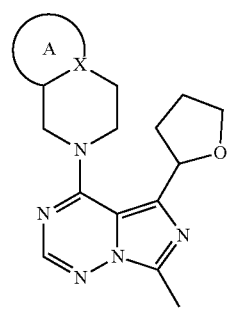

Ic'

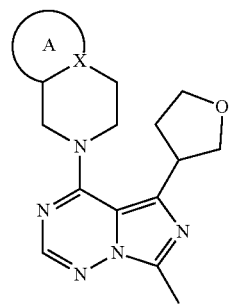

R$^1$ is represented by a tetrahydrofuran moiety as depicted, R$^2$ is represented by methyl, R$^3$ is represented by hydrogen and R$^4$ is absent. A and X are each as defined in Formula I. In a more specific embodiment of the compounds of Formula Ic and Ic', the combination of A, X and the carbon atom to which it is attached forms a phenyl ring, which may be optionally substituted with one or more substituents selected from the group consisting of methyl, methoxy, chloro, fluoro, 2-fluoroethoxy, cyano, —C(O)—OH, —C(O)—NH$_2$, and trifluoromethyl. In a more specific embodiment of the compounds of Formula Ic and Ic', the combination of A, X and the carbon atom to which it is attached forms a heteroaryl moiety selected from the group consisting of pyridine, pyridazine, pyrimidine, pyrazine, pyrrole, pyrazole, imidazole, isoxazole, oxazole, isothiazole, and thiazole, in which said heteroaryl moiety may be optionally substituted with one or more substituents selected from the group consisting of methyl, ethyl, trifluoromethyl, difluoromethyl, difluoromethoxy, methoxy, isopropyl, cyclopropyl, oxo, hydroxy, ethoxy, phenyl, 2-trifluoroethyl, dimethylamino, cyclobutylmethyl, methylamino, and cyclopentyl.

In a further embodiment of the invention, as depicted in formula Id immediately below:

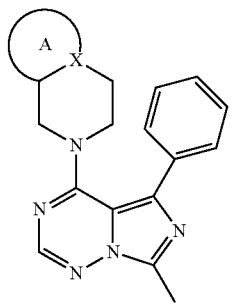

Id

R$^1$ is represented by a phenyl, as depicted, which may be optionally substituted with one or more substituents selected from the group consisting of methyl, fluoro, methoxy, and chloro, R$^2$ is represented by methyl, R$^3$ is represented by hydrogen and R$^4$ is absent. A and X are each as defined in Formula I. In a more specific embodiment of the compounds of Formula Id, the combination of A, X and the carbon atom to which it is attached forms a phenyl ring that may be optionally substituted with one or more substituents selected from the group consisting of methyl, methoxy, chloro, fluoro, 2-fluoroethoxy, cyano, —C(O)—OH, —C(O)—NH$_2$, and trifluoromethyl. Alternatively, the combination of A, X and the carbon atom to which it is attached forms a heteroaryl moiety selected from the group consisting of pyridine, pyridazine, pyrimidine, pyrazine, pyrrole, pyrazole, imidazole, isoxazole, oxazole, isothiazole, and thiazole, in which said heteroaryl moiety may be optionally substituted with one or more substituents selected from the group consisting of methyl, ethyl, trifluoromethyl, difluoromethyl, difluoromethoxy, methoxy, isopropyl, cyclopropyl, oxo, hydroxy, ethoxy, phenyl, 2-trifluoroethyl, dimethylamino, cyclobutylmethyl, methylamino, and cyclopentyl.

A more specific embodiment of the invention is the group of compounds (or their pharmaceutically acceptable salts) specified below:

i) 4-(3-cyclopropyl-6,7-dihydro[1,2]oxazolo[4,3-c]pyridin-5(4H)-yl)-7-methyl-5-[(3S)-tetrahydrofuran-3-yl]imidazo[5,1-f][1,2,4]triazine, ii) 4-(2-cyclopropyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine, iii) 4-(3-cyclopropyl-1-methyl-1,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine, iv) 2-cyclopropyl-6-[5-(2-fluorophenyl)-7-methylimidazo[5,1-f][1,2,4]triazin-4-yl]-5,6,7,8-tetrahydropyrido[4,3-d]pyrimidine, v) 4-(2-cyclopropyl-6,7-dihydro[1,3]oxazolo[5,4-c]pyridin-5(4H)-yl)-7-methyl-5-[(3S)-tetrahydrofuran-3-yl]imidazo[5,1-f][1,2,4]triazine, vi) 8-(2-fluoroethoxy)-7-methoxy-2-{7-methyl-5-[(3S)-tetrahydrofuran-3-yl]imidazo[5,1-f][1,2,4]triazin-4-yl}-1,2,3,4-tetrahydroisoquinoline, vii) 5-(2-fluorophenyl)-7-methyl-4-(1-methyl-1,4,5,7-tetrahydro-6H-pyrazolo[3,4-c]pyridin-6-yl)imidazo[5,1-f][1,2,4]triazine, viii) 7-methyl-4-(1-methyl-1,4,5,7-tetrahydro-6H-pyrazolo[3,4-c]pyridin-6-yl)-5-[(3S)-tetrahydrofuran-3-yl]imidazo[5,1-f][1,2,4]triazine, ix) 4-(1-cyclopropyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine, and;

x) 7-methyl-4-(1-methyl-1,4,5,7-tetrahydro-6H-pyrazolo[3,4-c]pyridin-6-yl)-5-[(2R)-tetrahydrofuran-2-yl]imidazo[5,1-f][1,2,4]triazine.

Synthesis

The compounds of Formula I can be prepared by a variety of methods that are analogously known in the art. The reaction schemes presented below illustrate alternative methods for preparing these compounds. Others, including modifications thereof, will be readily apparent to one skilled in the art. Any reference to an appropriately substituted entity refers to one that contains the same relevant substituents as that desired in the final product, or a protected entity that can be readily converted to the desired moiety. This is further illustrated below.

Generation of Compounds of Formula I

One potential synthetic approach to generate compounds of Formula I from imidazotriazinone intermediate A is shown in Scheme 1. The appropriately substituted imidazotriazinone (i.e., R$^1$, R$^2$ and R$^3$ are represented by the same moiety as desired in the final product or a protected variant thereof) is treated with an excess of phosphorus oxychloride, neat or in an appropriately inert solvent, at temperatures from 20° C. to 200° C. to generate intermediate B, where the leaving group (LG) for the subsequent S$_N$Ar reaction is a chloride. Alternatively, the S$_N$Ar precursor can be captured with 1H-1,2,4-triazole for a leaving group. This intermediate B can be synthesized by treating the appropriate imidazotriazinone A with an excess of phosphorus oxychloride in the presence of 1H-1,2,4-triazole and base (such as triethylamine, pyridine, N,N-diisopropylethylamine, cesium carbonate, etc.) at temperatures from 0° C. to 200° C. The leaving group (LG) of B can be displaced under S$_N$Ar conditions by stirring with an appropriately substituted amine C (i.e., A, X and R$^4$ are represented by the same moiety as in the final product, or a protected variant thereof) in the presence of a base (triethylamine, N,N-diisopropylethylamine, cesium carbonate, etc.) in a suitably inert solvent at temperatures from 20° C. to 200° C. to make compounds of Formula I.

Scheme 1

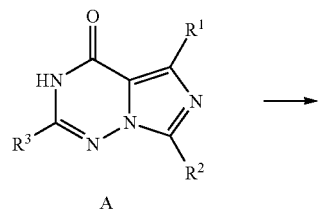

A

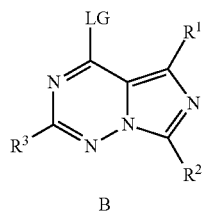

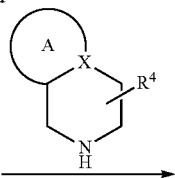

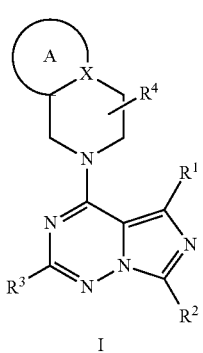

An alternate synthesis of compounds of Formula I is shown in Scheme 2. An appropriately substituted N'-hydroxyimidoformamide D (i.e., $R^2$ is represented by the same moiety as in the final product) and methyl propiolate E are stirred in an appropriate solvent and heated to elevated temperatures until the cyclization reaction to form imidazole intermediate F is completed. An example of a similar transformation is described by Paul et al., *J. Med. Chem.* 1985, 28, 1704-1716. The resultant imidazole F is brominated with an electrophilic bromine source such as bromine ($Br_2$), N-bromosuccinimide (NBS), etc., in an appropriate solvent usually at temperatures ≤20° C. to give intermediates represented by G. Bromoimidazole G can be N-aminated using a suitably strong base and an aminating reagent, such as (aminooxy)(diphenyl) phosphine oxide, an O-benzoylhydroxylamine derivative (Parlanti et al., *Org. Lett.* 2007, 9, 3821-3824), or hydroxylamine-O-sulfonic acid, in an appropriate solvent at temperatures below 20° C. The resulting aminated imidazole H is first condensed with an appropriately substituted imidoformamide J (i.e., $R^3$ is represented by the same moiety as desired in the final product) under elevated temperatures; a spontaneous intramolecular cyclization then affords the brominated imidazotriazinone K. The carbonyl of the imidazotriazinone K is transformed to the pendant 1,2,4-triazole in order to prepare the core for nucleophilic displacements via $S_NAr$ reactions. This transformation has been described previously by Knutsen et al., *J. Chem. Soc., Perkin Trans.* 1 (1972-1999) 1985, (3), 621-630. The pendant triazole is incorporated through treatment of the triazinone core K with phosphorus oxychloride in the presence of 1H-1,2,4-triazole at temperatures ranging from 20° C. to 200° C. to give intermediate L. Intermediate L readily undergoes $S_NAr$ displacement reactions upon treatment with appropriately substituted amines C using a wide variety of solvents (tetrahydrofuran, dimethyl sulfoxide, acetonitrile, toluene, etc.), bases (triethylamine, N, N-diisopropylethylamine, cesium carbonate, etc.), and temperatures (20° C. to 150° C.). Final compounds of Formula I can be generated by the transition metal-mediated (Suzuki reaction) installation of an alkyl or aryl group. The Suzuki reaction generally employs a halogenated starting material, which is treated with a catalytic amount of a palladium source, an appropriately substituted aryl or alkyl boronic acid or ester N (i.e., $R^1$ is represented by the same moiety as desired in the final product or a protected variant thereof), and a base in an appropriate solvent at temperatures from 20° C. to 200° C. Thorough reviews of this chemistry have been published; see N. Miyaura and A. Suzuki, *Chemical Reviews* 1995, 95, 2457-2483 and Heravi et al., *Tetrahedron* 2012, 68, 9145-9178.

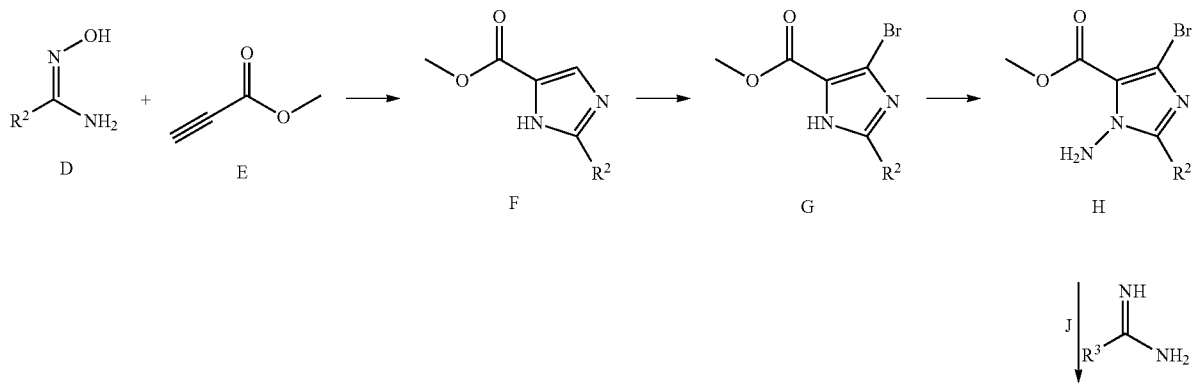

Scheme 2

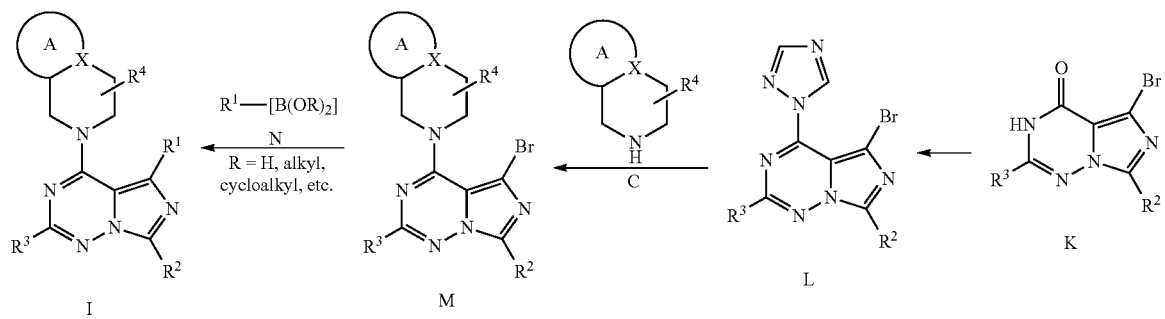

Generation of Substituted Triazinone Intermediates

Scheme 3 describes one potential synthetic route to the imidazotriazinone intermediate described by A in which $R^1$ is aryl or heteroaryl as defined above. Condensation of an α-bromoacetophenone P with intermediate S generates a Boc-protected substituted 4-phenyl-1H-imidazol-1-amine T. The α-bromoacetophenone P starting material is commercially available or prepared via bromination of a suitably substituted acetophenone O, while the Boc-protected amidrazone intermediate S is generated under basic conditions from tert-butyl hydrazinecarboxylate Q and an appropriately substituted ethyl imidoate R. Boc removal from intermediate T is accomplished under acidic conditions to generate intermediate U. A thorough review of Boc removal is described by Wuts, P. G. W. and Greene, T. W. *Greene's Protective Groups in Organic Synthesis*, 4$^{th}$ Edition, 2006. Intermediate U is condensed with an appropriately substituted imidamide salt V in an appropriate polar non-nucleophilic solvent at temperatures from 20° C. to 200° C. to give intermediates represented by structure W. The imidazotriazinone A can be formed by the addition of a carbonyl equivalent, such as 1,1'-carbonyldiimidazole (CDI), 1,1'-carbonyldi(1,2,4-triazole) (CTI), etc., to a preformed mixture of intermediate W and a base in an appropriate solvent at temperatures from 20° C. to 200° C. Similar chemistry to Scheme 3 has described by Helal et al., Imidazo-[5,1-f][1,2,4]triazines for the Treatment of Neurological Diseases, US 20120214791 A1.

Scheme 3

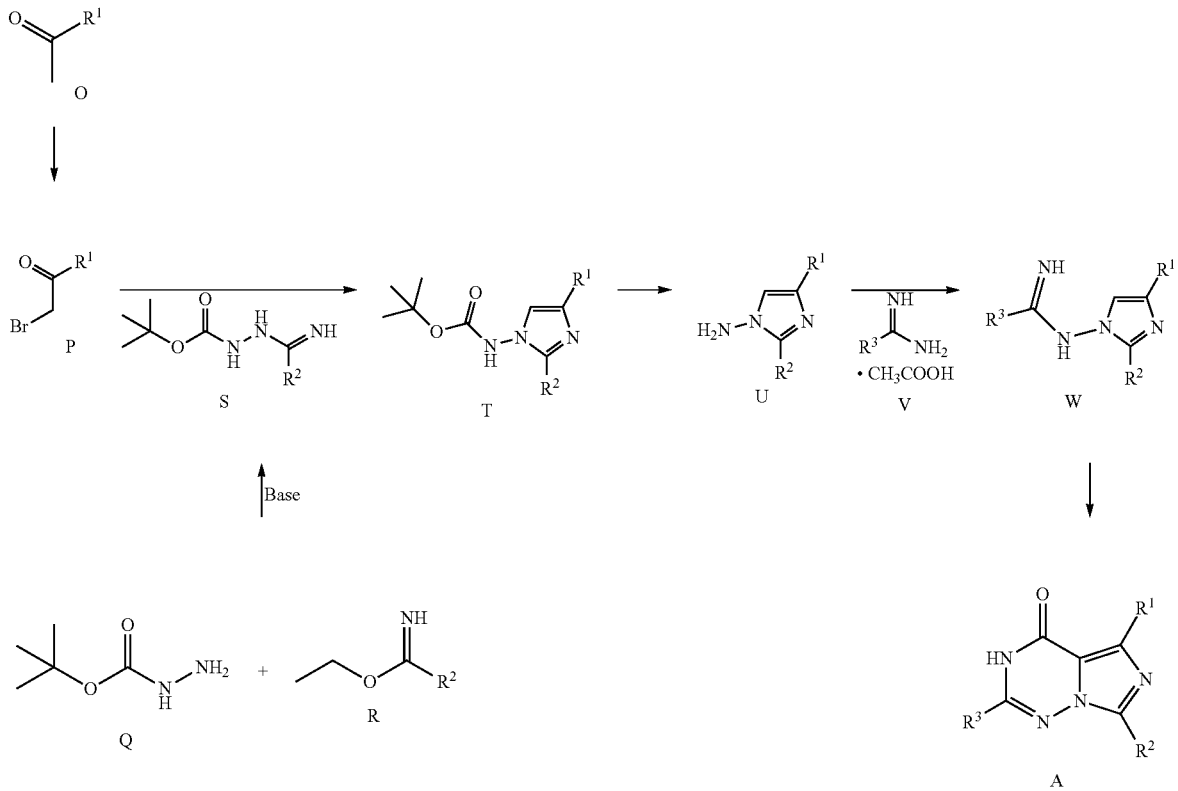

Scheme 4 describes a potential synthetic sequence to generate imidazotriazinone intermediates A. One method to generate key intermediate DD starts with the appropriate commercially available 3-ketoester Y. Treatment of 3-ketoester Y with a nitrating reagent such as sodium nitrite and an acid catalyst such as acetic acid, either neat or with an appropriate solvent, at temperatures below 20° C. can give intermediate Z. The nitro intermediate Z can then be reduced to the desired amine DD through a hydrogenation reaction. This transformation occurs by subjecting the nitro intermediate Z to a metal catalyst (usually palladium on a carbon support) under atmospheric or greater pressures of hydrogen in an appropriately inert solvent at temperatures around 20° C. to provide the desired DD intermediate. This reaction can also be done in the presence of reagents that speed the reduction process, such as acid catalysts and acid chlorides. A review of the generation of amines by reductive processes can be found in Schilling, Kirk-Othmer Encyclopedia of Chemical Technology (5th Edition) 2004, 2, 476-498. An alternate synthesis of compounds DD proceeds through a protected glycine derivative, such as the commercially available benzhydryl-protected glycine AA. The protected glycine AA is deprotonated by treatment with an appropriately strong base, such as lithium bis(trimethylsilyl)amide (LHMDS), lithium diisopropylamide (LDA), etc., in an appropriate solvent at temperatures from −78° C. to 20° C.; this anion is then added to an appropriately substituted acid chloride BB in a suitable solvent at temperatures<20° C. The resultant α-amino-protected dicarbonyl intermediate CC is treated in situ with aqueous acid, such as a 1 M to 6 M hydrochloric acid solution, for a period ranging from 15 min to several hours at 20° C. The resultant α-amino-β-dicarbonyl hydrochloride salt DD is stirred with an appropriately substituted imidoate FF under mildly basic conditions from 20° C. to 200° C. to give imidazole intermediate HH. Alternatively, intermediate DD can be transformed into intermediate HH through a process in which an oxazole intermediate GG is generated by treating DD with an appropriately substituted triethyl or trimethyl orthoester EE in the appropriate alcoholic solvent at 20° C. The oxazole intermediate GG can be treated in situ with an amine source (ammonium acetate, ammonium formate, ammonium chloride, etc.) in the presence of an acid catalyst (acetic acid, trifluoroacetic acid, etc.), neat or with an appropriate solvent, at temperatures from 20° C. to 200° C., to give the imidazole HH. HH can be N-aminated using a base and an aminating reagent, such as (aminooxy)(diphenyl)phosphine oxide, an O-benzoylhydroxylamine derivative, or hydroxylamine-O-sulfonic acid, in an appropriate solvent to give II. This transformation has previously been described by Heim-Riether et al., A Novel Method for the Synthesis of Imidazo [5,1-f][1,2,4]triazin-4(3H)-ones. *J. Org. Chem.* 2005, 70, 7331-7337. The resulting N-aminated intermediate II can then be cyclized to the desired imidazotriazinone intermediate A by stirring in the presence of the appropriately substituted amide JJ at temperatures of 20° C. and above.

Scheme 4

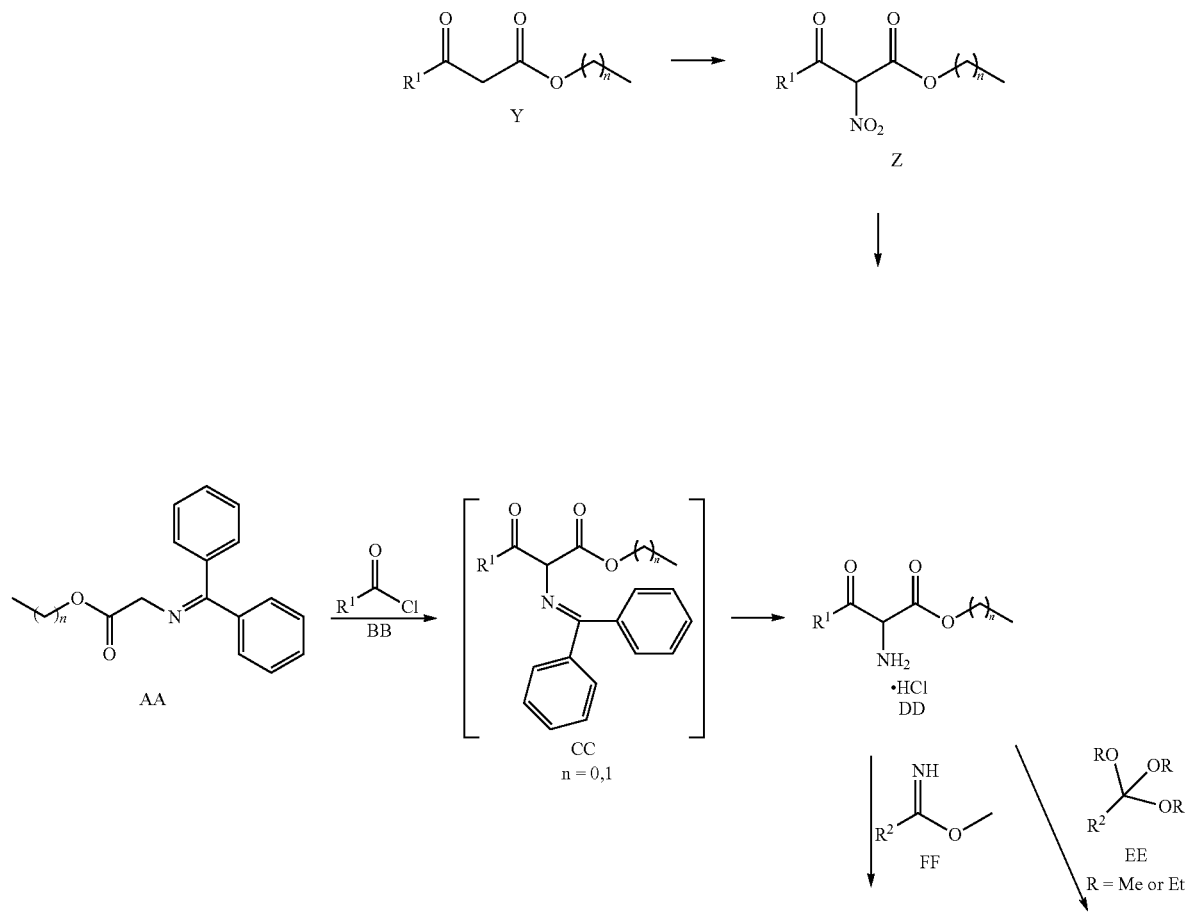

-continued

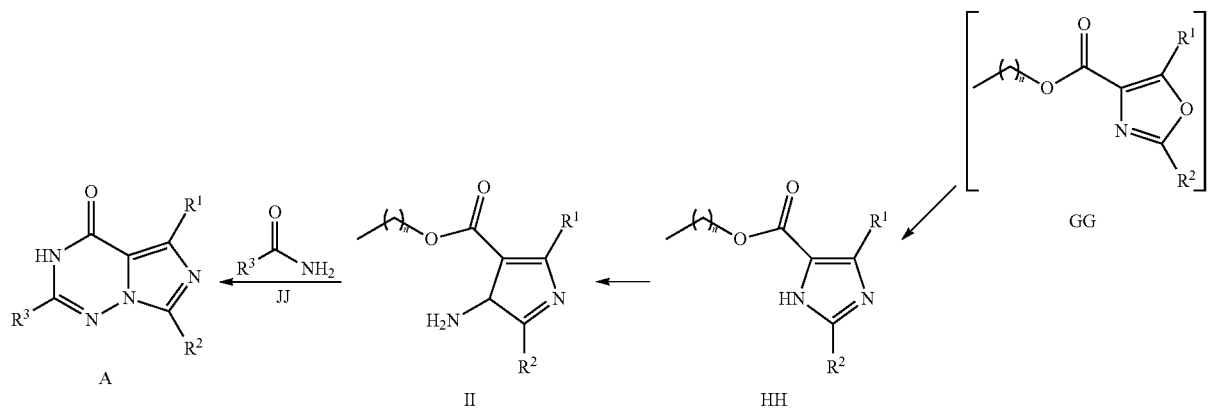

An alternative method for the generation of intermediate HH is depicted in Scheme 5. A glycine ester LL is acylated with an appropriately substituted acid, activated acid, acid chloride, or ester KK to generate an acylated intermediate MM, or a commercially available, appropriately substituted, acylated glycine ester MM may be employed. Compound MM can be C-acylated by treatment with an appropriately substituted activated acid BB, such as an acid chloride, in the presence of an imidazole, a Lewis acid such as titanium tetrachloride, and a base such as tri-n-butylamine in an appropriate solvent at temperatures generally below 20° C. to arrive at compounds represented by intermediate NN. Examples of this chemistry were previously described by Honda et al., WO 2008041571 and Misaki et al., J. Am. Chem. Soc. 2005, 127, 2854-2855. The cyclization of intermediate NN by the addition of an amine source (ammonium acetate, ammonium chloride, etc.) and an acid (acetic acid, trifluoroacetic acid, etc.), neat or in the presence of an acceptable solvent, at elevated temperatures results in the formation of the desired intermediate HH.

Generation of Substituted Amines C

In Schemes 6-18 Below, B' Represents the Corresponding Substituent on the A Moiety that is Desired in the Final Product (or a Protected Variant Thereof).

Scheme 6 illustrates one possible preparation of amines such as SA4 and SA6. Starting aldehyde SA1 can be reacted with hydrazine, or an appropriately substituted hydrazine OO, in a suitable solvent such as isopropyl alcohol at temperatures from 20° C. to 200° C. to form hydrazones such as SA2. Hydrazone intermediates SA2 can be cyclized under basic conditions at elevated temperatures to give pyrazole compounds SA3. For example, treatment of SA2 with sodium hydride in tetrahydrofuran under reflux gives SA3. Similar transformations have been described in WO 2009/074360. The pyridine ring of compounds SA3 can be reduced to give amines represented by structure SA4 by exposure to metal catalysts such as platinum under atmospheric to 100 psi of hydrogen in a suitably inert solvent system with an acid source at temperatures from 20° C. to 50° C. Intermediate SA3 can also give compounds such as SA5 by a metal- Scheme 5

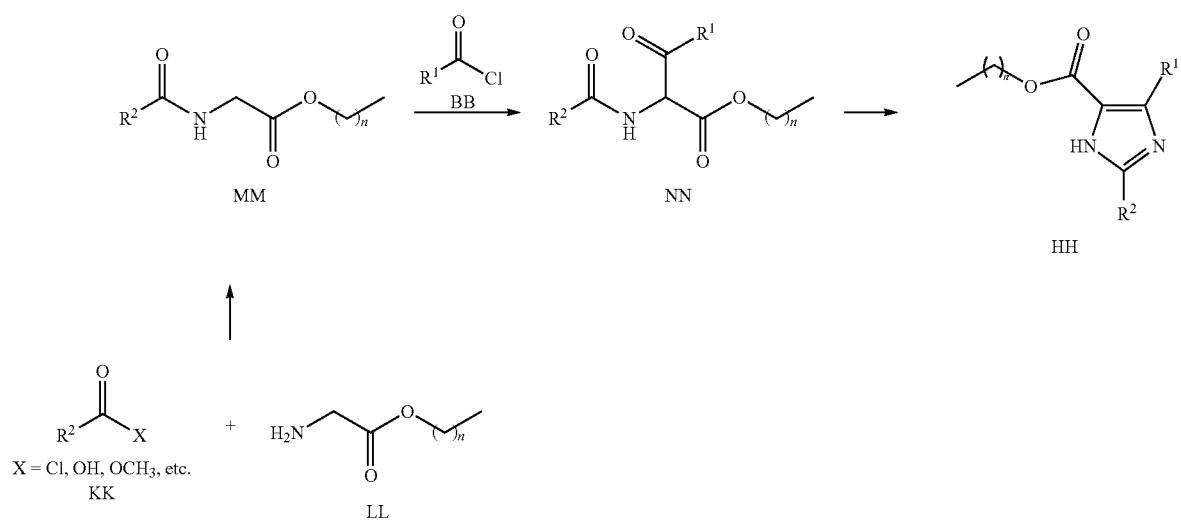

n = 0, 1 catalyzed (usually palladium) Suzuki reaction to install alkyl or aryl groups $R^4$ (generally from the alkyl or aryl boronic acids or esters N). A review of standard reaction conditions can be found at N. Miyaura and A. Suzuki, *Chemical Reviews* 1995, 95, 2457-2483. Intermediate SA5 can be reduced to a racemic intermediate SA6 following the pyridine ring reduction conditions described in the transformation of intermediate SA3 to intermediate SA4. The racemate SA6 can be separated into its constituent enantiomers through standard chiral separation methods.

with appropriate alkyl halides under basic conditions in a suitable solvent at a wide variety of temperatures. In the case where the substituent (B') is a cyclopropyl or aryl group, treatment of SA9 with the appropriate boronic acid or ester in the presence of oxygen, a copper source such as $Cu(OAc)_2$, and a copper ligand such as 2,2'-bipyridine in a suitable solvent at temperatures from 20° C. to 200° C. results in a mixture of compounds of formula SA10 and SA11. The regioisomeric mixtures of SA10 and SA11 can be separated using chromatographic methods. Deprotection of the Boc Scheme 6

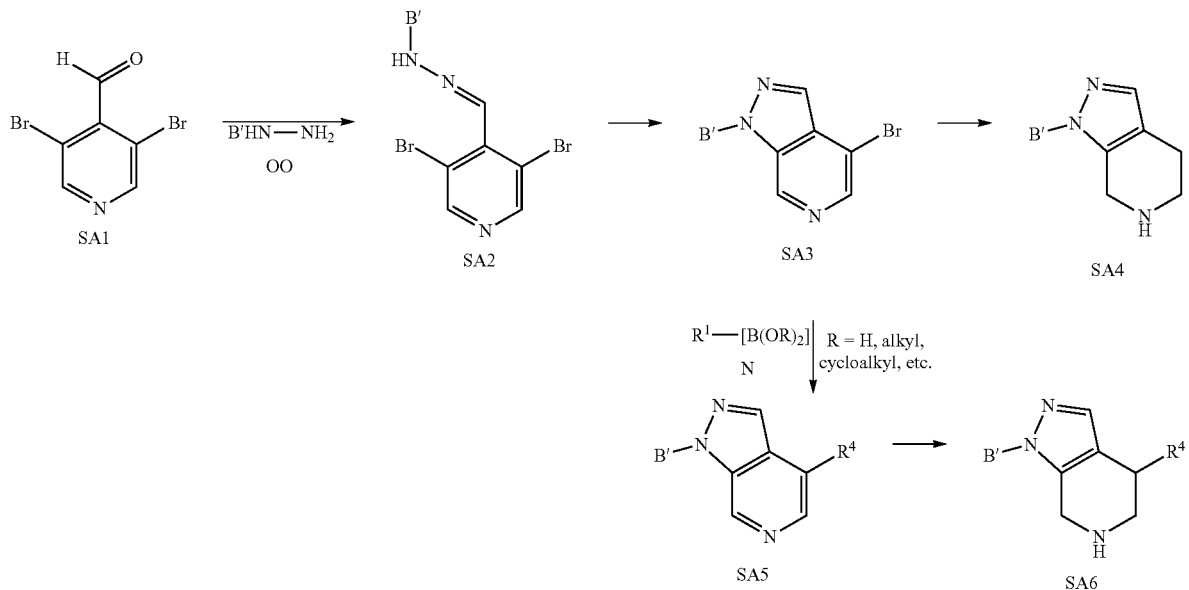

An alternative synthesis of compounds of formula SA4 and their regioisomers SA12 is depicted in Scheme 7. Boc-protected 3-piperidinone SA7 can be converted to enamine SA8 by treatment with N,N-dimethylformamide dimethyl acetal at elevated temperatures as described in US 2007167426. Treatment of SA8 with hydrazine in a suitable solvent at temperatures from 20° C. to 200° C. results in intermediate SA9. SA9 can be N-alkylated on the pyrazole ring by reaction group can be achieved by treatment of SA10 and SA11 with acids such as hydrochloric acid or trifluoroacetic acid, neat or in an appropriately inert solvent, at temperatures from 20° C. to 100° C. to give amines SA4 and SA12 respectively. Boc removal is thoroughly described by Wuts, P. G. W. and Greene, T. W. *Greene's Protective Groups in Organic Synthesis*, 4th Edition, 2006.

Scheme 7

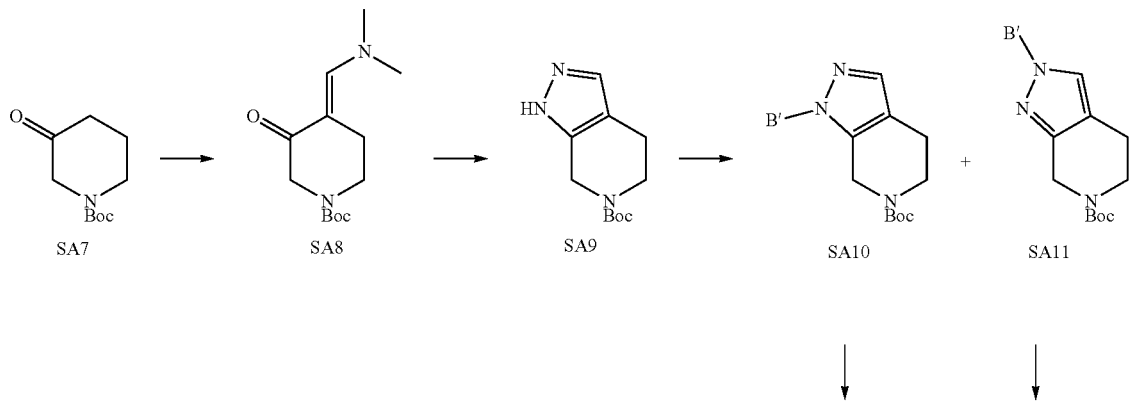

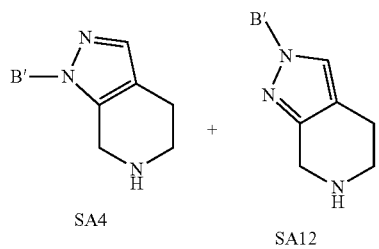

Scheme 8 illustrates an alternate route to compounds of formula SA4 and SA12. Commercially available 1H-pyrazolo[3,4-c]pyridine (SA13) can be optionally substituted with alkyl groups as described in Scheme 7 to give compounds of formula SA14 and SA15. The pyridine ring can be reduced under similar conditions to the pyridine ring reduction described in Scheme 6 for synthesis of intermediates SA4 and SA6. The resultant 4,5,6,7-tetrahydropyrazolo[3,4-c]pyridine regioisomers SA4 and SA12 can be separated using standard chromatographic methods.

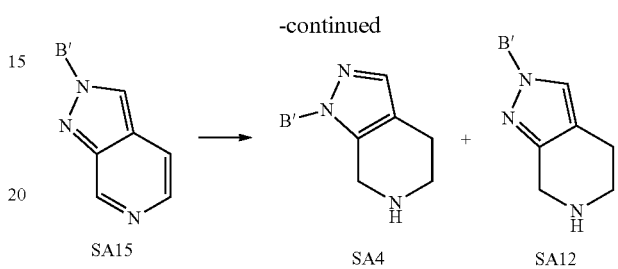

Scheme 8

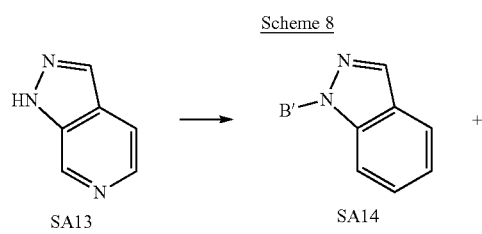

4,5,6,7-Tetrahydropyrazolo[4,3-c]pyridines of formula SA21 and SA22 can be prepared as outlined in Scheme 9. The synthesis of intermediate SA18 from SA16 via SA17 has been described in US 2007/0232600. Intermediate SA18 can be optionally substituted to provide SA19 and SA20 using chemistry described in the synthesis of intermediate SA10 and SA11 in Scheme 7. The Boc group can be removed under acidic conditions, as described by Wuts, P. G. W. and Greene, T. W. *Greene's Protective Groups in Organic Synthesis*, 4th Edition, 2006.

Scheme 9

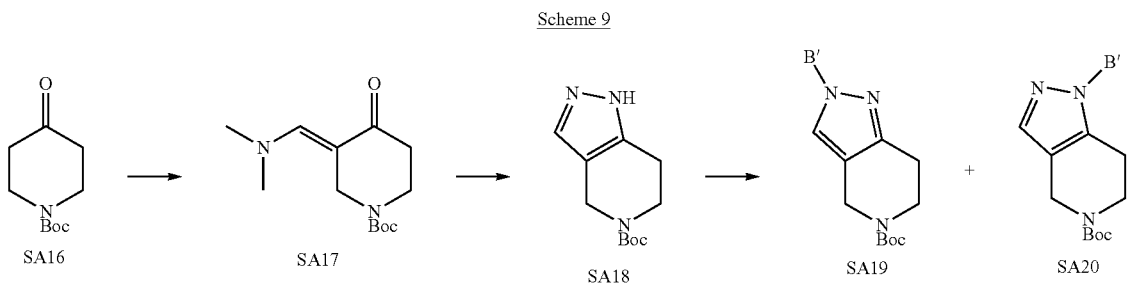

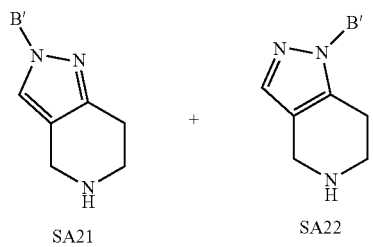

Scheme 10 refers to the preparation of disubstituted pyrazole amines of general structures SA27 and SA28. A synthesis of Boc-protected enamine SA23 has been described previously by Osata et al., *Org. Process Res. Dev.* 2011, 15, 1433-1437. SA23 can be reacted with various acyl chlorides BB' in the presence of bases such as N,N-diisopropylethylamine and pyridine, at temperatures<20° C. in appropriate solvents to give β-diketones SA24. β-Diketone intermediate SA24 can undergo condensation with appropriately substituted hydrazines OO in appropriate solvents (such as methanol, N,N-dimethylformamide, etc.) at 20° C. to 200° C., to give a regioisomeric mixture of pyrazoles SA25 and SA26. Standard chromatographic methods can be used to separate regioisomer SA25 from SA26. Removal of the Boc protecting groups from SA25 and SA26 to generate intermediates SA27 and SA28 can be achieved by treatment with acids under standard conditions.

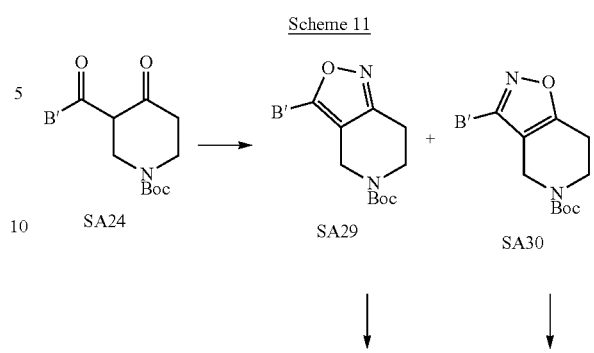

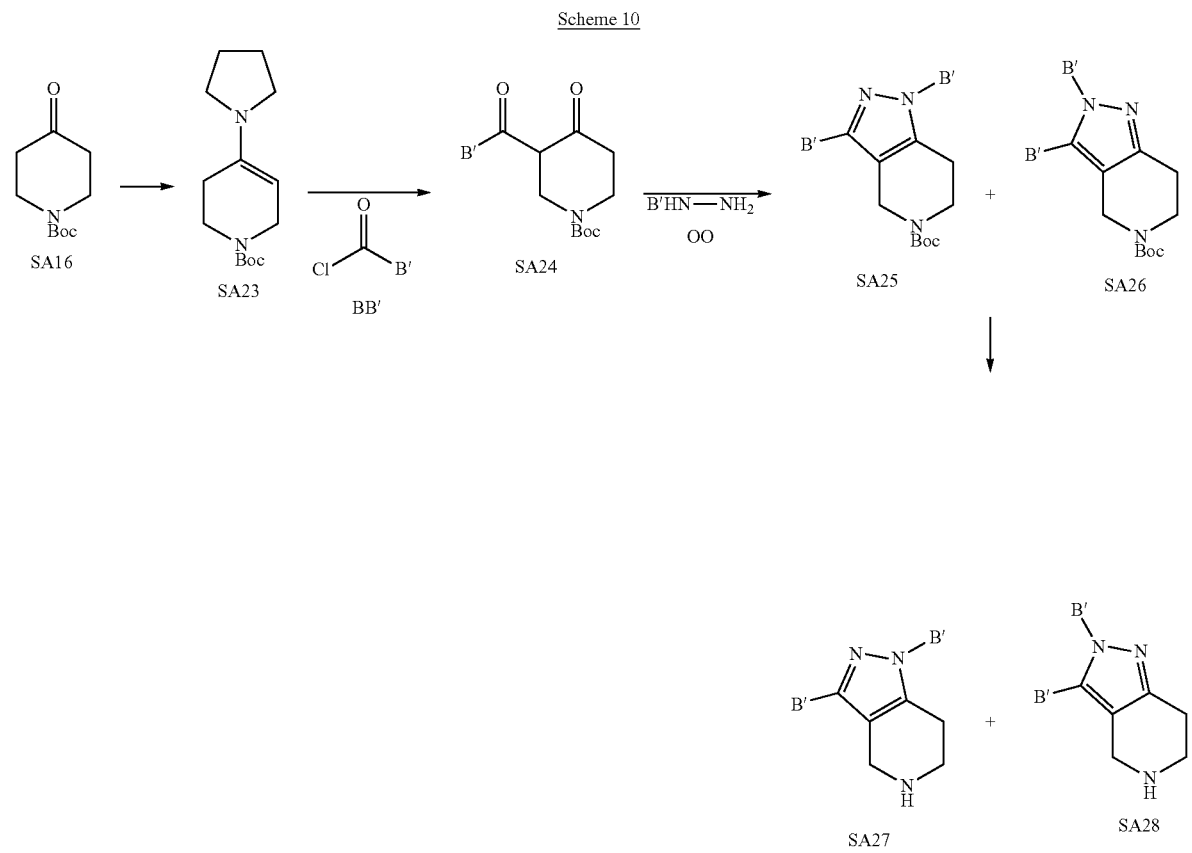

Scheme 11 illustrates a reaction sequence that can be used to obtain isoxazoles of general structure SA31 and SA32. β-Diketone intermediate SA24 (see Scheme 10) can be converted to isoxazoles SA29 and SA30 by treatment with hydroxylamine hydrochloride in the presence of a base in an appropriate solvent at temperatures from 20° C. to 200° C. Separation of the isoxazole isomers can be accomplished by standard chromatographic techniques. Removal of the Boc protecting group from SA29 and SA30 is carried out under acidic conditions, as described by Wuts, P. G. W. and Greene, T. W. *Greene's Protective Groups in Organic Synthesis*, 4th Edition, 2006 to furnish SA31 and SA32.

-continued

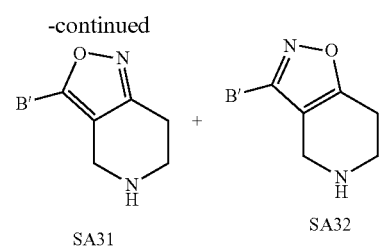

Scheme 12 depicts a synthetic sequence that can be used to access 4,5,6,7-tetrahydropyrazolo[1,5-a]pyrazines such as those represented by general structures SA36 and SA37.

Intermediate SA33 can be prepared as described by T. S. Mansour et al., PCT Intl. Appl. WO 2006/130588. The reaction of SA33 with terminal alkynes QQ in a sealed bomb reactor, at temperatures>200° C., gives a regioisomeric mixture of SA34 and SA35, which can be separated from each other via chromatographic methods. Removal of the benzyl carbamate (Cbz) protecting group from SA34 and SA35 can be achieved using hydrogenation conditions (catalytic metals such as palladium on a solid support, under hydrogen in an inert solvent) or other conditions described by Wuts, P. G. W. and Greene, T. W. *Greene's Protective Groups in Organic Synthesis*, 4$^{th}$ Edition, 2006 to give compounds represented by SA36 and SA37.

Scheme 12

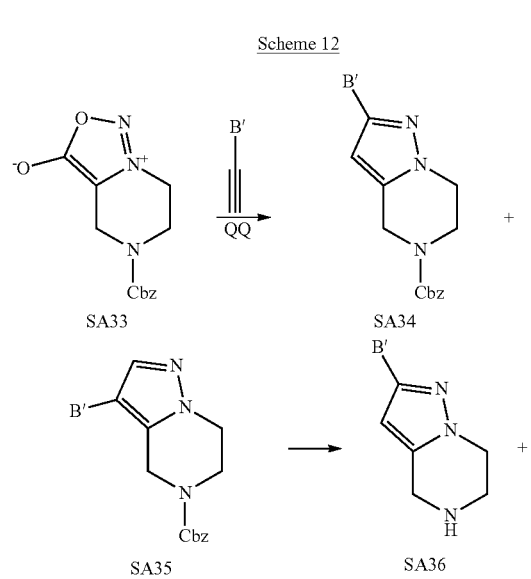

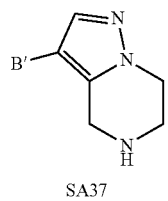

SA37

Potential access to 4,5,6,7-tetrahydro[1,3]oxazolo[5,4-c] pyridines such as SA42 is illustrated in Scheme 13 and is similar to what has been described previously by Ashton et al., *Bioorg. Med. Chem. Lett.* 2005, 15, 2253-2258. Amino alcohol SA38 (see US 2009/163472 and WO 2011/157793) can be acylated by treatment with appropriately substituted acyl chlorides BB' in the presence of a base such as N,N-diisopropylethylamine, pyridine, etc. at temperatures≤20° C. to give compounds represented by SA39. SA39 can be oxidized to ketone SA40 by treatment with an oxidizing agent such as Dess-Martin periodinane (a review of this and related reagents can be found at Zhdankin, V. V. *J. Org. Chem.* 2011, 76, 1185-1197). SA40 can be subjected to dehydration conditions with a reagent such as Burgess's reagent, which can result in a cyclization to generate isoxazoles such as SA41. Boc removal with acid provides compounds represented by SA42.

Scheme 13

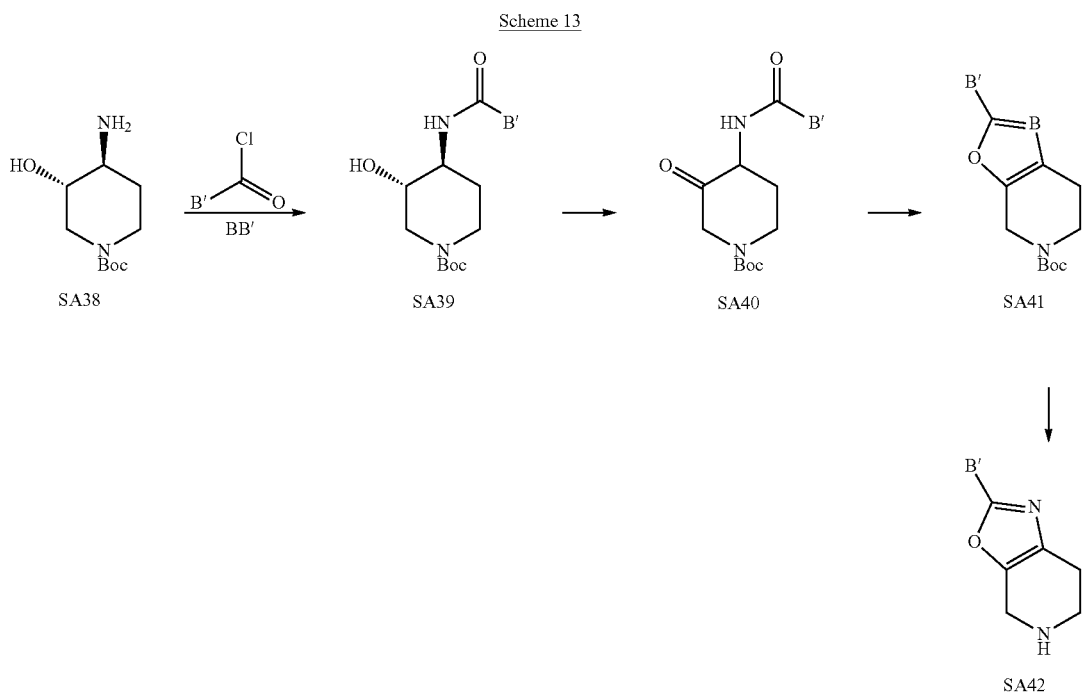

Scheme 14 describes the synthesis of 5,6,7,8-tetrahydropyrido[4,3-d]pyrimidines such as those represented by SA47 and SA49. Compounds such as SA47 and SA49 can be synthesized starting from compound SA43 (Dodd and Oehlschlager, *J. Org. Chem.* 1992, 57, 2794-2803) by an adaptation of the work described by Shireman et al., *Bioorg. Med. Chem. Lett.* 2008, 18, 2103-2108. Treatment of ketoester SA43 with appropriately substituted amidines V in the presence of base and solvent at temperatures from 20° C. to 200° C. gives hydroxypyrimidine compounds such as SA44. SA44 may be converted to chloride SA45 by treatment with a chlorinating reagent such as phosphorus oxychloride, either neat or in inert solvents, from 20° C. to 200° C. Chlorides SA45 can undergo $S_NAr$ substitution reactions by treatment with appropriately substituted alcohols or amines RR under basic conditions at temperatures ranging from 20° C. to 200° C. to give intermediate SA46. The benzyl carbamate-protected SA46 can be deprotected under various conditions, most commonly hydrogenation, as described by Wuts, P. G. W. and Greene, T. W. *Greene's Protective Groups in Organic Synthesis*, 4$^{th}$ Edition, 2006, to give amines SA47. Intermediate SA45 may also be used to generate compounds with carbon-based substitution of the pyrimidine. This substitution could occur through transition metal-catalyzed (usually palladium) cross couplings with appropriately substituted alkyl or aryl boronates N in the presence of base in appropriate solvents at temperatures from 20° C. to 200° C. to give compounds such as SA48. Removal of the benzyl carbamate protecting group of SA48 to generate the desired SA49 can be effected using similar conditions to those used to generate SA47 from SA46.

Scheme 15 shows one possible route to 5,6,7,8-tetrahydro-1,7-naphthyridine compounds SA53 and SA55. A synthesis of SA50 has been described by Strang et al., EP 1595 881. Compound SA50 can be chlorinated using a chlorinating reagent such as phosphorus oxychloride, neat or in an appropriately inert solvent, at temperatures of 20° C. to 200° C. to give SA51. The chloride of SA51 can be displaced in an $S_NAr$ reaction using appropriately substituted alcohols and amines RR in the presence of base in an appropriate solvent at temperatures of 20° C. to 200° C. to give compounds represented by SA52. Removal of the benzyl protecting group from SA52 can be carried out by a metal-catalyzed hydrogenation reaction. Many other conditions for benzyl removal can be found in Wuts, P. G. W. and Greene, T. W. *Greene's Protective Groups in Organic Synthesis*, 4$^{th}$ Edition, 2006. Intermediate SA51 may also be used to generate compounds with carbon-based substitution of the pyridine ring. This substitution could occur through transition metal-catalyzed (usually palladium) cross couplings with appropriately substituted alkyl or aryl boronates N in the presence of base in appropriate solvents at temperatures from 20° C. to 200° C. to give compounds such as SA54. Conditions for removal of the benzyl protecting group from SA54 to generate SA55 can be found in Wuts, P. G. W. and Greene, T. W. *Greene's Protective Groups in Organic Synthesis*, 4$^{th}$ Edition, 2006.

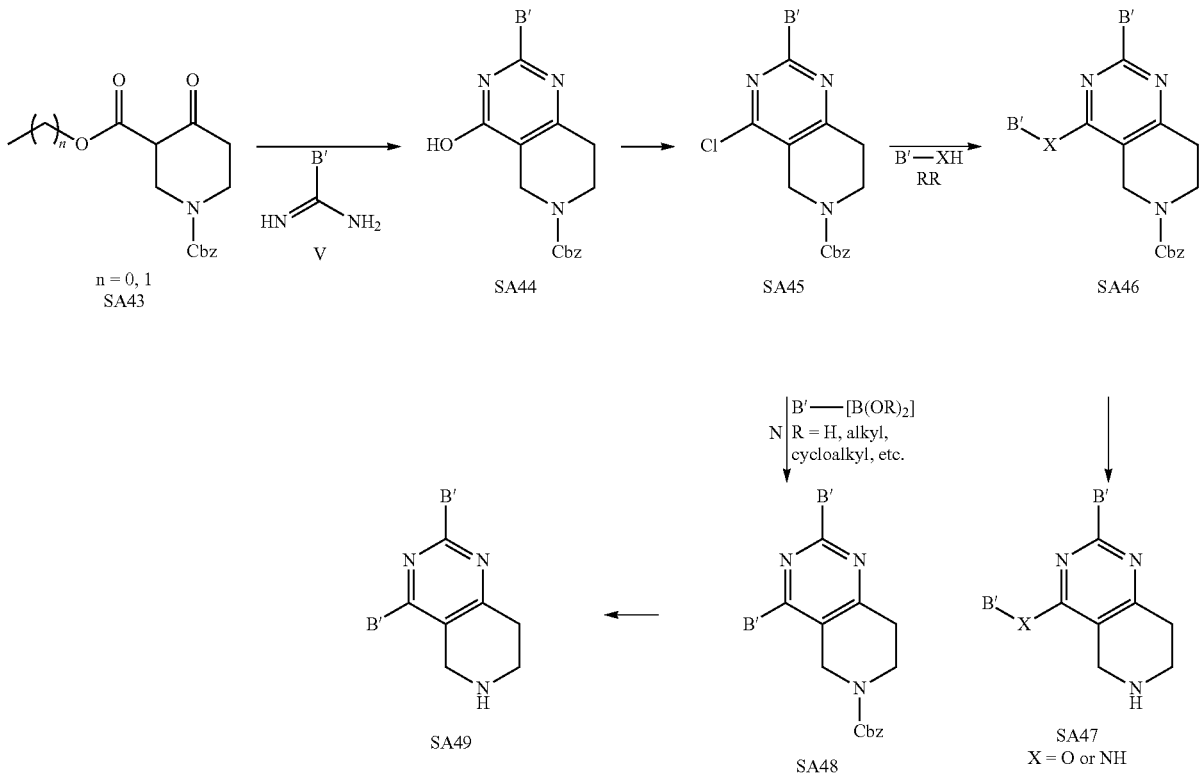

Scheme 14

Scheme 15

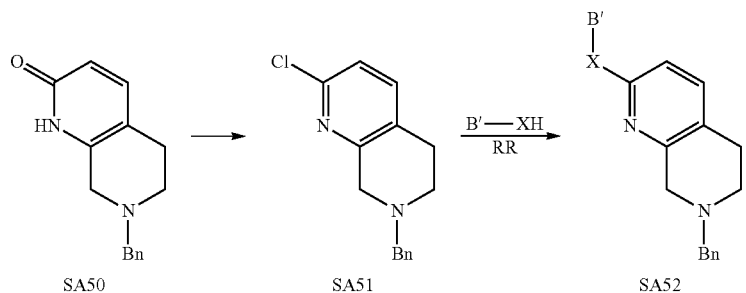

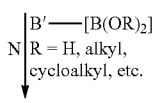

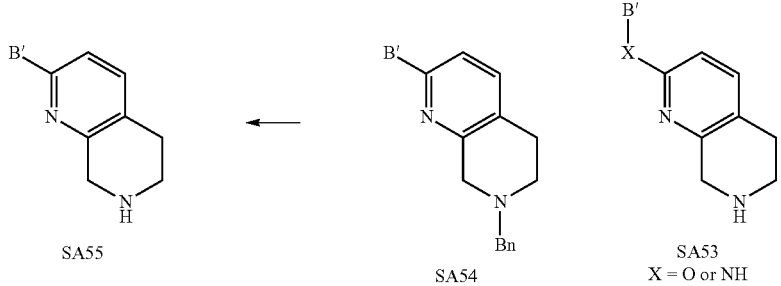

Scheme 16 describes a potential synthesis of substituted 5,6,7,8-tetrahydro-1,6-naphthyridine compounds represented by general structures SA58 and SA60. A synthesis of the starting chloropyridine SA56 has been described by Strang et al., EP 1595 881. General reaction conditions to make the desired carbon-, oxygen-, and nitrogen-substituted fused pyridines are described in Scheme 15 and can be applied to SA56 to generate appropriately substituted SA57 and SA59. Removal of the benzyl protecting group to generate the desired SA58 and SA60 can be carried out using conditions described by Wuts, P. G. W. and Greene, T. W. *Greene's Protective Groups in Organic Synthesis*, 4th Edition, 2006.

Scheme 16

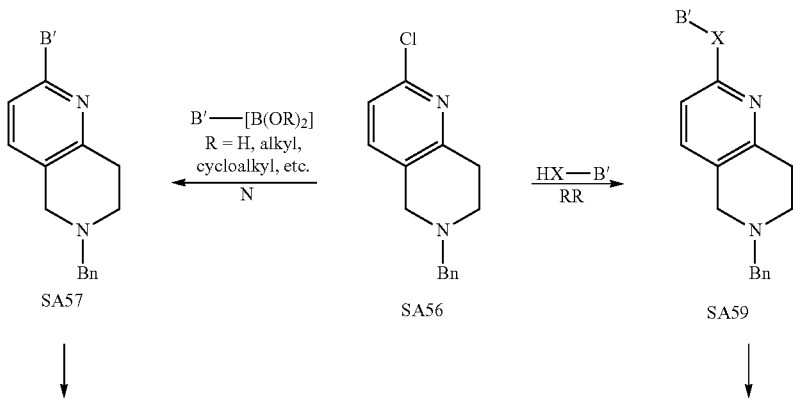

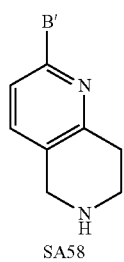

SA58

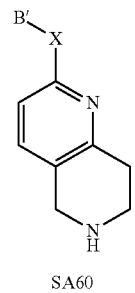

SA60

Scheme 17 refers to the synthesis of 1,2,3,4-tetrahydro-2,7-naphthyridines of general formula SA65 and SA67. The synthesis of the starting material SA61 has been described by Zhang et al., *J. Comb. Chem.* 2007, 9, 916. Treatment of SA61 with benzyl bromide followed by a reducing agent such as sodium borohydride in a suitable solvent provides SA62. Treatment of SA62 with a chlorinating reagent such as phosphorus oxychloride, neat or in a suitable solvent, at temperatures from 20° C. to 200° C. affords the chloropyridine intermediate SA63. Using chloropyridine SA63, in conjunction with the general conditions described in Scheme 15 for installing the appropriately substituted carbon, oxygen, or nitrogen substituent, provides benzyl-protected SA64 and SA66. Removal of the benzyl protecting group can be carried out using conditions described by Wuts, P. G. W. and Greene, T. W. *Greene's Protective Groups in Organic Synthesis*, 4th Edition, 2006 to generate SA65 and SA67.

et al., *ACS Med. Chem. Lett.* 2012, 3, 5-9. Treatment of SA68 with a bromine source (bromine, N-bromosuccinimide, etc.) at temperatures below 20° C. in an appropriate solvent such as chloroform can result in mono-brominated compounds represented by SA69. Intermediate SA69 can be cyclized to give compounds such as SA70 by treatment with 1,3,5-trioxane in the presence of an acid such as trifluoroacetic acid at temperatures of 20° C. to 100° C. The acetyl protecting group on SA70 can be removed by treatment with strong bases such as potassium hydroxide or strong acids such as hydrochloric acid at elevated temperature to give amine SA71. This acetyl deprotection has been described by Wuts, P. G. W. and Greene, T. W. *Greene's Protective Groups in Organic Synthesis*, 4th Edition, 2006. The removal of the bromine and the benzyl group from SA71 can occur simultaneously via metal-catalyzed hydrogenation using palladium on carbon catalyst under hydrogen (atmospheric to 100 psi) in an appropriate

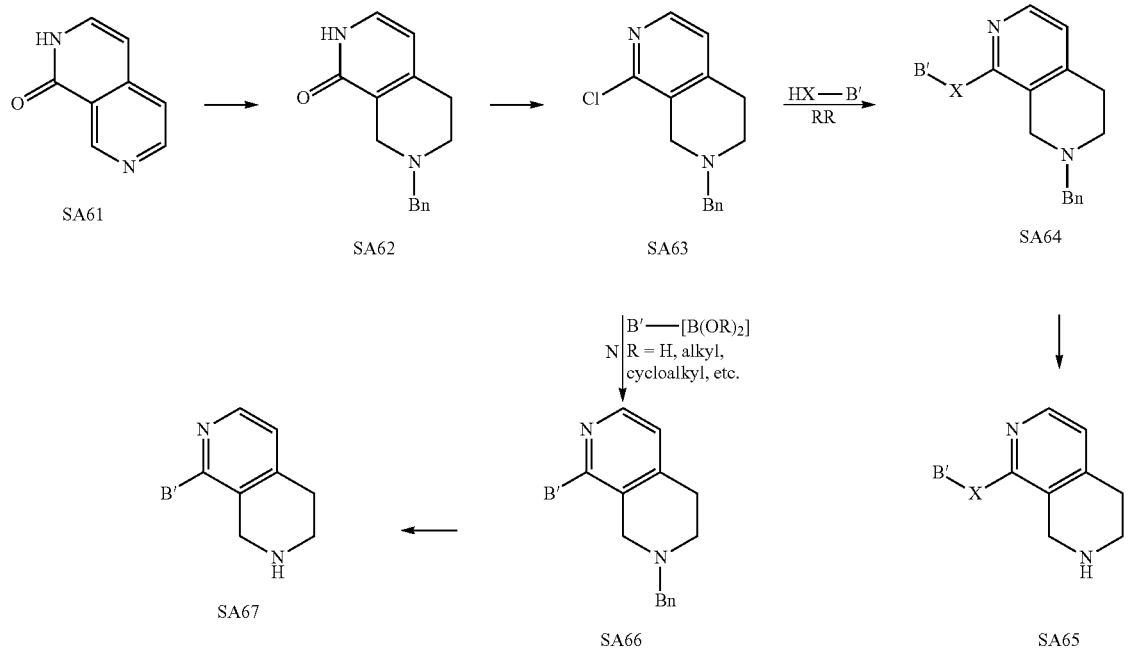

Scheme 18 describes a possible synthesis of compounds represented by the structure SA73. The benzyl-protected starting material SA68 can be prepared as described by Leese solvent such as methanol, to provide SA72. SA72 can be alkylated with appropriately substituted halogenated alkyls SS in the presence of base or through a Mitsunobu reaction (Swamy et al., *Chemical Reviews* 2009, 109, 2551-2651) with alcohol RR' to provide the desired amine SA73.

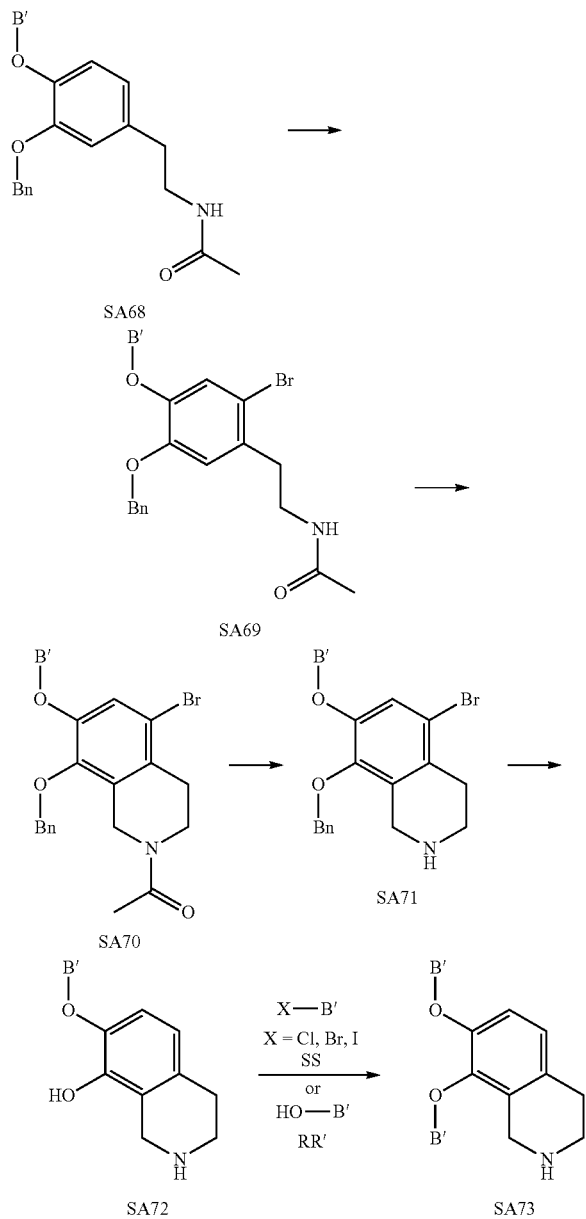

Scheme 18

Medical and Veterinary Uses

In one aspect, provided herein are methods for treating a disorder or disease by inhibiting a PDE10 enzyme. The methods, in general, comprise the step of administering a therapeutically effective amount of a compound of Formula I (or alternatively one of Ia, Ib, Ic, Ic' or Id) or a pharmaceutically acceptable salt thereof, to a patient in need thereof to treat the disorder or disease. A further aspect is the use of a compound as described herein in the manufacture of a medicament for treating a disorder or disease treatable by inhibition of PDE10.

The compounds of the present invention inhibit PDE10 enzymatic activity and hence raise the levels of cAMP or cGMP within cells that express PDE10. Accordingly, inhibition of PDE10 enzyme activity can be useful in the treatment of diseases caused by deficient amounts of cAMP or cGMP in cells. PDE10 inhibitors can also be beneficial in cases wherein raising the amount of cAMP or cGMP above normal levels results in a therapeutic effect. Inhibitors of PDE10 may be used to treat disorders of the peripheral and central nervous system, cardiovascular diseases, cancer, gastroenterological diseases, endocrinological diseases, urological diseases, etc.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, Huntington's disease, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, lupus, sarcoidosis, brain tumors, multiple sclerosis, dementia with Lewy bodies, or hypoglycemia. Other psychiatric disorders, such as post-traumatic stress disorder (PTSD) and schizoid personality disorder, can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long-term memory. Without wishing to be bound to any particular mechanism, it is proposed that, since PDE10 degrades cAMP or cGMP, the level of this enzyme affects memory in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long-term memory. The more active such genes are, the better is long-term memory. Thus, by inhibiting a phosphodiesterase, long-term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's disease, Parkinson's disease, Huntington's disease, Pick's disease), vascular (e.g., infarcts, hemorrhage, cardiac disorders), mixed vascular and Alzheimer's, bacterial meningitis, Creutzfeldt-Jakob disease, multiple sclerosis, traumatic (e.g., subdural hematoma or traumatic brain injury), infectious (e.g., HIV), genetic (Down's syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeldt-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amyotrophic lateral sclerosis (ALS), multiple systems atrophy (MSA), schizophrenia, Parkinson's disease, Huntington's disease, Pick's disease, Creutzfeldt-Jakob disease, depression, aging, head trauma, stroke, spinal cord injury, CNS hypoxia, cerebral senility, diabetes-associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntington. In individuals who do not have Huntington's disease, huntington has a polyglutamine region containing about 8 to 31 glutamine residues. For individuals who have Huntington's disease, huntington has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha IA voltage-dependent calcium channel); spinocerebellar ataxia type-7 (ataxin-7); and spinal and bulbar muscular atrophy (SBMA, also known as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S 17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amyotrophic lateral sclerosis (ALS), and multiple systems atrophy (MSA).

The invention further provides a method of treating a drug addiction, for example an alcohol, amphetamine, cocaine, or opiate addiction, in a mammal, including a human, which method comprises administering to said human an amount of a compound of formula I effective to treat said addiction. A "drug addiction", as used herein, means an abnormal desire for a drug and is generally characterized by motivational disturbances such a compulsion to take the desired drug and episodes of intense drug craving. Treating addiction also encompasses decreasing the amount of drug of abuse that the patient consumes and does not require total abstinence.

In addition to treating drug addiction, the compounds are also useful in preventing the relapse in drug and alcohol abuse associated with stress, especially chronic stress. Logrip et al. showed that stress induced up-regulation of PDE10 in rodents; Addiction Biology, 17, 920-933, 2012. Further, these authors demonstrated that stressed rodents consumed more alcohol than their non-stressed counterparts. The compounds of Formula I can be used to decrease the incidence of relapse associated with alcohol and drug addiction in stressed individuals.

Autoimmune diseases or infectious diseases that affect the basal ganglia may result in disorders of the basal ganglia including ADHD, OCD, tics, Tourette's disease, and Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

Tian et al. reported that PDE10 was present in the lung vasculature (PLoS One, April 11, Volume 6, Issue 4, e18136). Tian et al. also reported that infusion of papaverine, a PDE10 inhibitor, attenuated pulmonary hypertension and pulmonary vascular remodeling in a rodent model of this disease. These authors also determined that PDE10 is expressed in human lung tissues. Since PDE10 is present in lung tissue, the compounds of the invention can be used in the treatment of pulmonary arterial hypertension (PAH). PAH is a fatal disease characterized by progressively elevated pulmonary vascular resistance, which results from vasoconstriction, vascular remodeling and in situ thrombosis. These events ultimately lead to right ventricular hypertrophy and right heart failure. The compound of formula I will reduce pulmonary arterial hypertension and thus relieve or alleviate the patient's PAH.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE10, intracellular levels of cAMP are increased, thereby increasing the release of insulin-containing secretory granules and, therefore, increasing insulin secretion (see, for example, WO 2005/012485).

In a further embodiment of the invention, the compounds can be used in the treatment of a variety of neurological conditions due to the high levels of expression of PDE10 in the CNS. Examples of such conditions include anxiety disorders, movement disorders, mood disorders, amnesic disorders; post-traumatic stress; mental retardation; learning disorders, attention-deficit/hyperactivity, age-related cognitive decline, major depressive episodes (of the mild, moderate or severe type), a manic or mixed mood episode, a hypomania mood episode, a depressive episode with atypical features, a depressive episode with melancholic features, a depressive episode with catatonic features, a mood episode with postpartum onset, post-stroke depression, major depressive disorder, dysthymic disorder, minor depressive disorder, premenstrual dysphoric disorder, and cyclothymic disorder.

Administration and Pharmaceutical Compositions

The compounds of the invention may be administered either alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed thereby can then be readily administered in a variety of dosage forms such as tablets, powders, lozenges, liquid preparations, syrups, injectable solutions and the like. These pharmaceutical compositions can optionally contain additional ingredients such as flavorings, binders, excipients and the like. Thus, the compounds of the invention may be formulated for oral, buccal, intranasal, parenteral (e.g., intravenous, intramuscular or subcutaneous), transdermal (e.g., patch) or rectal administration, or in a form suitable for administration by inhalation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of the invention may be formulated for parenteral administration by injection, including using conventional catheterization techniques or infusion. Formulations for injection may be presented in unit dosage form, e.g., in ampoules or in multi-dose containers, with an added preservative. They may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The compounds of the invention may also be formulated in rectal compositions such as suppositories or retention enemas, e.g., containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, e.g., from gelatin) for use in an inhaler or insulator may be formulated containing a powder mix of a compound of the invention and a suitable powder base such as lactose or starch.

Aerosol formulations for treatment of the conditions referred to above (e.g., drug addiction) in the average adult human are preferably arranged so that each metered dose or "puff" of aerosol contains about 20 mg to about 1000 mg of the compound of the invention. The overall daily dose with an aerosol will be within the range of about 100 mg to about 10 mg. Administration may be several times daily, e.g., 2, 3, 4 or 8 times, giving for example, 1, 2 or 3 doses each time.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compound of Formula (I) based on the total formulation, with the balance being one or more suitable pharmaceutical excipients. Usually, the compound is present at a level of about 1-80 wt %.

In general, the compounds of this invention can be administered in a therapeutically effective amount by any of the accepted modes of administration for agents that serve similar utilities. The actual dosage administered to patients depends upon numerous factors, such as the severity of the disease to be treated, the age and relative health of the subject, the potency of the compound used, the route and form of administration, and other factors. The patient's physician will ultimately decide the appropriate dose, in light of clinical testing conducted on the compounds. However, a typical daily dose of the compound will range from about 0.01 mg to about 2000 mg, more typically from about 0.1 mg to about 200 mg, which may be administered, for example, 1 to 4 times per day.

The compounds can be administered as the sole active agent or in combination with other pharmaceutical agents used in the treatment of psychoses (especially schizophrenia and bipolar disorder), obsessive-compulsive disorder, Parkinson's disease, Alzheimer's disease, Huntington's disease, cognitive impairment and/or memory loss (e.g., dementia). Examples of such agents include nicotinic α-7 agonists, PDE4 inhibitors, other PDE10 inhibitors, calcium channel blockers, muscarinic M1 and M2 modulators, adenosine receptor modulators, ampakines, NMDA modulators, m-GluR modulators, dopamine modulators, serotonin modulators, cannabinoid modulators, and cholinesterase inhibitors (e.g., donepezil, rivastigmine, and galanthamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Desipramine, Nortriptyline, Paroxetine, Fluoxetine, Sertraline, Tetrabenazine, Haloperidol, Chlorpromazine, Thioridazine, Sulpride, Quetiapine, Clozapine, and Risperidone; agents useful in the treatment of diabetes, including, but not limited to, PPAR ligands (e.g., agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-IB inhibitors, DPP-IV inhibitors, and 11-beta-HSD inhibitors), hepatic glucose output lowering compounds (such as glucagon antagonists and metformin, e.g., Glucophage and Glucophage XR), insulin and insulin derivatives (both long- and short-acting forms and formulations of insulin); and anti-obesity drugs, including, but not limited to, β-3 agonists, CB-I agonists, neuropeptide Y5 inhibitors, ciliary neurotrophic factor and derivatives (e.g., Axokine), appetite suppressants (e.g., Sibutramine), and lipase inhibitors (e.g., Orlistat).

EXAMPLES

The following preparations and examples are given to enable those skilled in the art to more clearly understand and to practice the present invention. They should not be considered as limiting the scope of the invention, but merely as being illustrative and representative thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed, Commercial solvents and reagents were generally used without further purification. Anhydrous solvents were employed where appropriate, generally Sure-Seal™ products from the Aldrich Chemical Company, AcroSeal® products from Acros Organics or DriSoly® products from EMD Chemicals. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary, In general, reactions were followed by thin layer chromatography or mass spectrometry, and subjected to work-up when appropriate. Purifications may vary between experiments: in general, solvents and the solvent ratios used for eluents/gradients were chosen to provide appropriate Rfs or retention times.

EXAMPLES

Example 1

2-Cyclopropyl-6-[5-(2-fluorophenyl)-7-methylimidazo[5,1-f][1,2,4]triazin-4-yl]-5,6,7,8-tetrahydropyrido[4,3-d]pyrimidine (1)

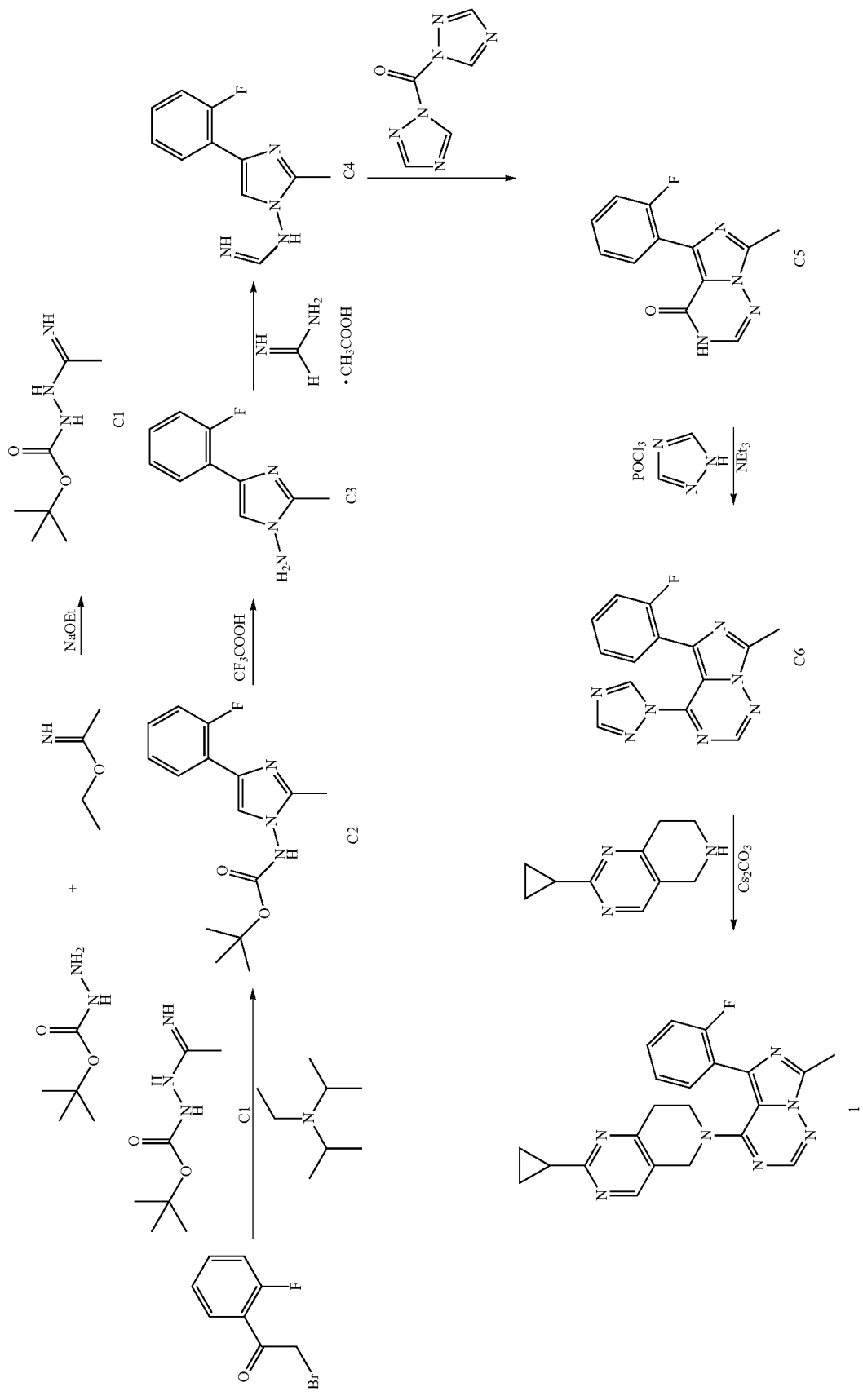

Step 1. Synthesis of tert-butyl 2-ethanimidoylhydrazinecarboxylate (C1)

Sodium hydroxide (16.0 g, 400 mmol) was dissolved in absolute ethanol (1 L) at 60° C. The solution was cooled to 0° C. and treated portion-wise with ethyl ethanimidoate hydrochloride (50 g, 400 mmol); after 10 minutes, tert-butyl hydrazinecarboxylate (52.9 g, 400 mmol) was added in a single portion. The reaction mixture was stirred at 70° C. for 2.5 hours, then cooled to 20° C. and filtered. The filtrate was concentrated in vacuo and treated with tert-butyl methyl ether (500 mL) and ethanol (20 mL). After seeding, the mixture was allowed to stir for 18 hours, whereupon the precipitated solid was collected via filtration and washed with ice-cold tert-butyl methyl ether (500 mL). The solid was dissolved in 2-methyltetrahydrofuran:methanol (9:1 mixture, 300 mL), and the solution was concentrated to dryness. The residue was washed with diethyl ether (3×200 mL) to afford the product as a very pale yellow solid. Yield: 50.2 g, 290 mmol, 72%. LCMS m/z 174.3 [M+H]+. 1H NMR (500 MHz, CD$_3$OD) δ 1.88 (s, 3H), 1.47 (s, 9H).

Step 2. Synthesis of tert-butyl [4-(2-fluorophenyl)-2-methyl-1H-imidazol-1-yl]carbamate (C2)

Compound C1 (11.4 g, 65.8 mmol), 2-bromo-1-(2-fluorophenyl)ethanone (13.0 g, 59.9 mmol) and N,N-diisopropylethylamine (23.0 mL, 132 mmol) were combined in a mixture of acetonitrile (100 mL) and 2-methyltetrahydrofuran (300 mL) and heated at reflux for 18 hours. After cooling, the reaction mixture was concentrated in vacuo; the residue was mixed with ethyl acetate, then washed sequentially with saturated aqueous ammonium chloride solution and with saturated aqueous sodium bicarbonate solution. The combined aqueous layers were extracted with ethyl acetate, and the combined organic layers were dried over magnesium sulfate, filtered, and concentrated under reduced pressure to provide the product as a pale brown foam. Yield: 18.1 g, assumed quantitative. LCMS m/z 292.4 [M+H]+. 1H NMR (500 MHz, CDCl$_3$), presumed to be a mixture of rotamers: δ 8.15 (v br s, 1H), 8.03-8.07 (m, 1H), 7.30 and 7.31 (2 s, 1H), 7.13-7.20 (m, 2H), 7.02-7.08 (m, 1H), 2.31 (s, 3H), 1.49 (br s, 9H).

Step 3. Synthesis of 4-(2-fluorophenyl)-2-methyl-1H-imidazol-1-amine (C3)

Compound C2 (17.4 g, 59.7 mmol) in dichloromethane (120 mL) was treated with trifluoroacetic acid (23.0 mL, 299 mmol) and allowed to stir for 18 hours at room temperature. Excess 1 N aqueous sodium hydroxide solution was added, and the mixture was stirred vigorously for 15 minutes. The organic layer was separated, dried over magnesium sulfate, filtered, and concentrated in vacuo to afford the product as a brown solid. Yield: 9.95 g, 52.0 mmol, 87%. LCMS m/z 192.3 [M+H]+.

Step 4. Synthesis of N-[4-(2-fluorophenyl)-2-methyl-1H-imidazol-1-yl]imidoformamide (C4)

Compound C3 (9.95 g, 52.0 mmol) and formamidine acetate (previously azeotroped with toluene, 13.5 g, 130 mmol) were combined in 2-butanol (160 mL) and heated at reflux for 3 hours. The reaction mixture was cooled and concentrated in vacuo. The residue was partitioned between ethyl acetate and saturated aqueous sodium bicarbonate solution, and the aqueous layer was extracted twice with ethyl acetate. The combined organic layers were dried over magnesium sulfate, filtered and concentrated in vacuo. The residue was suspended in a mixture of heptane and ethyl acetate; filtration provided the product as a pale brown powder. Yield: 8.20 g, 37.6 mmol, 72%. LCMS m/z 219.3 [M+H]+. 1H NMR (500 MHz, DMSO-d6), presumed to be a mixture of rotamers and/or tautomers; characteristic peaks: δ 7.99-8.07 (m, 1.6H), 7.51 and 7.52 (2 s [1:1 ratio], 0.6H), 7.30 (dd, J=9.8, 9.8 Hz, 0.4H), 7.16-7.21 (m, 3.4H), 2.26 and 2.18 (2 s [1.6:1 ratio], 3H).

Step 5. Synthesis of 5-(2-fluorophenyl)-7-methylimidazo[5,1-f][1,2,4]triazin-4(3H)-one (C5)

Compound C4 (8.16 g, 37.4 mmol) in tetrahydrofuran (187 mL) was heated to 55° C., treated with 1,1'-carbonyldi(1,2,4-triazole) (7.36 g, 44.8 mmol) and stirred at 55° C. for 5 hours. The reaction was then cooled and stirred for an additional 3 days at room temperature. Removal of solvent in vacuo gave a solid, which was stirred with water (200 mL) for 1 hour and filtered to afford a pale brown powder. This was stirred in heptane (~35 mL) and ethyl acetate (~35 mL) for 24 hours and filtered, providing the product as an off-white powder (5.08 g). The aqueous filtrate was extracted once with ethyl acetate; this organic layer was dried over magnesium sulfate, filtered and concentrated under reduced pressure. The residue was recrystallized from heptane/ethyl acetate to provide additional product as a white powder. Total yield: 5.33 g, 21.8 mmol, 58%. LCMS m/z 245.0 [M+H]+. 1H NMR (500 MHz, CD$_3$OD) δ 7.73 (s, 1H), 7.62 (ddd, J=7.6, 7.3, 1.7 Hz, 1H), 7.40-7.46 (m, 1H), 7.24 (ddd, J=7.6, 7.6, 1.0 Hz, 1H), 7.18 (br dd, J=10, 8.5 Hz, 1H), 2.63 (s, 3H).

Step 6. Synthesis of 5-(2-fluorophenyl)-7-methyl-4-(1H-1,2,4-triazol-1-yl)imidazo[5,1-f][1,2,4]triazine (C6)

1H-1,2,4-Triazole (15.1 g, 219 mmol) in acetonitrile (220 mL) was cooled to 0° C. and treated slowly with phosphorus oxychloride (5.99 mL, 65.4 mmol). After 10 minutes, triethylamine (36.5 mL, 262 mmol) was slowly added; the reaction was stirred for an additional 10 minutes at 0° C., then slowly warmed to room temperature over 15 minutes. C5 (5.33 g, 21.8 mmol) was added to the reaction mixture and stirring was continued at room temperature for 2 hours. After concentration in vacuo, the residue was diluted with ethyl acetate (~250 mL) and poured into ice-cold stirring aqueous potassium phosphate solution (25%, 250 mL). After stirring for 10 minutes, the layers were separated and the aqueous layer was extracted with ethyl acetate. The combined organic layers were dried over magnesium sulfate, filtered and concentrated under reduced pressure. Purification via silica gel chromatography (small plug of silica gel employed; Eluent: 2:1 heptane/ethyl acetate) provided the product as a bright yellow solid. Yield: 6.50 g, 21.8 mmol, 100%. LCMS m/z 296.0 [M+H]+. 1H NMR (500 MHz, CDCl3) δ 9.06 (s, 1H), 8.35 (s, 1H), 7.77 (s, 1H), 7.74 (ddd, J=7.6, 7.4, 1.8 Hz, 1H), 7.35-7.40 (m, 1H), 7.26 (ddd, J=7.6, 7.5, 1.2 Hz, 1H), 6.88 (ddd, J=10.2, 8.3, 1.1 Hz, 1H), 2.87 (s, 3H).

Step 7. Synthesis of 2-cyclopropyl-6-[5-(2-fluorophenyl)-7-methylimidazo[5,1-f][1,2,4]triazin-4-yl]-5,6,7,8-tetrahydropyrido[4,3-d]pyrimidine (1)

A mixture of C6 (6.40 g, 21.7 mmol), 2-cyclopropyl-5,6,7,8-tetrahydropyrido[4,3-d]pyrimidine (3.84 g, 21.9 mmol) and cesium carbonate (7.06 g, 21.7 mmol) was stirred in N,N-dimethylformamide (45 mL) for 2 hours at room temperature. The reaction mixture was concentrated in vacuo, then stirred with water (45 mL) for 18 hours. Filtration provided the product as an off-white powder. Yield: 6.68 g, 16.6 mmol, 76%. This material was combined with product from two similar runs (total weight: 20.37 g) and triturated with a mixture of heptane (100 mL) and ethyl acetate (100 mL) for 3 days at room temperature. Filtration provided the product as an off-white powder (19.6 g). LCMS m/z 402.1 [M+H]+. 1H NMR (500 MHz, CDCl3) δ 7.97 (s, 1H), 7.92 (br s, 1H), 7.63 (ddd, J=7.6, 7.4, 1.8 Hz, 1H), 7.36-7.41 (m, 1H), 7.27 (ddd, J=7.6, 7.6, 1.1 Hz, 1H), 7.07 (br ddd, J=9, 9, 1 Hz, 1H), 4.51 (s, 2H), 3.86-3.90 (m, 2H), 2.73 (s, 3H), 2.71-2.76 (m, 2H), 2.12-2.18 (m, 1H), 1.00-1.08 (m, 4H).

Example 2

5-(2-Fluorophenyl)-7-methyl-4-(1-methyl-1,4,5,7-tetrahydro-6H-pyrazolo[3,4-c]pyridin-6-yl)imidazo[5,1-f][1,2,4]triazine (2)

Step 2. Synthesis of 4-bromo-1-methyl-1H-pyrazolo[3,4-c]pyridine (C8)

Sodium hydride (60% in mineral oil, 0.524 g, 13.1 mmol) was added to a solution of C7 (3.20 g, 10.9 mmol) in tetrahydrofuran (20 mL), and the reaction mixture was heated at reflux for 1.5 hours, then allowed to sit at room temperature for 90 hours. Additional sodium hydride (1 equivalent) was added, and the reaction mixture was heated at reflux for 3 hours. After cooling to room temperature, the mixture was quenched with water, diluted with saturated aqueous sodium chloride solution, and extracted with ethyl acetate. The combined organic layers were dried over magnesium sulfate, filtered, and concentrated in vacuo. Purification via silica gel chromatography (Gradient: 0% to 100% ethyl acetate in heptane) afforded the product as a solid. Yield: 1.51 g, 7.12 mmol, 65%. $^1$H NMR (400 MHz, CDCl$_3$) δ 8.87 (s, 1H), 8.38 (s, 1H), 8.03 (s, 1H), 4.19 (s, 3H).

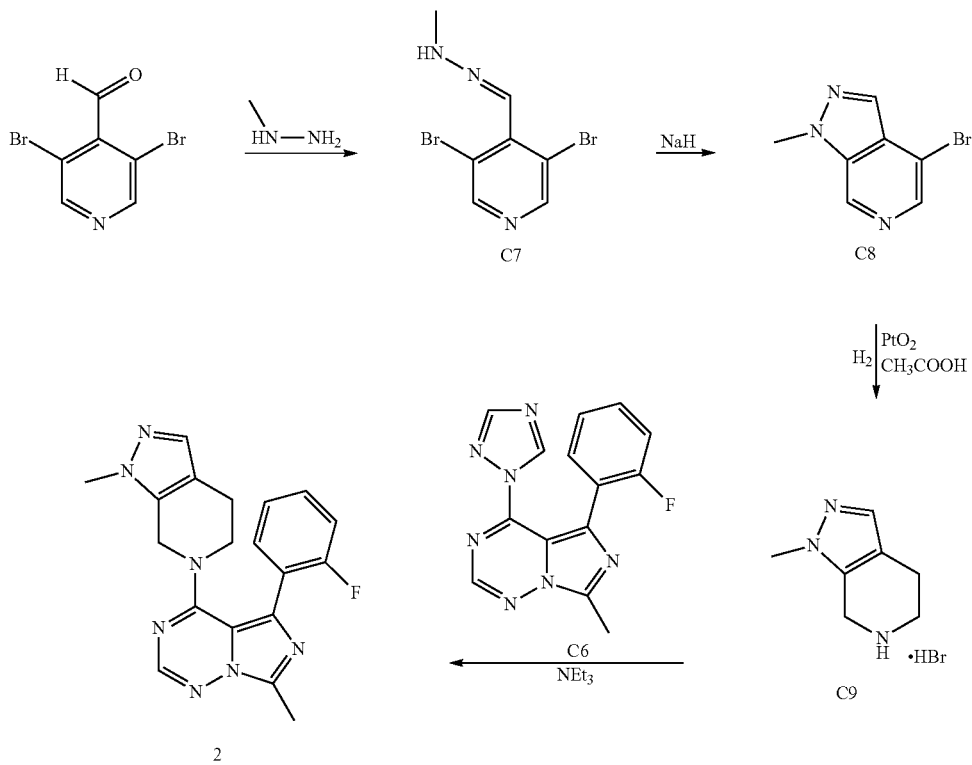

Step 1. Synthesis of 3,5-dibromo-4-[(2-methylhydrazinylidene)methyl]pyridine (C7)

Methylhydrazine (1.06 mL, 19.3 mmol) was added to a solution of 3,5-dibromopyridine-4-carbaldehyde (3.4 g, 13 mmol) in 2-propanol (20 mL). After 3 hours at room temperature, the reaction mixture was concentrated in vacuo, dissolved in ethyl acetate, and washed with saturated aqueous sodium chloride solution. The organic layer was dried over magnesium sulfate, filtered, and concentrated under reduced pressure to afford the product as a solid. Yield: 3.20 g, 10.9 mmol, 84%. $^1$H NMR (400 MHz, DMSO-d$_6$) δ 8.62 (s, 2H), 7.24-7.26 (m, 1H), 2.89-2.91 (m, 3H).

Step 3. Synthesis of 1-methyl-4,5,6,7-tetrahydro-1H-pyrazolo[3,4-c]pyridine, hydrobromide salt (C9)

Acetic acid (5 mL) was added to a solution of C8 (226 mg, 1.07 mmol) in ethanol (30 mL), and the mixture was hydrogenated (30 psi hydrogen) over platinum(IV) oxide monohydrate (78.4 mg, 0.320 mmol) for 18 hours. The reaction mixture was filtered through diatomaceous earth, and the filtrate was concentrated in vacuo to provide the product as a gum. Nuclear Overhauser Effect (NOE) studies supported the indicated regiochemistry of the methyl group. By $^1$H NMR, this material contained residual acetic acid. Corrected yield: 146 mg, 0.67 mmol, 63%. LCMS m/z 138.1 [M+H]$^+$. $^1$H NMR (400 MHz, CDCl₃) δ 7.33 (br s, 1H), 4.32 (br s, 2H), 3.79 (s, 3H), 3.31-3.39 (m, 2H), 2.87-2.94 (m, 2H).

Step 4. Synthesis of 5-(2-fluorophenyl)-7-methyl-4-(1-methyl-1,4,5,7-tetrahydro-6H-pyrazolo[3,4-c]pyridin-6-yl)imidazo[5,1-f][1,2,4]triazine (2)

Triethylamine (0.510 mL, 3.66 mmol) and C9 (0.333 g, 1.58 mmol) were added to a solution of C6 (0.360 g, 1.22 mmol) in dichloromethane (10 mL), and the reaction mixture was heated at 40° C. for 18 hours. The mixture was then washed with saturated aqueous sodium chloride solution, dried over magnesium sulfate, filtered, and concentrated in vacuo. Purification was effected first via silica gel chromatography (Gradient: 0% to 100% ethyl acetate in heptane), then by reversed phase HPLC (Column: Phenomenex Gemini C18, 5 μm; Mobile phase A: 0.1% ammonium hydroxide in water; Mobile phase B: 0.1% ammonium hydroxide in methanol; Gradient: 5% to 100% B). The product was obtained as a solid. Yield: 202 mg, 0.556 mmol, 46%. LCMS m/z 364.2 [M+H]⁺. ¹H NMR (400 MHz, CD₃OD) δ 7.98 (s, 1H), 7.63 (ddd, J=7.6, 7.5, 1.8 Hz, 1H), 7.52 (dddd, J=8.3, 7.5, 5.2, 1.8 Hz, 1H), 7.35 (ddd, J=7.6, 7.5, 1.1 Hz, 1H), 7.22 (br ddd, J=10.0, 8.3, 1.0 Hz, 1H), 7.16 (br s, 1H), 4.45 (br s, 2H), 3.76-3.84 (m, 2H), 3.43 (s, 3H), 2.67 (s, 3H), 2.35-2.41 (m, 2H).

Example 3

7-{7-Methyl-5-[(3S)-tetrahydrofuran-3-yl]imidazo[5,1-f][1,2,4]triazin-4-yl}-5,6,7,8-tetrahydro-1,7-naphthyridine (3)

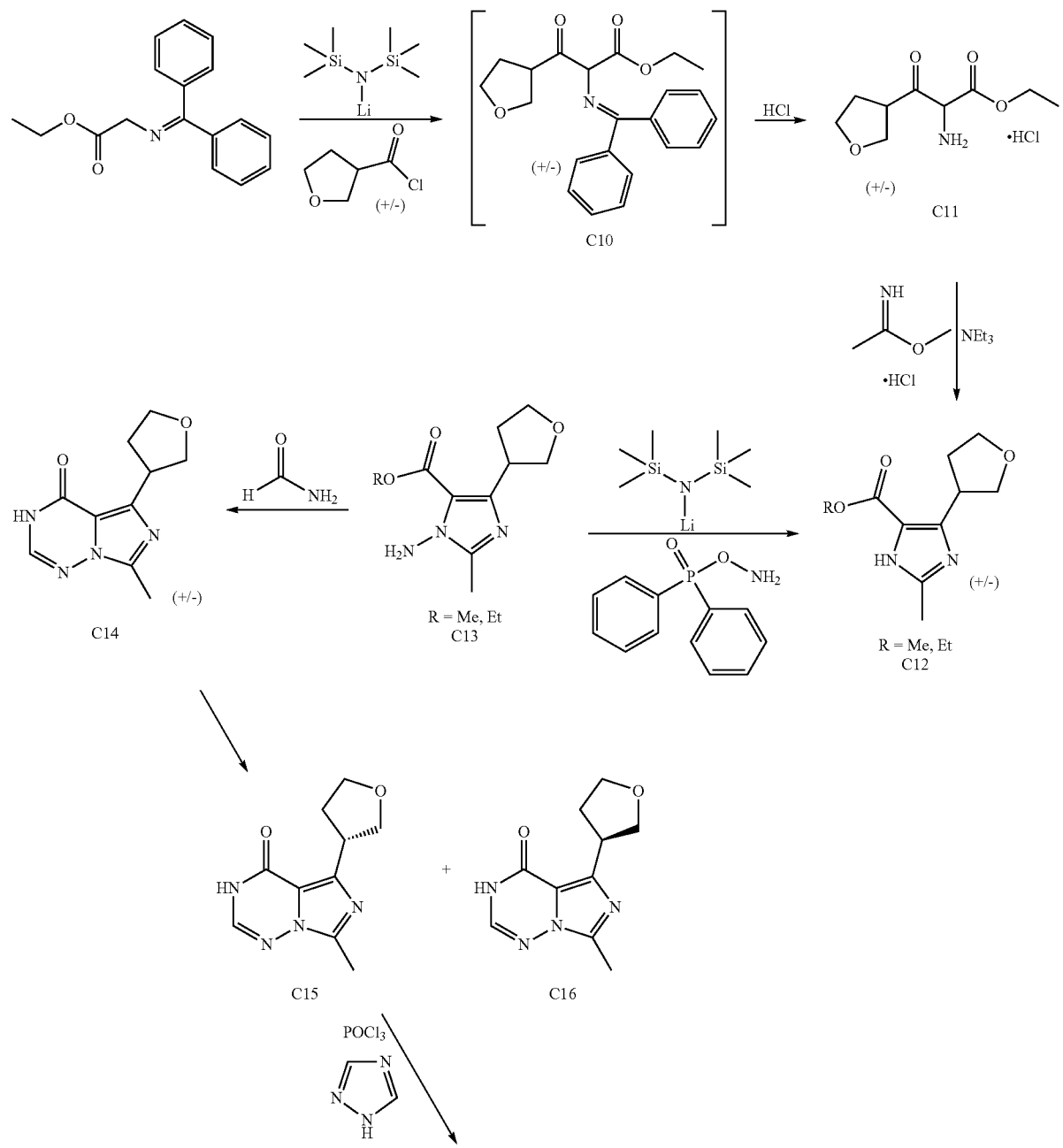

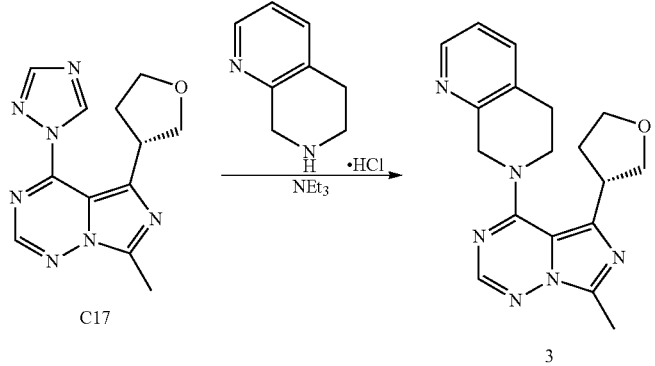

Step 1. Synthesis of ethyl 2-amino-3-oxo-3-(tetrahydrofuran-3-yl)propanoate, hydrochloride salt (C11)

Lithium bis(trimethysilyl)amide (1 M solution in tetrahydrofuran, 288 mL, 0.288 mol) was added drop-wise to a solution of ethyl (2E)-[(diphenylmethyl)imino]ethanoate (70 g, 0.26 mol) in tetrahydrofuran (1 L) at −70° C. The reaction mixture was stirred for 30 minutes, and the resulting suspension was transferred via cannula into a solution of tetrahydrofuran-3-carbonyl chloride (35.7 g, 0.26 mol) in tetrahydrofuran (200 mL) at −70° C. The reaction mixture was stirred at room temperature for 2 hours, at which time aqueous hydrochloric acid (2 M, 260 mL) was added. After the reaction mixture had stirred for 15 minutes, the tetrahydrofuran was removed in vacuo, and the aqueous residue was washed with ethyl acetate (4×200 mL). The aqueous layer was freeze-dried, affording the product as a light yellow solid. Yield: 40 g, 0.20 mol, 77%.

Step 2. Synthesis of methyl and ethyl 2-methyl-4-(tetrahydrofuran-3-yl)-1H-imidazole-5-carboxylates (C12)

To a solution of methyl ethanimidoate, hydrochloride salt (216 g, 1.97 mol) in methanol (1.5 L) at room temperature was added triethylamine (289 mL, 2.07 mol). A suspension of C11 (200 g, 0.84 mol) in methanol (2 L) was added portion-wise, at a rate that maintained the reaction temperature below 30° C. The reaction mixture was stirred at room temperature for 18 hours, then concentrated in vacuo to provide a light yellow solid, which was washed with ethyl acetate. The solid was dissolved in water (1 L) and extracted with ethyl acetate (4×500 mL); these extracts were combined with the ethyl acetate washes and concentrated in vacuo. Silica gel chromatography (Eluent:1:2 ethyl acetate/petroleum ether) afforded the product as a light yellow liquid. By $^1$H NMR analysis, this material was a mixture of the ethyl and methyl esters. Yield: 48 g, —0.22 mol, ~26%. $^1$H NMR (400 MHz, CDCl$_3$) δ 4.34 (q, J=7.0 Hz, <2H), 3.97-4.20 (m, 3H), 3.87 (s, <3H), 3.78-3.97 (m, 2H), 2.43 and 2.43 (2 s, 3H), 2.26-2.38 (m, 1H), 2.13-2.26 (m, 1H), 1.37 (t, J=7.0 Hz, <3H).

Step 3. Synthesis of ethyl and methyl 1-amino-2-methyl-4-(tetrahydrofuran-3-yl)-1H-imidazole-5-carboxylates (C13)

To a stirred −20° C. solution of C12 (from the previous step, 48 g, ~0.22 mol) in N,N-dimethylformamide (500 mL) was added lithium bis(trimethysilyl)amide (1 M solution in tetrahydrofuran, 257 mL, 0.257 mol). After 15 minutes, a suspension of (aminooxy)(diphenyl)phosphine oxide (prepared as described by E. W. Colvin et al., *Tetrahedron Letters* 1982, 23, 3835-3836; 60 g, 0.26 mol; Caution: (aminooxy)(diphenyl)phosphine oxide is a highly energetic substance that has shown the ability to explosively decompose under ambient conditions. Its use should be carefully monitored!) in N,N-dimethylformamide (500 mL) was added portion-wise, and the reaction mixture was stirred for 1 hour while the temperature was maintained below 0° C. Water (1.5 L) was added and the mixture was extracted with ethyl acetate (20× 500 mL). The combined extracts were concentrated in vacuo to afford the product as a light yellow liquid. By $^1$H NMR analysis, this material was a mixture of the ethyl and methyl esters. Yield: 40 g, −0.17 mol, −80%. $^1$H NMR (400 MHz, CDCl$_3$) δ 5.21-5.28 (br m, 2H), 4.31-4.39 (m, <2H), 4.01-4.11 (m, 2H), 3.88 (s, <3H), 3.87-3.98 (m, 2H), 3.72-3.80 (m, 1H), 2.42 (s, 3H), 2.28-2.39 (m, 1H), 2.14-2.24 (m, 1H), 1.38 (t, J=7.2 Hz, <3H).

Step 4. Synthesis of 7-methyl-5-(tetrahydrofuran-3-yl)imidazo[5,1-f][1,2,4]triazin-4(3H)-one (C14)

A solution of C13 (77 g, −0.33 mol) in formamide (600 mL) was heated at 170-180° C. for 3 hours. The reaction mixture was then cooled to room temperature and excess formamide was removed under reduced pressure at 110-120° C. The residue was cooled to room temperature and recrystallized from methanol to provide the product as an off-white solid. Yield: 18.62 g, 84.55 mmol, −26%. LCMS m/z 221.0 [M+H]$^+$. $^1$H NMR (400 MHz, DMSO-d$_6$) δ 7.80 (s, 1H), 3.99 (dd, J=7.7, 7.7 Hz, 1H), 3.84-3.94 (m, 2H), 3.76-3.84 (m, 1H), 3.66 (dd, J=7.7, 7.7 Hz, 1H), 2.46 (s, 3H), 2.14-2.22 (m, 2H).

Step 5. Isolation of 7-methyl-5-[(3S)-tetrahydrofuran-3-yl]imidazo[5,1-f][1,2,4]triazin-4(3H)-one (C15)

Racemic C14 (13.5 g, 61.3 mmol) was subjected to supercritical fluid chromatography (Column: Chiral Technologies, Chiralpak AD-H, 5 µm; Eluent: 88:12 carbon dioxide/methanol containing 0.2% isopropylamine). The second-eluting enantiomer was compound C15, obtained as a solid; the indicated absolute stereochemistry was assigned on the basis of an X-ray crystal structure obtained on compound 3 (vide infra). Yield: 6.5 g, 29.5 mmol, 48%. Retention time 10.48 minutes (Column: Chiral Technologies, Chiralpak AD-H, 4.6×250 mm, 5 µm; Eluent: 88:12 carbon dioxide/methanol containing 0.2% isopropylamine; Flow rate: 2.5 mL/minute).

Also isolated was the first-eluting enantiomer, 7-methyl-5-[(3R)-tetrahydrofuran-3-yl]imidazo[5,1-f][1,2,4]triazin-4(3H)-one (C16); this was obtained as a solid. Yield: 6.5 g, 29.5 mmol, 48%. Retention time 7.86 minutes (analytical HPLC conditions identical to those used for C15 above).

Step 6. Synthesis of 7-methyl-5-[(3S)-tetrahydrofuran-3-yl]-4-(1H-1,2,4-triazol-1-yl)imidazo[5,1-f][1,2,4]triazine (C17)

A solution of C15 (5.00 g, 22.7 mmol) in pyridine (70 mL) was cooled to 0° C. and treated with phosphorus oxychloride (6.24 mL, 68.1 mmol). After 15 minutes, 1H-1,2,4-triazole (7.84 g, 114 mmol) was added; the reaction mixture was stirred at 0° C. for 30 minutes, then allowed to warm to room temperature over 18 hours. After removal of volatiles under reduced pressure, the residue was mixed with dichloromethane, vigorously stirred, and filtered through a thin layer of silica gel. The filtrate was concentrated in vacuo, mixed with dichloromethane, and filtered once more. The resulting filtrate was concentrated under reduced pressure and purified via silica gel chromatography (Gradient: 0% to 10% methanol in ethyl acetate), affording the product as a yellow solid. Yield: 4.86 g, 17.9 mmol, 79%. LCMS m/z 272.2 [M+H]$^+$. $^1$H NMR (400 MHz, CDCl$_3$) δ 9.27 (s, 1H), 8.26 (s, 1H), 8.21 (s, 1H), 4.58-4.66 (m, 1H), 4.20 (dd, J=8.0, 7.8 Hz, 1H), 4.11-4.18 (m, 1H), 3.95-4.02 (m, 1H), 3.92 (dd, J=8.1, 7.2 Hz, 1H), 2.78 (s, 3H), 2.42-2.52 (m, 1H), 2.26-2.35 (m, 1H).

Step 7. Synthesis of 7-{7-methyl-5-[(3S)-tetrahydrofuran-3-yl]imidazo[5,1-f][1,2,4]triazin-4-yl}-5,6,7,8-tetrahydro-1,7-naphthyridine (3)

A solution of C17 (150 mg, 0.553 mmol), 5,6,7,8-tetrahydro-1,7-naphthyridine, dihydrochloride salt (126 mg, 0.608 mmol), and triethylamine (0.308 mL, 2.21 mmol) in dichloromethane (5 mL) was stirred at room temperature for 3 days. The reaction mixture was diluted with additional dichloromethane and washed sequentially with saturated aqueous sodium bicarbonate solution, water and saturated aqueous sodium chloride solution. The organic layer was dried over magnesium sulfate, filtered, and concentrated in vacuo. Silica gel chromatography (Gradient: 5% to 10% methanol in ethyl acetate) provided the product as a yellow solid. Yield: 181 mg, 0.538 mmol, 97%. LCMS m/z 337.3 [M+H]$^+$. $^1$H NMR (400 MHz, CDCl$_3$) δ 8.42-8.45 (m, 1H), 7.88 (s, 1H), 7.48-7.52 (m, 1H), 7.16 (dd, J=7.7, 4.8 Hz, 1H), 4.95 (br s, 2H), 4.21 (dd, J=7.9, 7.8 Hz, 1H), 4.14-4.20 (m, 1H), 4.05-4.12 (m, 1H), 3.92-4.04 (m, 3H), 3.72-3.81 (m, 1H), 3.12-3.21 (m, 1H), 3.02-3.11 (m, 1H), 2.65 (s, 3H), 2.40-2.50 (m, 2H).

Recrystallization of 3 from ethyl acetate/dichloromethane afforded a crystal for X-ray structural analysis, which established the absolute stereochemistry.

Single Crystal X-Ray Analysis

Data collection was performed on a Bruker APEX diffractometer at room temperature. Data collection consisted of 3 omega scans at low angle and three at high angle, each with 0.5 step. In addition, 2 phi scans were collected to improve the quality of the absorption correction.

The structure was solved by direct methods using SHELX software suite in the space group P2(1). The structure was subsequently refined by the full-matrix least squares method. All non-hydrogen atoms were found and refined using anisotropic displacement parameters.

All hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). The results indicate that the absolute structure has been correctly assigned. The method calculates that the probability that the structure is correct is 100.0%. The Hooft parameter is reported as 0.04 with an esd of 0.13 within range for absolute configuration with the assumption of an enantiopure sample.

The final R-index was 3.8%. A final difference Fourier revealed no missing or misplaced electron density.

Pertinent crystal, data collection and refinement are summarized in Table 1. Atomic coordinates, bond lengths, bond angles, torsion angles and displacement parameters are listed in Tables 2-5.

Software and References

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler and J. van de Streek, *J. Appl. Cryst.* 2006, 39, 453-457.
R. W. Hooft et al., *J. Appl. Cryst.* 2008, 41, 96-103.
H. D. Flack, *Acta Cryst.* 1983, A39, 867-881.

TABLE 1

Crystal data and structure refinement for 3.

| | |
|---|---|
| Empirical formula | $C_{18}H_{20}N_6O$ |
| Formula weight | 336.40 |
| Temperature | 296(2) K |
| Wavelength | 1.54178 Å |
| Crystal system | Monoclinic |
| Space group | P2(1) |
| Unit cell dimensions | a = 13.2475(12) Å   α = 90° |
| | b = 9.0155(9) Å    β = 101.312(4)° |
| | c = 14.0721(13) Å   γ = 90° |
| Volume | 1648.0(3) Å$^3$ |
| Z | 4 |
| Density (calculated) | 1.356 Mg/m$^3$ |
| Absorption coefficient | 0.722 mm$^{-1}$ |
| F(000) | 712 |
| Crystal size | 0.17 × 0.22 × 0.43 mm$^3$ |
| Theta range for data collection | 3.20 to 67.42° |
| Index ranges | −14 <= h <= 15, −10 <= k <= 10, −15 <= l <= 16 |
| Reflections collected | 10353 |
| Independent reflections | 4962 [R(int) = 0.0220] |
| Completeness to theta = 67.42° | 96.3% |
| Absorption correction | Empirical |
| Refinement method | Full-matrix least-squares on F$^2$ |
| Data/restraints/parameters | 4962/1/464 |
| Goodness-of-fit on F$^2$ | 1.033 |
| Final R indices [ I > 2sigma(I)] | R1 = 0.0351, wR2 = 0.0948 |
| R indices (all data) | R1 = 0.0372, wR2 = 0.0971 |
| Absolute structure parameter | 0.0(3) |
| Extinction coefficient | 0.0009(2) |
| Largest diff. peak and hole | 0.176 and −0.162 e.Å$^{-3}$ |

TABLE 2

Atomic coordinates (×10$^4$) and equivalent isotropic displacement parameters (Å$^2$ × 10$^3$) for 3. U(eq) is defined as one third of the trace of the orthogonalized U$^{ij}$ tensor.

|       | x       | y       | z       | U(eq) |
|-------|---------|---------|---------|-------|
| C(1)  | 5261(2) | 353(2)  | 3667(1) | 41(1) |
| C(2)  | 5729(2) | −451(3) | 4472(2) | 49(1) |
| C(3)  | 6618(2) | −1231(3)| 4444(2) | 55(1) |
| C(4)  | 7015(2) | −1188(3)| 3622(2) | 54(1) |
| C(5)  | 5717(1) | 307(2)  | 2860(1) | 37(1) |
| C(6)  | 5262(2) | 1085(3) | 1924(1) | 42(1) |
| C(7)  | 4112(2) | 2338(3) | 2808(2) | 51(1) |
| C(8)  | 4296(2) | 1258(3) | 3656(2) | 52(1) |
| C(9)  | 3387(2) | 871(2)  | 1385(1) | 40(1) |
| C(10) | 1740(2) | 8(3)    | 1279(2) | 60(1) |
| C(11) | 3412(1) | 164(2)  | 472(1)  | 38(1) |
| C(12) | 4005(2) | 42(2)   | −240(1) | 37(1) |
| C(13) | 2665(2) | −1378(3)| −703(2) | 45(1) |
| C(14) | 1912(2) | −2431(3)| −1250(2)| 63(1) |
| C(15) | 4971(2) | 822(2)  | −377(1) | 39(1) |
| C(16) | 5921(2) | −174(3) | −267(2) | 51(1) |
| C(17) | 6014(2) | 1327(3) | −1550(2)| 64(1) |
| C(18) | 4921(2) | 1427(3) | −1408(2)| 57(1) |
| C(19) | −52(2)  | 6472(2) | 1442(1) | 41(1) |
| C(20) | −567(2) | 7245(3) | 633(2)  | 52(1) |
| C(21) | −1525(2)| 7826(3) | 635(2)  | 56(1) |
| C(22) | −1953(2)| 7629(3) | 1445(2) | 53(1) |
| C(23) | −539(1) | 6366(2) | 2225(1) | 37(1) |
| C(24) | −42(2)  | 5641(3) | 3168(1) | 42(1) |
| C(25) | 1232(2) | 4664(3) | 2299(2) | 49(1) |
| C(26) | 986(2)  | 5771(3) | 1477(2) | 55(1) |
| C(27) | 1803(1) | 6096(2) | 3768(1) | 39(1) |
| C(28) | 3399(2) | 7187(3) | 3958(2) | 59(1) |
| C(29) | 1699(1) | 6735(2) | 4685(1) | 36(1) |
| C(30) | 1075(1) | 6725(2) | 5373(1) | 36(1) |
| C(31) | 2301(2) | 8307(2) | 5895(1) | 41(1) |
| C(32) | 2979(2) | 9417(3) | 6486(2) | 55(1) |
| C(33) | 179(2)  | 5781(2) | 5496(1) | 38(1) |
| C(34) | 306(2)  | 5080(3) | 6506(2) | 56(1) |
| C(35) | −1325(2)| 5949(4) | 6207(2) | 70(1) |
| C(36) | −845(2) | 6623(3) | 5436(2) | 51(1) |
| N(1)  | 6587(1) | −439(2) | 2825(1) | 47(1) |
| N(2)  | 4210(1) | 1592(2) | 1906(1) | 43(1) |
| N(3)  | 2530(1) | 846(3)  | 1743(1) | 54(1) |
| N(4)  | 1681(1) | −853(2) | 525(1)  | 54(1) |
| N(5)  | 2551(1) | −734(2) | 132(1)  | 42(1) |
| N(6)  | 3541(1) | −927(2) | −937(1) | 44(1) |
| N(7)  | −1473(1)| 6920(2) | 2235(1) | 46(1) |
| N(8)  | 1045(1) | 5317(2) | 3205(1) | 41(1) |
| N(9)  | 2681(1) | 6254(3) | 3460(1) | 53(1) |
| N(10) | 3371(1) | 8000(2) | 4710(1) | 52(1) |
| N(11) | 2491(1) | 7740(2) | 5068(1) | 41(1) |
| N(12) | 1454(1) | 7716(2) | 6095(1) | 41(1) |
| O(1)  | 6584(1) | 486(3)  | −798(2) | 86(1) |
| O(2A) | −724(3) | 4702(4) | 6600(2) | 69(1) |
| O(2B) | −388(4) | 5834(8) | 7009(3) | 72(2) |

TABLE 3

Bond lengths [Å] and angles [°] for 3.

| C(1)—C(2)   | 1.384(3) |
| C(1)—C(5)   | 1.388(3) |
| C(1)—C(8)   | 1.515(3) |
| C(2)—C(3)   | 1.379(3) |
| C(3)—C(4)   | 1.361(3) |
| C(4)—N(1)   | 1.337(3) |
| C(5)—N(1)   | 1.343(3) |
| C(5)—C(6)   | 1.510(3) |
| C(6)—N(2)   | 1.462(3) |
| C(7)—N(2)   | 1.464(3) |
| C(7)—C(8)   | 1.522(3) |
| C(9)—N(3)   | 1.330(3) |
| C(9)—N(2)   | 1.354(3) |
| C(9)—C(11)  | 1.441(3) |
| C(10)—N(4)  | 1.304(3) |
| C(10)—N(3)  | 1.350(3) |
| C(11)—C(12) | 1.393(3) |
| C(11)—N(5)  | 1.404(3) |
| C(12)—N(6)  | 1.366(3) |
| C(12)—C(15) | 1.505(3) |
| C(13)—N(6)  | 1.331(3) |
| C(13)—N(5)  | 1.346(3) |
| C(13)—C(14) | 1.478(3) |
| C(15)—C(16) | 1.529(3) |
| C(15)—C(18) | 1.539(3) |
| C(16)—O(1)  | 1.393(3) |
| C(17)—O(1)  | 1.396(3) |
| C(17)—C(18) | 1.503(3) |

TABLE 3-continued

Bond lengths [Å] and angles [°] for 3.

| | |
|---|---|
| C(19)—C(23) | 1.386(3) |
| C(19)—C(20) | 1.394(3) |
| C(19)—C(26) | 1.505(3) |
| C(20)—C(21) | 1.373(3) |
| C(21)—C(22) | 1.381(3) |
| C(22)—N(7) | 1.331(3) |
| C(23)—N(7) | 1.336(3) |
| C(23)—C(24) | 1.509(3) |
| C(24)—N(8) | 1.460(2) |
| C(25)—N(8) | 1.468(3) |
| C(25)—C(26) | 1.514(3) |
| C(27)—N(9) | 1.327(2) |
| C(27)—N(8) | 1.348(3) |
| C(27)—C(29) | 1.444(3) |
| C(28)—N(10) | 1.294(3) |
| C(28)—N(9) | 1.357(3) |
| C(29)—C(30) | 1.391(3) |
| C(29)—N(11) | 1.410(2) |
| C(30)—N(12) | 1.372(2) |
| C(30)—C(33) | 1.498(3) |
| C(31)—N(12) | 1.322(3) |
| C(31)—N(11) | 1.339(3) |
| C(31)—C(32) | 1.486(3) |
| C(33)—C(34) | 1.534(3) |
| C(33)—C(36) | 1.543(3) |
| C(34)—O(2B) | 1.437(5) |
| C(34)—O(2A) | 1.438(4) |
| C(35)—O(2A) | 1.424(5) |
| C(35)—C(36) | 1.491(3) |
| C(35)—O(2B) | 1.508(5) |
| N(4)—N(5) | 1.377(2) |
| N(10)—N(11) | 1.378(2) |
| C(2)—C(1)—C(5) | 117.20(19) |
| C(2)—C(1)—C(8) | 122.17(19) |
| C(5)—C(1)—C(8) | 120.63(18) |
| C(3)—C(2)—C(1) | 119.4(2) |
| C(4)—C(3)—C(2) | 119.0(2) |
| N(1)—C(4)—C(3) | 123.8(2) |
| N(1)—C(5)—C(1) | 123.98(18) |
| N(1)—C(5)—C(6) | 113.55(17) |
| C(1)—C(5)—C(6) | 122.46(17) |
| N(2)—C(6)—C(5) | 112.12(16) |
| N(2)—C(7)—C(8) | 110.98(18) |
| C(1)—C(8)—C(7) | 110.95(18) |
| N(3)—C(9)—N(2) | 117.37(19) |
| N(3)—C(9)—C(11) | 120.04(19) |
| N(2)—C(9)—C(11) | 122.59(18) |
| N(4)—C(10)—N(3) | 130.0(2) |
| C(12)—C(11)—N(5) | 104.17(17) |
| C(12)—C(11)—C(9) | 142.27(19) |
| N(5)—C(11)—C(9) | 113.56(17) |
| N(6)—C(12)—C(11) | 109.21(17) |
| N(6)—C(12)—C(15) | 118.72(17) |
| C(11)—C(12)—C(15) | 131.96(18) |
| N(6)—C(13)—N(5) | 109.69(18) |
| N(6)—C(13)—C(14) | 126.8(2) |
| N(5)—C(13)—C(14) | 123.5(2) |
| C(12)—C(15)—C(16) | 114.60(18) |
| C(12)—C(15)—C(18) | 113.99(16) |
| C(16)—C(15)—C(18) | 100.71(17) |
| O(1)—C(16)—C(15) | 106.7(2) |
| O(1)—C(17)—C(18) | 108.87(19) |
| C(17)—C(18)—C(15) | 103.91(19) |
| C(23)—C(19)—C(20) | 116.99(19) |
| C(23)—C(19)—C(26) | 120.70(18) |
| C(20)—C(19)—C(26) | 122.31(19) |
| C(21)—C(20)—C(19) | 119.6(2) |
| C(20)—C(21)—C(22) | 118.8(2) |
| N(7)—C(22)—C(21) | 123.0(2) |
| N(7)—C(23)—C(19) | 123.97(18) |
| N(7)—C(23)—C(24) | 113.55(17) |
| C(19)—C(23)—C(24) | 122.47(18) |
| N(8)—C(24)—C(23) | 112.09(16) |
| N(8)—C(25)—C(26) | 110.56(18) |
| C(19)—C(26)—C(25) | 111.09(18) |
| N(9)—C(27)—N(8) | 117.60(18) |
| N(9)—C(27)—C(29) | 119.50(18) |
| N(8)—C(27)—C(29) | 122.90(18) |
| N(10)—C(28)—N(9) | 130.1(2) |
| C(30)—C(29)—N(11) | 103.72(16) |
| C(30)—C(29)—C(27) | 142.48(19) |
| N(11)—C(29)—C(27) | 113.80(17) |
| N(12)—C(30)—C(29) | 109.31(17) |
| N(12)—C(30)—C(33) | 117.86(17) |
| C(29)—C(30)—C(33) | 132.57(18) |
| N(12)—C(31)—N(11) | 110.11(18) |
| N(12)—C(31)—C(32) | 126.65(19) |
| N(11)—C(31)—C(32) | 123.2(2) |
| C(30)—C(33)—C(34) | 113.28(16) |
| C(30)—C(33)—C(36) | 114.98(17) |
| C(34)—C(33)—C(36) | 100.93(17) |
| O(2B)—C(34)—O(2A) | 49.9(3) |
| O(2B)—C(34)—C(33) | 107.3(3) |
| O(2A)—C(34)—C(33) | 104.4(2) |
| O(2A)—C(35)—C(36) | 108.6(2) |
| O(2A)—C(35)—O(2B) | 48.7(3) |
| C(36)—C(35)—O(2B) | 99.7(2) |
| C(35)—C(36)—C(33) | 104.7(2) |
| C(4)—N(1)—C(5) | 116.62(19) |
| C(9)—N(2)—C(6) | 121.49(17) |
| C(9)—N(2)—C(7) | 119.42(18) |
| C(6)—N(2)—C(7) | 112.00(16) |
| C(9)—N(3)—C(10) | 117.75(19) |
| C(10)—N(4)—N(5) | 111.04(19) |
| C(13)—N(5)—N(4) | 124.30(18) |
| C(13)—N(5)—C(11) | 108.87(17) |
| N(4)—N(5)—C(11) | 126.60(18) |
| C(13)—N(6)—C(12) | 107.99(17) |
| C(22)—N(7)—C(23) | 117.62(18) |
| C(27)—N(8)—C(24) | 122.15(17) |
| C(27)—N(8)—C(25) | 119.13(18) |
| C(24)—N(8)—C(25) | 112.45(15) |
| C(27)—N(9)—C(28) | 117.94(19) |
| C(28)—N(10)—N(11) | 111.33(18) |
| C(31)—N(11)—N(10) | 124.67(17) |
| C(31)—N(11)—C(29) | 108.94(17) |
| N(10)—N(11)—C(29) | 126.11(17) |
| C(31)—N(12)—C(30) | 107.85(17) |
| C(16)—O(1)—C(17) | 109.56(19) |
| C(35)—O(2A)—C(34) | 104.2(2) |
| C(34)—O(2B)—C(35) | 100.1(3) |

Symmetry transformations used to generate equivalent atoms

TABLE 4

Anisotropic displacement parameters (Å$^2$ × 10$^3$) for 3. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(1) | 39(1) | 47(1) | 41(1) | −6(1) | 12(1) | −2(1) |
| C(2) | 48(1) | 60(1) | 42(1) | 4(1) | 14(1) | −4(1) |
| C(3) | 46(1) | 63(2) | 55(1) | 16(1) | 7(1) | 2(1) |
| C(4) | 42(1) | 59(1) | 61(1) | 4(1) | 9(1) | 10(1) |
| C(5) | 36(1) | 39(1) | 37(1) | −5(1) | 11(1) | −4(1) |
| C(6) | 40(1) | 49(1) | 39(1) | 1(1) | 13(1) | −1(1) |
| C(7) | 53(1) | 48(1) | 54(1) | −11(1) | 14(1) | 10(1) |
| C(8) | 53(1) | 63(1) | 44(1) | −7(1) | 19(1) | 10(1) |
| C(9) | 41(1) | 43(1) | 40(1) | 5(1) | 14(1) | 6(1) |

TABLE 4-continued

Anisotropic displacement parameters (Å² × 10³) for 3. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(10) | 43(1) | 82(2) | 61(1) | −1(1) | 26(1) | −5(1) |
| C(11) | 34(1) | 41(1) | 40(1) | 4(1) | 8(1) | 1(1) |
| C(12) | 37(1) | 39(1) | 36(1) | 5(1) | 9(1) | 4(1) |
| C(13) | 46(1) | 47(1) | 42(1) | 2(1) | 7(1) | −2(1) |
| C(14) | 57(2) | 72(2) | 60(1) | −6(1) | 6(1) | −15(1) |
| C(15) | 41(1) | 41(1) | 36(1) | 2(1) | 12(1) | −1(1) |
| C(16) | 43(1) | 53(1) | 62(1) | 2(1) | 21(1) | 2(1) |
| C(17) | 78(2) | 65(2) | 60(1) | −2(1) | 38(1) | −15(1) |
| C(18) | 59(1) | 73(2) | 41(1) | 12(1) | 14(1) | −9(1) |
| C(19) | 41(1) | 44(1) | 39(1) | −4(1) | 11(1) | −2(1) |
| C(20) | 52(1) | 66(2) | 39(1) | 6(1) | 13(1) | −1(1) |
| C(21) | 50(1) | 69(2) | 47(1) | 10(1) | 5(1) | 3(1) |
| C(22) | 40(1) | 66(1) | 53(1) | 3(1) | 8(1) | 8(1) |
| C(23) | 36(1) | 37(1) | 37(1) | −5(1) | 9(1) | −3(1) |
| C(24) | 39(1) | 48(1) | 41(1) | 2(1) | 12(1) | −2(1) |
| C(25) | 50(1) | 50(1) | 49(1) | −9(1) | 11(1) | 14(1) |
| C(26) | 54(1) | 73(2) | 41(1) | −4(1) | 20(1) | 13(1) |
| C(27) | 37(1) | 43(1) | 38(1) | 3(1) | 11(1) | 5(1) |
| C(28) | 41(1) | 81(2) | 60(1) | −4(1) | 24(1) | −7(1) |
| C(29) | 35(1) | 38(1) | 37(1) | 3(1) | 9(1) | 2(1) |
| C(30) | 36(1) | 36(1) | 36(1) | 4(1) | 9(1) | 6(1) |
| C(31) | 39(1) | 45(1) | 39(1) | −2(1) | 7(1) | 4(1) |
| C(32) | 50(1) | 60(2) | 53(1) | −9(1) | 7(1) | −9(1) |
| C(33) | 41(1) | 39(1) | 38(1) | 1(1) | 14(1) | 0(1) |
| C(34) | 60(1) | 61(2) | 50(1) | 15(1) | 20(1) | 1(1) |
| C(35) | 60(2) | 82(2) | 77(2) | −1(2) | 38(1) | 3(1) |
| C(36) | 41(1) | 52(1) | 62(1) | 6(1) | 17(1) | −1(1) |
| N(1) | 39(1) | 56(1) | 47(1) | −2(1) | 12(1) | 5(1) |
| N(2) | 43(1) | 43(1) | 43(1) | −1(1) | 12(1) | 5(1) |
| N(3) | 44(1) | 70(1) | 53(1) | −6(1) | 21(1) | −1(1) |
| N(4) | 42(1) | 70(1) | 55(1) | 2(1) | 20(1) | −9(1) |
| N(5) | 35(1) | 49(1) | 44(1) | 5(1) | 11(1) | −2(1) |
| N(6) | 41(1) | 49(1) | 41(1) | 0(1) | 10(1) | −1(1) |
| N(7) | 34(1) | 61(1) | 44(1) | −1(1) | 10(1) | 1(1) |
| N(8) | 41(1) | 42(1) | 39(1) | −2(1) | 10(1) | 5(1) |
| N(9) | 42(1) | 74(1) | 47(1) | −7(1) | 20(1) | −7(1) |
| N(10) | 40(1) | 69(1) | 51(1) | −1(1) | 17(1) | −10(1) |
| N(11) | 37(1) | 46(1) | 41(1) | 2(1) | 10(1) | −2(1) |
| N(12) | 40(1) | 44(1) | 39(1) | −3(1) | 10(1) | 3(1) |
| O(1) | 53(1) | 127(2) | 88(1) | 28(1) | 38(1) | 11(1) |
| O(2A) | 77(2) | 70(2) | 67(2) | 16(2) | 36(2) | −12(2) |
| O(2B) | 62(3) | 115(5) | 44(2) | 9(3) | 24(2) | 3(3) |

TABLE 5

Hydrogen coordinates (×10⁴) and isotropic displacement parameters (Å² × 10³) for 3.

| | x | y | z | U(eq) |
|---|---|---|---|---|
| H(2) | 5447 | −464 | 5027 | 59 |
| H(3) | 6942 | −1778 | 4978 | 66 |
| H(4) | 7619 | −1710 | 3615 | 65 |
| H(6A) | 5688 | 1931 | 1840 | 50 |
| H(6B) | 5262 | 412 | 1386 | 50 |
| H(7A) | 3428 | 2761 | 2738 | 61 |
| H(7B) | 4608 | 3141 | 2936 | 61 |
| H(8A) | 4362 | 1806 | 4258 | 63 |
| H(8B) | 3709 | 598 | 3606 | 63 |
| H(10) | 1146 | 51 | 1538 | 72 |
| H(14A) | 2089 | −2632 | −1867 | 95 |
| H(14B) | 1235 | −2006 | −1347 | 95 |
| H(14C) | 1924 | −3338 | −890 | 95 |
| H(15) | 5114 | 1643 | 87 | 46 |
| H(16A) | 6252 | −254 | 410 | 61 |
| H(16B) | 5729 | −1160 | −513 | 61 |
| H(17A) | 6033 | 863 | −2168 | 77 |
| H(17B) | 6307 | 2313 | −1550 | 77 |
| H(18A) | 4467 | 829 | −1882 | 68 |
| H(18B) | 4681 | 2446 | −1458 | 68 |
| H(20) | −264 | 7367 | 96 | 62 |
| H(21) | −1878 | 8344 | 100 | 67 |
| H(22) | −2607 | 8009 | 1438 | 64 |
| H(24A) | −106 | 6291 | 3701 | 50 |
| H(24B) | −401 | 4725 | 3246 | 50 |
| H(25A) | 806 | 3788 | 2142 | 59 |
| H(25B) | 1947 | 4364 | 2381 | 59 |
| H(26A) | 1510 | 6537 | 1563 | 65 |
| H(26B) | 993 | 5273 | 867 | 65 |
| H(28) | 4005 | 7253 | 3721 | 70 |
| H(32A) | 2570 | 10063 | 6800 | 82 |
| H(32B) | 3327 | 9991 | 6074 | 82 |
| H(32C) | 3477 | 8916 | 6966 | 82 |
| H(33) | 83 | 4993 | 5007 | 46 |
| H(34A) | 737 | 4202 | 6553 | 67 |
| H(34B) | 612 | 5779 | 7004 | 67 |
| H(35A) | −1350 | 6671 | 6713 | 84 |
| H(35B) | −2023 | 5638 | 5937 | 84 |
| H(36A) | −723 | 7674 | 5554 | 61 |
| H(36B) | −1285 | 6496 | 4803 | 61 |

Example 4

8-(2-Fluoroethoxy)-7-methoxy-2-{7-methyl-5-[(3S)-tetrahydrofuran-3-yl]imidazo[5,1-f][1,2,4]triazin-4-yl}-1,2,3,4-tetrahydroisoquinoline (4)

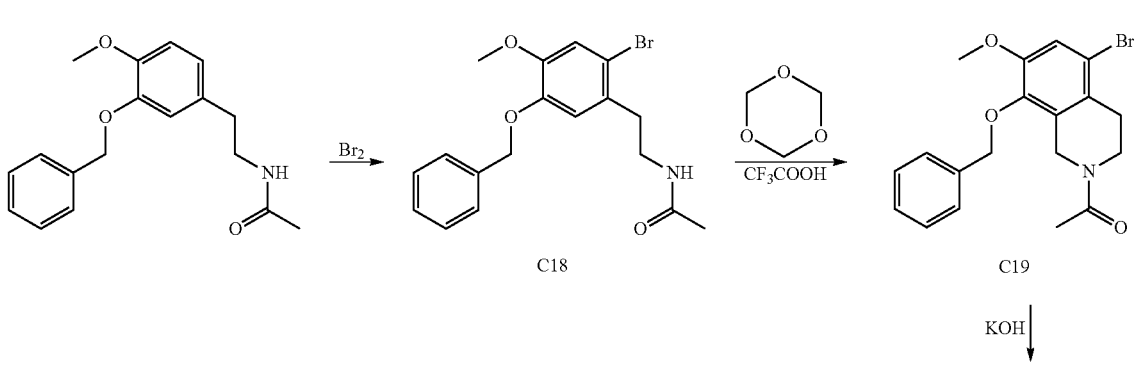

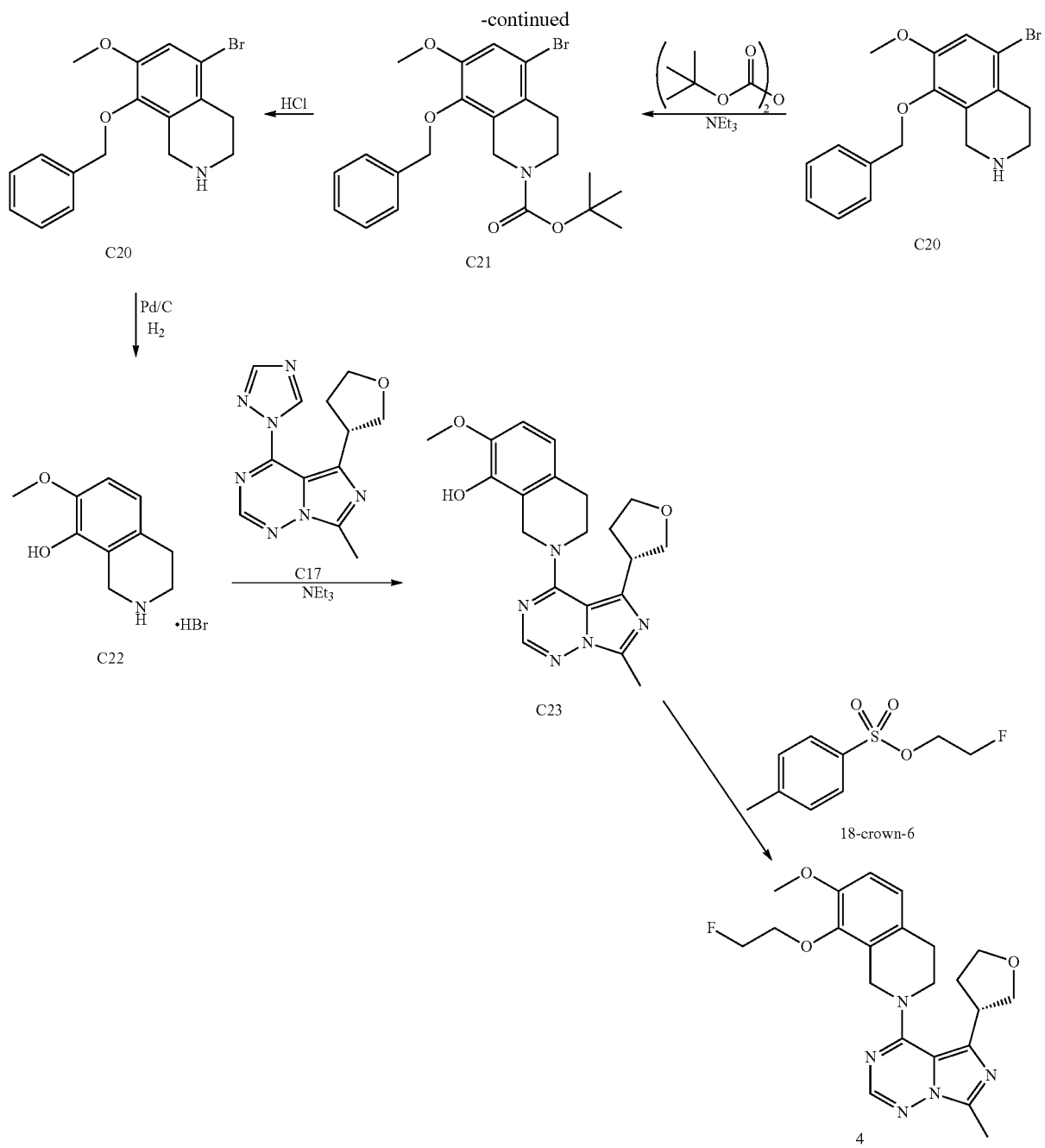

Step 1. Synthesis of N-{2-[5-(benzyloxy)-2-bromo-4-methoxyphenyl]ethyl}acetamide (C18)

A solution of bromine (16 mL, 0.31 mol) in chloroform (100 mL) was added drop-wise to a solution of N-{2-[3-(benzyloxy)-4-methoxyphenyl]ethyl}acetamide (see M. P. Leese et al., *ACS Med. Chem. Lett.* 2012, 3, 5-9) (80 g, 0.27 mol) in chloroform (1 L) at 10-15° C. The reaction mixture was stirred at 12° C. for 10 minutes, then washed sequentially with cooled saturated aqueous sodium bicarbonate solution (2×500 mL) and saturated aqueous sodium chloride solution (400 mL), dried, and concentrated in vacuo. Crystallization of the residue from ethyl acetate afforded the product as a yellow solid. Yield: 90 g, 0.24 mol, 88%. $^1$H NMR (400 MHz, CDCl$_3$) δ 7.41-7.46 (m, 2H), 7.37 (br dd, J=7.5, 7.0 Hz, 2H), 7.28-7.33 (m, 1H), 7.03 (s, 1H), 6.81 (s, 1H), 5.13 (s, 2H), 3.86 (s, 3H), 3.44-3.52 (m, 2H), 2.89 (t, J=7.0 Hz, 2H), 2.02 (s, 3H).

Step 2. Synthesis of 1-[8-(benzyloxy)-5-bromo-7-methoxy-3,4-dihydroisoquinolin-2(1H)-yl]ethanone (C19)

This reaction was carried out 32 times. A mixture of C18 (2.0 g, 5.3 mmol) and 1,3,5-trioxane (2.38 g, 26.4 mmol) in chloroform (20 mL) was treated with trifluoroacetic acid (10 mL), and the reaction mixture was heated at 50° C. for 50 minutes. The reaction mixture was poured into cooled saturated aqueous sodium bicarbonate solution (500 mL) and extracted with dichloromethane (2×300 mL). The combined organic layers were washed with saturated aqueous sodium chloride solution (400 mL), dried, and concentrated in vacuo; purification via silica gel chromatography (Gradient: 20% to 33% ethyl acetate in petroleum ether) provided the product as a yellow solid. From $^1$H NMR analysis, this compound was assumed to exist as a mixture of two rotamers. Yield of combined batches: 28 g, 72 mmol, 42%. $^1$H NMR (400 MHz, CDCl$_3$) δ 7.29-7.42 and 7.44-7.49 (m, 5H), 7.07 and 7.11 (2 s, total 1H), 5.04 and 5.08 (2 s, total 2H), 4.30 and 4.66 (2 s, total 2H), 3.88 and 3.92 (2 s, total 3H), 3.57-3.63 and 3.67-3.73 (2 m, total 2H), 2.69-2.75 and 2.79-2.84 (2 m, total 2H), 1.95 and 2.17 (2 s, total 3H).

Step 3. Synthesis of 8-(benzyloxy)-5-bromo-7-methoxy-1,2,3,4-tetrahydroisoquinoline (C20)

To a solution of C19 (23 g, 59 mmol) in ethanol (100 mL) was added aqueous potassium hydroxide solution (4 M, 90 mL), and the reaction mixture was stirred at 100-110° C. for 16 hours. The mixture was concentrated to remove ethanol, and the aqueous residue was extracted with dichloromethane (2×300 mL). The combined organic layers were washed with saturated aqueous sodium chloride solution (300 mL), dried over sodium sulfate, filtered, and concentrated to give the product as a yellow solid. Yield: 17.3 g, 49.7 mmol, 84%. Further purification was carried out via introduction of a tert-butoxycarbonyl group to facilitate chromatography (see following two steps).

Step 4. Synthesis of tert-butyl 8-(benzyloxy)-5-bromo-7-methoxy-3,4-dihydroisoquinoline-2(1H)-carboxylate (C21)

To a solution of C20 (15 g, 43 mmol) and di-tert-butyl dicarbonate (23 g, 105 mmol) in dichloromethane (150 mL) was added triethylamine (19 mL, 140 mmol), and the reaction mixture was stirred at room temperature for 4 hours. Solvents were removed in vacuo and the residue was purified by silica gel chromatography (Gradient: 5% to 10% ethyl acetate in petroleum ether) to afford the product (25 g) as a colorless solid. This material was used directly in the following step.

Step 5. Synthesis of 8-(benzyloxy)-5-bromo-7-methoxy-1,2,3,4-tetrahydroisoquinoline (C20)

To a solution of C21 (from the previous step, 25 g, 43 mmol) in methanol (200 mL) was added a solution of hydrogen chloride in methanol (50 mL). The reaction mixture was stirred at room temperature for 18 hours, then adjusted to pH 8-9 with 2 N aqueous sodium hydroxide solution. The mixture was extracted with dichloromethane (2×500 mL), and the combined organic layers were washed with saturated aqueous sodium chloride solution (3×300 mL), dried over sodium sulfate, and concentrated in vacuo, providing the product as a white solid. Yield: 10.3 g, 29.6 mmol, 69% over 2 steps. $^1$H NMR (400 MHz, CDCl$_3$) δ 7.41-7.46 (m, 2H), 7.30-7.41 (m, 3H), 7.06 (s, 1H), 4.98 (s, 2H), 3.91 (s, 2H), 3.87 (s, 3H), 3.02-3.09 (m, 2H), 2.61-2.68 (m, 2H).

Step 6. Synthesis of 7-methoxy-1,2,3,4-tetrahydroisoquinolin-8-ol, hydrobromide salt (C22)

To a solution of C20 (9.3 g, 27 mmol) in methanol (300 mL) was added 10% palladium on carbon (2 g), and the reaction mixture was hydrogenated at 50 psi for 24 hours at 40° C. The mixture was filtered and the filtrate was concentrated in vacuo to afford the product as a white solid. Yield: 7.0 g, 27 mmol, 100%. LCMS m/z 180.1 [M+H]$^+$. $^1$H NMR (400 MHz, CD$_3$OD) δ 6.91 (d, J=8.4 Hz, 1H), 6.70 (d, J=8.3 Hz, 1H), 4.25 (s, 2H), 3.85 (s, 3H), 3.40-3.46 (m, 2H), 3.00-3.05 (m, 2H).

Step 7. Synthesis of 7-methoxy-2-{7-methyl-5-[(3S)-tetrahydrofuran-3-yl]imidazo[5,1-f][1,2,4]triazin-4-yl}-1,2,3,4-tetrahydroisoquinolin-8-ol (C23)

A solution of C17 (2.00 g, 7.37 mmol), C22 (1.75 g, 8.12 mmol) and triethylamine (3.08 mL, 22.1 mmol) in dichloromethane (20 mL) was heated at 40° C. for 18 hours, then diluted with additional dichloromethane and washed sequentially with water and saturated aqueous sodium chloride solution. The organic layer was dried over magnesium sulfate, filtered, and concentrated in vacuo. Trituration with cold ethanol afforded the product as a white solid. Yield: 2.44 g, 6.40 mmol, 87%. LCMS m/z 382.2 [M+H]$^+$. $^1$H NMR (400 MHz, CDCl$_3$) δ 7.86 (s, 1H), 6.72 (AB quartet, $J_{AB}$=8.3 Hz, $\Delta v_{AB}$=34.2 Hz, 2H), 5.79 (s, 1H), 4.90 (AB quartet, $J_{AB}$=16.5 Hz, $\Delta v_{AB}$=11.3 Hz, 2H), 4.32 (dd, J=7.9, 7.8 Hz, 1H), 4.19 (ddd, J=8.4, 8.4, 5.1 Hz, 1H), 3.94-4.05 (m, 4H), 3.87 (s, 3H), 3.77-3.86 (m, 1H), 3.00-3.06 (m, 2H), 2.65 (s, 3H), 2.37-2.55 (m, 2H).

Step 8. Synthesis of 8-(2-fluoroethoxy)-7-methoxy-2-{7-methyl-5-[(3S)-tetrahydrofuran-3-yl]imidazo[5,1-f][1,2,4]triazin-4-yl}-1,2,3,4-tetrahydroisoquinoline (4)

2-Fluoroethyl 4-methylbenzenesulfonate (126 mg, 0.577 mmol) and 1,4,7,10,13,16-hexaoxacyclooctadecane (18-crown-6, 97%, 28.6 mg, 0.105 mmol) were added to a mixture of C23 (200 mg, 0.524 mmol) and potassium carbonate (99%, 146 mg, 1.06 mmol) in acetonitrile (7 mL). The reaction mixture was heated at 50° C. for 2 hours, and then at 75° C. for 18 hours. After cooling to room temperature, it was diluted with dichloromethane and washed sequentially with water and saturated aqueous sodium chloride solution. The organic layer was dried over magnesium sulfate, filtered, and concentrated in vacuo. Purification via chromatography on silica gel (Eluent: 5% methanol in ethyl acetate) afforded the product. This was combined with the material from an identical reaction run at twice the scale (400 mg of C23); trituration from cold ethanol afforded the product as a white solid. Yield: 553 mg, 1.29 mmol, 82%. LCMS m/z 428.2 [M+H]$^+$. $^1$H NMR (400 MHz, CDCl$_3$) δ 7.85 (s, 1H), 6.85 (AB quartet, $J_{AB}$=8.4 Hz, $\Delta v_{AB}$=22.9 Hz, 2H), 4.90-5.00 (m, 2H), 4.55-4.76 (m, $J_{HF}$=47.7 Hz, 2H), 4.26-4.44 (m, $J_{HF}$=30 Hz, 2H), 4.26 (dd, J=7.8, 7.8 Hz, 1H), 4.13-4.20 (m, 1H), 3.92-4.04 (m, 4H), 3.84 (s, 3H), 3.78-3.88 (m, 1H), 2.96-3.09 (m, 2H), 2.64 (s, 3H), 2.40-2.48 (m, 2H).

Example 5

4-(1-Cyclopropyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine (5)

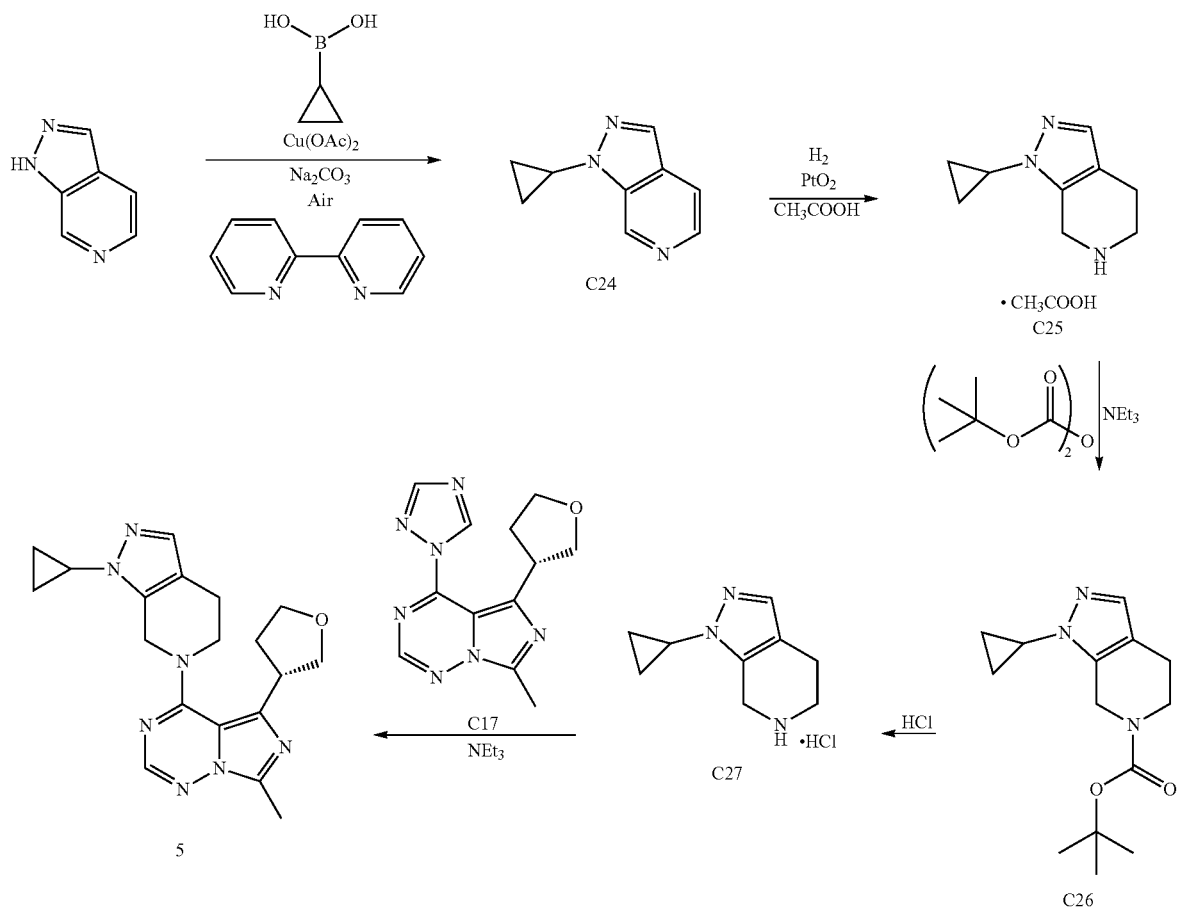

Step 1. Synthesis of 1-cyclopropyl-1H-pyrazolo[3,4-c]pyridine (C24)

Copper(II) acetate (3.02 g, 15.1 mmol), 2,2'-bipyridine (2.36 g, 15.1 mmol), and sodium carbonate (3.20 g, 30.2 mmol) were added to a solution of 1H-pyrazolo[3,4-c]pyridine (1.80 g, 15.1 mmol) and cyclopropylboronic acid (2.60 g, 30.3 mmol) in 1,2-dichloroethane (50 mL), and the reaction mixture was stirred at 70° C. for 3 hours while open to the atmosphere. The reaction mixture was partitioned between ethyl acetate (300 mL) and saturated aqueous ammonium chloride solution. The resulting aqueous layer was extracted with dichloromethane (2×100 mL), and the combined organic layers were dried, filtered, and concentrated in vacuo. Silica gel chromatography (Gradient: 0% to 30% methanol in ethyl acetate) afforded the product as a yellow oil. Yield: 1.20 g, 7.54 mmol, 50%. $^1$H NMR (400 MHz, CDCl$_3$) δ 9.17 (dd, J=1, 1 Hz, 1H), 8.34 (d, J=5.7 Hz, 1H), 8.01 (d, J=0.8 Hz, 1H), 7.63 (dd, J=5.7, 1.3 Hz, 1H), 3.70-3.76 (m, 1H), 1.21-1.32 (m, 4H).

Step 2. Synthesis of 1-cyclopropyl-4,5,6,7-tetrahydro-1H-pyrazolo[3,4-c]pyridine, acetate salt (C25)

Platinum(IV) oxide (100 mg, 0.44 mmol) was added to a solution of C24 (1.20 g, 7.54 mmol) in acetic acid (10 mL), and the mixture was hydrogenated on a Parr shaker for 3 hours at 40 psi. The mixture was then filtered through diatomaceous earth; after washing the filter pad with methanol, the combined filtrates were concentrated in vacuo, taken up in methanol and filtered once more through diatomaceous earth. The resulting filtrate was concentrated under reduced pressure and used directly in the following step. LCMS m/z 164.2 [M+H]$^+$.

Step 3. Synthesis of tert-butyl 1-cyclopropyl-1,4,5,7-tetrahydro-6H-pyrazolo[3,4-c]pyridine-6-carboxylate (C26)

Triethylamine (4.21 mL, 30.2 mmol) and di-tert-butyl dicarbonate (3.30 g, 15.1 mmol) were added to a solution of C25 (from the previous step, 7.54 mmol) in dichloromethane (15 mL). The reaction mixture was stirred for 18 hours at room temperature, then diluted with dichloromethane and water; the organic layer was washed with saturated aqueous sodium bicarbonate solution, dried, filtered, and concentrated in vacuo. Purification via supercritical fluid chromatography (Column: Chiral Technologies, Chiralcel OD-H, 5 μm; Eluent: 85:15 carbon dioxide/methanol) afforded the product as an oil. Yield: 910 mg, 3.44 mmol, 46% over 2 steps. $^1$H NMR (400 MHz, CD$_3$OD) δ 7.22 (s, 1H), 4.62 (s, 2H), 3.59-3.64 (m, 2H), 3.35-3.42 (m, 1H), 2.53-2.58 (m, 2H), 1.49 (s, 9H), 1.03-1.08 (m, 4H).

Step 4. Synthesis of 1-cyclopropyl-4,5,6,7-tetrahydro-1H-pyrazolo[3,4-c]pyridine, hydrochloride salt (C27)

Compound C26 (910 mg, 3.44 mmol) was dissolved in a mixture of ethyl acetate and methanol (1:1, 5 mL) and treated with concentrated hydrochloric acid (5 drops). After 3 hours, the reaction mixture was concentrated in vacuo to afford the product as a solid. Yield: 700 mg, quantitative. $^1$H NMR (500 MHz, CD$_3$OD) δ 8.09 (s, 1H), 4.69 (s, 2H), 3.73-3.78 (m, 1H), 3.54-3.60 (m, 2H), 3.00-3.06 (m, 2H), 1.26-1.36 (m, 4H).

Step 5. Synthesis of 4-(1-cyclopropyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine (5)

Triethylamine (387 μL, 2.78 mmol) and C27 (345 mg, 1.72 mmol) were added to a solution of C17 (466 mg, 1.72 mmol) in dichloromethane (10 mL). The reaction mixture was stirred at 40° C. for 18 hours, then diluted with dichloromethane (10 mL) and washed with water (20 mL). The organic layer was dried, filtered, and concentrated in vacuo; purification via silica gel chromatography (Gradient: 0% to 30% methanol in ethyl acetate) afforded the product as a yellow foam. Yield: 625 mg, 1.71 mmol, 99%. LCMS m/z 366.3 [M+H]$^+$. $^1$H NMR (400 MHz, CD$_3$OD) δ 7.90 (s, 1H), 7.28 (s, 1H), 4.86-4.96 (m, 2H), 4.12-4.21 (m, 2H), 3.80-4.03 (m, 5H), 3.40-3.46 (m, 1H), 2.79-2.92 (m, 2H), 2.60 (s, 3H), 2.28-2.47 (m, 2H), 1.03-1.13 (m, 4H).

Example 6

4-(3-Cyclopropyl-6,7-dihydro[1,2]oxazolo[4,3-c]pyridin-5(4H)-yl)-7-methyl-5-[(3S)-tetrahydrofuran-3-yl]imidazo[5,1-f][1,2,4]triazine (6)

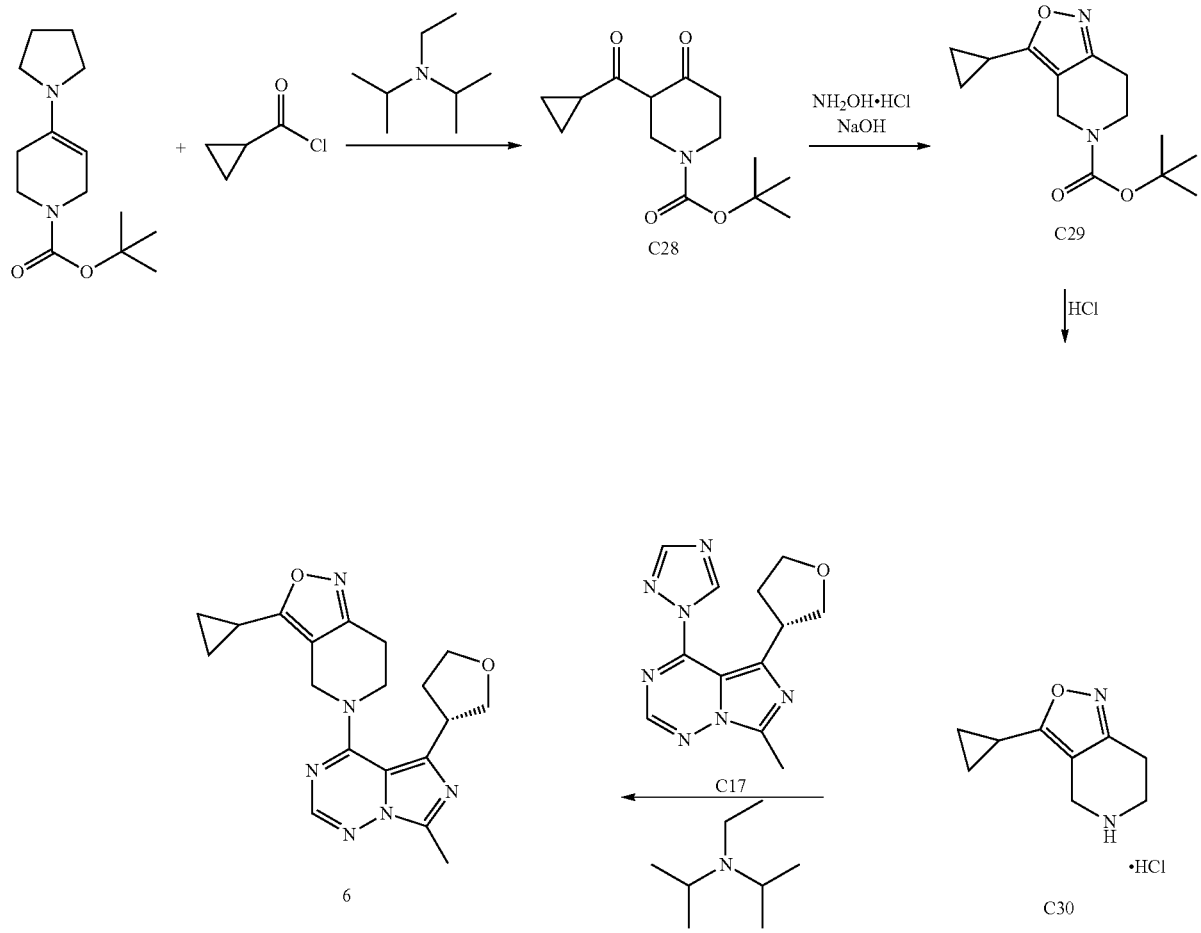

Step 1. Synthesis of tert-butyl 3-(cyclopropylcarbonyl)-4-oxopiperidine-1-carboxylate (C28)

N,N-Diisopropylethylamine (4.14 mL, 23.8 mmol) was added to a solution of tert-butyl 4-pyrrolidin-1-yl-3,6-dihydropyridine-1(2H)-carboxylate (5.00 g, 19.8 mmol) in 1,4-dioxane (10 mL). The reaction mixture was cooled in an ice bath and treated drop-wise with a solution of cyclopropanecarbonyl chloride (2.18 mL, 23.8 mmol) in 1,4-dioxane (3 mL). The mixture was allowed to stir at room temperature for 16 hours; water (10 mL) was added, and the solution was heated at reflux for 30 minutes. After cooling, the reaction was diluted with additional water (10 mL), and extracted with diethyl ether. The combined organic layers were washed sequentially with water, with 5% aqueous citric acid solution and with saturated aqueous sodium chloride solution. The organic layer was dried over magnesium sulfate, filtered and concentrated in vacuo. Purification using silica gel chromatography (Gradient: 0% to 100% ethyl acetate in heptane) provided the product as a yellow oil. Yield: 4.23 g, 15.8 mmol, 80%. $^1$H NMR (400 MHz, CDCl$_3$) δ 4.39 (br s, 2H), 3.59 (br dd, J=5.9, 5.9 Hz, 2H), 2.43 (br dd, J=5.7, 5.9 Hz, 2H), 1.74-1.85 (br m, 1H), 1.50 (s, 9H), 1.17-1.22 (m, 2H), 0.96-1.02 (m, 2H).

Step 2. Synthesis of tert-butyl 3-cyclopropyl-6,7-dihydroisoxazolo[4,3-c]pyridine-5(4H)-carboxylate (C29)

Sodium hydroxide (590 mg, 14.8 mmol) was added to a solution of C28 (3.95 g, 14.8 mmol) and hydroxylamine hydrochloride (98%, 1.05 g, 14.8 mmol) in ethanol (30 mL), and the reaction mixture was heated at reflux for 16 hours. After cooling, the reaction was concentrated in vacuo. The residue was dissolved in diethyl ether, washed consecutively with water, 5% aqueous citric acid solution, and saturated aqueous sodium chloride solution, then dried over magnesium sulfate, filtered and concentrated under reduced pressure to afford the product. Yield: 3.90 g, 14.8 mmol, quantitative. LCMS m/z 265.1 [M+H]$^+$. $^1$H NMR (400 MHz, CDCl$_3$) δ 4.44 (br s, 2H), 3.61-3.70 (br m, 2H), 2.78 (br dd, J=5.8, 5.8 Hz, 2H), 1.84-1.91 (m, 1H), 1.49 (s, 9H), 1.01-1.08 (m, 4H).

Step 3. Synthesis of 3-cyclopropyl-4,5,6,7-tetrahydroisoxazolo[4,3-c]pyridine, hydrochloride salt (C30)

A solution of C29 (3.90 g, 14.8 mmol) in 2-propanol (74 mL) was treated with a solution of hydrogen chloride in 1,4-dioxane (4 M, 18.4 mL, 73.6 mmol). After stirring for 18 hours, the reaction mixture was concentrated in vacuo, and the residue was triturated with diethyl ether to provide the product as a solid. Yield: 2.55 g, 12.7 mmol, 86%. $^1$H NMR (400 MHz, CD$_3$OD) δ 4.31 (br s, 2H), 3.53 (dd, J=6.4, 6.4 Hz, 2H), 3.08 (dd, J=6.4, 6.3 Hz, 2H), 2.06-2.13 (m, 1H), 1.10-1.16 (m, 2H), 1.02-1.08 (m, 2H).

Step 4. Synthesis of 4-(3-cyclopropyl-6,7-dihydro[1,2]oxazolo[4,3-c]pyridin-5(4H)-yl)-7-methyl-5-[(3S)-tetrahydrofuran-3-yl]imidazo[5,1-f][1,2,4]triazine (6)

Compound C17 (4.89 g, 18.0 mmol) was added to a mixture of C30 (4.34 g, 21.6 mmol) and N,N-diisopropylethylamine (9.71 mL, 54.1 mmol) in dichloromethane (50 mL), and the reaction mixture was heated to 40° C. for 18 hours. After cooling to room temperature, it was washed with saturated aqueous sodium chloride solution, dried over sodium sulfate, filtered, and concentrated in vacuo. Purification was effected via silica gel chromatography [Gradient: 0% to 20% methanol in (0.1% triethylamine in ethanol)] followed by supercritical fluid chromatography (Column: Chiral Technologies, Chiralcel OJ-H, 5 μm; Eluent: 3:1 carbon dioxide/methanol). The product was obtained as a solid. Yield: 3.49 g, 9.52 mmol, 53%. LCMS m/z 367.2 [M+H]$^+$. $^1$H NMR (400 MHz, CD$_3$OD) δ 7.91 (s, 1H), 4.76 (AB quartet, J$_{AB}$=15.3 Hz, Δv$_{AB}$=8.4 Hz, 2H), 4.18 (dd, J=7.9, 7.8 Hz, 1H), 4.11-4.17 (m, 1H), 3.89-4.05 (m, 4H), 3.77-3.86 (m, 1H), 2.98-3.11 (m, 2H), 2.60 (s, 3H), 2.37-2.46 (m, 1H), 2.27-2.37 (m, 1H), 1.98-2.06 (m, 1H), 1.05-1.12 (m, 2H), 0.98-1.05 (m, 2H).

Example 7

6-[5-(2-Chloro-4-fluorophenyl)-7-methylimidazo[5,1-f][1,2,4]triazin-4-yl]-2-cyclopropyl-5,6,7,8-tetrahydropyrido[4,3-d]pyrimidine (7)

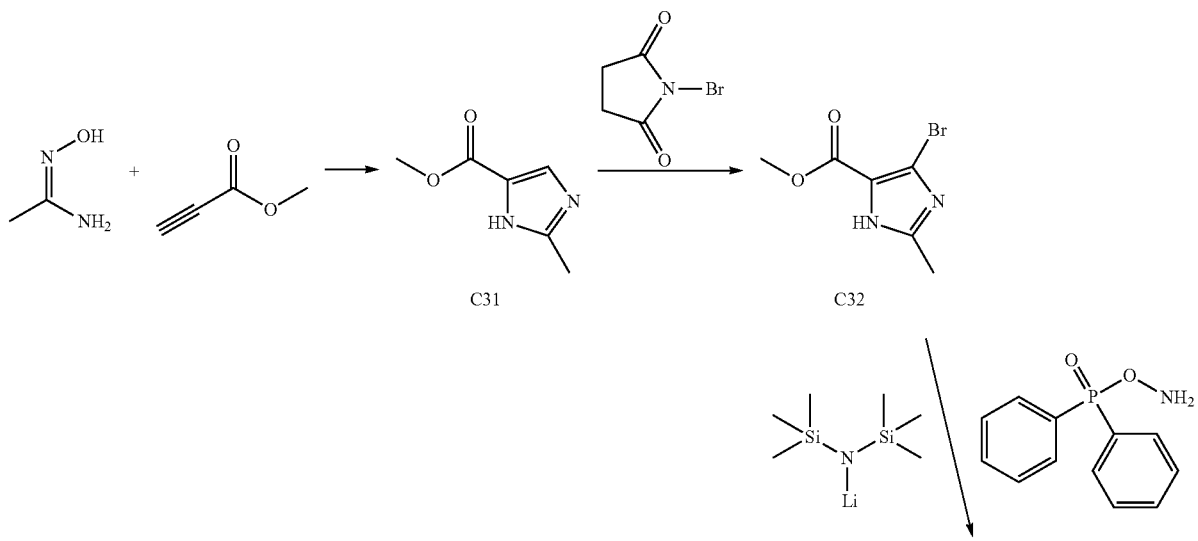

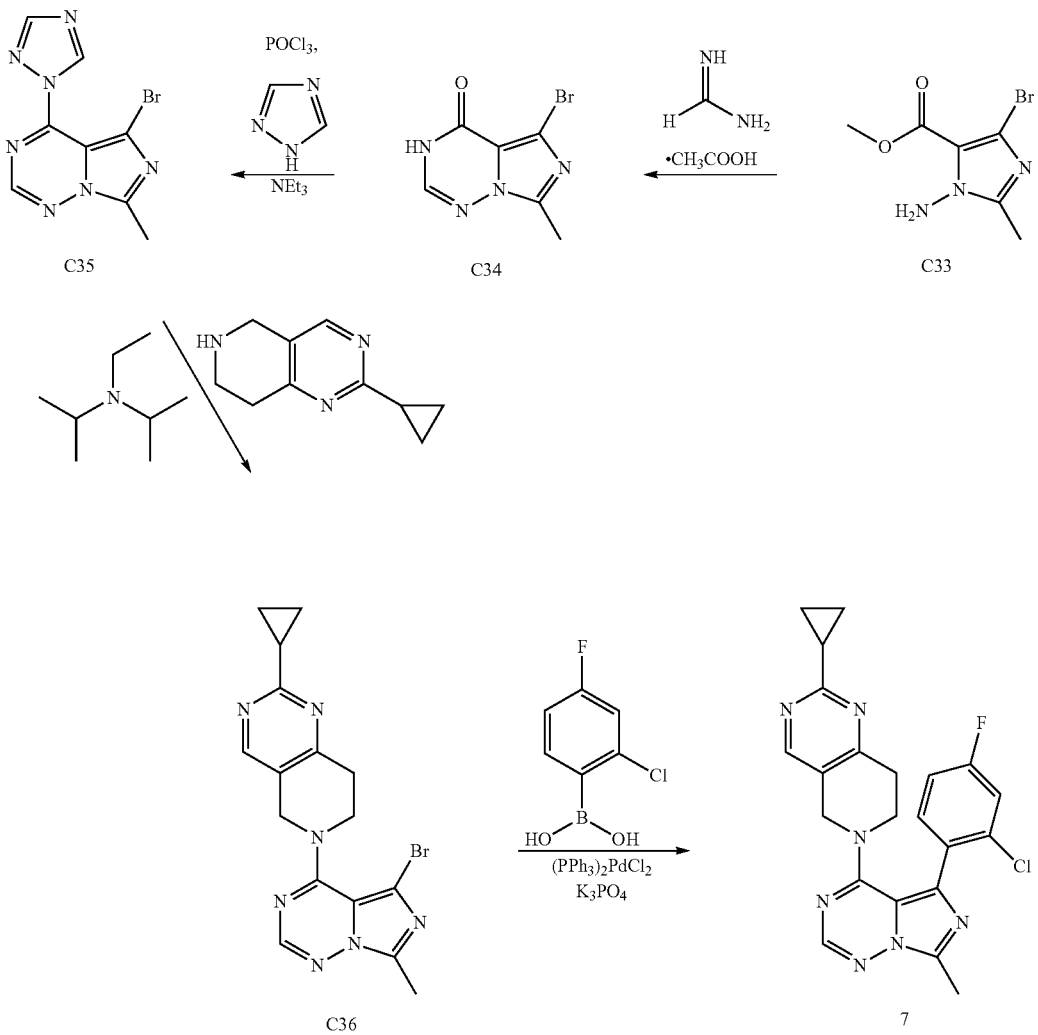

Step 1. Synthesis of methyl 2-methyl-1H-imidazole-5-carboxylate (C31)

A solution of N'-hydroxyethanimidamide (65 g, 880 mmol) in anhydrous methanol (2 L) was treated with methyl propiolate (100 g, 1.19 mol), and the reaction was heated at reflux for 4 hours. The reaction mixture was concentrated in vacuo, and the residue was diluted with diphenyl ether (1 L) and heated at reflux for 4 hours. The hot solution was filtered, and the filtrate was cooled to room temperature and diluted with hexanes (2 L). The resulting solid was washed with diethyl ether (1 L), to afford the product as a brown solid. Yield: 60 g, 430 mmol, 49%.

Step 2. Synthesis of methyl 4-bromo-2-methyl-1H-imidazole-5-carboxylate (C32)

N-Bromosuccinimide (92 g, 520 mmol) was added to a cold solution of C31 (60 g, 430 mmol) in N,N-dimethylformamide. The resulting mixture was stirred for 1 hour, concentrated in vacuo, diluted with water (1 L) and extracted with 1:1 dichloromethane/diethyl ether (1 L). The combined organic layers were dried, then concentrated under reduced pressure; purification via silica gel chromatography (Eluent: 50% ethyl acetate in dichloromethane) afforded the product as a yellow solid. Yield: 45 g, 200 mmol, 47%. LCMS m/z 219.0, 221.1 [M+H]$^+$.

Step 3. Synthesis of methyl 1-amino-4-bromo-2-methyl-1H-imidazole-5-carboxylate (C33)

A solution of C32 (37.6 g, 172 mmol) in N,N-dimethylformamide (2 L) was converted to the product using the general procedure described for synthesis of C13 in Example 3. In this case, the final reaction mixture was filtered, and the filtrate was concentrated in vacuo to provide the crude product as a brown solid (68.5 g); this material was used directly in the following step. LCMS m/z 234.0 and 236.1 [M+H]$^+$.

Step 4. Synthesis of 5-bromo-7-methylimidazo[5,1-f][1,2,4]triazin-4(3H)-one (C34)

Formamidine acetate (178.7 g, 1.716 mol) was added to a solution of C33 (68.5 g, ≤172 mmol) in ethanol (1.2 L), and the reaction was heated at reflux for 18 hours. After cooling to room temperature, the mixture was concentrated under reduced pressure, and the residue was suspended in water. The resulting solid was collected by filtration to afford the product as a brown solid. Yield: 9.5 g, 41 mmol, 24% from C32. LCMS m/z 228.9, 231.0 [M+H]$^+$. $^1$H NMR (300 MHz, DMSO-d$_6$) δ 7.86 (s, 1H), 2.46 (s, 3H).

Step 5. Synthesis of 5-bromo-7-methyl-4-(1H-1,2,4-triazol-1-yl)imidazo[5,1-f][1,2,4]triazine (C35)

Compound C35 was prepared from C34 according to the general procedure for the synthesis of C6 in Example 1. The product was obtained as a bright yellow solid. Yield: 1.85 g, 6.63 mmol, 43%.

Step 6. Synthesis of 6-(5-bromo-7-methylimidazo[5,1-f][1,2,4]triazin-4-yl)-2-cyclopropyl-5,6,7,8-tetrahydropyrido[4,3-d]pyrimidine (C36)

Compound C35 (335 mg, 1.20 mmol), 2-cyclopropyl-5,6,7,8-tetrahydropyrido[4,3-d]pyrimidine (266 mg, 1.26 mmol) and N,N-diisopropylethylamine (97%, 319 mg, 2.39 mmol) were dissolved in acetonitrile, and the reaction was stirred at room temperature for 18 hours. Solvent was removed in vacuo, and the residue was dissolved in ethyl acetate, then washed with water, dried, filtered and concentrated under reduced pressure. The residue was slurried in diethyl ether, and the resulting solid was collected to afford the product. Yield: 445 mg, 1.15 mmol, 96%. LCMS m/z 386.0 [M+H]$^+$. $^1$H NMR (500 MHz, CDCl$_3$) δ 8.38 (s, 1H), 7.91 (s, 1H), 4.88 (br s, 2H), 4.15 (dd, J=6.0, 6.0 Hz, 2H), 3.23 (dd, J=6.0, 6.0 Hz, 2H), 2.66 (s, 3H), 2.19-2.25 (m, 1H), 1.11-1.15 (m, 2H), 1.04-1.10 (m, 2H).

Step 7. Synthesis of 6-[5-(2-chloro-4-fluorophenyl)-7-methylimidazo[5,1-f][1,2,4]triazin-4-yl]-2-cyclopropyl-5,6,7,8-tetrahydropyrido[4,3-d]pyrimidine (7)

Compound C36 (45 mg, 0.12 mmol), (2-chloro-4-fluorophenyl)boronic acid (50 mg, 0.29 mmol), dichlorobis(triphenylphosphine)palladium(II) (7.0 mg, 10 µmol) and potassium phosphate (95%, 68.5 mg, 0.31 mmol) were combined and degassed. 1,2-Dimethoxyethane (0.3 mL) and water (0.3 mL) were added, and the reaction was stirred at 80° C. for 18 hours. The reaction was dried over magnesium sulfate, then filtered through a syringe filter. Purification was carried out by reversed phase HPLC (Mobile phase A: 0.1% ammonium hydroxide in water; Mobile phase B: 0.1% ammonium hydroxide in acetonitrile; Gradient: 20% to 80% B) to afford the product as a glass. Yield: 13.3 mg, 30.5 µmol, 25%. LCMS m/z 436.6, 438.6 [M+H]$^+$. $^1$H NMR (500 MHz, CDCl$_3$), δ 7.99 (br s, 1H), 7.98 (s, 1H), 7.53 (dd, J=8.5, 6.0 Hz, 1H), 7.24 (dd, J=8.4, 2.6 Hz, 1H), 7.11 (ddd, J=8.3, 8.0, 2.6 Hz, 1H), 4.34-4.55 (m, 2H), 3.85 (dd, J=5.9, 5.7 Hz, 2H), 2.73 (s, 3H), 2.65-2.80 (br m, 2H), 2.13-2.19 (m, 1H), 1.01-1.10 (m, 4H).

Example 8

7-Methyl-4-(1-methyl-1,4,5,7-tetrahydro-6H-pyrazolo[3,4-c]pyridin-6-yl)-5-[(3S)-tetrahydrofuran-3-yl]imidazo[5,1-f][1,2,4]triazine (8)

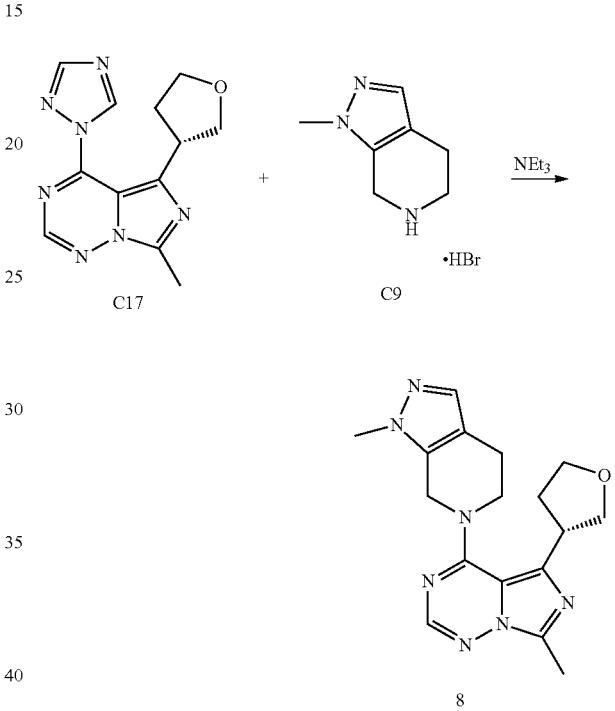

Triethylamine (2.8 mL, 20 mmol) was added to a mixture of C17 (2.0 g, 7.4 mmol) and C9 (1.78 g, 8.16 mmol) in dichloromethane (14 mL), and the reaction mixture was stirred at 40° C. for 24 hours, then cooled to room temperature. The reaction mixture was washed with water (3×10 mL), diluted with propan-2-yl acetate (15 mL), and concentrated in vacuo. The residue (2.33 g) was crystallized from propan-2-yl acetate (10 mL) to afford the product as a beige solid. Yield: 1.03 g, 3.03 mmol, 41%. A second crystallization was carried out: dissolution in hot propan-2-yl acetate (4 volumes) was followed by cooling to room temperature and treatment of the heterogeneous mixture with heptane (4 volumes), followed by heating to reflux. After the mixture had cooled to room temperature and stirred for 16 hours, the product, a beige solid, was collected via filtration and rinsed with a 1:2 mixture of propan-2-yl acetate and heptane. LCMS m/z 340.2 [M+H]$^+$. $^1$H NMR (400 MHz, DMSO-d$_6$) δ 7.96 (s, 1H), 7.25 (s, 1H), 4.74-4.84 (s, 2H), 4.09 (dd, J=7.8, 7.7 Hz, 1H), 3.98 (ddd, J=8.0, 7.9, 5.6 Hz, 1H), 3.71 (s, 3H), 3.67-3.91 (m, 5H), 2.75-2.81 (m, 2H), 2.53 (s, 3H), 2.17-2.34 (m, 2H).

Example 9

4-(2-Cyclopropyl-6,7-dihydro[1,3]oxazolo[5,4-c]pyridin-5(4H)-yl)-7-methyl-5-[(3S)-tetrahydrofuran-3-yl]imidazo[5,1-f][1,2,4]triazine (9)

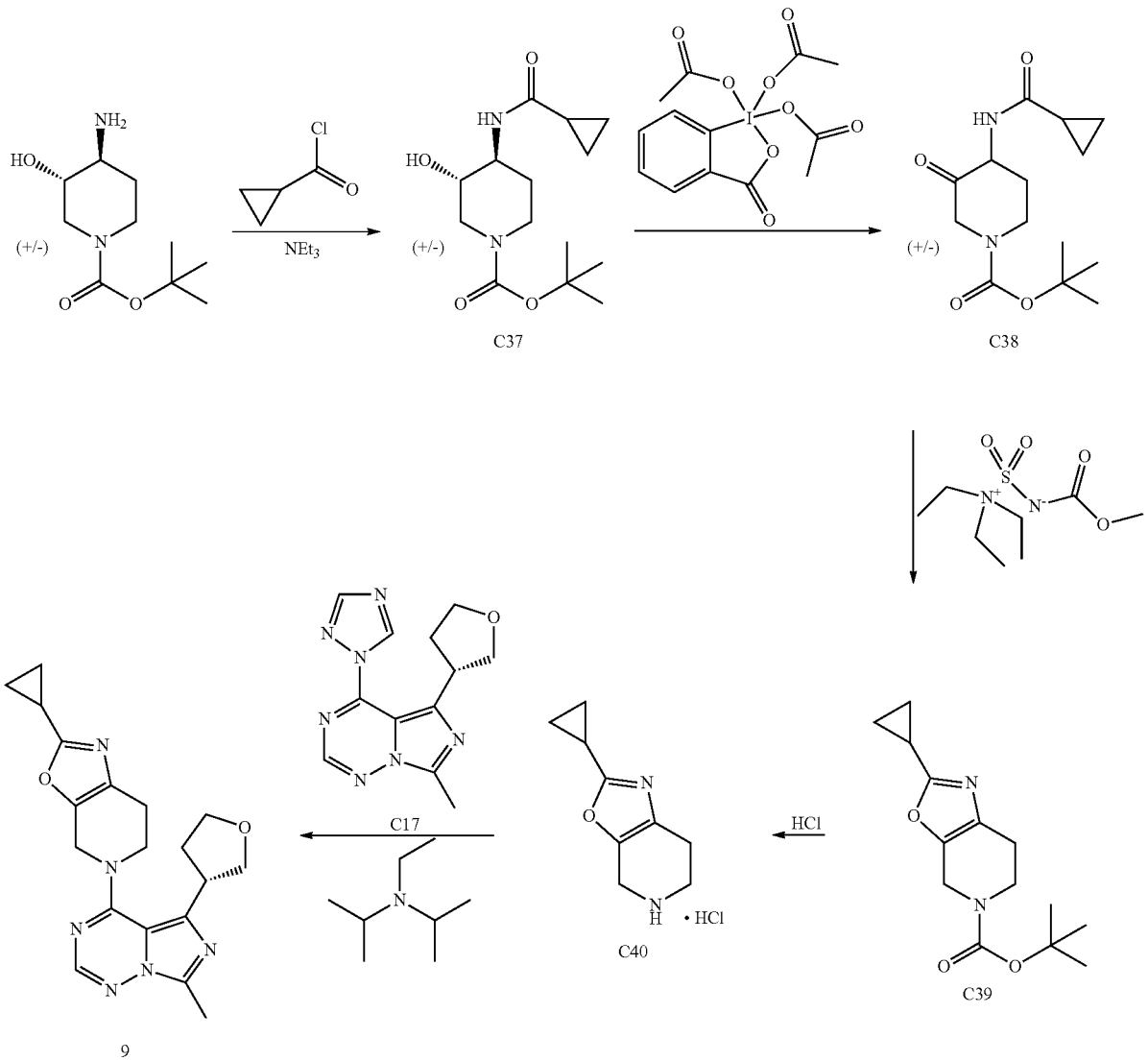

Step 1. Synthesis of tert-butyl trans-4-[(cyclopropylcarbonyl)amino]-3-hydroxypiperidine-1-carboxylate (C37)

Triethylamine (4.85 mL, 34.8 mmol) and cyclopropanecarbonyl chloride (3.18 mL, 35.0 mmol) were added to a 0° C. solution of tert-butyl trans-4-amino-3-hydroxypiperidine-1-carboxylate (7.52 g, 34.8 mmol) in tetrahydrofuran (100 mL), and the reaction was allowed to warm to room temperature and stir for 18 hours. After concentration in vacuo, the crude product was diluted with ethyl acetate, insoluble material was removed by filtration, and the solids were washed with ethyl acetate (3×50 mL). The combined filtrates were concentrated under reduced pressure, and the residue was purified by silica gel chromatography (Gradient: 0% to 5% methanol in ethyl acetate) to afford the product as a solid. Yield: 1.30 g, 4.57 mmol, 13%. LCMS m/z 285.6 [M+H]$^+$. $^1$H NMR (400 MHz, CDCl$_3$), observed peaks: δ 5.79 (br d, J=5 Hz, 1H), 4.21-4.34 (br m, 1H), 4.03-4.21 (br m, 1H), 3.70-3.79 (m, 1H), 3.34-3.42 (m, 1H), 2.66-2.79 (br m, 1H), 2.59 (br dd, J=12, 11 Hz, 1H), 1.88-1.96 (m, 1H), 1.46 (s, 9H), 1.37-1.44 (m, 1H), 1.01-1.05 (m, 2H), 0.77-0.87 (m, 2H).

Step 2. Synthesis of tert-butyl 4-[(cyclopropylcarbonyl)amino]-3-oxopiperidine-1-carboxylate (C38)

Dess-Martin periodinane [1,1,1-tris(acetyloxy)-1,1-dihydro-1,2-benziodoxol-3-(1H)-one] (3.88 g, 9.15 mmol) was added to a solution of C37 (1.30 g, 4.57 mmol) in dichloromethane (200 mL), and the reaction mixture was stirred at room temperature for 3 hours. The reaction was quenched with aqueous sodium thiosulfate solution (20%, 20 mL) and saturated aqueous sodium bicarbonate solution (80 mL), and the mixture was stirred until the aqueous layer was clear. The aqueous layer was extracted with dichloromethane (3×50 mL), and the combined organic layers were dried over sodium sulfate, filtered, and concentrated in vacuo, providing the product as a yellow oil. Yield: 1.25 g, 4.43 mmol, 97%. LCMS m/z 283.6 [M+H]+. 1H NMR (400 MHz, CDCl3) δ 6.42-6.55 (br s, 1H), 4.58-4.65 (m, 1H), 4.32 (br d, J=17 Hz, 1H), 3.81-4.12 (br m, 2H), 3.40-3.57 (br m, 1H), 2.63-2.71 (m, 1H), 1.59-1.69 (m, 1H, assumed; partially obscured by water peak), 1.47 (s, 9H), 1.42-1.47 (m, 1H, assumed; partially obscured by tert-butyl signal), 0.94-1.02 (m, 2H), 0.76-0.82 (m, 2H).

Step 3. Synthesis of tert-butyl 2-cyclopropyl-6,7-dihydro[1,3]oxazolo[5,4-c]pyridine-5(4H)-carboxylate (C39)

A mixture of C38 (3.50 g, 12.4 mmol) and Burgess reagent [(methoxycarbonylsulfamoyl)triethylammonium hydroxide, inner salt] (97%, 6.09 g, 24.8 mmol) in tetrahydrofuran (50 mL) was stirred at reflux for 18 hours. The tetrahydrofuran phase was decanted away from an oily residue, and was concentrated in vacuo. The residue was subjected to silica gel chromatography (Gradient: 10% to 30% ethyl acetate in hexanes), providing the product. Yield: 1.02 g, 3.86 mmol, 31%. 1H NMR (400 MHz, CDCl3) δ 4.40-4.46 (br m, 2H), 3.62-3.71 (br m, 2H), 2.54-2.60 (br m, 2H), 1.99-2.06 (m, 1H), 1.48 (s, 9H), 1.00-1.05 (m, 4H).

Step 4. Synthesis of 2-cyclopropyl-4,5,6,7-tetrahydro[1,3]oxazolo[5,4-c]pyridine, hydrochloride salt (C40)

Compound C39 (1.02 g, 3.86 mmol) was added to a mixture of tetrahydrofuran (20 mL) and concentrated hydrochloric acid (12 M, 0.662 mL, 7.9 mmol), and the reaction was stirred at room temperature for 18 hours. The layers were separated, and the bottom layer, a thick oil, was basified with 1 N aqueous sodium hydroxide solution and extracted with dichloromethane (3×10 mL). The combined organic extracts were dried over sodium sulfate, filtered and concentrated in vacuo to provide the free base of the product as an oil. Yield: 214 mg, 1.30 mmol, 34%. A mixture of methanol (3 mL) and acetyl chloride (93 μL, 1.30 mmol) was allowed to stir for 15 minutes. To this mixture was added the free base of the product (214 mg, 1.30 mmol), and stirring was continued for an additional 15 minutes. Solvent was removed under reduced pressure, and the residue was dissolved in a minimal quantity of methanol, then recrystallized by addition of diethyl ether, to afford the product as a tan solid. Yield for formation of the hydrochloride salt: 250 mg, 1.25 mmol, 96%. 1H NMR (400 MHz, CD3OD) δ 4.25 (dd, J=2.0, 2.0 Hz, 2H), 3.46 (dd, J=6.0, 6.0 Hz, 2H), 2.77-2.82 (m, 2H), 2.07-2.14 (m, 1H), 1.06-1.13 (m, 2H), 1.00-1.05 (m, 2H).

Step 5. Synthesis of 4-(2-cyclopropyl-6,7-dihydro[1,3]oxazolo[5,4-c]pyridin-5(4H)-yl)-7-methyl-5-[(3S)-tetrahydrofuran-3-yl]imidazol[5,1-f][1,2,4]triazine (9)

Compound C17 (300 mg, 1.11 mmol) was added to a mixture of C40 (244 mg, 1.22 mmol) and N,N-diisopropylethylamine (97%, 0.605 mL, 3.31 mmol) in dichloromethane (10 mL), and the reaction mixture was heated at 40° C. for 18 hours. It was then concentrated in vacuo and purified using silica gel chromatography (Gradient: 0% to 20% methanol in ethyl acetate), affording the product as a solid. Yield: 168 mg, 0.458 mmol, 41%. LCMS m/z 367.3 [M+H]+. 1H NMR (400 MHz, DMSO-d6) δ 7.97 (s, 1H), 4.70 (br s, 2H), 4.06 (dd, J=7.8, 7.6 Hz, 1H), 3.81-4.00 (m, 4H), 3.78 (dd, J=7.8, 7.6 Hz, 1H), 3.63-3.72 (m, 1H), 2.70-2.76 (m, 2H), 2.52 (s, 3H), 2.15-2.32 (m, 2H), 2.03-2.11 (m, 1H), 0.86-1.03 (m, 4H).

Example 10

4-(3-Isopropyl-1-methyl-1,4,6,7-tetrahydro-5H-pyrazolo[4,3-c]pyridin-5-yl)-7-methyl-5-(2-methylphenyl)imidazo[5,1-f][1,2,4]triazine (10)

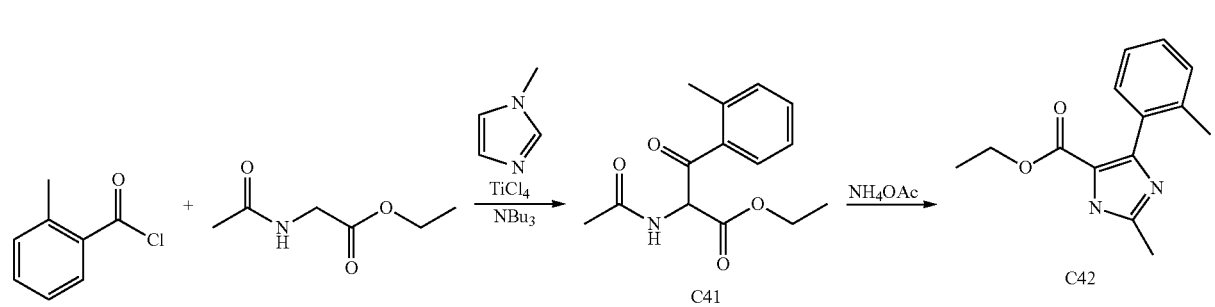
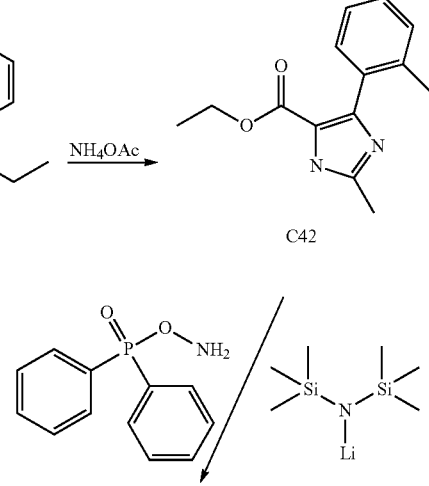

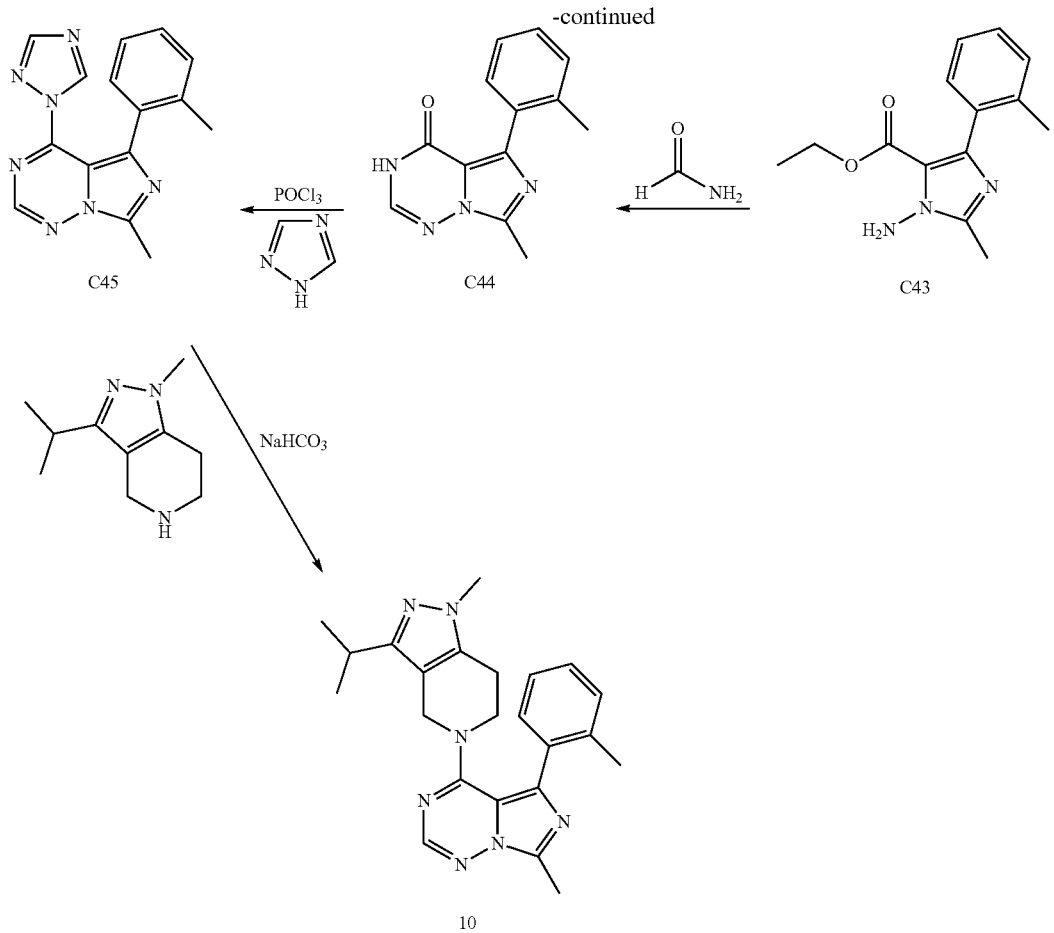

Step 1. Synthesis of ethyl N-acetyl-2-methyl-β-oxophenylalaninate (C41)

A solution of ethyl N-acetylglycinate (98%, 7.41 g, 50.0 mmol) and 1-methyl-1H-imidazole (99%, 4.81 mL, 60.0 mmol) in dichloromethane (100 mL) was cooled to −45° C. and treated with 2-methylbenzoyl chloride (99%, 6.59 mL, 50.0 mmol). The reaction was stirred at −45° C. for 10 minutes. Titanium(IV) chloride (19.2 mL, 175 mmol) was added, followed by tri-n-butylamine (98%, 48.6 mL, 200 mmol), and stirring was continued at the same temperature for 30 minutes. The reaction was quenched with water and extracted with diethyl ether; the combined organic layers were washed with saturated aqueous sodium chloride solution, dried over magnesium sulfate, filtered and concentrated in vacuo. Silica gel chromatography (Eluents: 1:5 ethyl acetate/heptane followed by 1:2 ethyl acetate/heptane) afforded the product. Yield: 6.00 g, 22.8 mmol, 46%. APCI m/z 264.1 [M+H]$^+$. $^1$H NMR (400 MHz, CDCl$_3$) δ 7.93 (dd, J=7.8, 1.2 Hz, 1H), 7.44 (ddd, J=7.6, 7.5, 1.4 Hz, 1H), 7.26-7.34 (m, 2H), 6.89 (br d, J=7 Hz, 1H), 6.05 (d, J=7.2 Hz, 1H), 4.04-4.19 (m, 2H), 2.45 (br s, 3H), 2.11 (s, 3H), 1.06 (t, J=7.1 Hz, 3H).

Step 2. Synthesis of ethyl 2-methyl-4-(2-methylphenyl)-1H-imidazole-5-carboxylate (C42)

A mixture of C41 (6.00 g, 22.8 mmol) and ammonium acetate (8.78 g, 114 mmol) in acetic acid (30 mL) was stirred at reflux for 16 hours. After concentration of the reaction mixture in vacuo, the residue was dissolved in ethyl acetate, washed with saturated aqueous sodium bicarbonate solution, dried over magnesium sulfate, filtered, and concentrated under reduced pressure. Silica gel chromatography (Gradient: 25% to 75% ethyl acetate in heptane) provided the product. Yield: 3.00 g, 12.3 mmol, 54%. LCMS m/z 245.2 [M+H]$^+$. $^1$H NMR (400 MHz, CDCl$_3$) δ 7.12-7.26 (m, 4H), 4.15 (q, J=7.1 Hz, 2H), 2.27 (s, 3H), 2.18 (s, 3H), 1.13 (t, J=7.1 Hz, 3H).

Step 3. Synthesis of ethyl 1-amino-2-methyl-4-(2-methylphenyl)-1H-imidazole-5-carboxylate (C43)

Compound C43 was prepared from C42 according to the procedure for the synthesis of C13 in Example 3. Yield: 2.30 g, 8.87 mmol, 72%. APCI m/z 260.1 [M+H]$^+$. $^1$H NMR (400 MHz, CDCl$_3$) δ 7.12-7.26 (m, 4H), 5.37 (br s, 2H), 4.08 (q, J=7.1 Hz, 2H), 2.47 (s, 3H), 2.19 (s, 3H), 0.98 (t, J=7.1 Hz, 3H).

Step 4. Synthesis of 7-methyl-5-(2-methylphenyl)imidazo[5,1-f][1,2,4]triazin-4(3H)-one (C44)

A mixture of C43 (2.20 g, 8.48 mmol) and formamide (7.0 mL) was heated at reflux for 2 hours. The reaction mixture was cooled to room temperature, diluted with water, and filtered. The resulting solid was washed with water to provide the product. Yield: 1.25 g, 5.20 mmol, 61%. LCMS m/z 241.1 [M+H]$^+$. $^1$H NMR (400 MHz, DMSO-d$_6$) δ 11.69 (br s, 1H), 7.89 (s, 1H), 7.13-7.40 (m, 4H), 2.55 (s, 3H), 2.28 (s, 3H).

Step 5. Synthesis of 7-methyl-5-(2-methylphenyl)-4-(1H-1,2,4-triazol-1-yl)imidazo[5,1-f][1,2,4]triazine (C45)

A solution of C44 (1.01 g, 4.22 mmol) in pyridine (9 mL) was cooled to 0° C. and treated with phosphorus oxychloride (1.16 mL, 12.7 mmol). After 30 minutes, 1H-1,2,4-triazole (1.49 g, 21.6 mmol) was added to the cold reaction mixture, and the ice bath was removed. The reaction was stirred at room temperature for 18 hours, then concentrated in vacuo. The residue was suspended in dichloromethane and filtered. Removal of solvent from the filtrate under reduced pressure provided a residue; purification by silica gel chromatography (Gradient: 0% to 100% ethyl acetate in heptane) afforded the product as a yellow solid. Yield: 435 mg, 1.49 mmol, 35%. LCMS m/z 292.0 [M+H]$^+$. $^1$H NMR (400 MHz, CDCl$_3$) δ 8.65 (s, 1H), 8.38 (s, 1H), 7.73 (s, 1H), 7.31 (ddd, J=7.5, 7.5, 1.6 Hz, 1H), 7.22 (br d, J=7.7 Hz, 1H), 7.13 (br dd, J=7.6, 7.3 Hz, 1H), 7.07 (dd, J=7.6, 1.6 Hz, 1H), 2.88 (s, 3H), 2.09 (br s, 3H).

Bioorg. Med. Chem. Lett. 2005, 15, 2253-2258; 49.5 mg, 0.196 mmol) in tetrahydrofuran (1.0 mL) and water (0.4 mL) was treated with sodium bicarbonate (252 mg, 3.00 mmol) and allowed to react at room temperature for 18 hours. Solvents were removed in vacuo; purification via silica gel chromatography (Gradient: 30% to 100% ethyl acetate in heptane) provided the product as a glassy white foam. Yield: 35.6 mg, 88.7 μmol, 60%. APCI m/z 402.1 [M+H]$^+$. $^1$H NMR (400 MHz, CDCl$_3$) δ 7.93 (s, 1H), 7.29-7.38 (m, 4H), 3.75-4.16 (br m, 4H), 3.60 (s, 3H), 2.73 (s, 3H), 2.45-2.66 (br m, 3H), 2.36 (s, 3H), 1.02 (br d, J=7 Hz, 6H).

Example 11

4-(2-Cyclopropyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine (11)

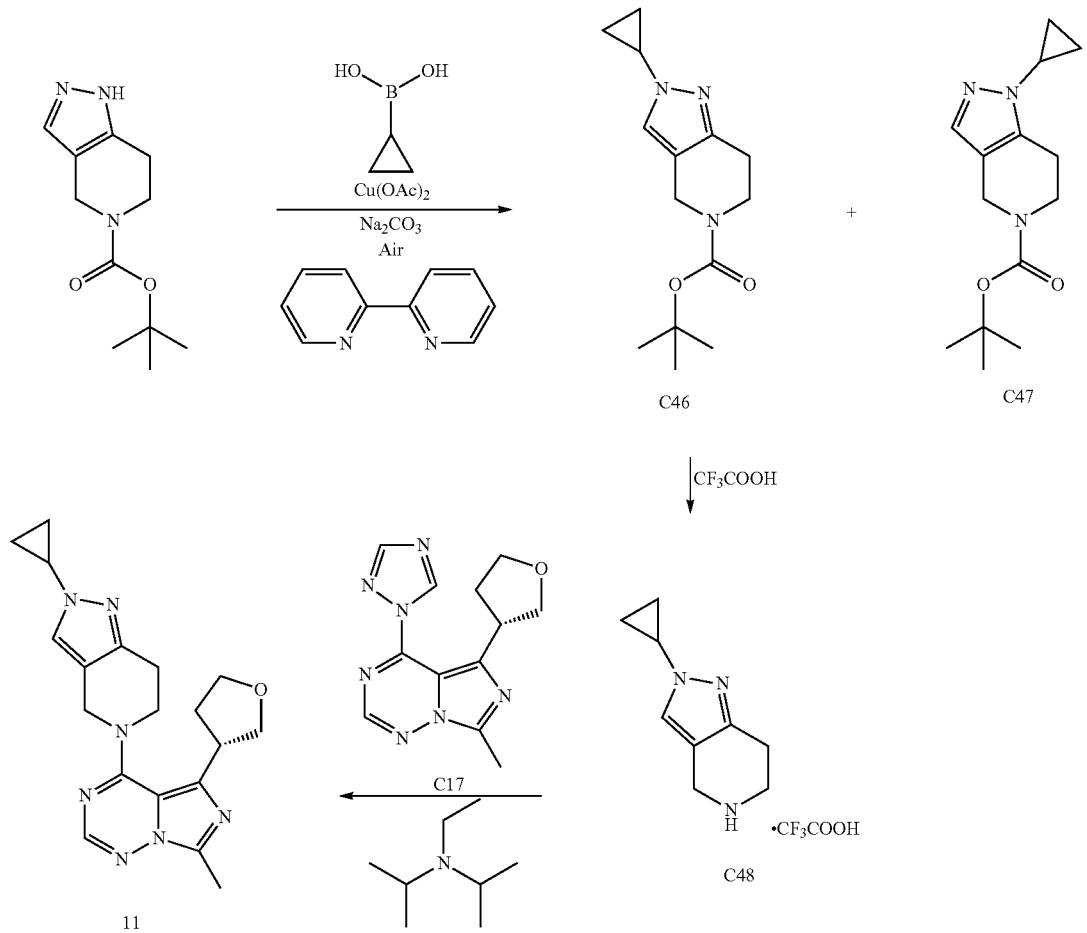

Step 6. Synthesis of 4-(3-isopropyl-1-methyl-1,4,6,7-tetrahydro-5H-pyrazolo[4,3-c]pyridin-5-yl)-7-methyl-5-(2-methylphenyl)imidazo[5,1-f][1,2,4]triazine (10)

A solution of C45 (43.3 mg, 0.149 mmol) and 3-isopropyl-1-methyl-4,5,6,7-tetrahydro-1H-pyrazolo[4,3-c]pyridine (which may be prepared by the method of W. T. Ashton et al., Step 1. Synthesis of tert-butyl 2-cyclopropyl-2,4,6,7-tetrahydro-5H-pyrazolo[4,3-c]pyridine-5-carboxylate (C46)

tert-Butyl 1,4,6,7-tetrahydro-5H-pyrazolo[4,3-c]pyridine-5-carboxylate (4.0 g, 18 mmol) and cyclopropylboronic acid (3.08 g, 35.8 mmol) were combined in dichloroethane (200 mL). After sequential addition of sodium carbonate (3.80 g, 35.8 mmol), copper(II) acetate (3.58 g, 17.9 mmol) and 2,2'-bipyridine (2.80 g, 17.9 mmol), the reaction mixture was stirred at 60° C. for 18 hours while open to the atmosphere. The reaction mixture was then diluted with ethyl acetate (500 mL) and filtered through diatomaceous earth; the filtrate was washed with saturated ammonium chloride solution and concentrated in vacuo. Purification via silica gel chromatography (Gradient: 0% to 100% ethyl acetate in heptane) was followed by supercritical fluid chromatography (Column: Chiral Technologies, Chiralpak AD-H, 5 μm; Eluent: 85:15 carbon dioxide/methanol) to obtain the major regioisomer, which was the first-eluting peak. The indicated regiochemistry was assigned on the basis of NOE studies carried out on C46. Yield: 1.7 g, 6.5 mmol, 36%. LCMS m/z 264.5 [M+H]$^+$. $^1$H NMR (400 MHz, CD$_3$OD) δ 7.43 (br s, 1H), 4.42 (br s, 2H), 3.65-3.70 (m, 2H), 3.52-3.58 (m, 1H), 2.64-2.69 (m, 2H), 1.47 (s, 9H), 0.98-1.03 (m, 4H).

Step 2. Synthesis of 2-cyclopropyl-4,5,6,7-tetrahydro-2H-pyrazolo[4,3-c]pyridine, trifluoroacetate salt (C48)

Trifluoroacetic acid (1 mL) was added to a solution of C46 (169 mg, 0.642 mmol) in dichloromethane (5 mL), and the reaction mixture was stirred for 1 hour at room temperature. Removal of solvents in vacuo afforded the crude product, which was used without additional purification. LCMS m/z 164.0 [M+H]$^+$.

Step 3. Synthesis of 4-(2-cyclopropyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine (11)

N,N-Diisopropylethylamine (97%, 0.318 mL, 1.74 mmol) and C48 (from the previous step, ≤0.642 mmol) were added to a solution of C17 (158 mg, 0.582 mmol) in dichloromethane (5 mL), and the reaction mixture was stirred at 40° C. for 18 hours. Additional dichloromethane was added, and the mixture was washed with saturated aqueous sodium chloride solution. The organic layer was dried over magnesium sulfate, filtered, and concentrated in vacuo. Purification via silica gel chromatography (Gradient: 0% to 20% ethyl acetate in heptane) afforded the product as a solid. Yield: 154 mg, 0.421 mmol, 72% over two steps. LCMS m/z 366.2 [M+H]$^+$. $^1$H NMR (400 MHz, CD$_3$OD) δ 7.87 (s, 1H), 7.52 (br s, 1H), 4.73 (br AB quartet, J$_{AB}$=15.5 Hz, Δv$_{AB}$=5.6 Hz, 2H), 4.10-4.18 (m, 2H), 3.92-4.07 (m, 3H), 3.90 (dd, J=8.2, 8.1 Hz, 1H), 3.74-3.83 (m, 1H), 3.54-3.61 (m, 1H), 2.95-3.01 (m, 2H), 2.59 (s, 3H), 2.25-2.43 (m, 2H), 0.99-1.04 (m, 4H).

Example 12

4-(3-Cyclopropyl-1-methyl-1,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine (12)

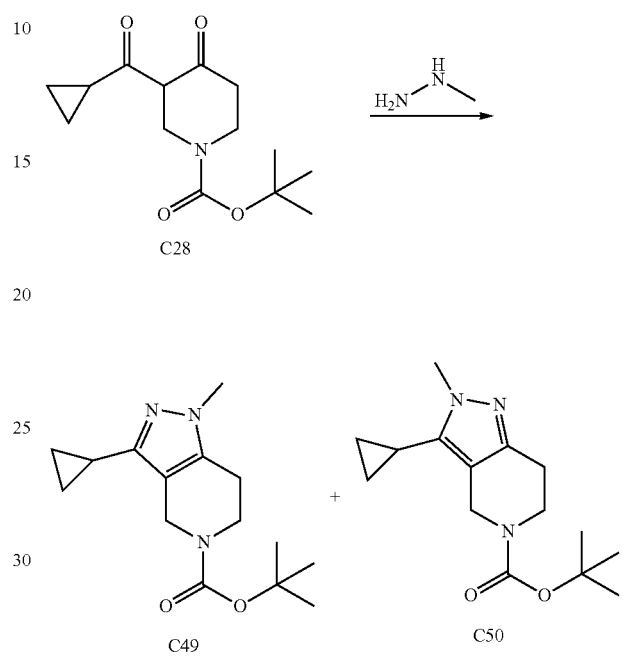

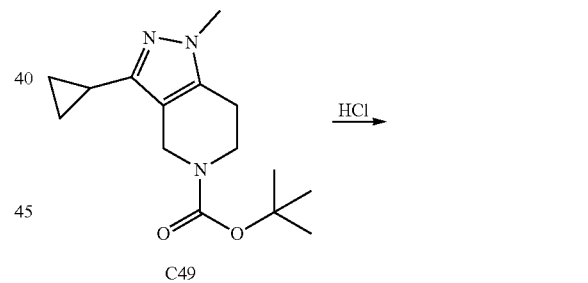

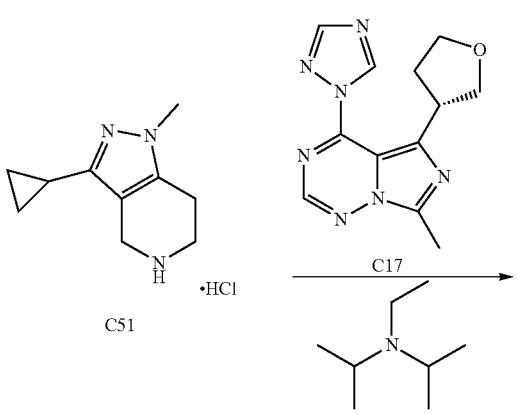

-continued

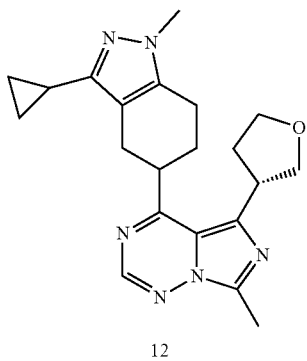

12

Step 1. Synthesis of tert-butyl 3-cyclopropyl-1-methyl-1,4,6,7-tetrahydro-5H-pyrazolo[4,3-c]pyridine-5-carboxylate (C49)

To a solution of C28 (100 g, 0.374 mol) in methanol (1.2 L) was added methylhydrazine (40% solution in water, 47.4 g, 0.411 mol). The reaction mixture was heated at reflux for 2 hours, then concentrated to dryness. Purification via silica gel chromatography (Gradient: 5% to 9% ethyl acetate in petroleum ether) provided a mixture of product C49 and tert-butyl 3-cyclopropyl-2-methyl-2,4,6,7-tetrahydro-5H-pyrazolo[4,3-c]pyridine-5-carboxylate (C50). LCMS m/z 278.0 [M+H]$^+$. Separation via supercritical fluid chromatography (Column: Chiral Technologies, Chiralcel OJ-H, 5 um; Eluent: 97:3 carbon dioxide/methanol) afforded the product C49 as the second-eluting isomer, isolated as a solid. NOE studies supported the indicated regiochemical assignment. Yield: 33 g, 120 mmol, 32%. $^1$H NMR (400 MHz, CDCl$_3$) δ 4.40 (br s, 2H), 3.65-3.73 (br m, 2H), 3.65 (s, 3H), 2.57-2.64 (m, 2H), 1.68-1.76 (m, 1H), 1.49 (s, 9H), 0.77-0.89 (m, 4H).
The first-eluting isomer, C50, was obtained as a gum. Yield: 24 g, 86 mmol, 23%. $^1$H NMR (400 MHz, CDCl$_3$) δ 4.39 (br s, 2H), 3.83 (s, 3H), 3.60-3.67 (m, 2H), 2.65-2.72 (m, 2H), 1.59-1.68 (m, 1H), 1.47 (s, 9H), 0.89-0.98 (m, 2H), 0.63-0.69 (m, 2H).

Step 2. Synthesis of 3-cyclopropyl-1-methyl-4,5,6,7-tetrahydro-1H-pyrazolo[4,3-c]pyridine, hydrochloride salt (C51)

A mixture of C49 (15.0 g, 54.1 mmol) and hydrogen chloride (4 M solution in 1,4-dioxane, 100 mL) was allowed to stir at room temperature for 2 hours, whereupon it was concentrated in vacuo. The crude product, obtained as a solid, was used without additional purification. Yield: 10.4 g, 48.8 mmol, 90%. LCMS m/z 178.3 [M+H]$^+$. $^1$H NMR (400 MHz, DMSO-d$_6$) δ 9.86 (br s, 2H), 4.02-4.08 (m, 2H), 3.64 (s, 3H), 3.26-3.34 (m, 2H), 2.86-2.93 (m, 2H), 1.75-1.84 (m, 1H), 0.81-0.87 (m, 2H), 0.71-0.77 (m, 2H).

Step 3. Synthesis of 4-(3-cyclopropyl-1-methyl-1,4,6,7-tetrahydro-5H-pyrazolo[4,3-q]pyridin-5-yl)-7-methyl-5-[(3S)-tetrahydrofuran-3-yl]imidazo[5,1-f][1,2,4]triazine (12)

N,N-Diisopropylethylamine (6.7 mL, 37 mmol) was added to a solution of C51 (4.94 g, 23.1 mmol) in dichloromethane (60 mL), and the reactants were allowed to stir for a few minutes. Compound C17 (4.93 g, 18.2 mmol) was then added, and the reaction mixture was heated to 40° C. for 18 hours. After cooling to room temperature, it was washed with saturated aqueous sodium chloride solution, dried over magnesium sulfate, filtered, and concentrated in vacuo. Purification was effected via supercritical fluid chromatography (Column: Chiral Technologies, Chiralpak AD-H, 5 μm; Eluent: 4:1 carbon dioxide/methanol) to afford the product as a solid. Yield: 4.18 g, 11.0 mmol, 60%. LCMS m/z 380.3 [M+H]$^+$. $^1$H NMR (400 MHz, CD$_3$OD) δ 7.85 (s, 1H), 4.72 (br AB quartet, $J_{AB}$=15 Hz, $\Delta v_{AB}$=8.3 Hz, 2H), 4.12-4.22 (m, 2H), 3.89-4.11 (m, 4H), 3.79-3.88 (m, 1H), 3.65 (s, 3H), 2.89-3.03 (m, 2H), 2.58 (s, 3H), 2.38-2.48 (m, 1H), 2.26-2.37 (m, 1H), 1.68-1.76 (m, 1H), 0.82-0.89 (m, 2H), 0.69-0.75 (m, 2H).

Example 13

7-Methyl-4-(1-methyl-1,4,5,7-tetrahydro-6H-pyrazolo[3,4-c]pyridin-6-yl)-5-[(2R)-tetrahydrofuran-2-yl]imidazo[5,1-f][1,2,4]triazine (13)

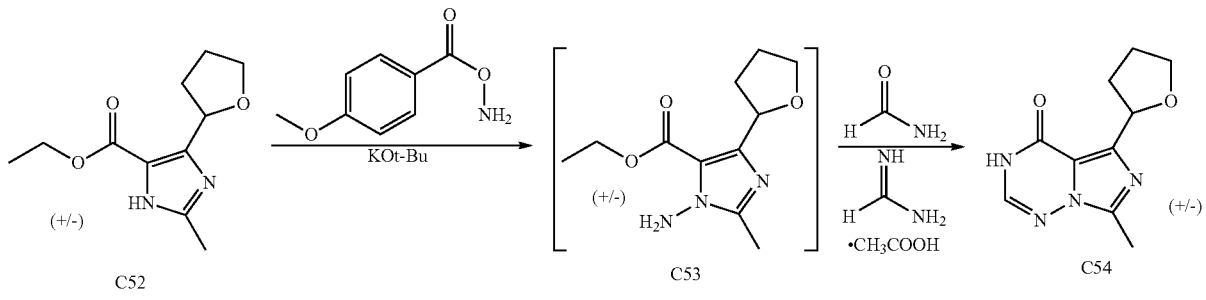

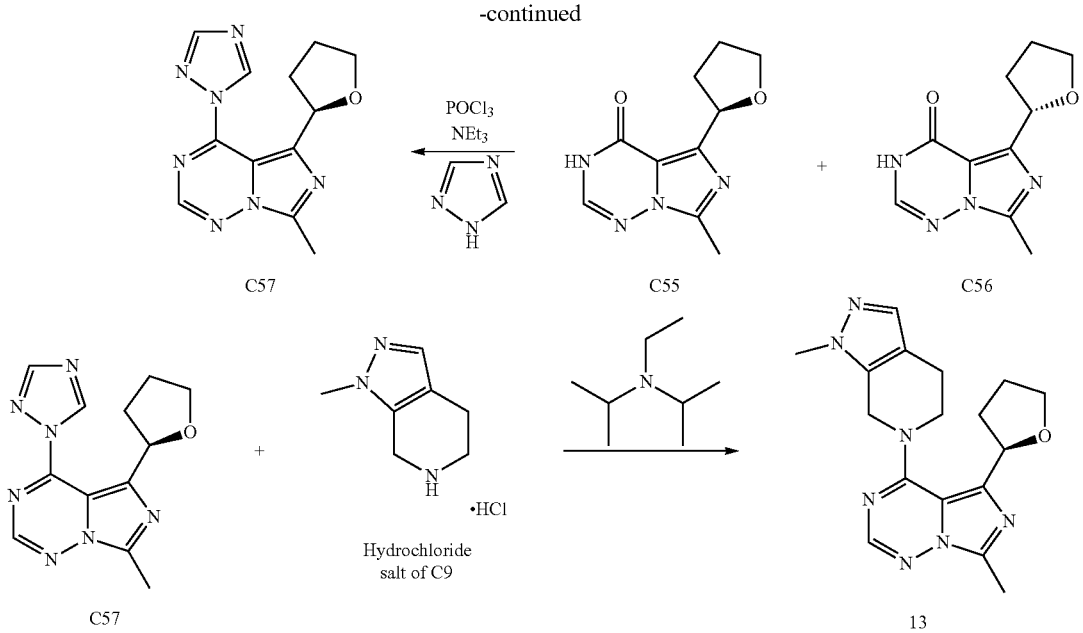

Step 1. Synthesis of 7-methyl-5-(tetrahydrofuran-2-yl)imidazo[5,1-f][1,2,4]triazin-4(3H)-one (C54)

Ethyl 2-methyl-4-(tetrahydrofuran-2-yl)-1H-imidazole-5-carboxylate (C52) [prepared in an analogous manner to C63 in Preparation P2, by employing tetrahydrofuran-2-carbonyl chloride as starting material] (0.4 mol) was converted to ethyl 1-amino-2-methyl-4-(tetrahydrofuran-2-yl)-1H-imidazole-5-carboxylate (C53) using the general method for synthesis of C64 in Preparation P2. In this case, due to enhanced water-solubility, extraction was carried out with a mixture of ethyl acetate and tetrahydrofuran. The isolated material was judged by proton NMR analysis to be a 3:1 mixture of C53 and its regioisomer ethyl 1-amino-2-methyl-5-(tetrahydrofuran-2-yl)-1H-imidazole-4-carboxylate. The mixture was subjected to reaction with formamide and formamidine acetate, as described for the synthesis of P2 in Preparation P2. After the reaction was cooled to room temperature, it was partitioned between water and a mixture of ethyl acetate and tetrahydrofuran. The extracts were concentrated in vacuo, dissolved in a small volume of ethyl acetate, and the product was extracted into aqueous potassium carbonate solution. Adjustment of the aqueous layer to a mildly acidic pH resulted in precipitation of the product. Additional product was obtained by evaporating the aqueous layer to dryness, triturating the residue with methanol and filtering. The filtrate was treated with a small amount of water, and the methanol was removed in vacuo. Additional product precipitated from the aqueous residue. Combined yield: 13.5 g, 61 mmol, 15%. LCMS m/z 221.1 [M+H]$^+$. $^1$H NMR (500 MHz, DMSO-d$_6$) δ 11.71 (br s, 1H), 7.81 (s, 1H), 5.33 (dd, J=6.8, 6.8 Hz, 1H), 3.87-3.93 (m, 1H), 3.70-3.76 (m, 1H), 2.46 (s, 3H), 2.04-2.18 (m, 3H), 1.85-1.96 (m, 1H).

Step 2. Separation of 7-methyl-5-[(2R)-tetrahydrofuran-2-yl]imidazo[5,1-f][1,2,4]triazin-4(3H)-one (C55) and 7-methyl-5-[(2S)-tetrahydrofuran-2-yl]imidazo[5,1-f][1,2,4]triazin-4(3H)-one (C56)

Compound C54 (3 g) was subjected to supercritical fluid chromatography (Column: Chiral Technologies, Chiralcel OD-H, 5 um; Eluent: 4:1 carbon dioxide/methanol). The first-eluting enantiomer (1 g), which exhibited a (−) optical rotation, was arbitrarily assigned as the (2R)-enantiomer C55. $^1$H NMR (400 MHz, CD$_3$OD) δ 7.68 (s, 1H), 5.46 (dd, J=7.5, 6.9 Hz, 1H), 4.09-4.15 (m, 1H), 3.87-3.93 (m, 1H), 2.57 (s, 3H), 2.12-2.30 (m, 3H), 1.99-2.10 (m, 1H).

The second-eluting enantiomer (1 g), which exhibited a (+) optical rotation, was consequently assigned as the (2S)-enantiomer C56. $^1$H NMR (400 MHz, CD$_3$OD) δ 7.68 (s, 1H), 5.46 (dd, J=7.3, 7.0 Hz, 1H), 4.09-4.15 (m, 1H), 3.87-3.93 (m, 1H), 2.57 (s, 3H), 2.12-2.30 (m, 3H), 1.99-2.10 (m, 1H).

Step 3. Synthesis of 7-methyl-5-[(2R)-tetrahydrofuran-2-yl]-4-(1H-1,2,4-triazol-1-yl)imidazo[5,1-f][1,2,4]triazine (C57)

Compound C55 was converted to the product using the general method described for synthesis of C6 in Example 1. In this case, when the reaction had reached completion, it was quenched with 30 mM aqueous potassium phosphate solution that had been cooled to 10° C. The aqueous layer was extracted with ethyl acetate, and the combined organic layers were dried over sodium sulfate, filtered, and concentrated in vacuo. Silica gel chromatography (Gradient: 30% to 100% ethyl acetate in heptane) afforded the product as a gum. Yield: 1.39 g, 5.12 mmol, 86%. LCMS m/z 272.1 [M+H]$^+$. $^1$H NMR (400 MHz, CDCl$_3$) δ 9.28 (s, 1H), 8.26 (s, 1H), 8.25 (s, 1H), 5.99 (dd, J=7.0, 6.9 Hz, 1H), 4.13-4.19 (m, 1H), 3.92 (ddd, J=8.0, 7.8, 5.8 Hz, 1H), 2.80 (s, 3H), 2.33-2.43 (m, 1H), 2.13-2.32 (m, 2H), 1.98-2.11 (m, 1H).

Step 4. Synthesis of 7-methyl-4-(1-methyl-1,4,5,7-tetrahydro-6H-pyrazolo[3,4-c]pyridin-6-yl)-5-[(2R)-tetrahydrofuran-2-yl]imidazo[5,1-f][1,2,4]triazine (13)

Compound C57 was reacted with the hydrochloride salt of C9 using the general method described for synthesis of 9 in Example 9. In this case, purification was carried out via reversed phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 5% to 50% B), affording the product as a solid. Yield: 20.2 mg, 59.5 μmol, 33%. LCMS m/z 340.4 [M+H]$^+$. $^1$H NMR (400 MHz, CD$_3$OD) δ 7.92 (s, 1H), 7.29 (s, 1H), 5.20 (dd, J=8.1, 6.5 Hz, 1H), 5.09 (d, J=16.1 Hz, 1H), 4.81 (br d, J=16.1 Hz, 1H), 4.45 (ddd, J=13, 4, 4 Hz, 1H), 4.09-4.17 (m, 1H), 3.94 (ddd, J=7.9, 7.8, 5.5 Hz, 1H), 3.77 (s, 3H), 3.61 (ddd, J=13.4, 9.5, 4.3 Hz, 1H), 2.94 (ddd, J=16, 9, 5 Hz, 1H), 2.71 (ddd, J=15, 4, 4 Hz, 1H), 2.61 (s, 3H), 2.47-2.57 (m, 1H), 2.23-2.32 (m, 1H), 2.05-2.23 (m, 2H).

Preparation P1

3-(Trifluoromethyl)-4,5,6,7-tetrahydropyrazolo[1,5-a]pyrazine (P1)

Step 1. Synthesis of benzyl 3-(trifluoromethyl)-6,7-dihydropyrazolo[1,5-a]pyrazine-5(4H)-carboxylate (C60)

5-[(Benzyloxy)carbonyl]-4,5,6,7-tetrahydro[1,2,3]oxadiazolo[3,4-a]pyrazin-8-ium-3-olate (C58, prepared from 4-[(benzyloxy)carbonyl]piperazine-2-carboxylic acid using the general procedure described by T. S. Mansour et al., 2006, PCT Intl. Appl. WO 2006/130588) (65 g, 0.24 mol) was dissolved in o-xylene (250 mL) and cooled to −78° C. in a bomb reactor. 3,3,3-Trifluoroprop-1-yne (25 g, 0.27 mol) was injected into the reaction mixture, and the bomb was heated to 270° C. for 24 hours. After cooling to room temperature, the reaction was concentrated in vacuo, and the residue was purified by silica gel chromatography to provide C60 as white crystals. Yield: 7.5 g, 23 mmol, 10%. [The major regioisomer, benzyl 2-(trifluoromethyl)-6,7-dihydropyrazolo[1,5-a]pyrazine-5(4H)-carboxylate (C59), was also isolated, in 61% yield.]

Step 2. Synthesis of 3-(trifluoromethyl)-4,5,6,7-tetrahydropyrazolo[1,5-a]pyrazine (P1)

Compound C60 (7.5 g, 23 mmol) was dissolved in methanol (300 mL) and treated with 10% palladium on carbon (2 g). The reaction mixture was hydrogenated in a Parr apparatus at room temperature and 40 psi hydrogen, until hydrogen uptake ceased. The mixture was filtered, and the filtrate was concentrated in vacuo and recrystallized from hexanes to provide the product as a white solid. Yield: 2.9 g, 15 mmol, 65%. LCMS m/z 192.1 [M+H]$^+$. $^1$H NMR (500 MHz, DMSO-d$_6$) δ 7.80 (s, 1H), 4.01 (dd, J=5.6, 5.4 Hz, 2H), 3.96 (s, 2H), 3.12 (dd, J=5.6, 5.4 Hz, 2H), 2.72 (br s, 1H).

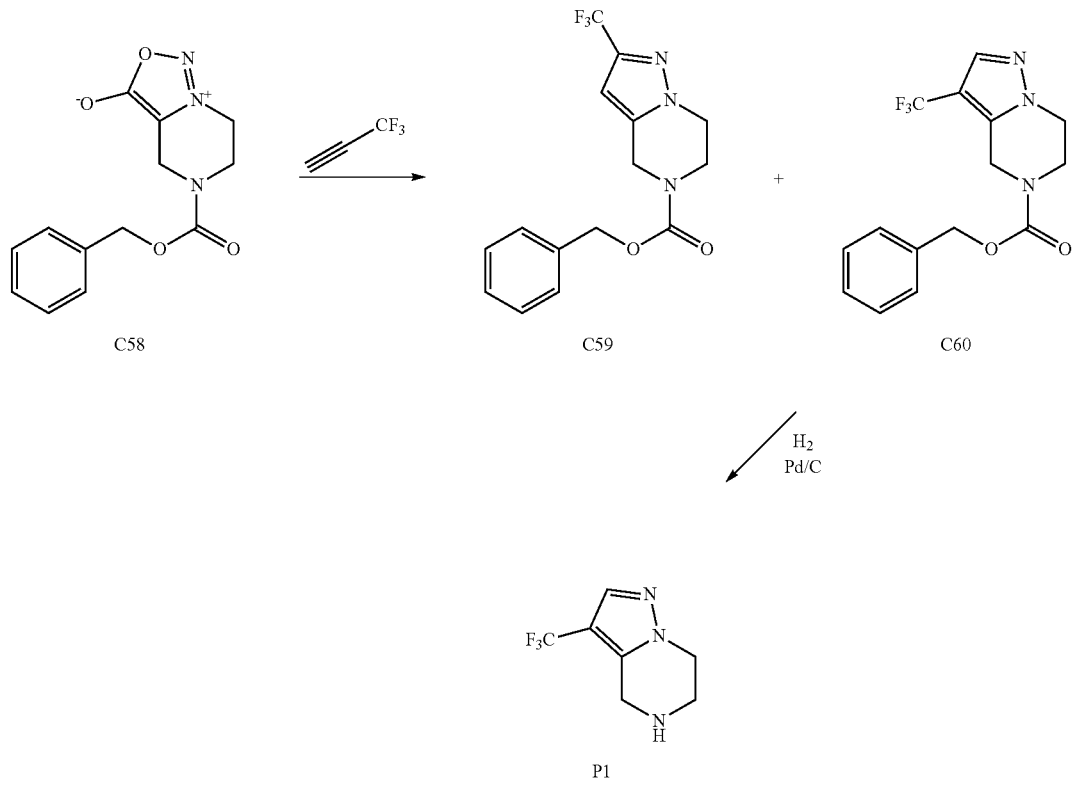

Preparation P2

7-Methyl-5-(tetrahydro-2H-pyran-4-yl)imidazo[5,1-f][1,2,4]triazin-4(3H)-one (P2)

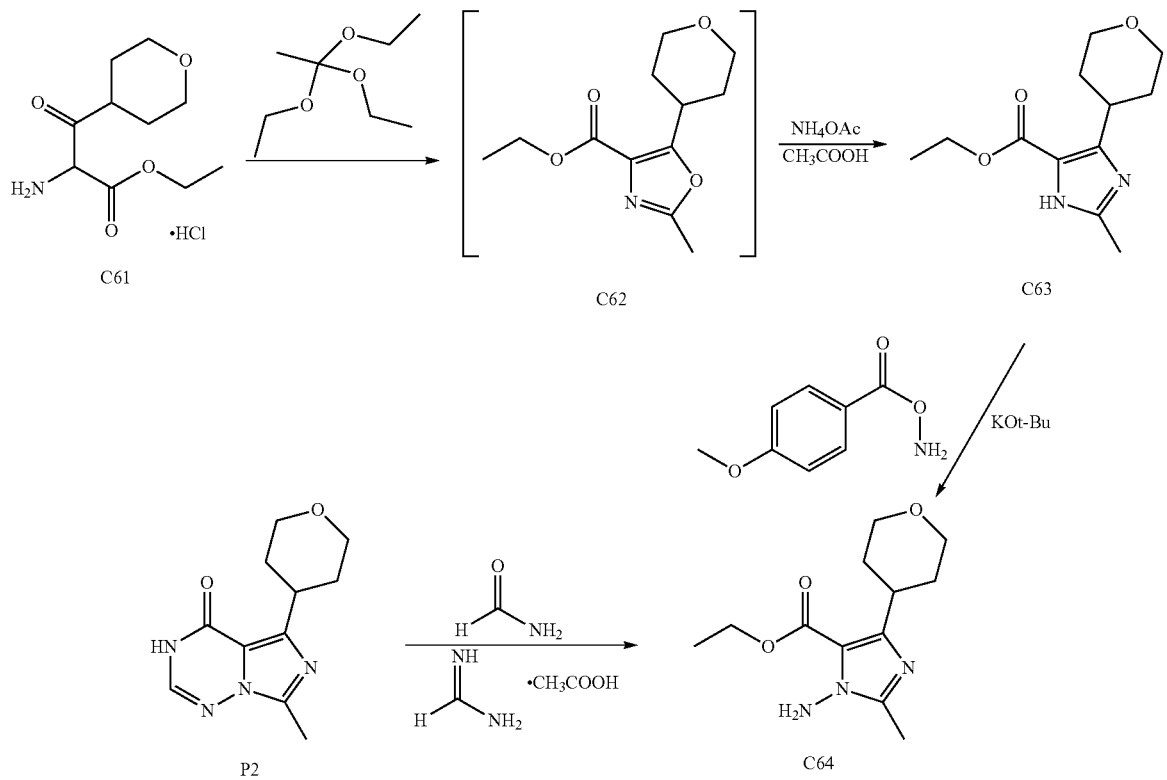

Step 1. Synthesis of ethyl 2-methyl-4-(tetrahydro-2H-pyran-4-yl)-1H-imidazole-5-carboxylate (C63)

Ethyl 2-amino-3-oxo-3-(tetrahydro-2H-pyran-4-yl)propanoate, hydrochloride salt [C61, which may be prepared according to the general procedure for synthesis of ethyl 2-amino-3-oxo-3-(tetrahydrofuran-3-yl)propanoate, hydrochloride salt (C11) in Example 3, through the use of tetrahydro-2H-pyran-4-carbonyl chloride in place of tetrahydrofuran-3-carbonyl chloride] (200 g, ≤0.56 mol) was combined with triethyl orthoacetate (200 mL, 1.1 mol) in methanol (200 mL), and the reaction was stirred at room temperature for 2 days. Concentration in vacuo afforded the crude intermediate, ethyl 2-methyl-5-(tetrahydro-2H-pyran-4-yl)-1,3-oxazole-4-carboxylate (C62). This was mixed with acetic acid (500 mL), treated with ammonium acetate (600 g, 7.8 mol) and heated to 99° C. for 2 days. At this point, additional ammonium acetate (100 g, 1.3 mol) was added, and heating was continued for 24 hours. The reaction mixture was then diluted with ethyl acetate (4 L) and water (2 L), and the pH was adjusted to ~9 with aqueous ammonium hydroxide solution. The aqueous layer was extracted with ethyl acetate (1 L), and the combined organic layers were diluted with cyclohexane (1 L), washed with saturated aqueous potassium bicarbonate solution (1 L), washed with saturated aqueous sodium chloride solution (1 L), and concentrated under reduced pressure. The residue was dissolved in diethyl ether (1 L) and seeded; the resulting crystals were isolated by filtration, affording the product as a solid. Yield: 75 g, 0.31 mol, 55% from tetrahydro-2H-pyran-4-carboxylic acid.

Step 2. Synthesis of ethyl 1-amino-2-methyl-4-(tetrahydro-2H-pyran-4-yl)-1H-imidazole-5-carboxylate (C64)

A solution of potassium tert-butoxide (36.1 g, 0.32 mol) in tetrahydrofuran (200 mL) was added over 15 minutes to a solution of C63 (70 g, 0.29 mol) in N,N-dimethylformamide (175 mL) at −18° C., while keeping the temperature below −10° C. The mixture was stirred at −15° C. for an additional 25 minutes, then cooled to −25° C., at which point a solution of O-(4-methoxybenzoyl)hydroxylamine (L. Parlanti et al., *Org. Lett* 2007, 9, 3821-3824) (58.5 g, 0.35 mol) in N,N-dimethylformamide (100 mL) was added over 5 minutes, while the reaction temperature was maintained below −15° C. {Caution: in the course of this work, there were indications of slow decomposition of the aminating reagent, as evidenced by gas evolution, potentially triggered by contact of neat reagent or concentrated solution with sharp items.} The reaction was then allowed to warm to room temperature and stir for 3 hours. Water (150 mL) and saturated aqueous sodium chloride solution (250 mL) were added, and the mixture was extracted with ethyl acetate (2×300 mL). The combined organic layers were washed with saturated aqueous sodium chloride solution (3×200 mL), dried over magnesium sulfate, filtered and evaporated under reduced pressure. The combined aqueous layers were further extracted with ethyl acetate (2×300 mL); these combined organic layers were concentrated, redissolved in tert-butyl methyl ether (500 mL), washed with saturated aqueous sodium chloride solution (2×200 mL), dried over magnesium sulfate, filtered, and concentrated in vacuo. The combined residues were purified by silica gel chromatography (Gradient: 0% to 4% methanol in ethyl acetate) to provide the product as a pale yellow oil, which solidified on standing. Yield: 60 g, 0.24 mol, 83%.

Step 3. Synthesis of 7-methyl-5-(tetrahydro-2H-pyran-4-yl)imidazo[5,1-f][1,2,4]triazin-4(3H)-one (P2)

Compound C64 (57 g, 0.23 mol), formamide (57 mL) and formamidine acetate (57 g) were combined and heated to 95° C. for 24 hours. After the mixture had cooled to room temperature, it was triturated with an aqueous solution of potassium bicarbonate (60 g in 300 mL of water) and filtered. The collected solid was washed first with water (3×80 mL) and then with tert-butyl methyl ether (2×100 mL), affording the product as a white powder. Yield: 45.7 g, 0.195 mol, 85%. LCMS m/z 235.1 [M+H]$^+$. $^1$H NMR (500 MHz, DMSO-$d_6$) δ 11.55 (br s, 1H), 7.74 (s, 1H), 3.89 (br dd, J=11, 3 Hz, 2H), 3.27-3.42 (m, 3H), 2.43 (s, 3H), 1.77-1.88 (m, 2H), 1.62 (br d, J=12.7 Hz, 2H).

Preparation P3

5-Isobutyl-7-methylimidazo[5,1-f][1,2,4]triazin-4(3H)-one (P3)

with water (2.5 L), with aqueous sodium bicarbonate solution (2.5 L), and with saturated aqueous sodium chloride solution (1.0 L). After drying over sodium sulfate, the organic extracts were concentrated in vacuo to afford the product as a yellow liquid, which was used directly in the next step. Yield: 456 g, 2.24 mol, 89%.

Step 2. Synthesis of methyl 2-amino-5-methyl-3-oxohexanoate, hydrochloride salt (C66)

To a solution of C65 (151 g, 0.743 mol) in methanol (500 mL) at 10° C. was added acetyl chloride (105.5 mL, 1.48 mol) in a drop-wise manner. After completion of the addition, the reaction was maintained at 10° C. for 30 minutes, and then 10% palladium on carbon (15 g) was cautiously added. The mixture was hydrogenated under 50 psi of hydrogen for 24 hours at room temperature, then filtered through a pad of diatomaceous earth. The filtrate was concentrated in vacuo, and the residue was suspended in diethyl ether (1 L), filtered and washed with additional diethyl ether to provide the product as a white solid. Yield: 138 g, 0.658 mol, 89%. $^1$H NMR (400 MHz, DMSO-$d_6$) δ 8.98 (br s, 3H), 5.26 (br s, 1H), 3.80 (s, 3H), 2.66 (d, J=6.8 Hz, 2H), 1.99-2.13 (m, 1H), 0.90 (d, J=6.5 Hz, 3H), 0.85 (d, J=6.5 Hz, 3H).

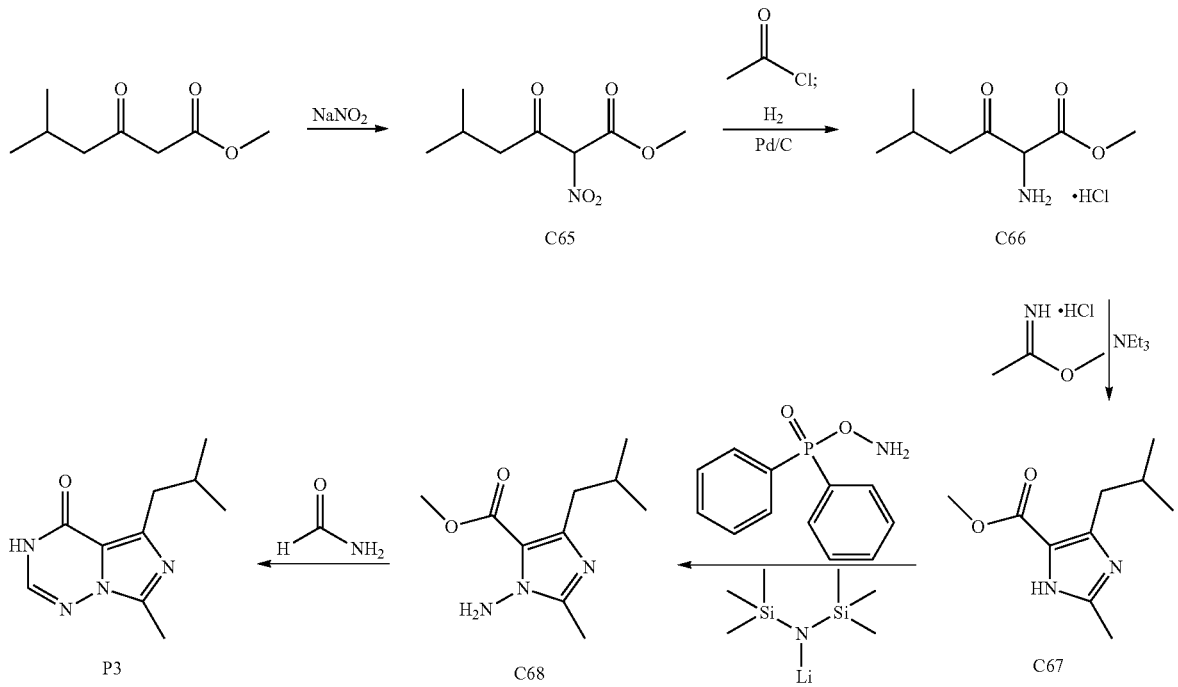

Step 1. Synthesis of methyl 5-methyl-2-nitro-3-oxohexanoate (C65)

A solution of sodium nitrite (232 g, 3.36 mol) in water (560 mL) was added drop-wise over 1.5 hours to a solution of methyl 5-methyl-3-oxohexanoate (400 g, 2.53 mol) in glacial acetic acid (510 mL) at 20 to 25° C. Stirring was continued at room temperature for 2 hours. Water (1.3 L) was added, and the reaction mixture was stirred for an additional 18 hours. The mixture was then extracted with ethyl acetate (3×2.5 L), and the combined organic layers were washed sequentially Step 3. Synthesis of methyl 4-isobutyl-2-methyl-1H-imidazole-5-carboxylate (C67)

Triethylamine (140 mL, 1.00 mol) was added drop-wise to a solution of methyl ethanimidoate, hydrochloride salt (88 g, 0.80 mol) in methanol (520 mL). A solution of C66 (42 g, 0.20 mol) in methanol (200 mL) was then added in a drop-wise manner, and the reaction mixture was stirred at room temperature for 60 hours. After concentration in vacuo, the residue was partitioned between ethyl acetate (800 mL) and water (500 mL), and the aqueous phase was extracted with ethyl acetate (3×200 mL). The combined organic layers were washed with water (300 mL) and with saturated aqueous sodium chloride solution (300 mL), then dried over sodium sulfate and concentrated under reduced pressure. The residue was recrystallized from ethyl acetate/petroleum ether (1:5) to give the product as a light yellow solid. Yield: 16.2 g, 82.5 mmol, 41%. $^1$H NMR (400 MHz, DMSO-$d_6$) δ 12.2 (v br s, 1H), 3.70 (s, 3H), 2.64 (d, J=7.0 Hz, 2H), 2.23 (s, 3H), 1.85-1.96 (m, 1H), 0.84 (d, J=6.6 Hz, 6H).

Step 4. Synthesis of methyl 1-amino-4-isobutyl-2-methyl-1H-imidazole-5-carboxylate (C68)

A solution of C67 (51 g, 0.26 mol) in N,N-dimethylformamide (1 L) was cooled to −10 to −20° C. Lithium bis(trimethylsilyl)amide (1.0 M solution in tetrahydrofuran, 286 mL, 0.286 mol) was added drop-wise and the reaction was stirred for 10 minutes. A suspension of (aminooxy)(diphenyl)phosphine oxide (72.7 g, 0.312 mol; Caution: (aminooxy)(diphenyl)phosphine oxide is a highly energetic substance that has shown the ability to explosively decompose under ambient conditions. Its use should be carefully monitored!) in N,N-dimethylformamide (1 L) was added in portions; after completion of the addition, the mixture was stirred for 1 hour at −10 to −20° C. Water was added until the slurry became clear, and the mixture was extracted with diethyl ether (3×1 L). The combined organic layers were washed with water (1 L) and with saturated aqueous sodium chloride solution (1 L), dried over sodium sulfate, and concentrated in vacuo to afford the product as a yellow liquid. Yield: 37 g, 0.175 mol, 67%. $^1$H NMR (400 MHz, CDCl$_3$) δ 5.22 (br s, 2H), 3.86 (s, 3H), 2.66 (d, J=7.2 Hz, 2H), 2.42 (s, 3H), 1.94-2.05 (m, 1H), 0.91 (d, J=6.6 Hz, 6H).

Step 5. Synthesis of 5-isobutyl-7-methylimidazo[5,1-f][1,2,4]triazin-4(3H)-one (P3)

A mixture of C68 (137 g, 0.648 mol) in formamide (800 mL) was heated to 170° C. for 2 hours. After cooling to room temperature, the reaction mixture was poured into water (2 L), and the resulting mixture was extracted with ethyl acetate (4×600 mL). The combined organic layers were washed with water (1 L) and with saturated aqueous sodium chloride solution (1 L), dried over sodium sulfate and concentrated in vacuo. The residue was recrystallized from ethyl acetate to provide the product as a white solid. Yield: 54 g, 0.26 mol, 40%. LCMS m/z 207.3 [M+H]$^+$. $^1$H NMR (400 MHz, CDCl$_3$) δ 10.2 (br s, 1H), 7.49 (s, 1H), 2.88 (d, J=7.3 Hz, 2H), 2.63 (s, 3H), 2.10-2.21 (m, 1H), 0.97 (d, J=6.6 Hz, 6H).

Method A

Introduction of a 4-amino substituent onto an imidazo[5,1-f][1,2,4]triazine core via a chloro intermediate

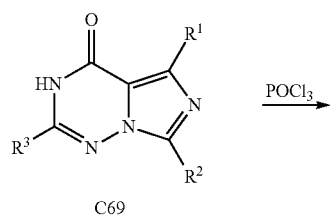

C69

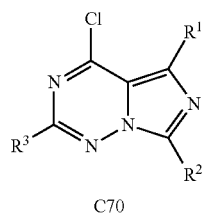

C70

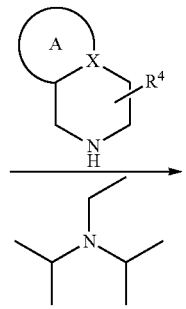

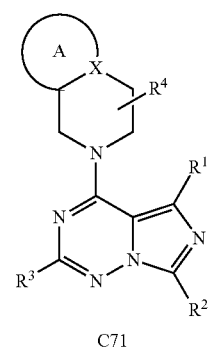

C71

Step 1. Synthesis of 4-chloro-imidazo[5,1-f][1,2,4]triazines C70

The appropriately substituted imidazo[5,1-f][1,2,4]triazin-4(3H)-one C69 (1 equivalent) was mixed with phosphorus oxychloride (roughly 20 equivalents), and the mixture was heated at 100° C. for 3 hours. Volatiles were removed in vacuo, and the crude product was used directly in the next step.

Step 2. Synthesis of 4-amino-substituted imidazo[5,1-f][1,2,4]triazines C71

The amine reagent (roughly 0.1 mmol) was dissolved in acetonitrile (250 μL) and N,N-diisopropylethylamine (250 μL), and treated with a solution of chloride C70 (roughly 0.125 mmol) in acetonitrile (0.5 mL). The reaction mixture was shaken until the reaction was judged to be complete by MS analysis, then diluted with methanol (1 mL), filtered, and concentrated in vacuo. Purification was carried out via reversed phase HPLC (Column: Waters XBridge C$_{18}$; Mobile phase A: 0.03% ammonium hydroxide in water (v/v); Mobile phase B: 0.03% ammonium hydroxide in acetonitrile (v/v); Gradient: 5% to 100% B) to afford the product.

Method B

Introduction of a 4-amino substituent onto an imidazo[5,1-f][1,2,4]triazine core via triazole displacement

Method C

Alternative introduction of a 4-amino substituent onto an imidazo[5,1-f][1,2,4]triazine core via triazole displacement

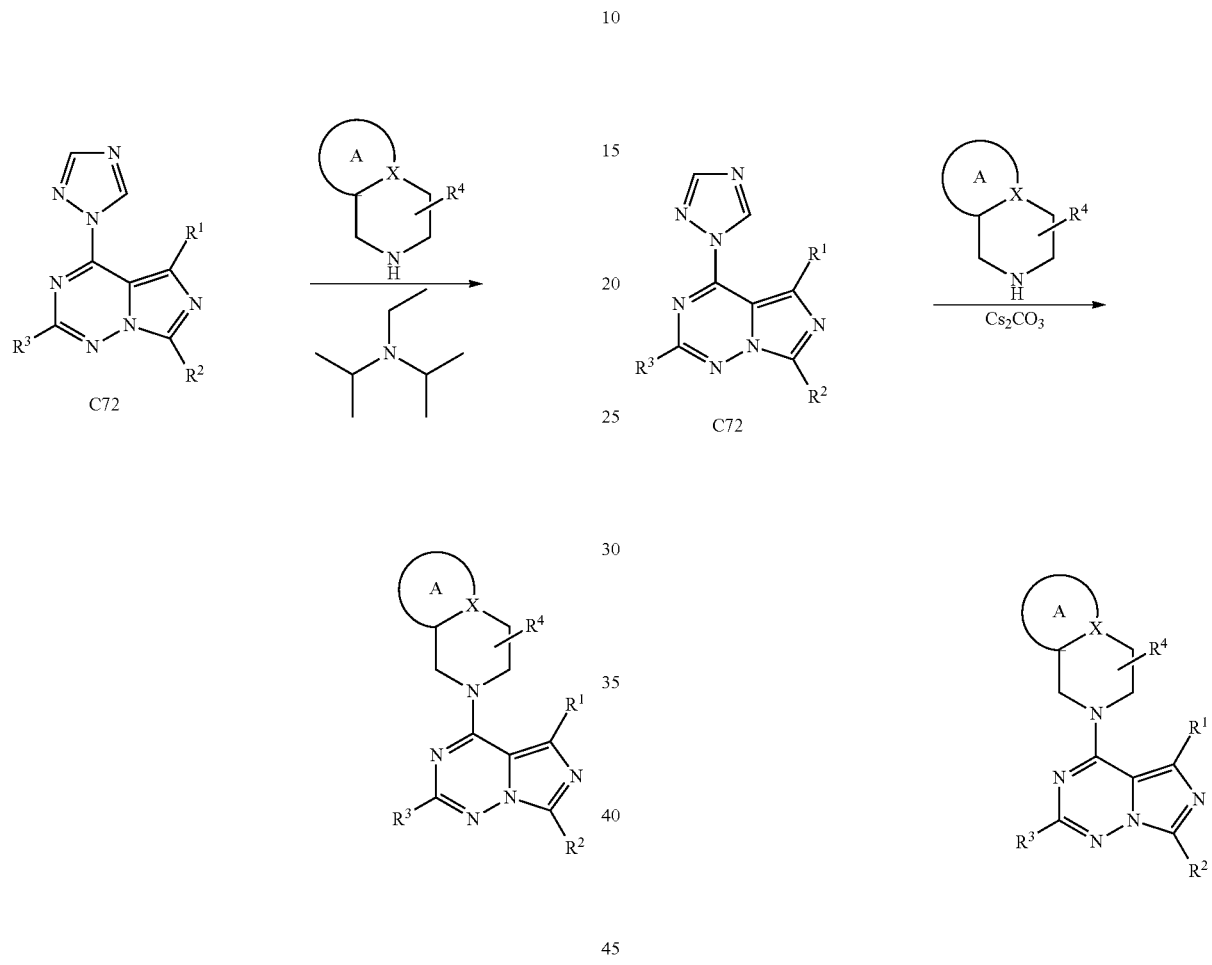

The amine reagent (roughly 0.11 mmol) was dissolved in 1,2-dichloroethane (250 μL) and treated with a solution of the appropriate triazole C72 (roughly 0.1 mmol) in 1,2-dichloroethane (0.25 mL) and N,N-diisopropylethylamine (28 μL). The reaction mixture was shaken at 50° C. for 44 hours, then partitioned between water (1.5 mL) and ethyl acetate (2.5 mL). The organic layer was eluted through a 6 mL solid phase extraction cartridge filled with sodium sulfate (approximately 1 g). This extraction was repeated twice, and the combined eluates from the cartridge were concentrated in vacuo and purified via reversed phase HPLC (Column: Waters XBridge $C_{18}$; Mobile phase A: 0.03% ammonium hydroxide in water (v/v); Mobile phase B: 0.03% ammonium hydroxide in acetonitrile (v/v), using an appropriate gradient) to afford the product.

The amine reagent (82.5 μmol) was treated with a solution of the appropriate triazole C72 (75 μmol) in N,N-dimethylformamide (0.3 mL). Cesium carbonate (roughly 25 mg, ~75 μmol) was added, and the reaction mixture was shaken at room temperature for 18 hours, then partitioned between water (1.5 mL) and ethyl acetate (2.5 mL). The organic layer was eluted through a 6 mL solid phase extraction cartridge filled with sodium sulfate (approximately 1 g). This extraction was repeated twice, and the combined eluates from the cartridge were concentrated in vacuo and purified via reversed phase HPLC (Column: Waters XBridge $C_{18}$; Mobile phase A: 0.03% ammonium hydroxide in water (v/v); Mobile phase B: 0.03% ammonium hydroxide in acetonitrile (v/v), using an appropriate gradient) to afford the product.

TABLE 6

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 14 | 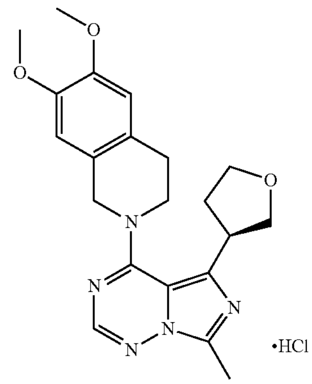 [SMILES: COc1cc2c(cc1OC)CN(c1ncnn3c(C)nc([C@H]4CCOC4)c13)CC2 ; Cl] | Example 10; C16 | $^1$H NMR (400 MHz, CD$_3$OD) δ 8.16 (s, 1H), 6.80 (s, 1H), 6.76 (s, 1H), 4.86-4.97 (m, 2H), 4.20-4.27 (m, 1H), 4.11-4.19 (m, 2H), 3.98-4.10 (m, 2H), 3.88-3.97 (m, 2H), 3.81 (s, 3H), 3.81 (s, 3H), 2.97-3.12 (m, 2H), 2.83 (s, 3H), 2.60-2.70 (m, 1H), 2.17-2.28 (m, 1H); APCI m/z 396.1 [M + H]$^+$ |
| 15 | 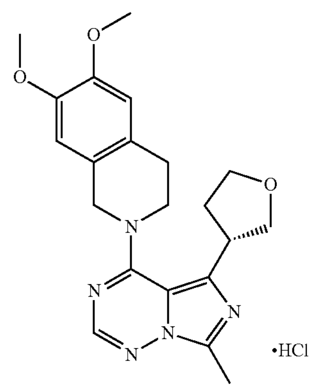 [SMILES: COc1cc2c(cc1OC)CN(c1ncnn3c(C)nc([C@@H]4CCOC4)c13)CC2 ; Cl] | Example 10; C17 | $^1$H NMR (400 MHz, CD$_3$OD) δ 8.16 (s, 1H), 6.80 (s, 1H), 6.76 (s, 1H), 4.91 (s, 2H, assumed; partially obscured by water signal), 4.24 (ddd, J = 8.6, 8.6, 4.1 Hz, 1H), 4.12-4.18 (m, 2H), 3.99-4.09 (m, 2H), 3.89-3.96 (m, 2H), 3.81 2 singlets, 6H), 2.98-3.11 (m, 2H), 2.83 (s, 3H), 2.65 (m, 1H), 2.23 (m, 1H); APCI m/z 396.0 [M + H]$^+$ |
| 16 | 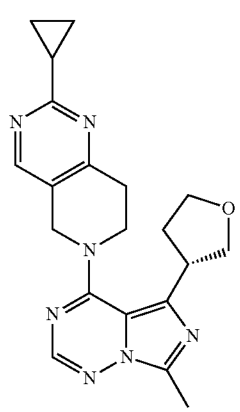 | Example 10; C17 | $^1$H NMR (400 MHz, CD$_3$OD) δ 8.83 (s, 1H), 8.23 (s, 1H), 5.13 (br s, 2H), 4.04-4.32 (m, 5H), 3.92-4.00 (m, 2H), 3.32-3.38 (m, 2H), 2.86 (s, 3H), 2.67-2.76 (m, 1H), 2.31-2.39 (m, 1H), 2.19-2.30 (m, 1H), 1.34-1.40 (m, 4H); APCI m/z 378.2 [M + H]$^+$ |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 17 | 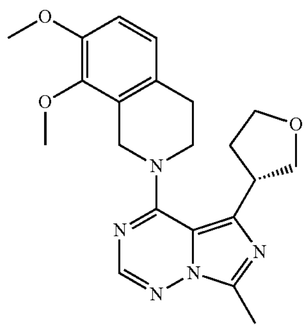 [SMILES: COc1ccc2c(c1OC)CN(c1ncnn3c(C)nc([C@@H]4CCOC4)c13)CC2] | Method A; C15[1] | 7.88 (s, 1H), 6.85 (AB quartet, J$_{AB}$ = 8.4 Hz, Δν$_{AB}$ = 16.7 Hz, 2H), 4.91 (br s, 2H), 4.27 (dd, J = 7.8, 7.8 Hz, 1H), 4.19-4.27 (m, 1H), 3.89-4.07 (m, 4H), 3.87 (s, 3H), 3.85 (s, 3H), 3.76-3.85 (m, 1H), 2.97-3.10 (m, 2H), 2.68 (br s, 3H), 2.42-2.53 (m, 2H); 396.2 |
| 18 | ·HCl | Example 10; C17[2] | $^1$H NMR (400 MHz, CD$_3$OD) δ 8.15 (s, 1H), 4.81 (br s, 2H), 4.19-4.29 (m, 2H), 4.14 (dd, J = 8.4, 7.3 Hz, 1H), 3.99-4.08 (m, 2H), 3.92-3.98 (m, 2H), 3.75 (s, 3H), 2.99-3.14 (m, 2H), 2.80 (s, 3H), 2.58-2.66 (m, 1H), 2.61 (q, J = 7.7 Hz, 2H), 2.19-2.29 (m, 1H), 1.23 (t, J = 7.6 Hz, 3H); APCI m/z 368.1 [M + H]$^+$ |
| 19 | 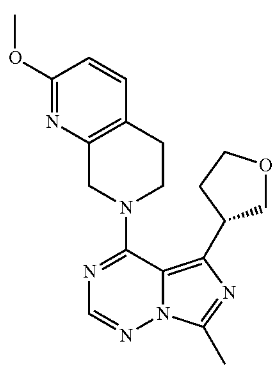 [SMILES: COc1ccc2c(n1)CN(c1ncnn3c(C)nc([C@@H]4CCOC4)c13)CC2] | Example 6 | 7.89 (s, 1H), 7.36 (br d, J = 8.4 Hz, 1H), 6.61 (br d, J = 8.4 Hz, 1H), 4.81 (br s, 2H), 4.27 (dd, J = 7.9, 7.8 Hz, 1H), 4.17-4.24 (m, 1H), 3.98-4.06 (m, 4H), 3.88 (s, 3H), 3.71-3.80 (m, 1H), 2.97-3.02 (m, 2H), 2.67 (s, 3H), 2.40-2.50 (m, 2H); 367.1 |
| 20 | 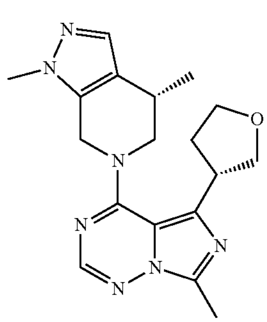 [SMILES: Cc1nc([C@@H]2CCOC2)c2c(N3Cc4c(cnn4C)[C@H](C)C3)ncnn12] | Example 6[3] | $^1$H NMR (400 MHz, CD$_3$OD) δ 7.88 (s, 1H), 7.37 (s, 1H), 4.95 (d, half of AB quartet, J = 15.9 Hz, 1H), 4.68 (dd, half of ABX pattern, J = 15.9, 1.5 Hz, 1H), 4.31 (br dd, J = 13.3, 4.4 Hz, 1H), 4.17 (ddd, J = 8.3, 8.3, 5.1 Hz, 1H), 3.97-4.10 (m, 2H), 3.8-3.89 (m, 2H), 3.78 (s, 3H), 3.17-3.28 (m, 1H), 3.02 (dd, J = 13.2, 10.4 Hz, 1H), 2.59 (s, 3H), 2.32-2.54 (m, 2H), 1.24 (d, J = 6.8 Hz, 3H); 354.3 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 21 | 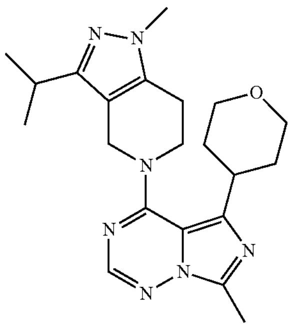 [SMILES: Cc1nc(C2CCOCC2)c2c(N3CCc4c(c(C(C)C)nn4C)C3)ncnn12] | Example 10; P2[2] | 7.85 (s, 1H), 4.69 (br s, 2H), 4.14 (dd, J = 11.5, 3.3 Hz, 2H), 3.97 (dd, J = 5.7, 5.6 Hz, 2H), 3.72 (s, 3H), 3.55 (br dd, J = 12, 11 Hz, 2H), 3.16 (tt, J = 11.6, 3.4 Hz, 1H), 2.97 (dd, J = 5.7, 5.6 Hz, 2H), 2.87 (septet, J = 7.0 Hz, 1H), 2.65 (s, 3H), 2.19-2.31 (m, 2H), 1.75 (br d, J = 13 Hz, 2H), 1.24 (d, J = 7.0 Hz, 6H); APCI m/z 396.4 [M + H]$^+$ |
| 22 | (+/−) •HCl | Example 10; C54[4] | $^1$H NMR (400 MHz, CD$_3$OD) δ 8.76 (s, 1H), 8.26 (s, 1H), 5.49-5.52 (m, 1H), 5.09 (AB quartet, J$_{AB}$ = 16.3 Hz, Δν$_{AB}$ = 19.8 Hz, 2H), 4.39-4.45 (m, 1H), 4.16-4.22 (m, 1H), 3.98-4.07 (m, 2H), 3.3-3.39 (m, 1H, assumed; partially obscured by solvent signal), 3.17-3.25 (m, 1H), 2.85 (s, 3H), 2.52-2.60 (m, 1H), 2.27-2.33 (m, 1H), 2.08-2.19 (m, 3H), 1.31-1.35 (m, 4H); 378.1 |
| 23 | •HCl | Example 10; C16 | $^1$H NMR (400 MHz, CD$_3$OD) δ 8.19 (s, 1H), 5.01 (br s, 2H), 3.90-4.26 (m, 7H), 3.04-3.19 (m, 2H), 2.82 (s, 3H), 2.72 (s, 3H), 2.57-2.66 (m, 1H), 2.16-2.26 (m, 1H); 357.1 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 24 | 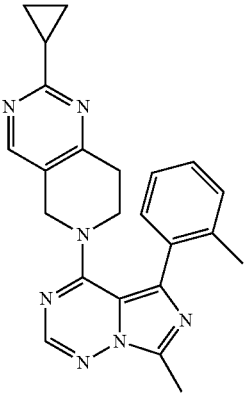 [SMILES: Cc1ccccc1-c1nc(C)n2ncnc(N3CCc4nc(C5CC5)ncc4C3)c12] | Example 10; C45 | 7.96 (s, 1H), 7.91 (br s, 1H), 7.21-7.35 (m, 4H), 4.23-4.47 (br m, 2H), 3.66-3.92 (br m, 2H), 2.72 (s, 3H), 2.54-2.62 (br m, 2H), 2.28 (s, 3H), 2.09-2.16 (m, 1H), 0.98-1.07 (m, 4H); APCI m/z 398.1 [M + H]$^+$ |
| 25 | 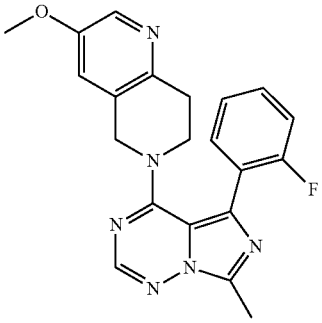 [SMILES: COc1cnc2c(c1)CN(c1ncnn3c(C)nc(-c4ccccc4F)c13)CC2] | Example 2 | $^1$H NMR (600 MHz, DMSO-d$_6$) δ 8.05-8.07 (m, 2H), 7.60-7.64 (m, 1H), 7.44-7.49 (m, 1H), 7.31 (dd, J = 7.6, 7.4 Hz, 1H), 7.20 (br dd, J = 9.3, 9.2 Hz, 1H), 6.83 (br s, 1H), 4.60 (br s, 2H), 3.75-3.79 (m, 2H), 3.74 (s, 3H), 2.61 (s, 3H), 2.54-2.58 (m, 2H); 391.1 |
| 26 | 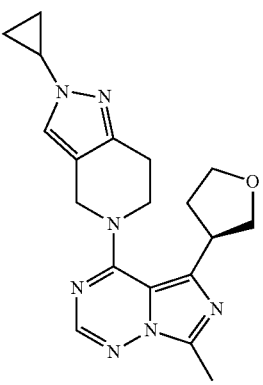 [SMILES: Cc1nc([C@H]2CCOC2)c2c(N3CCc4nn(C5CC5)cc4C3)ncnn12] | Example 10; C16, C48 | 7.89 (s, 1H), 7.26 (s, 1H), 4.71 (AB quartet, J$_{AB}$ = 15.1 Hz, Δv$_{AB}$ = 11.2 Hz, 2H), 4.17-4.24 (m, 1H), 4.16 (dd, J = 7.9, 7.8 Hz, 1H), 3.92-4.05 (m, 4H), 3.66-3.75 (m, 1H), 3.52-3.58 (m, 1H), 3.05 (dd, J = 6.0, 5.8 Hz, 2H), 2.68 (s, 3H), 2.38-2.49 (m, 1H), 2.28-2.38 (m, 1H), 0.99-1.11 (m, 4H); APCI m/z 366.1 [M + H]$^+$ |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 27 | 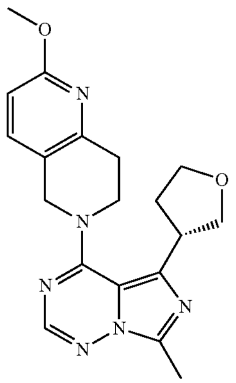 [SMILES: COc1ccc2c(n1)CCN(c1ncnn3c(C)nc([C@@H]4CCOC4)c13)C2] | Example 6 | $^1$H NMR (400 MHz, CD$_3$OD) δ 7.89 (s, 1H), 7.48 (d, J = 8.6 Hz, 1H), 6.65 (d, J = 8.4 Hz, 1H), 4.78 (s, 2H), 3.89-4.20 (m, 6H), 3.89 (s, 3H), 3.77-3.87 (m, 1H), 3.07-3.12 (m, 2H), 2.59 (s, 3H), 2.27-2.46 (m, 2H); 367.2 |
| 28 | 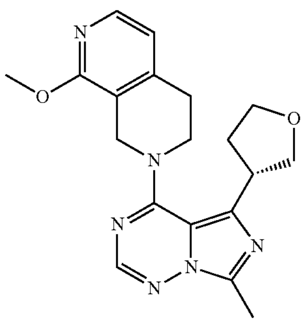 [SMILES: COc1nccc2c1CN(c1ncnn3c(C)nc([C@@H]4CCOC4)c13)CC2] | Example 6$^5$ | 7.96 (br d, J = 5.3 Hz, 1H), 7.85 (s, 1H), 6.70 (br d, J = 5.2 Hz, 1H), 4.76 (br AB quartet, J$_{AB}$ = 17.5 Hz, Δv$_{AB}$ = 5.1 Hz, 2H), 4.29 (dd, J = 7.9, 7.8 Hz, 1H), 4.21 (ddd, J = 8.1, 8.1, 5.7 Hz, 1H), 3.96-4.08 (m, 4H), 3.95 (s, 3H), 3.73-3.82 (m, 1H), 3.01-3.06 (m, 2H), 2.64 (s, 3H), 2.39-2.50 (m, 2H); 367.1 |
| 29 | 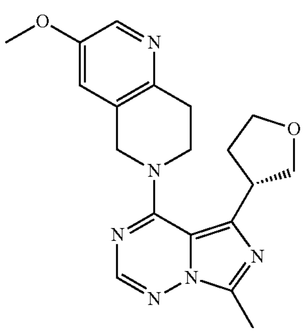 [SMILES: COc1cnc2c(c1)CN(c1ncnn3c(C)nc([C@@H]4CCOC4)c13)CC2] | Example 6 | $^1$H NMR (600 MHz, DMSO-d$_6$) δ 8.14 (d, J = 2.7 Hz, 1H), 7.95 (s, 1H), 7.30 (br d, J = 2.7 Hz, 1H), 4.85 (br AB quartet, J$_{AB}$ = 17 Hz, Δv$_{AB}$ = 8 Hz, 2H), 4.12 (dd, J = 7.8, 7.6 Hz, 1H), 3.96-4.02 (m, 2H), 3.96 (ddd, J = 8.1, 8.0, 5.3 Hz, 1H), 3.80 (s, 3H), 3.79-3.88 (m, 2H), 3.71-3.78 (m, 1H), 3.02-3.07 (m, 2H), 2.53 (s, 3H), 2.28-2.35 (m, 1H), 2.20-2.26 (m, 1H); 367.1 |
| 30 | 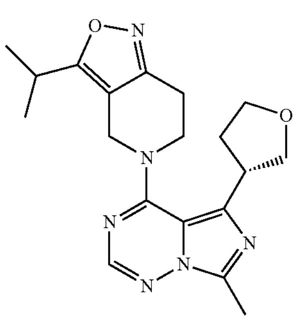 [SMILES: Cc1nc([C@@H]2CCOC2)c2c(N3CCc4noc(C(C)C)c4C3)ncnn12] | Example 10; C17$^2$ | 7.90 (s, 1H), 4.69 (AB quartet, J$_{AB}$ = 15.2 Hz, Δv$_{AB}$ = 14.5 Hz, 2H), 4.14-4.22 (m, 2H), 3.83-4.05 (m, 4H), 3.65-3.74 (m, 1H), 3.06-3.16 (m, 3H), 2.66 (s, 3H), 2.28-2.46 (m, 2H), 1.34 (d, J = 7.0 Hz, 3H), 1.34 (d, J = 7.0 Hz, 3H) |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 31 | 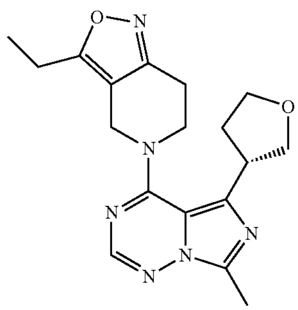 [SMILES: CCc1onc2c1CN(c1ncnn3c(C)nc([C@@H]4CCOC4)c13)CC2] | Example 10; C17[2,6] | 7.89 (s, 1H), 4.66 (AB quartet, J$_{AB}$ = 15.1 Hz, Δν$_{AB}$ = 14.5 Hz, 2H), 4.14-4.23 (m, 2H), 3.84-4.06 (m, 4H), 3.64-3.74 (m, 1H), 3.11-3.16 (m, 2H), 2.75 (q, J = 7.7 Hz, 2H), 2.66 (s, 3H), 2.28-2.47 (m, 2H), 1.31 (t, J = 7.6 Hz, 3H) |
| 32 | 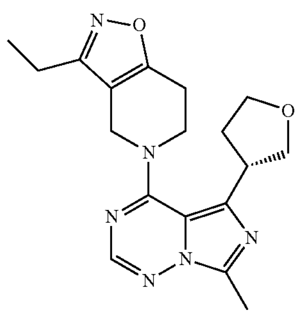 [SMILES: CCc1noc2c1CN(c1ncnn3c(C)nc([C@@H]4CCOC4)c13)CC2] | Example 10; C17[2,6] | 7.88 (s, 1H), 4.52-4.63 (m, 2H), 4.14-4.23 (m, 2H), 3.89-4.07 (m, 4H), 3.65-3.74 (m, 1H), 3.07-3.13 (m, 2H), 2.66 (s, 3H), 2.65 (q, J = 7.6 Hz, 2H), 2.28-2.49 (m, 2H), 1.29 (t, J = 7.6 Hz, 3H) |
| 33 | 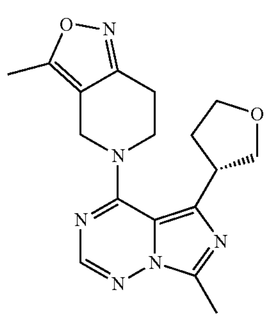 [SMILES: Cc1onc2c1CN(c1ncnn3c(C)nc([C@@H]4CCOC4)c13)CC2] | Example 10; C17[2,7] | 7.89 (s, 1H), 4.63 (br AB quartet, J$_{AB}$ = 15 Hz, Δν$_{AB}$ = 14 Hz, 2H), 4.14-4.23 (m, 2H), 3.85-4.06 (m, 4H), 3.64-3.74 (m, 1H), 3.10-3.15 (m, 2H), 2.66 (s, 3H), 2.38 (br s, 3H), 2.28-2.48 (m, 2H) |
| 34 | 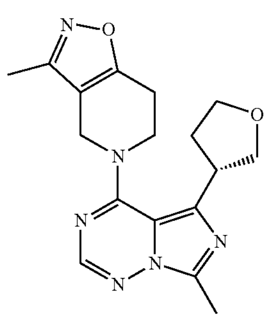 [SMILES: Cc1noc2c1CN(c1ncnn3c(C)nc([C@@H]4CCOC4)c13)CC2] | Example 10; C17[2,7] | 7.88 (s, 1H), 4.50-4.61 (m, 2H), 4.15-4.23 (m, 2H), 3.91-4.07 (m, 4H), 3.65-3.74 (m, 1H), 3.07-3.13 (m, 2H), 2.66 (s, 3H), 2.28-2.50 (m, 2H), 2.25 (s, 3H) |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 35 | 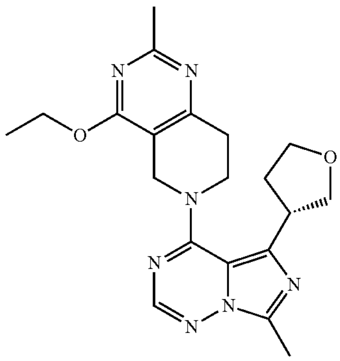 [SMILES: CCOc1nc(C)nc2c1CN(c1ncnn3c(C)nc([C@@H]4CCOC4)c13)CC2] | Example 6[8] | $^1$H NMR (400 MHz, CD$_3$OD) δ 7.88 (s, 1H), 4.76 (br AB quartet, J$_{AB}$ = 16.5 Hz, Δν$_{AB}$ = 16.0 Hz, 2H), 4.47 (q, J = 7.1 Hz, 2H), 4.27 (dd, J = 7.5, 7.4 Hz, 1H), 4.17 (ddd, J = 8.3, 8.3, 4.7 Hz, 1H), 3.82-4.13 (m, 5H), 3.01-3.07 (m, 2H), 2.59 (s, 3H), 2.51 (s, 3H), 2.44-2.5 (m, 1H), 2.28-2.38 (m, 1H), 1.41 (t, J = 7.1 Hz, 3H); 396.3 |
| 36 | 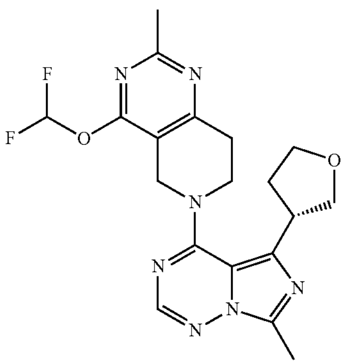 [SMILES: Cc1nc2c(c(OC(F)F)n1)CN(c1ncnn3c(C)nc([C@@H]4CCOC4)c13)CC2] | Example 6[9] | $^1$H NMR (400 MHz, CD$_3$OD) δ 7.88 (s, 1H), 7.66 (t, J$_{HF}$ = 71.6 Hz, 1H), 4.83 (br AB quartet, J$_{AB}$ = 17.0 Hz, Δν$_{AB}$ = 9.6 Hz, 2H), 4.23 (dd, J = 7.6, 7.6 Hz, 1H), 4.10-4.20 (m, 2H), 3.81-4.07 (m, 4H), 3.05-3.19 (m, 2H), 2.58 (s, 3H), 2.57 (s, 3H), 2.44-2.54 (m, 1H), 2.27-2.38 (m, 1H); 418.3 |
| 37 | 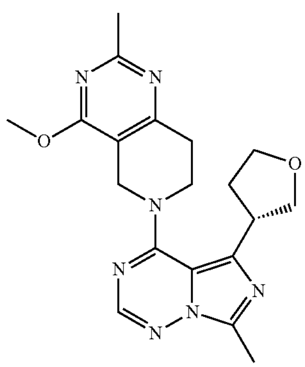 [SMILES: COc1nc(C)nc2c1CN(c1ncnn3c(C)nc([C@@H]4CCOC4)c13)CC2] | Method B; C17[10] | 1.53 minutes[11]; 382.3 |
| 38 | 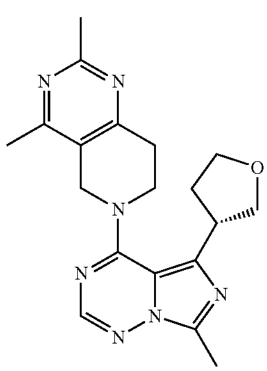 [SMILES: Cc1nc(C)c2c(n1)CCN(c1ncnn3c(C)nc([C@@H]4CCOC4)c13)C2] | Method B; C17[12] | 1.46 minutes[11]; 366.3 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 39 | 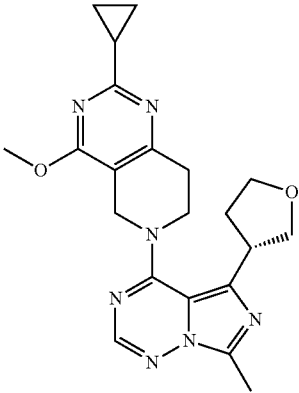 [SMILES: COc1nc(C2CC2)nc2c1CN(c1ncnn3c(C)nc([C@@H]4CCOC4)c13)CC2] | Example 35 | $^1$H NMR (400 MHz, CD$_3$CN) δ 7.81 (s, 1H), 4.63 (br AB quartet, J$_{AB}$ = 16.7 Hz, Δν$_{AB}$ = 13.1 Hz, 2H), 4.13 (dd, J = 7.7, 7.7 Hz, 1H), 4.04 (ddd, J = 8.2, 8.1, 5.1 Hz, 1H), 3.92 (s, 3H), 3.82-4.00 (m, 4H), 3.71-3.80 (m, 1H), 2.92-2.97 (m, 2H), 2.52 (s, 3H), 2.31-2.40 (m, 1H), 2.20-2.30 (m, 1H), 1.99-2.06 (m, 1H), 0.98-1.04 (m, 2H), 0.92-0.98 (m, 2H); 408.3 |
| 40 | 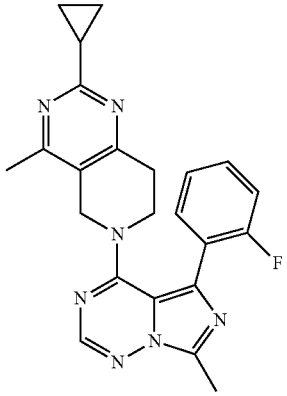 [SMILES: Cc1nc(C2CC2)nc2c1CN(c1ncnn3c(C)nc(-c4ccccc4F)c13)CC2] | Example 38; C6$^{13}$ | $^1$H NMR (400 MHz, CD$_3$OD) δ 8.01 (s, 1H), 7.68 (ddd, J = 7.6, 7.5, 1.8 Hz, 1H), 7.50 (dddd, J = 8.3, 7.4, 5.2, 1.9 Hz, 1H), 7.35 (ddd, J = 7.5, 7.5, 1.2 Hz, 1H), 7.19 (ddd, J = 10.0, 8.3, 1.1 Hz, 1H), 4.40 (br s, 2H), 4.00 (v br s, 2H), 2.75-2.81 (m, 2H), 2.67 (s, 3H), 2.02-2.09 (m, 1H), 1.91 (s, 3H), 0.95-1.04 (m, 4H); 416.2 |
| 41 | 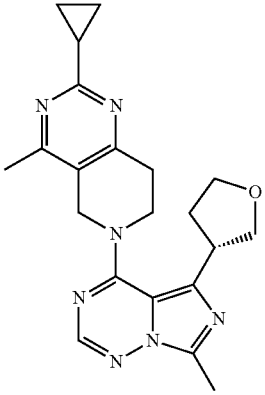 [SMILES: Cc1nc(C2CC2)nc2c1CN(c1ncnn3c(C)nc([C@@H]4CCOC4)c13)CC2] | Example 40; C17 | $^1$H NMR (400 MHz, CD$_3$CN) δ 7.84 (s, 1H), 4.66-4.76 (m, 2H), 4.10 (dd, J = 7.6, 7.5 Hz, 1H), 4.03 (ddd, J = 8.1, 8.0, 5.4 Hz, 1H), 3.83-4.01 (m, 4H), 3.75-3.83 (m, 1H), 2.95-3.09 (m, 2H), 2.53 (s, 3H), 2.34 (s, 3H), 2.21-2.38 (m, 2H), 2.04-2.11 (m, 1H), 0.94-0.99 (m, 4H); 392.3 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 42 | 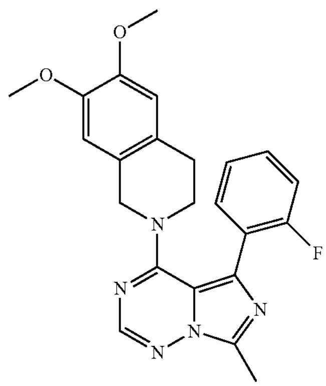 [SMILES: COc1cc2c(cc1OC)CN(c1ncnn3c(C)nc(-c4ccccc4F)c13)CC2] | Example 10; C6 | 7.96 (s, 1H), 7.64-7.73 (br m, 1H), 7.35-7.43 (m, 1H), 7.26-7.31 (m, 1H), 7.08 (br dd, J = 9, 9 Hz, 1H), 6.55 (s, 1H), 6.15 (br s, 1H), 4.50 (br s, 2H), 3.84-3.90 (br m, 2H), 3.83 (s, 3H), 3.76 (s, 3H), 2.74 (br s, 3H), 2.65-2.72 (br m, 2H); APCI m/z 420.0 [M + H]$^+$ |
| 43 | 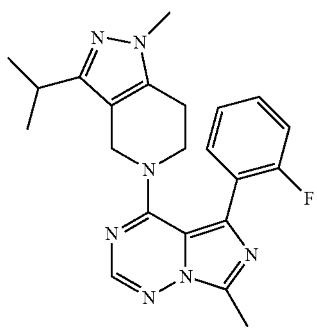 [SMILES: Cc1nc(-c2ccccc2F)c2c(N3CCc4c(c(C(C)C)nn4C)C3)ncnn12] | Example 10; C6$^2$ | 7.90 (s, 1H), 7.67 (ddd, J = 7.6, 7.5, 1.8 Hz, 1H), 7.38-7.45 (m, 1H), 7.29 (ddd, J = 7.6, 7.5, 1.1 Hz, 1H), 7.17 (ddd, J = 10.0, 8.3, 1.0 Hz, 1H), 4.23 (br s, 2H), 3.6-4.4 (v br m, 2H), 3.60 (s, 3H), 2.70 (s, 3H), 2.62-2.7 (br m, 2H), 2.57 (septet, J = 7.0 Hz, 1H), 0.92 (d, J = 7.0 Hz, 6H); APCI m/z 406.1 [M + H]$^+$ |
| 44 | 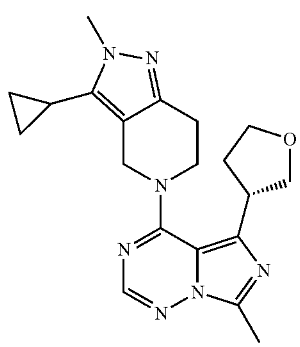 [SMILES: Cc1nc([C@@H]2CCOC2)c2c(N3CCc4nn(C)c(C5CC5)c4C3)ncnn12] | Example 10; C17, C50 and C49$^{14}$ | 7.87 (s, 1H), 4.68 (AB quartet, J$_{AB}$ = 14.7 Hz, Δν$_{AB}$ = 15.9 Hz, 2H), 4.16-4.23 (m, 2H), 3.87-4.04 (m, 4H), 3.86 (s, 3H), 3.69-3.78 (m, 1H), 3.01 (dd, J = 6.1, 5.9 Hz, 2H), 2.65 (s, 3H), 2.33-2.44 (m, 2H), 1.6-1.70 (m, 1H, assumed; partially obscured by water peak), 0.97-1.02 (m, 2H), 0.62-0.67 (m, 2H); 380.4 |
| 45 | 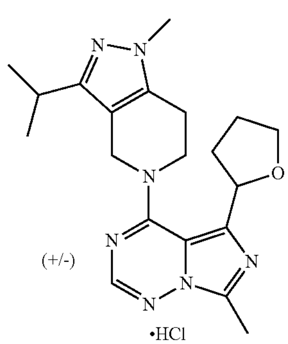 [SMILES: Cc1nc(C2CCCO2)c2c(N3CCc4c(c(C(C)C)nn4C)C3)ncnn12 ; Cl] | Example 10; C54$^2$ | 7.88 (s, 1H), 5.15 (dd, J = 8.1, 6.5 Hz, 1H), 5.06 (br d, J = 15 Hz, 1H), 4.60 (br d, J = 15 Hz, 1H), 4.49-4.55 (m, 1H), 4.16-4.23 (m, 1H), 3.91 (ddd, J = 8.1, 8.0, 5.6 Hz, 1H), 3.71 (s, 3H), 3.64 (ddd, J = 13.2, 9.5, 4.6 Hz, 1H), 3.06 (br ddd, J = 16, 9.5, 5 Hz, 1H), 2.96 (septet, J = 7.0 Hz, 1H), 2.78 (br ddd, J = 16, 4, 4 Hz, 1H), 2.66 (s, 3H), 2.60-2.70 (m, 1H), 2.26-2.35 (m, 1H), 2.03-2.21 (m, 2H), 1.27 (d, J = 7.0 Hz, 3H), 1.26 (d, J = 7.0 Hz, 3H)$^{15}$; 382.1 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 46 | 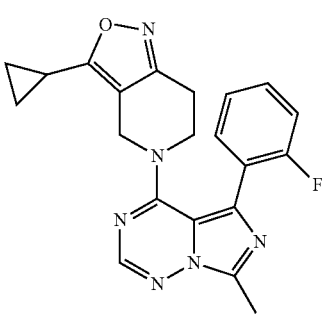 [SMILES: Cc1nc(-c2ccccc2F)c2c(N3CCc4noc(C5CC5)c4C3)ncnn12] | Example 10; C6, C30 | 7.97 (s, 1H), 7.66 (ddd, J = 7.6, 7.4, 1.8 Hz, 1H), 7.41-7.47 (m, 1H), 7.30 (ddd, J = 7.6, 7.6, 1.2 Hz, 1H), 7.17 (ddd, J = 9.9, 8.3, 1.0 Hz, 1H), 4.35 (br s, 2H), 3.83-3.96 (br m, 2H), 2.74 (s, 3H), 2.69-2.75 (m, 2H), 1.51-1.58 (m, 1H), 0.79-0.94 (m, 4H); 391.0 |
| 47 | 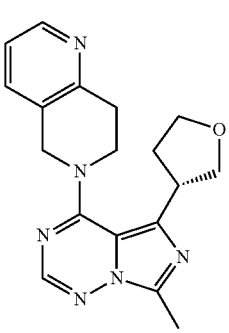 [SMILES: Cc1nc([C@@H]2CCOC2)c2c(N3CCc4ncccc4C3)ncnn12] | C17[16] | 8.50 (br d, J = 4.8 Hz, 1H), 7.90 (s, 1H), 7.46 (br d, J = 7.8 Hz, 1H), 7.19 (dd, J = 7.8, 4.8 Hz, 1H), 4.83 (br s, 2H), 4.15-4.22 (m, 2H), 3.97-4.11 (m, 4H), 3.69-3.79 (m, 1H), 3.22-3.35 (m, 2H), 2.66 (s, 3H), 2.30-2.47 (m, 2H); APCI m/z 336.7 [M + H]$^+$ |
| 48 | 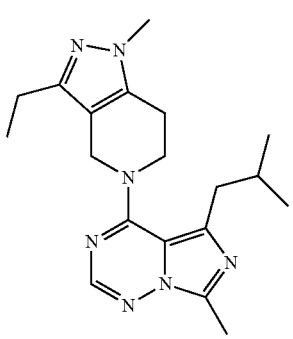 [SMILES: CCc1nn(C)c2c1CN(c1ncnn3c(C)nc(CC(C)C)c13)CC2] | Example 10; P3[2] | $^1$H NMR (500 MHz, CDCl$_3$), δ 7.83 (s, 1H), 4.64 (br s, 2H), 3.97 (dd, J = 5.9, 5.7 Hz, 2H), 3.72 (s, 3H), 2.93 (br dd, J = 5.7, 5.7 Hz, 2H), 2.81 (d, J = 7.2 Hz, 2H), 2.64 (s, 3H), 2.56 (q, J = 7.6 Hz, 2H), 2.20-2.32 (m, 1H), 1.22 (t, J = 7.6 Hz, 3H), 0.93 (d, J = 6.6 Hz, 6H); 354.1 |
| 49 | 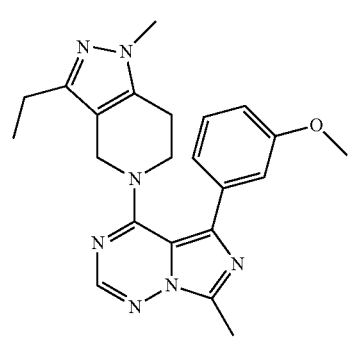 [SMILES: CCc1nn(C)c2c1CN(c1ncnn3c(C)nc(-c4cccc(OC)c4)c13)CC2] | Example 7; C35[17] | 7.94 (s, 1H), 7.34-7.38 (m, 1H), 7.18-7.22 (m, 2H), 6.93-6.97 (m, 1H), 4.18 (br s, 2H), 3.92-3.98 (br m, 2H), 3.84 (s, 3H), 3.62 (s, 3H), 2.72 (s, 3H), 2.64-2.70 (br m, 2H), 2.27 (br q, J = 7.6 Hz, 2H), 0.95 (t, J = 7.6 Hz, 3H); APCI m/z 403.6 [M + H]$^+$ |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 50 | (structure) | Example 10; C16, P1 | $^1$H NMR (500 MHz, CDCl$_3$), δ 7.92 (s, 1H), 7.72 (br s, 1H), 5.02 (AB quartet, J$_{AB}$ = 17.0 Hz, Δν$_{AB}$ = 12.8 Hz, 2H), 4.43-4.54 (m, 2H), 4.27 (br ddd, J = 14, 6, 5 Hz, 1H), 4.15-4.22 (m, 2H), 3.96-4.13 (m, 3H), 3.64-3.71 (m, 1H), 2.67 (s, 3H), 2.32-2.44 (m, 2H); 394.1 |
| 51 | (structure) | C16[16] | $^1$H NMR (500 MHz, CDCl$_3$), δ 7.88 (s, 1H), 7.29 (br s, 1H), 7.22 (br s, 1H), 4.77 (br s, 2H), 4.15-4.21 (m, 2H), 3.96-4.04 (m, 2H), 3.88-3.97 (m, 2H), 3.66-3.73 (m, 1H), 3.00-3.10 (m, 2H), 2.65 (s, 3H), 2.39-2.47 (m, 1H), 2.30-2.38 (m, 1H); 404.6 |
| 52 | (structure) •CF$_3$COOH | Example 10; C17[18] | 1.64 minutes[19]; 394.1 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 53 | 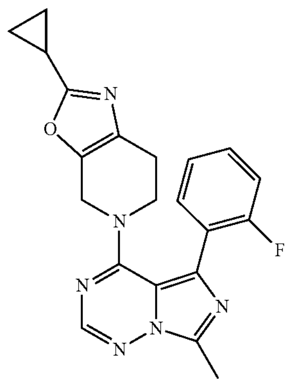 [SMILES: Cc1nc(-c2ccccc2F)c2c(N3CCc4nc(C5CC5)oc4C3)ncnn12] | Example 10; C6, C40 | 7.96 (s, 1H), 7.63 (ddd, J = 7.6, 7.5, 1.8 Hz, 1H), 7.42 (dddd, J = 8.2, 7.4, 5.1, 1.9 Hz, 1H), 7.28 (ddd, J = 7.5, 7.5, 1.2 Hz, 1H), 7.17 (ddd, J = 9.9, 8.3, 1.1 Hz, 1H), 4.36-4.39 (m, 2H), 3.76-3.89 (br m, 2H), 2.74 (s, 3H), 2.35-2.43 (br m, 2H), 1.93-2.00 (m, 1H), 0.99 (apparent br d, J = 6.7 Hz, 4H) |
| 54 | 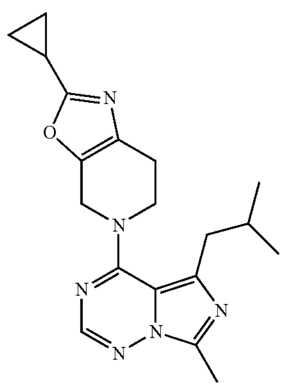 [SMILES: Cc1nc(CC(C)C)c2c(N3CCc4nc(C5CC5)oc4C3)ncnn12] | Example 10; P3, C40 | 7.87 (s, 1H), 4.66 (br s, 2H), 3.91-3.96 (m, 2H), 2.84-2.89 (m, 2H), 2.80 (d, J = 7.2 Hz, 2H), 2.66 (s, 3H), 2.20-2.31 (m, 1H), 2.00-2.08 (m, 1H), 1.02-1.08 (m, 4H), 0.91 (d, J = 6.6 Hz, 6H); 353.6 |
| 55 | 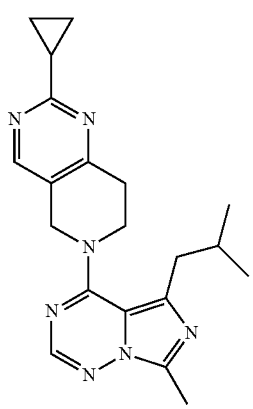 [SMILES: Cc1nc(CC(C)C)c2c(N3CCc4nc(C5CC5)ncc4C3)ncnn12] | Example 10; P3 | $^1$H NMR (500 MHz, CDCl$_3$), δ 8.36 (s, 1H), 7.88 (s, 1H), 4.76 (s, 2H), 3.98 (dd, J = 6.1, 6.0 Hz, 2H), 3.15 (dd, J = 6.0, 5.9 Hz, 2H), 2.80 (d, J = 7.2 Hz, 2H), 2.66 (s, 3H), 2.23-2.31 (m, 1H), 2.18-2.25 (m, 1H), 1.11-1.14 (m, 2H), 1.04-1.10 (m, 2H), 0.92 (d, J = 6.6 Hz, 6H); 364.1 |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 56 | ·HCl | C16[20] | $^1$H NMR (400 MHz, CD$_3$OD) δ 8.63 (s, 1H), 8.20 (s, 1H), 5.04 (s, 2H), 4.22-4.29 (m, 2H), 4.02-4.19 (m, 3H), 3.91-3.98 (m, 2H), 3.19-3.3 (m, 2H), 2.82 (s, 3H), 2.64-2.72 (m, 1H), 2.17-2.28 (m, 2H), 1.24 (br d, J = 6.1 Hz, 2H), 1.15 (br d, J = 6.2 Hz, 2H); APCI m/z 378.1 [M + H]$^+$ |
| 57 | ·HCl | C15[2,20] | $^1$H NMR (400 MHz, CD$_3$OD), δ 8.16 (s, 1H), 4.84 (s, 2H), 3.85-4.28 (m, 7H), 3.79 (s, 3H), 2.93-3.09 (m, 2H), 2.81 (s, 3H), 2.70 (q, J = 7.7 Hz, 2H), 2.57-2.66 (m, 1H), 2.13-2.27 (m, 1H), 1.22 (t, J = 7.7 Hz, 3H); APCI m/z 368.1 [M + H]$^+$ |
| 58 | ·HCl | Example 10; C15 | $^1$H NMR (400 MHz, CD$_3$OD) δ 8.15 (s, 1H), 7.11 (d, J = 8.3 Hz, 1H), 6.79-6.82 (m, 2H), 4.91 (s, 2H), 4.24 (ddd, J = 8.5, 8.5, 4.0 Hz, 1H), 4.00-4.17 (m, 4H), 3.89-3.96 (m, 2H), 3.78 (s, 3H), 3.03-3.16 (m, 2H), 2.82 (s, 3H), 2.65 (m, 1H), 2.22 (m, 1H); APCI m/z 366.1 [M + H]$^+$. |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 59 | 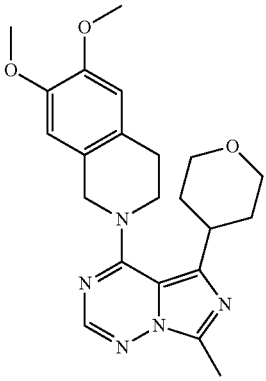 [SMILES: COc1cc2c(cc1OC)CN(c1ncnn3c(C)nc(C4CCOCC4)c13)CC2] | Example 10; P2 | 7.88 (s, 1H), 6.69 (s, 1H), 6.60 (s, 1H), 4.74 (s, 2H), 4.12 (br dd, J = 11.2, 3.5 Hz, 2H), 3.92 (t, J = 5.7 Hz, 2H, assumed; partially obscured by methyl signal), 3.90 (s, 3H), 3.87 (s, 3H), 3.52 (br dd, J = 12, 12 Hz, 2H), 3.15 (tt, J = 11.6, 3.6 Hz, 1H), 3.08 (t, J = 5.7 Hz, 2H), 2.66 (s, 3H), 2.23 (dddd, J = 13, 12, 12, 4 Hz, 2H), 1.75 (br d, J = 13.3 Hz, 2H); 410.4 |
| 60 | 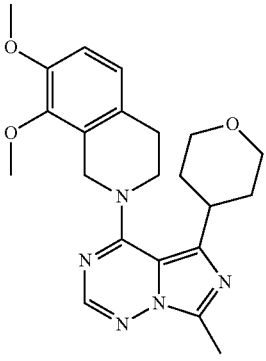 [SMILES: COc1ccc2c(c1OC)CN(c1ncnn3c(C)nc(C4CCOCC4)c13)CC2] | Method A; P2$^1$ | 7.86 (s, 1H), 6.86 (AB quartet, J$_{AB}$ = 8.4 Hz, Δν$_{AB}$ = 22.3 Hz, 2H), 4.89 (s, 2H), 4.14 (br dd, J = 11, 4 Hz, 2H), 3.95 (t, J = 5.8 Hz, 2H), 3.85 (s, 3H), 3.84 (s, 3H), 3.51-3.58 (m, 2H), 3.21 (tt, J = 11.6, 3.5 Hz, 1H), 3.04 (t, J = 5.8 Hz, 2H), 2.64 (s, 3H), 2.23 (dddd, J = 13, 12, 12, 4 Hz, 2H), 1.83 (br d, J = 13 Hz, 2H); 410.4 |
| 61 | 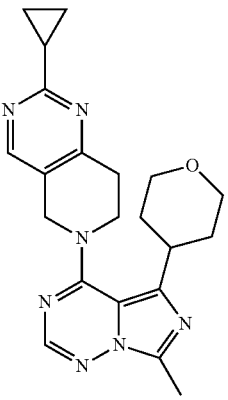 [SMILES: Cc1nc(C2CCOCC2)c2c(N3CCc4nc(C5CC5)ncc4C3)ncnn12] | Example 10; P2 | 8.36 (s, 1H), 7.91 (s, 1H), 4.72 (s, 2H), 4.12 (br dd, J = 11.5, 4 Hz, 2H), 3.94 (t, J = 6.0 Hz, 2H), 3.52 (br dd, J = 12, 12 Hz, 2H), 3.20 (t, J = 5.9 Hz, 2H), 3.10 (tt, J = 11.6, 3.6 Hz, 1H), 2.67 (s, 3H), 2.19-2.30 (m, 3H), 1.73 (br d, J = 13.3 Hz, 2H), 1.11-1.16 (m, 2H), 1.06-1.11 (m, 2H); APCI m/z 392.2 [M + H]$^+$ |

TABLE 6-continued

Structures, Method of Preparation and Physicochemical Data for Examples 14-64.

| Example Number | Structure | Method of Preparation; Source of Non-commercial Starting Materials | $^1$H NMR (400 MHz, CDCl$_3$), δ (ppm); LCMS, observed ion m/z [M + H]$^+$ or HPLC retention time (minutes); LCMS m/z [M + H]$^+$ (unless otherwise indicated) |
|---|---|---|---|
| 62 | 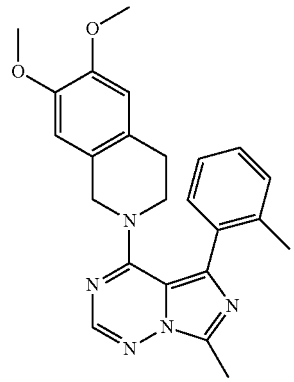 [SMILES: COc1cc2c(cc1OC)CN(c1ncnn3c(C)nc(-c4ccccc4C)c13)CC2] | Example 10 | 7.94 (s, 1H), 7.26-7.38 (m, 4H), 6.51 (s, 1H), 6.0-6.3 (v br s, 1H), 4.2-4.5 (br m, 2H), 3.82 (s, 3H), 3.79 (s, 3H), 3.6-3.9 (br m, 2H), 2.73 (s, 3H), 2.43-2.64 (br m, 2H), 2.30 (s, 3H); APCI m/z 416.1 [M + H]$^+$ |
| 63 | ·HCl | Example 10; C16 | $^1$H NMR (400 MHz, CD$_3$OD), δ 8.99 (s, 1H), 8.65 (s, 1H), 8.16 (s, 1H), 5.03 (s, 2H), 3.92-4.27 (m, 7H), 3.21-3.28 (m, 2H), 2.79 (s, 3H), 2.59-2.68 (m, 1H), 2.19-2.28 (m, 1H); 338.0 |
| 64 | 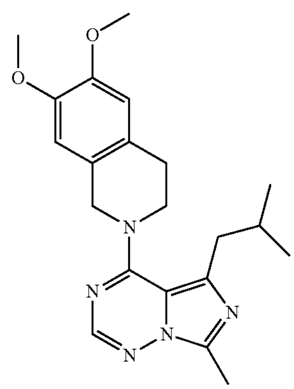 [SMILES: COc1cc2c(cc1OC)CN(c1ncnn3c(C)nc(CC(C)C)c13)CC2] | Example 10; P3 | $^1$H NMR (500 MHz, CDCl$_3$), δ 7.84 (s, 1H), 6.67 (s, 1H), 6.61 (s, 1H), 4.78 (s, 2H), 3.95 (dd, J = 5.9, 5.9 Hz, 2H), 3.87 (s, 3H), 3.86 (s, 3H), 3.02 (dd, J = 5.9, 5.6 Hz, 2H), 2.83 (d, J = 7.3 Hz, 2H), 2.63 (s, 3H), 2.19-2.29 (m, 1H), 0.91 (d, J = 6.6 Hz, 6H); 382.1 |

1. The amine side chain may be prepared according to C. Lamas et al., *Tetrahedron Lett.* 1988, 29, 3865-3868, followed by reduction of the imine moiety using sodium borohydride in methanol.

2. The amine side chain was prepared according to the general procedure of W. T. Ashton et al., *Bioorg. Med. Chem. Lett.* 2005, 15, 2253-2258.

3. The requisite (4S)-1,4-dimethyl-4,5,6,7-tetrahydro-1H-pyrazolo[3,4-c]pyridine was prepared in the following manner. Reaction of C8 at elevated temperature with trimethylboroxin in the presence of sodium carbonate and tetrakis(triphenylphosphine)palladium(0) afforded 1,4-dimethyl-1H-pyrazolo[3,4-c]pyridine. This material was reduced using the method described for synthesis of C9 from C8 in Example 2; the product was subjected to supercritical fluid chromatography to separate the enantiomers (Column: Chiral Technologies, Chiralpak IC, 5 μm; Eluent: 4:1 carbon dioxide/methanol). The second-eluting enantiomer was collected and used for synthesis of Example 20. The absolute stereochemistry was arbitrarily assigned.

4. The hydrochloride salt of the product was generated using a solution of acetyl chloride in methanol.

5. 4-Iodo-2-methoxypyridine-3-carbaldehyde was converted to 1-methoxy-2,7-naphthyridine using the methods described by A. Numata et al., *Synthesis* 1999, 306-311.

Subsequent hydrogenation in acetic acid, under platinum(IV) oxide catalysis, afforded the requisite 8-methoxy-1,2,3,4-tetrahydro-2,7-naphthyridine.

6. Synthesized as a mixture of Examples 31 and 32. Separation via supercritical fluid chromatography (Column: Chiral Technologies, Chiralcel OJ-H, 5 μm; Eluent: 3:1 carbon dioxide/methanol) provided Example 31 as the first-eluting isomer and Example 32 as the second-eluting isomer.

7. Synthesized as a mixture of Examples 33 and 34. Separation via supercritical fluid chromatography (Column: Chiral Technologies, Chiralcel OJ-H, 5 μm; Eluent: 3:1 carbon dioxide/methanol) provided Example 33 as the first-eluting isomer and Example 34 as the second-eluting isomer.

8. Benzyl 4-hydroxy-2-methyl-7,8-dihydropyrido[4,3-d]pyrimidine-6(5H)-carboxylate, which may be prepared using the general method of E. Kretzschmar and P. Meisel, *Pharmazie* 1988, 43, 475-476, was converted to benzyl 4-chloro-2-methyl-7,8-dihydropyrido[4,3-d]pyrimidine-6(5H)-carboxylate via treatment with phosphorus oxychloride. Chloride displacement with sodium ethoxide was followed by hydrogenolytic removal of the protecting group to afford the requisite 4-ethoxy-2-methyl-5,6,7,8-tetrahydropyrido[4,3-d]pyrimidine.

9. Benzyl 4-hydroxy-2-methyl-7,8-dihydropyrido[4,3-d]pyrimidine-6(5H)-carboxylate (see footnote 8) was reacted with sodium chloro(difluoro)acetate and cesium carbonate to generate benzyl 4-(difluoromethoxy)-2-methyl-7,8-dihydropyrido[4,3-d]pyrimidine-6(5H)-carboxylate; hydrogenolytic removal of the protecting group provided the requisite 4-(difluoromethoxy)-2-methyl-5,6,7,8-tetrahydropyrido[4,3-d]pyrimidine.

10. The requisite amine may be prepared in analogous fashion to the synthesis described in footnote 8.

11. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

12. Benzyl 4-chloro-2-methyl-7,8-dihydropyrido[4,3-d]pyrimidine-6(5H)-carboxylate (see footnote 8) was reacted with methylboronic acid and [1,1'-bis(diphenylphosphino)ferrocene]dichloropalladium(II) to generate benzyl 2,4-dimethyl-7,8-dihydropyrido[4,3-d]pyrimidine-6(5H)-carboxylate; hydrogenolytic removal of the protecting group provided the requisite 2,4-dimethyl-5,6,7,8-tetrahydropyrido[4,3-d]pyrimidine.

13. In this case, the benzyloxycarbonyl protecting group was removed through use of trimethylsilyl iodide.

14. This Example was prepared using a mixture of C50 and C49. The isomers of the final product were separated by HPLC (Column: Chiralcel OJ-H; Mobile phase: 3:1 carbon dioxide/methanol). Example 44 was the earlier-eluting isomer. The regiochemistry was assigned as shown, on the basis of NOE experiments.

15. The NMR data was obtained on the free base, prior to generation of the hydrochloride salt.

16. The final step in the synthesis was carried out in a microwave reactor using N,N-diisopropylethylamine in acetonitrile.

17. The final two steps in this case were carried out in a microwave reactor at 150° C. The catalyst used in the final step was [1,1'-bis(diphenylphosphino)ferrocene]dichloropalladium(II), and the overall yield for these two steps was less than 5%.

18. The amine in this case may be prepared by the method of B. T. Shireman et al., *Bioorg. Med. Chem. Lett.* 2008, 18, 2103-2108, followed by removal of the tert-butoxycarbonyl group.

19. Conditions for analytical HPLC. Column: Waters XBridge C18, 4.6×50 mm, 5 μm; Mobile phase A: 0.03% ammonium hydroxide in water (v/v); Mobile phase B: 0.03% ammonium hydroxide in acetonitrile (v/v); Gradient: 5.0% to 95% B, linear over 4.0 minutes; Flow rate: 2 mL/minute).

20. The final step was carried out via a condensation using benzotriazol-1-yloxytris(dimethylamino)phosphonium hexafluorophosphate and 1,8-diazabicyclo[5.4.0]undec-7-ene.

TABLE 7

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 65 | 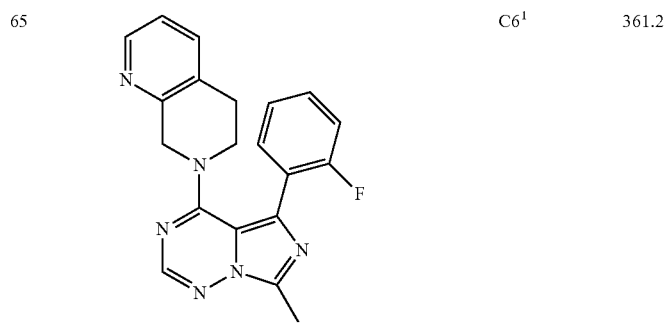 | C6[1] | 361.2 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 66 | 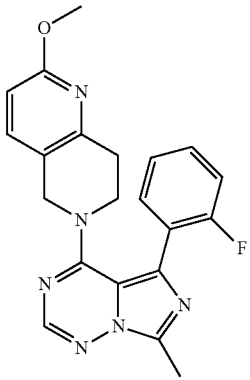 [SMILES: COc1ccc2c(n1)CCN(c1ncnn3c(C)nc(-c4ccccc4F)c13)C2] | C6[1] | 391.1 |
| 67 | 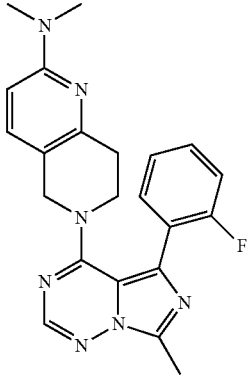 [SMILES: Cc1nc(-c2ccccc2F)c2c(N3CCc4nc(N(C)C)ccc4C3)ncnn12] | C6[1,2] | 404.2 |
| 68 | 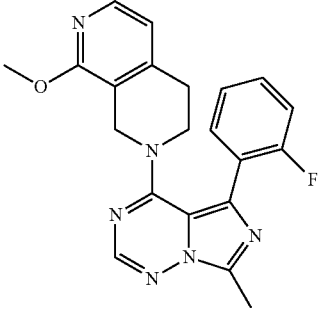 [SMILES: COc1nccc2c1CN(c1ncnn3c(C)nc(-c4ccccc4F)c13)CC2] | C6[1,3] | 391.1 |
| 69 | 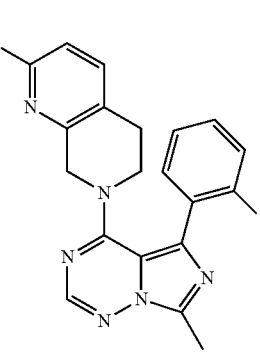 | C6[1] | 391.2 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 70 | 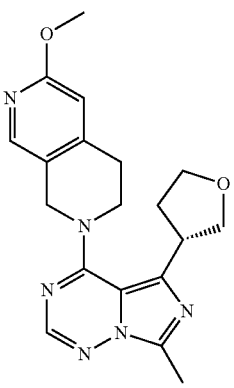 [SMILES: COc1cc2c(cn1)CN(c1ncnn3c(C)nc([C@@H]4CCOC4)c13)CC2] | Example 6 | 367.3 |
| 71 | 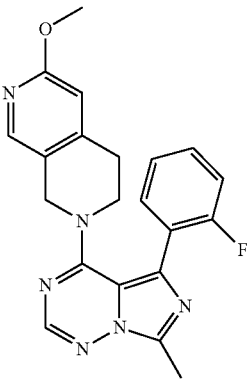 [SMILES: COc1cc2c(cn1)CN(c1ncnn3c(C)nc(-c4ccccc4F)c13)CC2] | C6[1] | 391.0 |
| 72 | 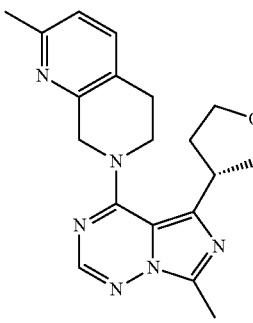 | Example 6 | 351.1 |
| 73 | 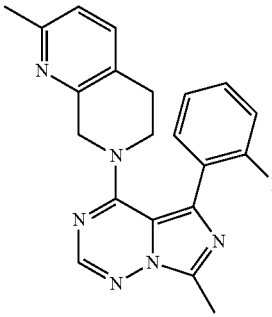 | Example 6; C[6] | 375.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 74 | 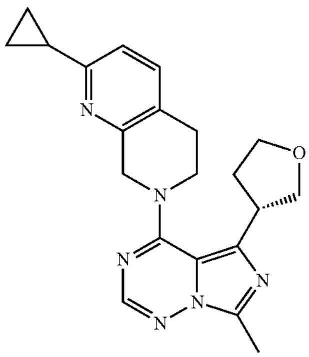 [SMILES: Cc1nc([C@@H]2CCOC2)c2c(N3CCc4ccc(C5CC5)nc4C3)ncnn12] | Example 6[4] | 377.1 |
| 75 | 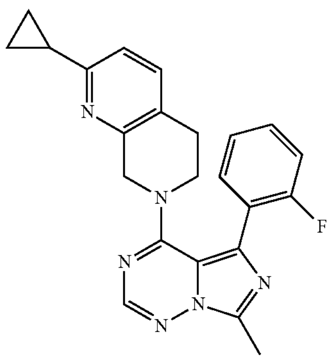 [SMILES: Cc1nc(-c2ccccc2F)c2c(N3CCc4ccc(C5CC5)nc4C3)ncnn12] | Example 6; C6[4] | 401.0 |
| 76 | 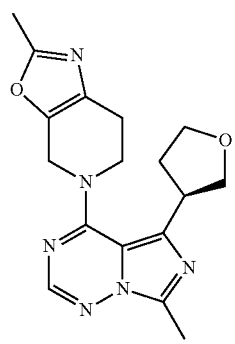 [SMILES: Cc1nc2c(o1)CN(c1ncnn3c(C)nc([C@H]4CCOC4)c13)CC2] | Example 10; C16 | 341.1 |
| 77 | 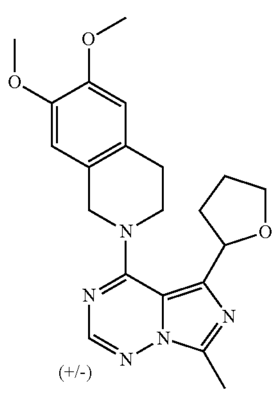 [SMILES: COc1cc2c(cc1OC)CN(c1ncnn3c(C)nc(C4CCCO4)c13)CC2] | C54[5,6] | 396.0 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 78 | 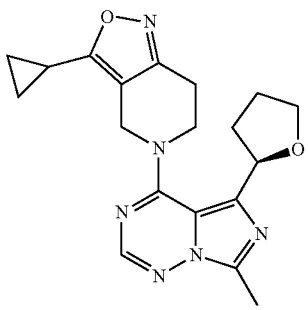 [SMILES: Cc1nc([C@H]2CCCO2)c2c(N3CCc4noc(C5CC5)c4C3)ncnn12] | C57[7], C30[5] | 367.1 |
| 79 | 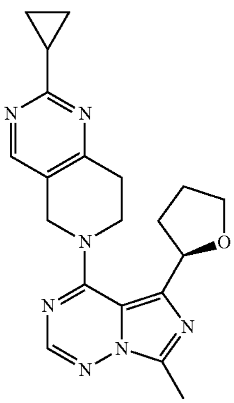 [SMILES: Cc1nc([C@H]2CCCO2)c2c(N3CCc4nc(C5CC5)ncc4C3)ncnn12] | C57[7,5] | 378.2 |
| 80 | 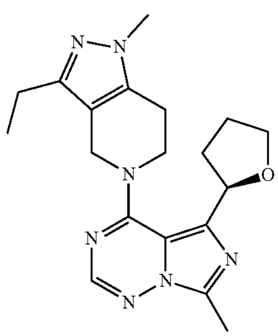 [SMILES: CCc1nn(C)c2c1CN(c1ncnn3c(C)nc([C@H]4CCCO4)c13)CC2] | C57[7,5,8] | 368.2 |
| 81 | 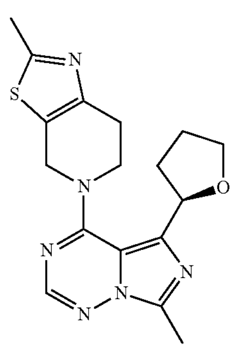 [SMILES: Cc1nc2c(s1)CN(c1ncnn3c(C)nc([C@H]4CCCO4)c13)CC2] | C57[7,5] | 357.1 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 82 | 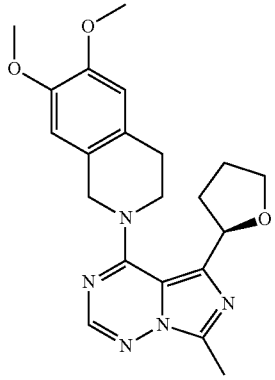 [SMILES: COc1cc2c(cc1OC)CN(c1ncnn3c(C)nc([C@H]4CCCO4)c13)CC2] | C57[7,5] | 396.2 |
| 83 | 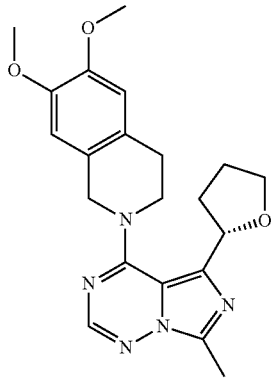 [SMILES: COc1cc2c(cc1OC)CN(c1ncnn3c(C)nc([C@@H]4CCCO4)c13)CC2] | C56[7,5,6] | 396.2 |
| 84 | 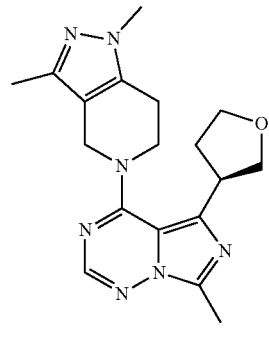 [SMILES: Cc1nn(C)c2c1CN(c1ncnn3c(C)nc([C@H]4CCOC4)c13)CC2] | Example 10; C16[8] | 354.1 (APCI) |
| 85 | 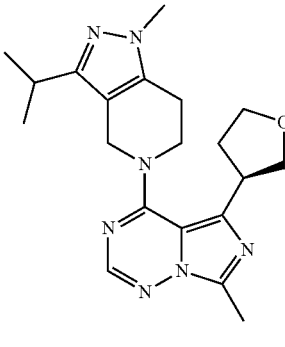 | Example 10; C16[8] | 382.1 (APCI) |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 86 | 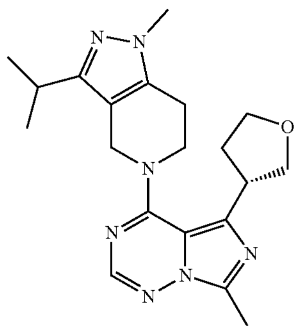 [SMILES: Cc1nc([C@@H]2CCOC2)c2c(N3CCc4c(c(C(C)C)nn4C)C3)ncnn12] | Example 10; C17[8] | 382.1 (APCI) |
| 87 | 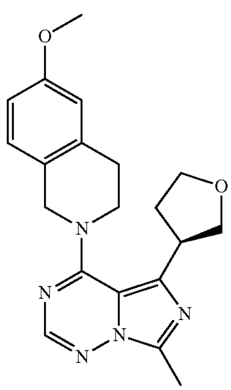 [SMILES: COc1ccc2c(c1)CCN(c1ncnn3c(C)nc([C@H]4CCOC4)c13)C2] | Example 10; C16 | 366.1 (APCI) |
| 88 | 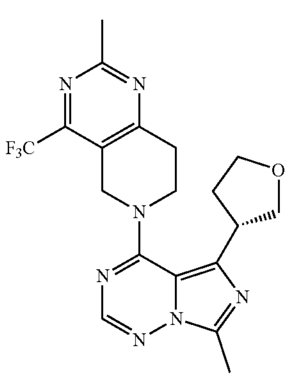 [SMILES: Cc1nc2c(c(C(F)(F)F)n1)CN(c1ncnn3c(C)nc([C@@H]4CCOC4)c13)CC2] | Example 6[9] | 420.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 89 | 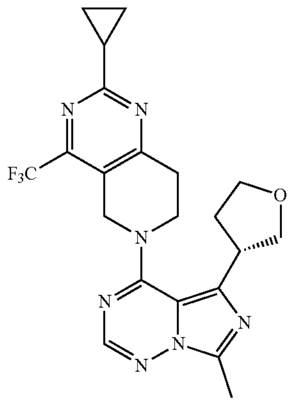 [SMILES: Cc1nc([C@@H]2CCOC2)c2c(N3CCc4nc(C5CC5)nc(C(F)(F)F)c4C3)ncnn12] | Example 6[9] | 446.1 |
| 90 | 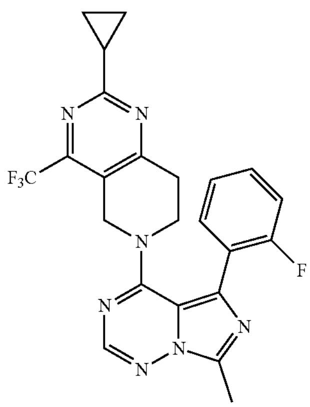 [SMILES: Cc1nc(-c2ccccc2F)c2c(N3CCc4nc(C5CC5)nc(C(F)(F)F)c4C3)ncnn12] | Example 6; C6[9] | 470.0 |
| 91 | 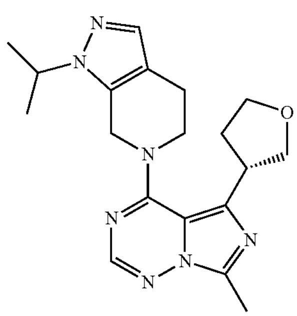 [SMILES: Cc1nc([C@@H]2CCOC2)c2c(N3CCc4cnn(C(C)C)c4C3)ncnn12] | Example 2; C17 | 368.2 |
| 92 | 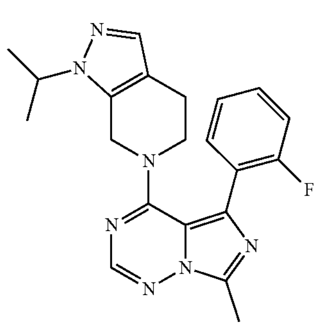 [SMILES: Cc1nc(-c2ccccc2F)c2c(N3CCc4cnn(C(C)C)c4C3)ncnn12] | Example 2 | 392.2 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 93 | 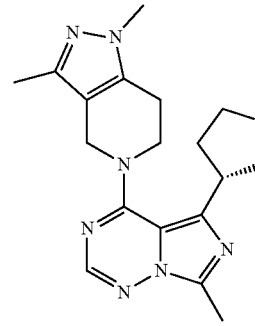 | Example 10; C17[8] | 354.4 |
| 94 | 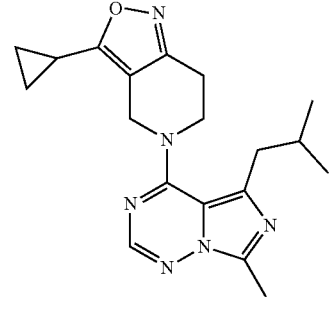 [SMILES: Cc1nc(CC(C)C)c2c(N3CCc4noc(C5CC5)c4C3)ncnn12] | Example 10; P3, C30 | 353.1 |
| 95 | 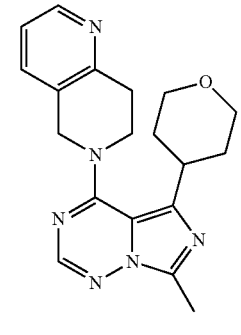 [SMILES: Cc1nc(C2CCOCC2)c2c(N3CCc4ncccc4C3)ncnn12] | Example 10; P2 | 351.1 |
| 96 | 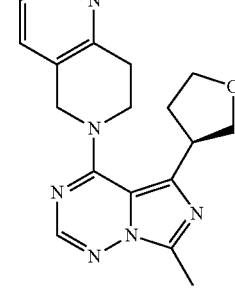 | Example 3; C16 | 336.7 (APCI) |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 97 | 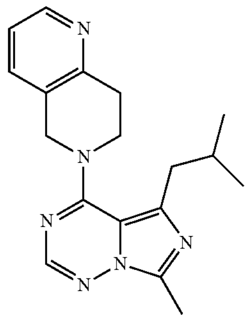 [SMILES: Cc1nc(CC(C)C)c2c(N3CCc4ncccc4C3)ncnn12] | Example 3; P3 | 322.8 (APCI) |
| 98 | 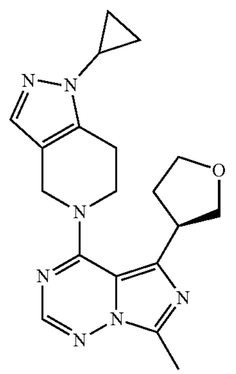 [SMILES: Cc1nc([C@H]2CCOC2)c2c(N3CCc4c(cnn4C4CC4)C3)ncnn12] | Example 10; C16[10] | 366.1 (APCI) |
| 99 | 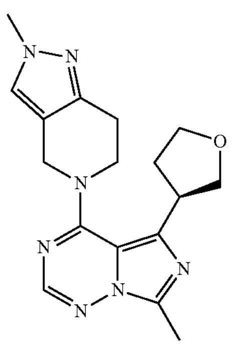 [SMILES: Cc1nc([C@H]2CCOC2)c2c(N3CCc4nn(C)cc4C3)ncnn12] | Example 10; C16 | 340.2 (APCI) |
| 100 | 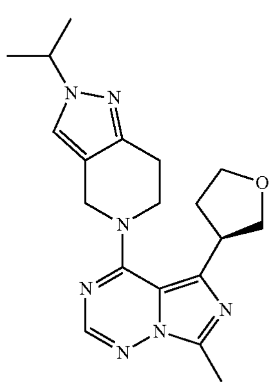 [SMILES: Cc1nc([C@H]2CCOC2)c2c(N3CCc4nn(C(C)C)cc4C3)ncnn12] | Example 10; C16[11] | 368.3 (APCI) |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 101 | 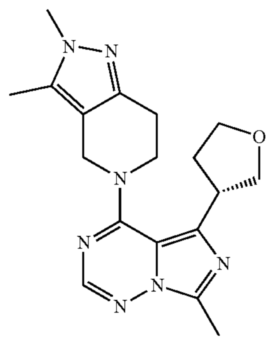 [SMILES: Cc1c2c(nn1C)CCN(c1ncnn3c(C)nc([C@@H]4CCOC4)c13)C2] | C15[12,8] | 354.2 |
| 102 | 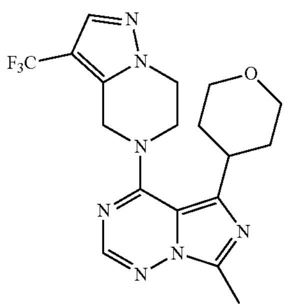 [SMILES: Cc1nc(C2CCOCC2)c2c(N3CCn4ncc(C(F)(F)F)c4C3)ncnn12] | Method A; P2, P1 | 408.1 |
| 103 | 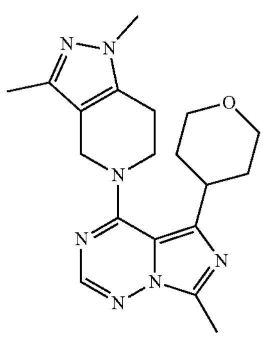 [SMILES: Cc1nn(C)c2c1CN(c1ncnn3c(C)nc(C4CCOCC4)c13)CC2] | Method A; P2[8] | 368.2 |
| 104 | 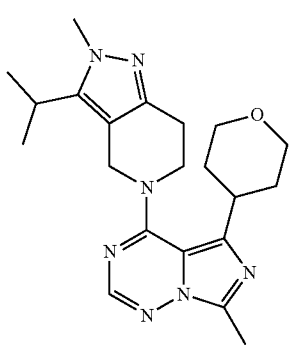 [SMILES: Cc1nc(C2CCOCC2)c2c(N3CCc4nn(C)c(C(C)C)c4C3)ncnn12] | Method A; P2[8] | 396.2 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 105 | 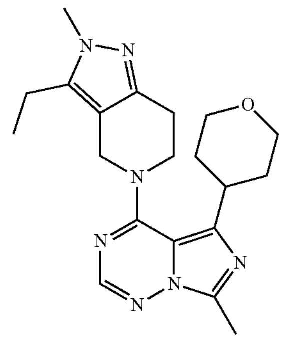 [SMILES: CCc1c2c(nn1C)CCN(c1ncnn3c(C)nc(C4CCOCC4)c13)C2] | Method A; P2[8] | 382.2 |
| 106 | 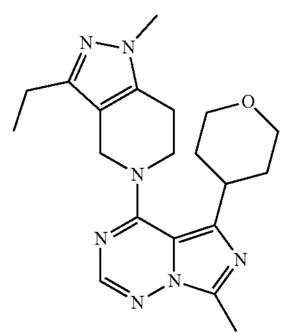 [SMILES: CCc1nn(C)c2c1CN(c1ncnn3c(C)nc(C4CCOCC4)c13)CC2] | Example 10; P2[8] | 382.2 (APCI) |
| 107 | 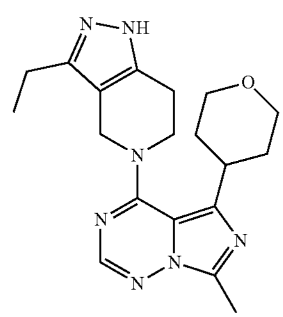 [SMILES: CCc1n[nH]c2c1CN(c1ncnn3c(C)nc(C4CCOCC4)c13)CC2] | Method A; P2[8] | 368.2 |
| 108 | 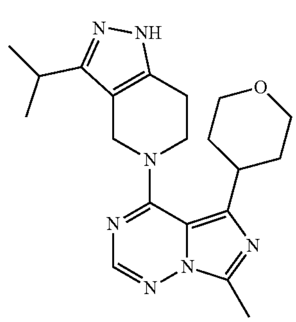 [SMILES: Cc1nc(C2CCOCC2)c2c(N3CCc4[nH]nc(C(C)C)c4C3)ncnn12] | Method A; P2[8] | 382.2 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 109 | 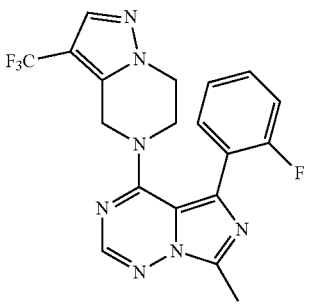 [SMILES: Cc1nc(-c2ccccc2F)c2c(N3CCn4ncc(C(F)(F)F)c4C3)ncnn12] | Method C; C6, P1 | 418.2 |
| 110 | 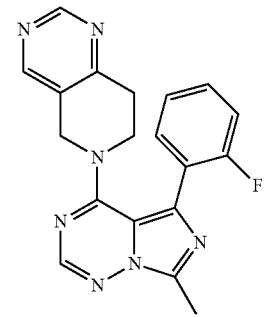 [SMILES: Cc1nc(-c2ccccc2F)c2c(N3CCc4ncncc4C3)ncnn12] | Method C; C6 | 362.1 |
| 111 | 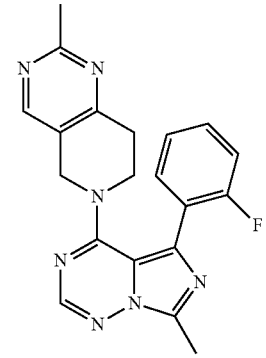 [SMILES: Cc1ncc2c(n1)CCN(c1ncnn3c(C)nc(-c4ccccc4F)c13)C2] | Example 2 | 376.4 |
| 112 | 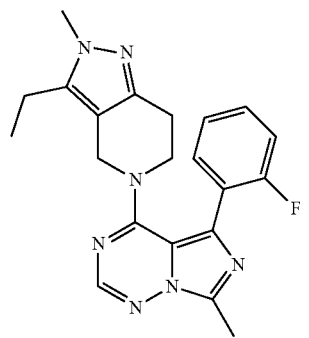 [SMILES: CCc1c2c(nn1C)CCN(c1ncnn3c(C)nc(-c4ccccc4F)c13)C2] | Method C; C6[8] | 392.2 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 113 | 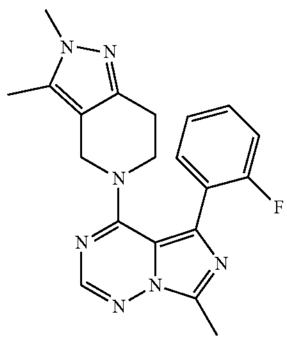 [SMILES: Cc1c2c(nn1C)CCN(c1ncnn3c(C)nc(-c4ccccc4F)c13)C2] | Method C; C6[8] | 378.2 |
| 114 | 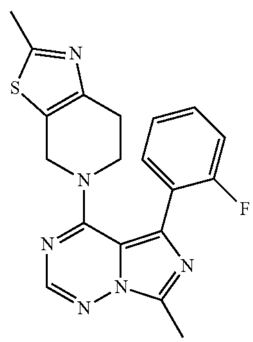 [SMILES: Cc1nc2c(s1)CN(c1ncnn3c(C)nc(-c4ccccc4F)c13)CC2] | Method C; C6 | 381.2 |
| 115 | 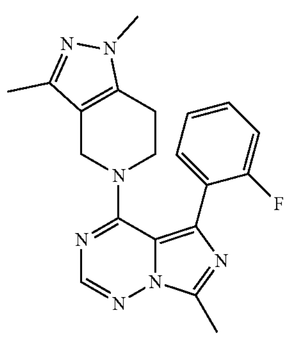 [SMILES: Cc1nn(C)c2c1CN(c1ncnn3c(C)nc(-c4ccccc4F)c13)CC2] | Method C; C6[8] | 378.2 |
| 116 | 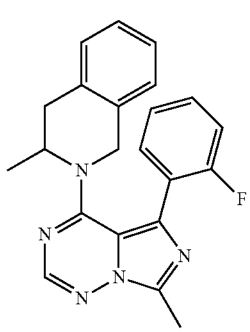 [SMILES: Cc1nc(-c2ccccc2F)c2c(N3Cc4ccccc4CC3C)ncnn12] | Method C; C6 | 374.2 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 117 | 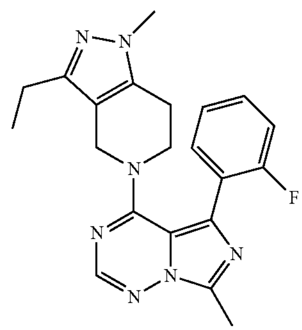 [SMILES: CCc1nn(C)c2c1CN(c1ncnn3c(C)nc(-c4ccccc4F)c13)CC2] | Method C; C6[8] | 392.2 |
| 118 | 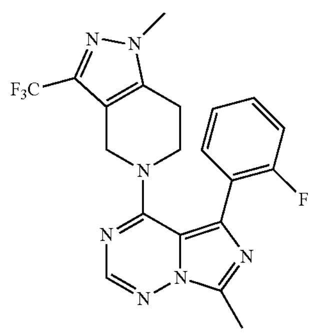 [SMILES: Cc1nc(-c2ccccc2F)c2c(N3CCc4c(c(C(F)(F)F)nn4C)C3)ncnn12] | Example 6; C6[8] | 432.2 |
| 119 | 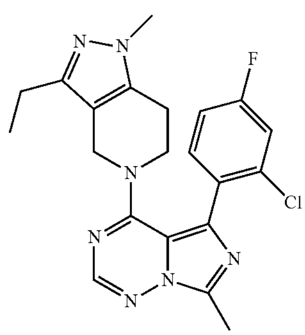 [SMILES: CCc1nn(C)c2c1CN(c1ncnn3c(C)nc(-c4ccc(F)cc4Cl)c13)CC2] | Method C[13,8] | 426.1, 428.1 |
| 120 | 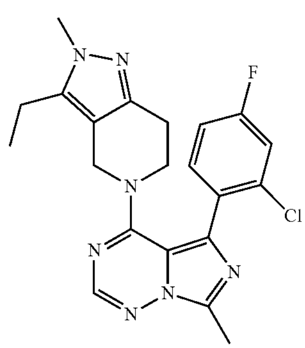 [SMILES: CCc1c2c(nn1C)CCN(c1ncnn3c(C)nc(-c4ccc(F)cc4Cl)c13)C2] | Method C[13] [8] | 426.1, 428.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 121 | 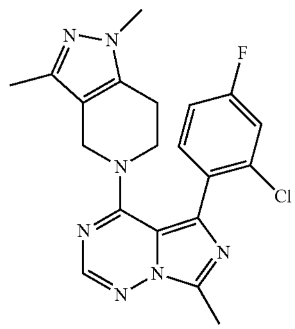 [SMILES: Cc1nn(C)c2c1CN(c1ncnn3c(C)nc(-c4ccc(F)cc4Cl)c13)CC2] | Method C[13,8] | 412.1, 414.1 |
| 122 | 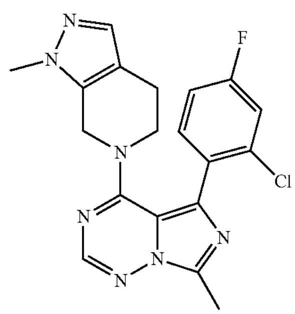 [SMILES: Cc1nc(-c2ccc(F)cc2Cl)c2c(N3CCc4cnn(C)c4C3)ncnn12] | Method C; C9[13] | 398.1, 400.1 |
| 123 | 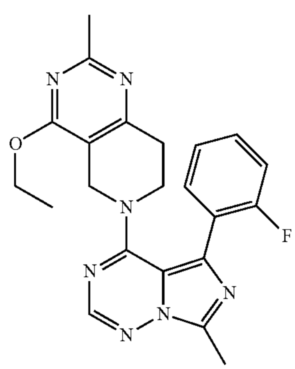 [SMILES: CCOc1nc(C)nc2c1CN(c1ncnn3c(C)nc(-c4ccccc4F)c13)CC2] | Method B; C6[14] | 420.1 |
| 124 | 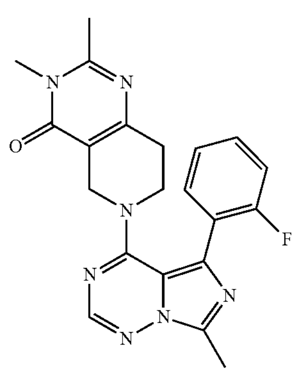 [SMILES: Cc1nc2c(c(=O)n1C)CN(c1ncnn3c(C)nc(-c4ccccc4F)c13)CC2] | Method B; C6[15] | 406.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 125 | 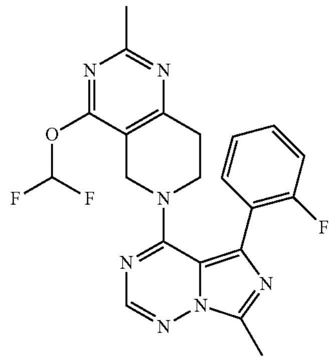 [SMILES: Cc1nc2c(c(OC(F)F)n1)CN(c1ncnn3c(C)nc(-c4ccccc4F)c13)CC2] | Method B; C6[16] | 442.1 |
| 126 | 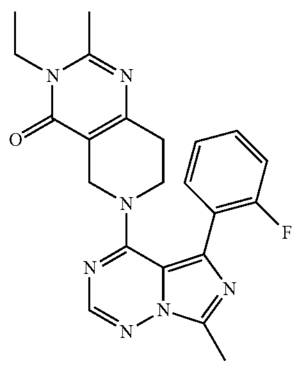 [SMILES: CCn1c(C)nc2c(c1=O)CN(c1ncnn3c(C)nc(-c4ccccc4F)c13)CC2] | Method B; C6[15] | 420.1 |
| 127 | 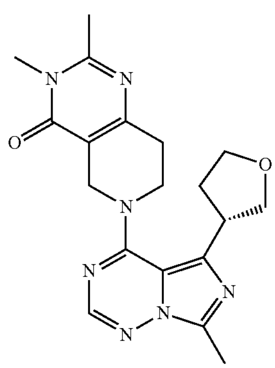 [SMILES: Cc1nc2c(c(=O)n1C)CN(c1ncnn3c(C)nc([C@@H]4CCOC4)c13)CC2] | Method B; C17[15] | 382.1 |
| 128 | 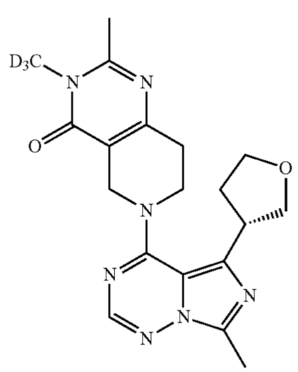 [SMILES: [2H]C([2H])([2H])n1c(C)nc2c(c1=O)CN(c1ncnn3c(C)nc([C@@H]4CCOC4)c13)CC2] | Method B; C17[15] | 385.2 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 129 | 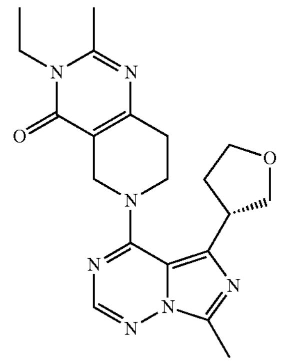 [SMILES: CCn1c(C)nc2c(c1=O)CN(c1ncnn3c(C)nc([C@@H]4CCOC4)c13)CC2] | Method B; C17[15] | 396.1 |
| 130 | 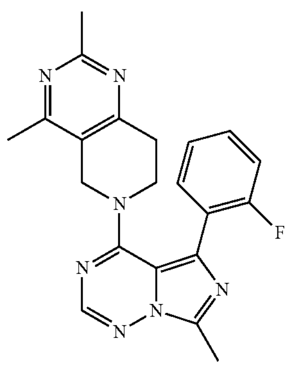 [SMILES: Cc1nc(C)c2c(n1)CCN(c1ncnn3c(C)nc(-c4ccccc4F)c13)C2] | Method B; C6[17] | 390.2 |
| 131 | 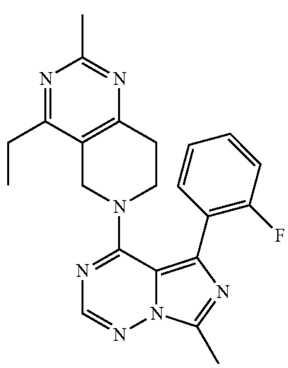 [SMILES: CCc1nc(C)nc2c1CN(c1ncnn3c(C)nc(-c4ccccc4F)c13)CC2] | Method B; C6[18] | 404.2 |
| 132 | 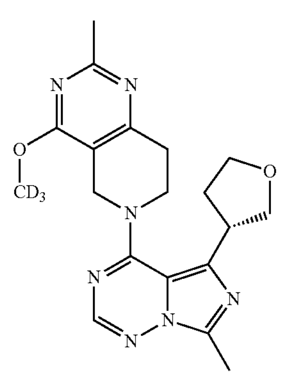 [SMILES: [2H]C([2H])([2H])Oc1nc(C)nc2c1CN(c1ncnn3c(C)nc([C@@H]4CCOC4)c13)CC2] | Method B; C17[14] | 385.3 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 133 | 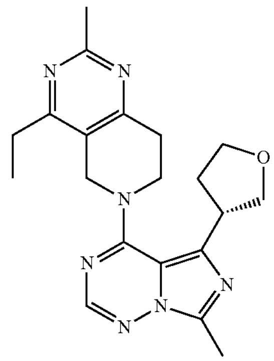 [SMILES: CCc1nc(C)nc2c1CN(c1ncnn3c(C)nc([C@@H]4CCOC4)c13)CC2] | Method B; C17[18] | 380.3 |
| 134 | 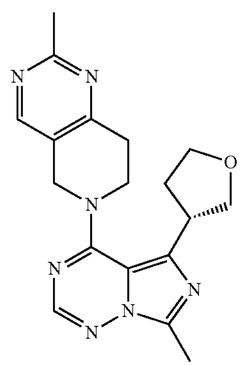 [SMILES: Cc1ncc2c(n1)CCN(c1ncnn3c(C)nc([C@@H]4CCOC4)c13)C2] | Example 2; C[17] | 352.2 |
| 135 | 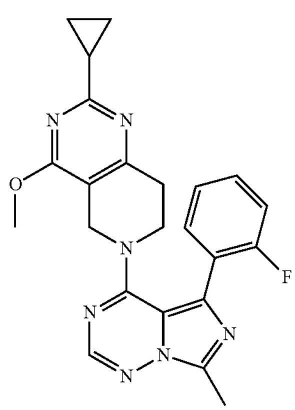 [SMILES: COc1nc(C2CC2)nc2c1CN(c1ncnn3c(C)nc(-c4ccccc4F)c13)CC2] | Example 2; C6[14] | 432.1 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 136 | 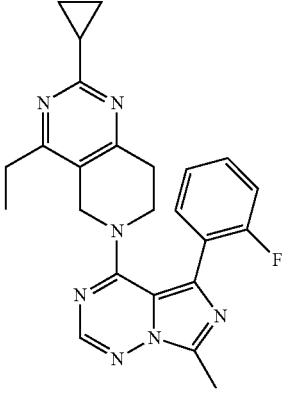 [SMILES: CCc1nc(C2CC2)nc2c1CN(c1ncnn3c(C)nc(-c4ccccc4F)c13)CC2] | Example 2; C6[19] | 430.2 |
| 137 | 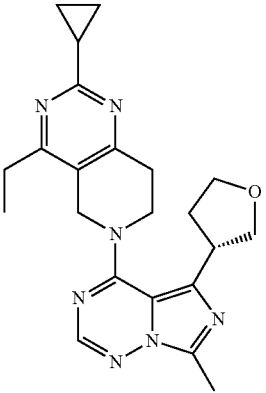 [SMILES: CCc1nc(C2CC2)nc2c1CN(c1ncnn3c(C)nc([C@@H]4CCOC4)c13)CC2] | Example 2; C17[19] | 406.3 |
| 138 | 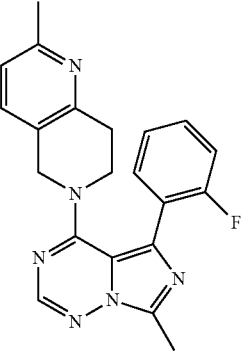 [SMILES: Cc1ccc2c(n1)CCN(c1ncnn3c(C)nc(-c4ccccc4F)c13)C2] | Example 2; C6 | 375.3 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 139 | 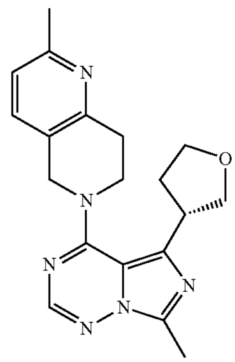 [SMILES: Cc1ccc2c(n1)CCN(c1ncnn3c(C)nc([C@@H]4CCOC4)c13)C2] | Example 2; C17 | 351.3 |
| 140 | 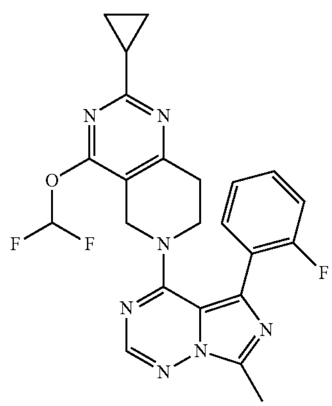 [SMILES: Cc1nc(-c2ccccc2F)c2c(N3CCc4nc(C5CC5)nc(OC(F)F)c4C3)ncnn12] | Example 2; C6[16] | 468.1 |
| 141 | 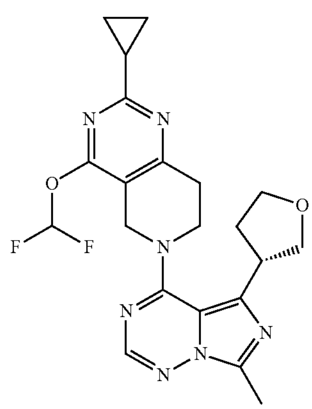 [SMILES: Cc1nc([C@@H]2CCOC2)c2c(N3CCc4nc(C5CC5)nc(OC(F)F)c4C3)ncnn12] | Example 2; C17[16] | 444.3 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 142 | 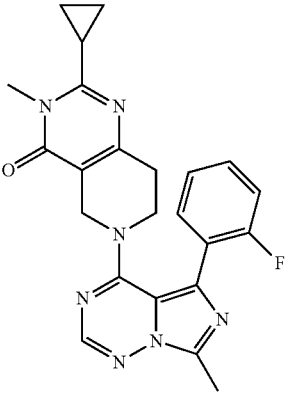 [SMILES: Cc1nc(-c2ccccc2F)c2c(N3CCc4nc(C5CC5)n(C)c(=O)c4C3)ncnn12] | Example 2; C6[15] | 432.1 |
| 143 | 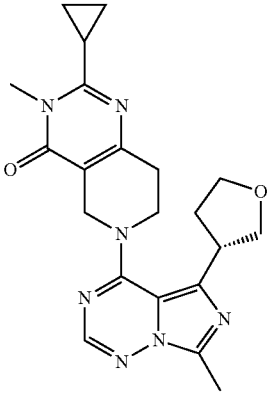 [SMILES: Cc1nc([C@@H]2CCOC2)c2c(N3CCc4nc(C5CC5)n(C)c(=O)c4C3)ncnn12] | Example 2; C17[15] | 408.2 |
| 144 | 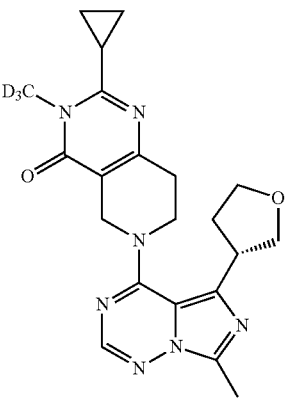 [SMILES: [2H]C([2H])([2H])n1c(C2CC2)nc2c(c1=O)CN(c1ncnn3c(C)nc([C@@H]4CCOC4)c13)CC2] | Example 2; C17[15] | 411.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 145 | 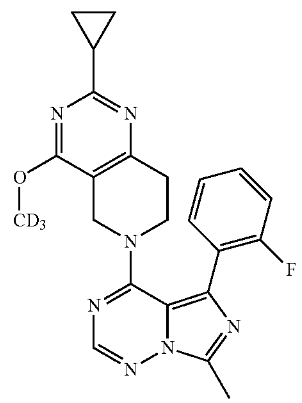 [SMILES: [2H]C([2H])([2H])Oc1nc(C2CC2)nc2c1CN(c1ncnn3c(C)nc(-c4ccccc4F)c13)CC2] | Example 2; C6[15] | 435.1 |
| 146 | 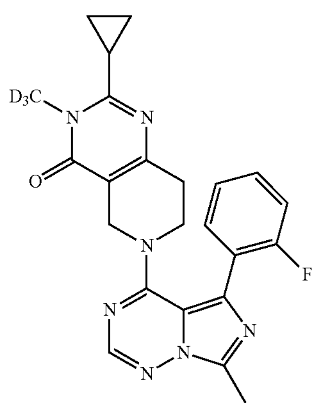 [SMILES: [2H]C([2H])([2H])n1c(C2CC2)nc2c(c1=O)CN(c1ncnn3c(C)nc(-c4ccccc4F)c13)CC2] | Example 2; C6[15] | 435.1 |
| 147 | 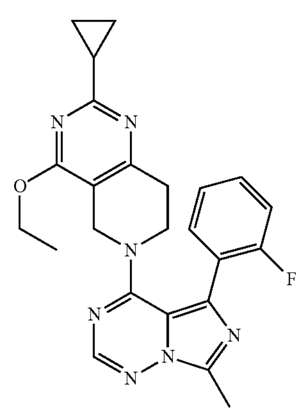 | Example 2; C6[15] | 446.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 148 | 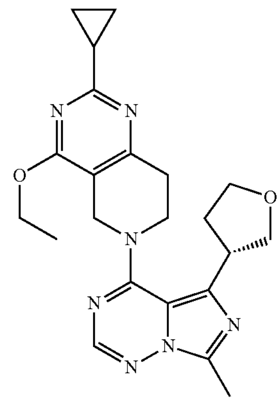 [SMILES: CCOc1nc(C2CC2)nc2c1CN(c1ncnn3c(C)nc([C@@H]4CCOC4)c13)CC2] | Example 2; C17[15] | 422.1 |
| 149 | 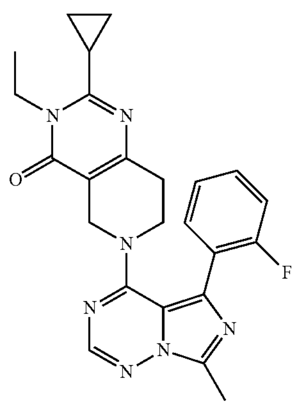 | Example 2; C6[15] | 446.1 |
| 150 | 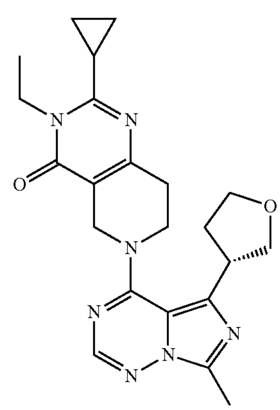 [SMILES: CCn1c(C2CC2)nc2c(c1=O)CN(c1ncnn3c(C)nc([C@@H]4CCOC4)c13)CC2] | Example 2; C17[15] | 422.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 151 | 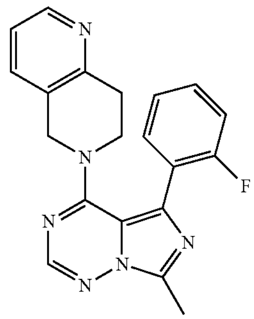 [SMILES: Cc1nc(-c2ccccc2F)c2c(N3CCc4ncccc4C3)ncnn12] | Example 2; C6 | 361.1 |
| 152 | 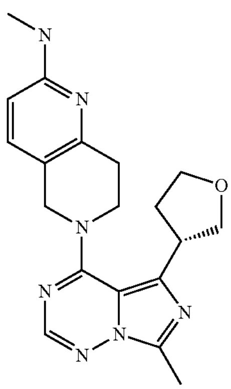 [SMILES: CNc1ccc2c(n1)CCN(c1ncnn3c(C)nc([C@@H]4CCOC4)c13)C2] | C17[1,20] | 366.2 |
| 153 | 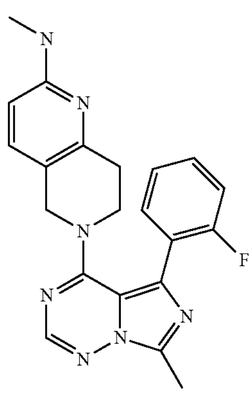 | C6[1,20] | 390.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 154 | 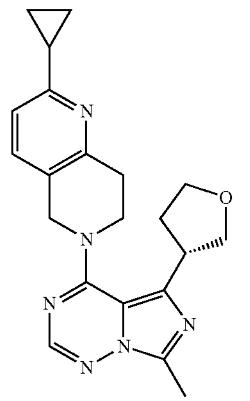 [SMILES: Cc1nc([C@@H]2CCOC2)c2c(N3CCc4nc(C5CC5)ccc4C3)ncnn12] | C17[1,21] | 377.2 |
| 155 | 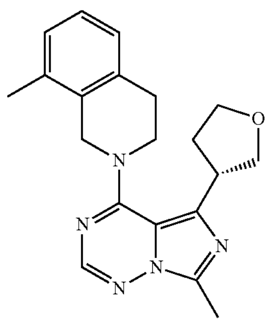 [SMILES: Cc1cccc2c1CN(c1ncnn3c(C)nc([C@@H]4CCOC4)c13)CC2] | Example 2; C17 | 350.3 |
| 156 | 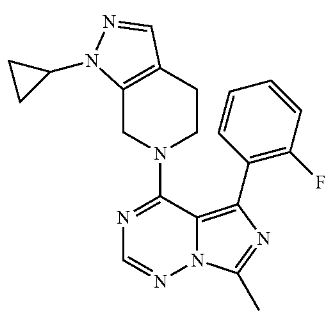 [SMILES: Cc1nc(-c2ccccc2F)c2c(N3CCc4cnn(C5CC5)c4C3)ncnn12] | C6, C27[1] | 390.1 |
| 157 | 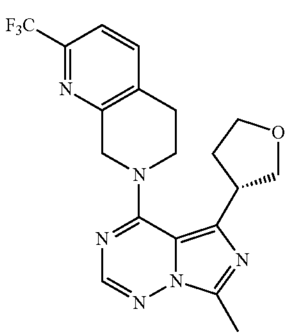 [SMILES: Cc1nc([C@@H]2CCOC2)c2c(N3CCc4ccc(C(F)(F)F)nc4C3)ncnn12] | Example 2; C17 | 405.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 158 | 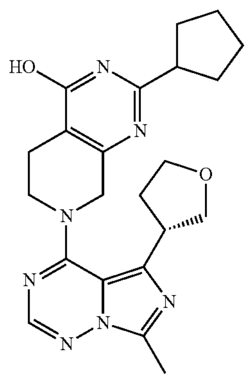 [SMILES: Cc1nc([C@@H]2CCOC2)c2c(N3CCc4c(O)nc(C5CCCC5)nc4C3)ncnn12] | Example 2; C17[14] | 422.1 |
| 159 | 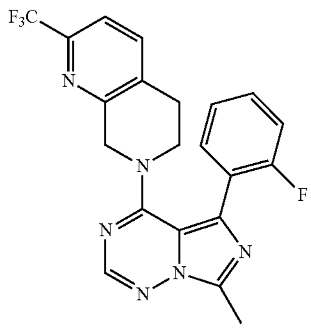 [SMILES: Cc1nc(-c2ccccc2F)c2c(N3CCc4ccc(C(F)(F)F)nc4C3)ncnn12] | Example 2; C6 | 429.0 |
| 160 | 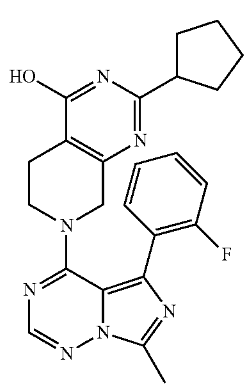 [SMILES: Cc1nc(-c2ccccc2F)c2c(N3CCc4c(O)nc(C5CCCC5)nc4C3)ncnn12] | Example 2; C6[14] | 446.1 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 161 | 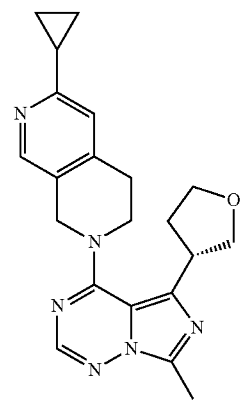 [SMILES: Cc1nc([C@@H]2CCOC2)c2c(N3CCc4cc(C5CC5)ncc4C3)ncnn12] | Example 2; C17[21] | 377.1 |
| 162 | 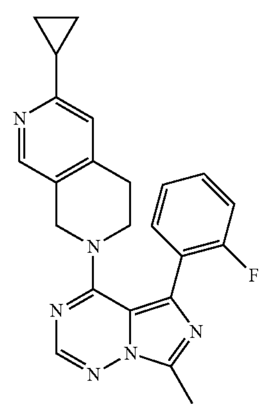 [SMILES: Cc1nc(-c2ccccc2F)c2c(N3CCc4cc(C5CC5)ncc4C3)ncnn12] | Example 2; C6[21] | 401.0 |
| 163 | 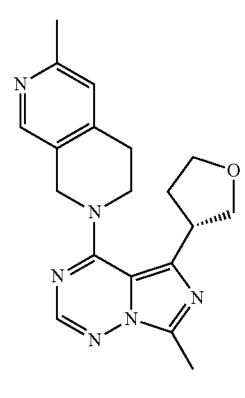 [SMILES: Cc1cc2c(cn1)CN(c1ncnn3c(C)nc([C@@H]4CCOC4)c13)CC2] | Example 2; C17[21] | 351.1 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 164 | 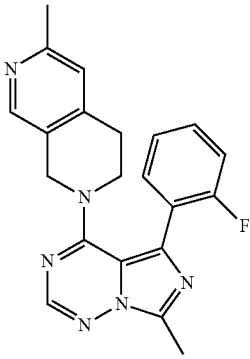 | Example 2; C6[21] | 375.0 |
| 165 | 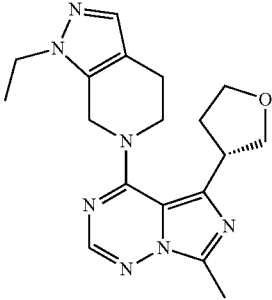 [SMILES: CCn1ncc2c1CN(c1ncnn3c(C)nc([C@@H]4CCOC4)c13)CC2] | Example 2; C17 | 354.1 |
| 166 | 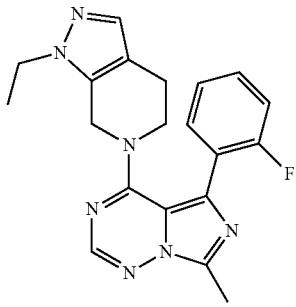 [SMILES: CCn1ncc2c1CN(c1ncnn3c(C)nc(-c4ccccc4F)c13)CC2] | Example 2; C6 | 378.0 |
| 167 | 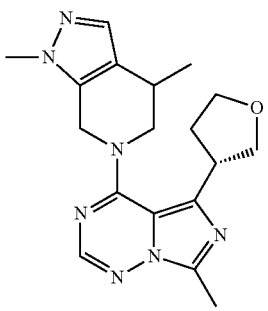 [SMILES: Cc1nc([C@@H]2CCOC2)c2c(N3Cc4c(cnn4C)C(C)C3)ncnn12] | Example 6; C17[22] | 354.1 |

TABLE 7-continued
Structures, Method of Preparation and Physicochemical Data for Examples 65-175.
| Example Number | Structure | Method of Preparation; Source of Non-commercial Starting Materials | LCMS m/z [M + H]+ |
|---|---|---|---|
| 168 | 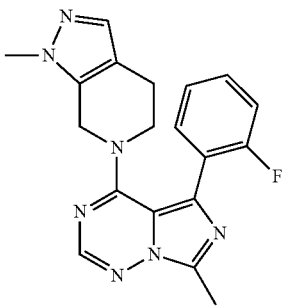 [SMILES: Cc1nc(-c2ccccc2F)c2c(N3CCc4cnn(C)c4C3)ncnn12] | Example 6; C6[22] | 378.0 |
| 169 | 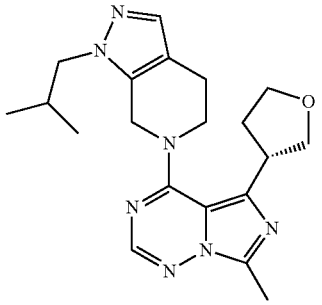 [SMILES: Cc1nc([C@@H]2CCOC2)c2c(N3CCc4cnn(CC(C)C)c4C3)ncnn12] | Example 2; C17 | 382.1 |
| 170 | 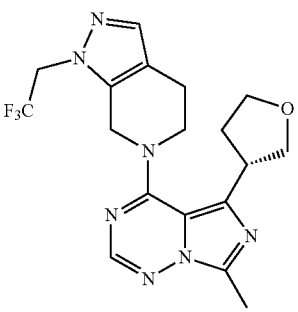 [SMILES: Cc1nc([C@@H]2CCOC2)c2c(N3CCc4cnn(CC(F)(F)F)c4C3)ncnn12] | Example 6: C17[23] | 408.1 |
| 171 | 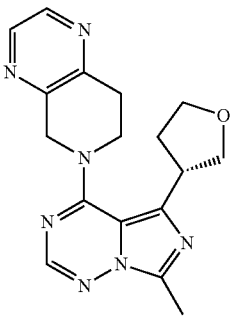 [SMILES: Cc1nc([C@@H]2CCOC2)c2c(N3CCc4nccnc4C3)ncnn12] | Example 6; C17 | 338.2 |

TABLE 7-continued

Structures, Method of Preparation and Physicochemical Data for Examples 65-175.

| Example Number | Structure | Method of Preparation; Source of Non-commercial Starting Materials | LCMS m/z [M + H]+ |
|---|---|---|---|
| 172 | 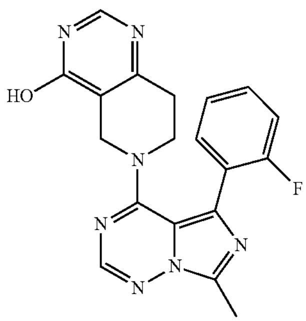 [SMILES: Cc1nc(-c2ccccc2F)c2c(N3CCc4ncnc(O)c4C3)ncnn12] | Example 1; C6 | 378.2 |
| 173 | 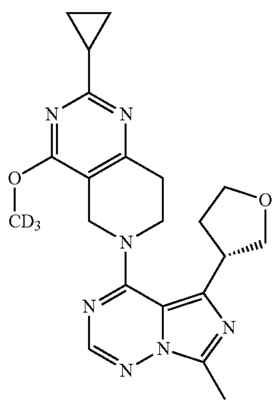 [SMILES: [2H]C([2H])([2H])Oc1nc(C2CC2)nc2c1CN(c1ncnn3c(C)nc([C@@H]4CCOC4)c13)CC2] | Example 2; C17[15] | 411.1 |
| 174 | 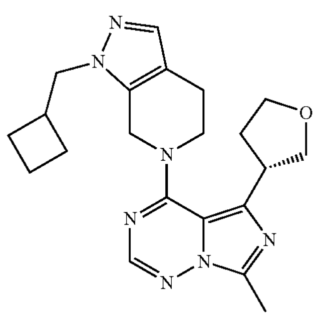 [SMILES: Cc1nc([C@@H]2CCOC2)c2c(N3CCc4cnn(CC5CCC5)c4C3)ncnn12] | Example 2; C17 | 394.2 |
| 175 | 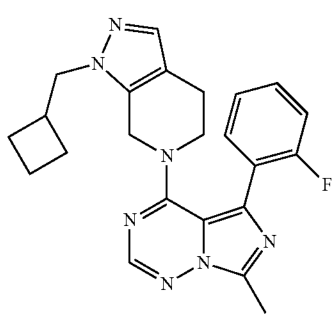 [SMILES: Cc1nc(-c2ccccc2F)c2c(N3CCc4cnn(CC5CCC5)c4C3)ncnn12] | Example 2; C6 | 418.3 |

1. The final coupling was carried out using cesium carbonate in dimethyl sulfoxide at 50° C.

2. N,N-Dimethyl-5,6,7,8-tetrahydro-1,6-naphthyridin-2-amine was prepared via reaction of 6-benzyl-2-chloro-5,6,7,8-tetrahydro-1,6-naphthyridine with dimethylamine, followed by hydrogenation to remove the protecting group.

3. See footnote 5 in Table 6.

4. 2-Chloro-1,7-naphthyridine was subjected to a Suzuki reaction with cyclopropylboronic acid; the product was reacted with benzyl bromide, and then reduced with sodium borohydride to afford 7-benzyl-2-cyclopropyl-5,6,7,8-tetrahydro-1,7-naphthyridine. Protecting group removal with 1-chloroethyl carbonochloridate provided 2-cyclopropyl-5,6,7,8-tetrahydro-1,7-naphthyridine.

5. The coupling was carried out in a microwave reactor using N,N-diisopropylethylamine in acetonitrile.

6. The 7-methylimidazo[5,1-f][1,2,4]triazin-4(3H)-one was converted to the corresponding triazole with phosphorus oxychloride.

7. The absolute stereochemistry of this intermediate or its precursor was arbitrarily assigned.

8. The amine side chain was, or may be, prepared according to the general procedure of W. T. Ashton et al., *Bioorg. Med. Chem. Lett.* 2005, 15, 2253-2258.

9. Reaction of tert-butyl 4-oxo-3-(trifluoroacetyl)piperidine-1-carboxylate with the appropriate amidine, followed by protecting group removal, afforded the 2-substituted-4-(trifluoromethyl)-5,6,7,8-tetrahydropyrido[4,3-d]pyrimidine.

10. A mixture of C46 and C47 was deprotected and used in synthesis of this Example. Regioisomers of the final product were separated via silica gel chromatography.

11. tert-Butyl (3E)-3-[(dimethylamino)methylidene]-4-oxopiperidine-1-carboxylate was condensed with propan-2-ylhydrazine; removal of the protecting group provided 2-(propan-2-yl)-4,5,6,7-tetrahydro-2H-pyrazolo[4,3-c]pyridine.

12. The final step was carried out via a condensation using benzotriazol-1-yloxytris(dimethylamino)phosphonium hexafluorophosphate and N,N-diisopropylethylamine.

13. 5-(2-Chloro-4-fluorophenyl)-7-methyl-4-(1H-1,2,4-triazol-1-yl)imidazo[5,1-f][1,2,4]triazine was prepared in similar fashion to C6 in Example 1, by employing 2-bromo-1-(2-chloro-4-fluorophenyl)ethanone.

14. Benzyl 4-hydroxy-2-methyl-7,8-dihydropyrido[4,3-d]pyrimidine-6(5H)-carboxylate, which may be prepared using the general method of E. Kretzschmar and P. Meisel, *Pharmazie* 1988, 43, 475-476, was converted to benzyl 4-chloro-2-methyl-7,8-dihydropyrido[4,3-d]pyrimidine-6(5H)-carboxylate via treatment with phosphorus oxychloride. Chloride displacement with the appropriate sodium alkoxide was followed by hydrogenolytic removal of the protecting group to afford the requisite 4-alkoxy-2-methyl-5,6,7,8-tetrahydropyrido[4,3-d]pyrimidine. Related compounds with other alkyl groups at the 2-position may be prepared in similar fashion.

15. Benzyl 4-hydroxy-2-alkyl-7,8-dihydropyrido[4,3-d]pyrimidine-6(5H)-carboxylate (see footnote 14) was reacted with cesium carbonate and the appropriate alkyl halide; benzyloxycarbonyl removal the provided the requisite amine.

16. Benzyl 4-hydroxy-2-alkyl-7,8-dihydropyrido[4,3-d]pyrimidine-6(5H)-carboxylate (see footnote 14) was reacted with sodium chloro(difluoro)acetate and cesium carbonate, followed by protecting group removal, to afford the amine.

17. See footnote 12 in Table 6.

18. Benzyl 4-oxo-3-propanoylpiperidine-1-carboxylate, prepared in similar manner to C28 in Example 6, was condensed with ethanimidamide hydrochloride; deprotection afforded the requisite 4-ethyl-2-methyl-5,6,7,8-tetrahydropyrido[4,3-d]pyrimidine.

19. Benzyl 4-chloro-2-cyclopropyl-7,8-dihydropyrido[4,3-d]pyrimidine-6(5H)-carboxylate, which was made using the general route described in footnote 14, was reacted with ethylmagnesium bromide under [1,2-bis(diphenylphosphino)ethane]dichloronickel(II) catalysis. Upon deprotection, the requisite 2-cyclopropyl-4-ethyl-5,6,7,8-tetrahydropyrido[4,3-d]pyrimidine was isolated.

20. 6-Benzyl-2-chloro-5,6,7,8-tetrahydro-1,6-naphthyridine was reacted with methylamine; deprotection afforded N-methyl-5,6,7,8-tetrahydro-1,6-naphthyridin-2-amine.

21. A Suzuki reaction between 6-benzyl-2-chloro-5,6,7,8-tetrahydro-1,6-naphthyridine and the appropriate boronic acid, followed by deprotection, provided the 2-substituted-5,6,7,8-tetrahydro-1,6-naphthyridine. Similar chemistry was employed for other regioisomers.

22. See footnote 3 in Table 6.

23. 1H-Pyrazolo[3,4-c]pyridine was alkylated with 1,1,1-trifluoro-2-iodoethane, then reduced via hydrogenation over platinum(IV) oxide to afford 1-(2,2,2-trifluoroethyl)-4,5,6,7-tetrahydro-1H-pyrazolo[3,4-c]pyridine.

Example 176

Inhibition of PDE10 Enzymatic Activity

The ability of a compound to inhibit PDE10 enzymatic activity can be demonstrated by any number of assays that are known in the art. The products of Examples 1-175 were tested in the assay described below.

PDE10 activity was measured using a scintillation assay (SPA-based method) similar to that previously described by Seeger, T. F. et al., Brain Research 985 (2003) 113-126. The compounds' relative activity as PDE10 inhibitors was investigated by assaying a fixed amount of enzyme in the presence of the test compound and low substrate concentration (cAMP) such that an $IC_{50}$ could be determined. More specifically, this assay uses a Scintillation Proximity Assay (SPA) to measure the inhibition of rat[1] and human recombinant[2] PDE10 enzyme activity by compounds in vitro (preparation of enzymes described below). The assay is performed in a 384-well format with 50 µL assay buffer (50 mM TRIS pH 7.5; 1.3 mM $MgCl_2$; 0.01% Brij) containing enough PDE10 to convert ~20% of 20 nM $^3$H-cAMP, and a range of inhibitors. Reactions are incubated for 30 minutes at 25° C. The addition of 20 µL of 8 mg/ml yttrium silicate SPA beads (PerkinElmer) stops the reaction. The plates are sealed (TopSeal, PerkinElmer) and the beads are allowed to settle for 8 hrs, after which they are read on the Trilux Microbeta overnight.

[1]Rat enzyme preparation:

[2]Human enzyme preparation:

Rat PDE10 coding sequence (amino acids 24 to 794 from the sequence with accession number NM_022236.1) was amplified from total rat brain RNA and cloned into the baculovirus expression vector pFastBac (Invitrogen) engineered to include a C-terminal His6 affinity tag to aid in purification as described in Seeger, T. F. et al., Brain Research 985 (2003) 113-126. The recombinant Bacmid was isolated and used to transfect sf9 insect cells to generate a viral stock. To generate cell paste for purification, sf21 cells were infected with the virus stock and cells were harvested 72 hours after infection as described in Seeger, T. F. et al., Brain Research 985 (2003) 113-126. Insect cell paste was lysed and after centrifugation, the supernatant was chromatographed on Ni-NTA agarose (Qiagen) followed by Mono Q (GE Healthcare Life Sciences) as described in Seeger, T. F. et al., Brain Research 985 (2003) 113-126.

Human PDE10A coding sequence (amino acids 21 to 797 from the sequence with accession number NP_001124162.1) was synthesized using codon optimization for insect expression and cloned into the baculovirus expression vector pFastBac (Invitrogen) engineered to include a N-terminal His6 affinity tag to aid in purification as described in Seeger, T. F. et al., Brain Research 985 (2003) 113-126. The recombinant Bacmid was isolated and used to transfect sf9 insect cells to generate a viral stock. To generate cell paste for purification, sf21 cells were infected with the virus stock and cells were harvested 72 hours after infection as described in Seeger, T. F. et al., Brain Research 985 (2003) 113-126. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE10A were chromatographed on Superdex 200 (GE Healthcare Life Sciences) in 50 mM Tris HCl pH 7.5, 150 mM NaCl, 1 mM EDTA, 10% glycerol, 2 mM TCEP, 1.5 mM benzamidine, EDTA-free protease inhibitors (Roche), and 5 µM E-64.

The following results were obtained:

TABLE 8

Biological Activity of Examples 1-175.

| Example Number | Rat PDE10 IC$_{50}$ (nm)$^a$ | Human PDE10A IC$_{50}$ (nm)$^a$ | IUPAC Name |
|---|---|---|---|
| 1 | 4.23$^b$ | 5.93$^b$ | 2-cyclopropyl-6-[5-(2-fluorophenyl)-7-methylimidazo[5,1-f][1,2,4]triazin-4-yl]-5,6,7,8-tetrahydropyrido[4,3-d]pyrimidine |
| 2 | 2.95$^b$ | 3.28 | 5-(2-fluorophenyl)-7-methyl-4-(1-methyl-1,4,5,7-tetrahydro-6H-pyrazolo[3,4-c]pyridin-6-yl)imidazo[5,1-f][1,2,4]triazine |
| 3 | 0.607$^b$ | 0.785$^b$ | 7-{7-methyl-5-[(3S)-tetrahydrofuran-3-yl]imidazo[5,1-f][1,2,4]triazin-4-yl}-5,6,7,8-tetrahydro-1,7-naphthyridine |
| 4 | 0.205 | 0.0386 | 8-(2-fluoroethoxy)-7-methoxy-2-{7-methyl-5-[(3S)-tetrahydrofuran-3-yl]imidazo[5,1-f][1,2,4]triazin-4-yl}-1,2,3,4-tetrahydroisoquinoline |
| 5 | 0.299 | 0.427 | 4-(1-cyclopropyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine |
| 6 | 0.364$^b$ | 0.406$^b$ | 4-(3-cyclopropyl-6,7-dihydro[1,2]oxazolo[4,3-c]pyridin-5(4H)-yl)-7-methyl-5-[(3S)-tetrahydrofuran-3-yl]imidazo[5,1-f][1,2,4]triazine |
| 7 | 8.44 | N.D.$^d$ | 6-[5-(2-chloro-4-fluorophenyl)-7-methylimidazo[5,1-f][1,2,4]triazin-4-yl]-2-cyclopropyl-5,6,7,8-tetrahydropyrido[4,3-d]pyrimidine |
| 8 | 2.36$^b$ | 3.41$^b$ | 7-methyl-4-(1-methyl-1,4,5,7-tetrahydro-6H-pyrazolo[3,4-c]pyridin-6-yl)-5-[(3S)-tetrahydrofuran-3-yl]imidazo[5,1-f][1,2,4]triazine |
| 9 | 0.892$^c$ | 1.14$^b$ | 4-(2-cyclopropyl-6,7-dihydro[1,3]oxazolo[5,4-c]pyridin-5(4H)-yl)-7-methyl-5-[(3S)-tetrahydrofuran-3-yl]imidazo[5,1-f][1,2,4]triazine |
| 10 | 0.560$^b$ | N.D. | 4-(3-isopropyl-1-methyl-1,4,6,7-tetrahydro-5H-pyrazolo[4,3-c]pyridin-5-yl)-7-methyl-5-(2-methylphenyl)imidazo[5,1-f][1,2,4]triazine |
| 11 | 0.174$^b$ | 0.265 | 4-(2-cyclopropyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine |
| 12 | 0.194$^b$ | 0.257$^b$ | 4-(3-cyclopropyl-1-methyl-1,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine |
| 13 | N.D. | 7.59$^b$ | 7-methyl-4-(1-methyl-1,4,5,7-tetrahydro-6H-pyrazolo[3,4-c]pyridin-6-yl)-5-[(2R)-tetrahydrofuran-2-yl]imidazo[5,1-f][1,2,4]triazine |
| 14 | 1.62 | N.D. | 6,7-dimethoxy-2-{7-methyl-5-[(3R)-tetrahydrofuran-3-yl]imidazo[5,1-f][1,2,4]triazin-4-yl}-1,2,3,4-tetrahydroisoquinoline, hydrochloride salt |
| 15 | 0.716$^b$ | N.D. | 6,7-dimethoxy-2-{7-methyl-5-[(3S)-tetrahydrofuran-3-yl]imidazo[5,1-f][1,2,4]triazin-4-yl}-1,2,3,4-tetrahydroisoquinoline, hydrochloride salt |
| 16 | 6.55 | N.D. | 2-cyclopropyl-6-{7-methyl-5-[(3S)-tetrahydrofuran-3-yl]imidazo{5,1-f][1,2,4]triazin-4-yl}-5,6,7,8-tetrahydropyrido[4,3-d]pyrimidine, hydrochloride salt |
| 17 | <0.240 | N.D. | 7,8-dimethoxy-2-{7-methyl-5-[(3S)-tetrahydrofuran-3-yl]imidazo[5,1-f][1,2,4]triazin-4-yl}-1,2,3,4-tetrahydroisoquinoline |
| 18 | 0.147$^b$ | 0.486$^b$ | 4-(3-ethyl-1-methyl-1,4,6,7-tetrahydro-5H-pyrazolo[4,3-c]pyridin-5-yl)-7-methyl-5-[(3S)- |

TABLE 8-continued

Biological Activity of Examples 1-175.

| Example Number | Rat PDE10 IC$_{50}$ (nm)$^a$ | Human PDE10A IC$_{50}$ (nm)$^a$ | IUPAC Name |
|---|---|---|---|
| | | | tetrahydrofuran-3-yl]imidazo[5,1-f][1,2,4]triazine, hydrochloride salt |
| 19 | 2.04$^b$ | 2.75 | 2-methoxy-7-{7-methyl-5-[(3S)-tetrahydrofuran-3-yl]imidazo[5,1-f][1,2,4]triazin-4-yl}-5,6,7,8-tetrahydro-1,7-naphthyridine |
| 20 | 1.72$^b$ | 2.51$^b$ | 4-[(4S)-1,4-dimethyl-1,4,5,7-tetrahydro-6H-pyrazolo[3,4-c]pyridin-6-yl]-7-methyl-5-[(3S)-tetrahydrofuran-3-yl]imidazo[5,1-f][1,2,4]triazine |
| 21 | 0.510$^b$ | 0.876$^b$ | 4-(3-isopropyl-1-methyl-1,4,6,7-tetrahydro-5H-pyrazolo[4,3-c]pyridin-5-yl)-7-methyl-5-(tetrahydro-2H-pyran-4-yl)imidazo[5,1-f][1,2,4]triazine |
| 22 | 5.20 | N.D. | 2-cyclopropyl-6-[7-methyl-5-(tetrahydrofuran-2-yl)imidazo[5,1-f][1,2,4]triazin-4-yl]-5,6,7,8-tetrahydropyrido[4,3-d]pyrimidine, hydrochloride salt |
| 23 | <5.55$^b$ | 2.53 | 7-methyl-4-(2-methyl-6,7-dihydro[1,3]thiazolo[5,4-c]pyridin-5(4H)-yl)-5-[(3R)-tetrahydrofuran-3-yl]imidazo[5,1-f][1,2,4]triazine, hydrochloride salt |
| 24 | <3.29$^b$ | N.D. | 2-cyclopropyl-6-[7-methyl-5-(2-methylphenyl)imidazo[5,1-f][1,2,4]triazin-4-yl]-5,6,7,8-tetrahydropyrido[4,3-d]pyrimidine |
| 25 | 1.12 | 1.41 | 6-[5-(2-fluorophenyl)-7-methylimidazo[5,1-f][1,2,4]triazin-4-yl]-3-methoxy-5,6,7,8-tetrahydro-1,6-naphthyridine |
| 26 | <2.26$^b$ | N.D. | 4-(2-cyclopropyl-2,4,6,7-tetrahydro-5H-pyrazolo[4,3-c]pyridin-5-yl)-7-methyl-5-[(3R)-tetrahydrofuran-3-yl]imidazo[5,1-f][1,2,4]triazine |
| 27 | 0.617 | 0.891 | 2-methoxy-6-{7-methyl-5-[(3S)-tetrahydrofuran-3-yl]imidazo[5,1-f][1,2,4]triazin-4-yl}-5,6,7,8-tetrahydro-1,6-naphthyridine |
| 28 | 0.236 | 0.582 | 8-methoxy-2-{7-methyl-5-[(3S)-tetrahydrofuran-3-yl]imidazo[5,1-f][1,2,4]triazin-4-yl}-1,2,3,4-tetrahydro-2,7-naphthyridine |
| 29 | 0.307 | 0.384$^b$ | 3-methoxy-6-{7-methyl-5-[(3S)-tetrahydrofuran-3-yl]imidazo[5,1-f][1,2,4]triazin-4-yl}-5,6,7,8-tetrahydro-1,6-naphthyridine |
| 30 | 3.52 | N.D. | 7-methyl-4[3-(propan-2-yl)-6,7-dihydro[1,2]oxazolo[4,3-c]pyridin-5(4H)-yl]-5-[(3S)-tetrahydrofuran-3-yl]imidazo[5,1-f][1,2,4]triazine |
| 31 | 3.73$^b$ | N.D. | 4-(3-ethyl-6,7-dihydro[1,2]oxazolo[4,3-c]pyridin-5(4H)-yl)-7-methyl-5-[(3S)-tetrahydrofuran-3-yl]imidazo[5,1-f][1,2,4]triazine |
| 32 | 3.74$^b$ | N.D. | 4-(3-ethyl-6,7-dihydro[1,2]oxazolo[4,5-c]pyridin-5(4H)-yl)-7-methyl-5-[(3S)-tetrahydrofuran-3-yl]imidazo[5,1-f][1,2,4]triazine |
| 33 | 23.3 | N.D. | 7-methyl-4-(3-methyl-6,7-dihydro[1,2]oxazolo[4,3-c]pyridin-5(4H)-yl)-5-[(3S)-tetrahydrofuran-3-yl]imidazo[5,1-f][1,2,4]triazine |
| 34 | 16.5 | N.D. | 7-methyl-4-(3-methyl-6,7-dihydro[1,2]oxazolo[4,5-c]pyridin-5(4H)-yl)-5-[(3S)-tetrahydrofuran-3-yl]imidazo[5,1-f][1,2,4]triazine |
| 35 | 0.123$^b$ | 0.275 | 4-ethoxy-2-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 36 | 0.440 | N.D. | 4-(difluoromethoxy)-2-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 37 | 0.177 | 0.277 | 4-methoxy-2-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 38 | 1.78 | 2.92 | 2,4-dimethyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 39 | 0.193$^b$ | N.D. | 2-cyclopropyl-4-methoxy-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 40 | 0.442 | 0.98 | 2-cyclopropyl-6-[5-(2-fluorophenyl)-7-methylimidazo[5,1-f][1,2,4]triazin-4-yl]-4-methyl-5,6,7,8-tetrahydropyrido[4,3-d]pyrimidine |

TABLE 8-continued

Biological Activity of Examples 1-175.

| Example Number | Rat PDE10 IC$_{50}$ (nm)[a] | Human PDE10A IC$_{50}$ (nm)[a] | IUPAC Name |
|---|---|---|---|
| 41 | <0.175 | N.D. | 2-cyclopropyl-4-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 42 | <3.23 | N.D. | 2-[5-(2-fluorophenyl)-7-methylimidazo[5,1-f][1,2,4]triazin-4-yl]-6,7-dimethoxy-1,2,3,4-tetrahydroisoquinoline |
| 43 | 0.465[b] | N.D. | 5-(2-fluorophenyl)-4-(3-isopropyl-1-methyl-1,4,6,7-tetrahydro-5H-pyrazolo[4,3-c]pyridin-5-yl)-7-methylimidazo[5,1-f][1,2,4]triazine |
| 44 | 0.102[b] | 0.11 | 4-(3-cyclopropyl-2-methyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine |
| 45 | 3.84 | N.D. | 4-(3-isopropyl-1-methyl-1,4,6,7-tetrahydro-5H-pyrazolo[4,3-c]pyridin-5-yl)-7-methyl-5-(tetrahydrofuran-2-yl)imidazo[5,1-f][1,2,4]triazine, hydrochloride salt |
| 46 | 1.98 | N.D. | 4-(3-cyclopropyl-6,7-dihydroisoxazolo[4,3-c]pyridin-5(4H)-yl)-5-(2-fluorophenyl)-7-methylimidazo[5,1-f][1,2,4]triazine |
| 47 | 0.758[b] | 1.42 | 6-{7-methyl-5-[(3S)-tetrahydrofuran-3-yl]imidazo[5,1-f][1,2,4]triazin-4-yl}-5,6,7,8-tetrahydro-1,6-naphthyridine |
| 48 | <1.00 | N.D. | 4-(3-ethyl-1-methyl-1,4,6,7-tetrahydro-5H-pyrazolo[4,3-c]pyridin-5-yl)-5-isobutyl-7-methylimidazo[5,1-f][1,2,4]triazine |
| 49 | 2.70 | N.D. | 4-(3-ethyl-1-methyl-1,4,6,7-tetrahydro-5H-pyrazolo[4,3-c]pyridin-5-yl)-5-(3-methoxyphenyl)-7-methylimidazo[5,1-f][1,2,4]triazine |
| 50 | 2.25 | 3.27 | 7-methyl-5-[(3R)-tetrahydrofuran-3-yl]-4-[3-(trifluoromethyl)-6,7-dihydropyrazolo[1,5-a]pyrazin-5(4H)-yl]imidazo[5,1-f][1,2,4]triazine |
| 51 | 13.5 | N.D. | 6,7-dichloro-2-{7-methyl-5-[(3R)-tetrahydrofuran-3-yl]imidazo[5,1-f][1,2,4]triazin-4-yl}-1,2,3,4-tetrahydroisoquinoline |
| 52 | 0.101[c] | N.D. | 2-cyclopropyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidin-4-ol, trifluoroacetate salt |
| 53 | 1.79 | N.D. | 4-(2-cyclopropyl-6,7-dihydro[1,3]oxazolo[5,4-c]pyridin-5(4H)-yl)-5-(2-fluorophenyl)-7-methylimidazo[5,1-f][1,2,4]triazine |
| 54 | 4.52 | N.D. | 4-(2-cyclopropyl-6,7-dihydro[1,3]oxazolo[5,4-c]pyridin-5(4H)-yl)-5-isobutyl-7-methylimidazo[5,1-f][1,2,4]triazine |
| 55 | 2.19 | N.D. | 2-cyclopropyl-6-(5-isobutyl-7-methylimidazo[5,1-f][1,2,4]triazin-4-yl)-5,6,7,8-tetrahydropyrido[4,3-d]pyrimidine |
| 56 | 5.34 | N.D. | 2-cyclopropyl-6-{7-methyl-5-[(3R)-tetrahydrofuran-3-yl]imidazo[5,1-f][1,2,4]triazin-4-yl}-5,6,7,8-tetrahydropyrido[4,3-d]pyrimidine, hydrochloride salt |
| 57 | 0.364[b] | 13.8 | 4-(3-ethyl-2-methyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine, hydrochloride salt |
| 58 | <1.16 | 1.12[b] | 6-methoxy-2-{7-methyl-5-[(3S)-tetrahydrofuran-3-yl]imidazo[5,1-f][1,2,4]triazin-4-yl}-1,2,3,4-tetrahydroisoquinoline, hydrochloride salt |
| 59 | 3.10[b] | N.D. | 6,7-dimethoxy-2-[7-methyl-5-(tetrahydro-2H-pyran-4-yl)imidazo[5,1-f][1,2,4]triazin-4-yl]-1,2,3,4-tetrahydroisoquinoline |
| 60 | 1.35[b] | N.D. | 7,8-dimethoxy-2-[7-methyl-5-(tetrahydro-2H-pyran-4-yl)imidazo[5,1-f][1,2,4]triazin-4-yl]-1,2,3,4-tetrahydroisoquinoline |
| 61 | <3.52[b] | N.D. | 2-cyclopropyl-6-[7-methyl-5-(tetrahydro-2H-pyran-4-yl)imidazo[5,1-f][1,2,4]triazin-4-yl]-5,6,7,8-tetrahydropyrido[4,3-d]pyrimidine |
| 62 | 3.87[b] | N.D. | 6,7-dimethoxy-2-[7-methyl-5-(2-methylphenyl)imidazo[5,1-f][1,2,4]triazin-4-yl]-1,2,3,4-tetrahydroisoquinoline |
| 63 | 133[b] | N.D. | 6-{7-methyl-5-[(3R)-tetrahydrofuran-3-yl]imidazo[5,1-f][1,2,4]triazin-4-yl}-5,6,7,8-tetrahydropyrido[4,3-d]pyrimidine, hydrochloride salt |

TABLE 8-continued

Biological Activity of Examples 1-175.

| Example Number | Rat PDE10 IC$_{50}$ (nm)[a] | Human PDE10A IC$_{50}$ (nm)[a] | IUPAC Name |
|---|---|---|---|
| 64 | 1.18 | N.D. | 2-(5-isobutyl-7-methylimidazo[5,1-f][1,2,4]triazin-4-yl)-6,7-dimethoxy-1,2,3,4-tetrahydroisoquinoline |
| 65 | 2.98 | N.D. | 7-[5-(2-fluorophenyl)-7-methylimidazo[5,1-f]1,2,4]triazin-4-yl]-5,6,7,8-tetrahydro-1,7-naphthyridine |
| 66 | 2.60 | N.D. | 6-[5-(2-fluorophenyl)-7-methylimidazo[5,1-f][1,2,4]triazin-4-yl]-2-methoxy-5,6,7,8-tetrahydro-1,6-naphthyridine |
| 67 | 0.325 | N.D. | 6-[5-(2-fluorophenyl)-7-methylimidazo[5,1-f][1,2,4]triazin-4-yl]-N,N-dimethyl-5,6,7,8-tetrahydro-1,6-naphthyridin-2-amine |
| 68 | 0.895 | N.D. | 2-[5-(2-fluorophenyl)-7-methylimidazo[5,1-f][1,2,4]triazin-4-yl]-8-methoxy-1,2,3,4-tetrahydro-2,7-naphthyridine |
| 69 | 7.30 | N.D. | 7-[5-(2-fluorophenyl)-7-methylimidazo[5,1-f][1,2,4]triazin-4-yl]-2-methoxy-5,6,7,8-tetrahydro-1,7-naphthyridine |
| 70 | 1.52[b] | 1.95 | 6-methoxy-2-{7-methyl-5-[(3S)-tetrahydrofuran-3-yl]imidazo[5,1-f][1,2,4]triazin-4-yl}-1,2,3,4-tetrahydro-2,7-naphthyridine |
| 71 | 3.41 | 5.77[b] | 2-[5-(2-fluorophenyl)-7-methylimidazo[5,1-f][1,2,4]triazin-4-yl]-6-methoxy-1,2,3,4-tetrahydro-2,7-naphthyridine |
| 72 | 0.255 | 0.539[b] | 2-methyl-7-{7-methyl-5-[(3S)-tetrahydrofuran-3-yl]imidazo[5,1-f][1,2,4]triazin-4-yl}-5,6,7,8-tetrahydro-1,7-naphthyridine |
| 73 | 6.81 | N.D. | 7-[5-(2-fluorophenyl)-7-methylimidazo[5,1-f][1,2,4]triazin-4-yl]-2-methyl-5,6,7,8-tetrahydro-1,7-naphthyridine |
| 74 | 0.0896 | 0.211 | 2-cyclopropyl-7-{7-methyl-5-[(3S)-tetrahydrofuran-3-yl]imidazo[5,1-f][1,2,4]triazin-4-yl}-5,6,7,8-tetrahydro-1,7-naphthyridine |
| 75 | 3.56 | 6.03 | 2-cyclopropyl-7-[5-(2-fluorophenyl)-7-methylimidazo[5,1-f][1,2,4]triazin-4-yl]-5,6,7,8-tetrahydro-1,7-naphthyridine |
| 76 | 22.9 | N.D. | 7-methyl-4-(2-methyl-6,7-dihydro[1,3]oxazolo[5,4-c]pyridin-5(4H)-yl)-5-[(3R)-tetrahydrofuran-3-yl]imidazo[5,1-f][1,2,4]triazine |
| 77 | 30 | N.D. | 6,7-dimethoxy-2-[7-methyl-5-(tetrahydrofuran-2-yl)imidazo[5,1-f][1,2,4]triazin-4-yl]-1,2,3,4-tetrahydroisoquinoline |
| 78 | 3.89[c] | N.D. | 4-(3-cyclopropyl-6,7-dihydro[1,2]oxazolo[4,3-c]pyridin-5(4H)-yl)-7-methyl-5-[(2R)-tetrahydrofuran-2-yl]imidazo[5,1-f][1,2,4]triazine |
| 79 | 11.2[c] | N.D. | 2-cyclopropyl-6-{7-methyl-5-[(2R)-tetrahydrofuran-2-yl]imidazo[5,1-1[1,2,4]triazin-4-yl}-5,6,7,8-tetrahydropyrido[4,3-d]pyrimidine |
| 80 | 17.6[c] | N.D. | 4-(3-ethyl-1-methyl-1,4,6,7-tetrahydro-5H-pyrazolo[4,3-c]pyridin-5-yl)-7-methyl-5-[(2R)-tetrahydrofuran-2-yl]imidazo[5,1-f][1,2,4]triazine |
| 81 | 9.73[c] | N.D. | 7-methyl-442-methyl-6,7-dihydro[1,3]thiazolo[5,4-c]pyridin-5(4H)-yl)-5-[(2R)-tetrahydrofuran-2-yl]imidazo[5,1-f][1,2,4]triazine |
| 82 | 37.2[c] | N.D. | 6,7-dimethoxy-2-{7-methyl-5-[(2R)-tetrahydrofuran-2-yl]imidazo[5,1-f][1,2,4]triazin-4-yl}-1,2,3,4-tetrahydroisoquinoline |
| 83 | 29.7[c] | N.D. | 6,7-dimethoxy-2-{7-methyl-5-[(2S)-tetrahydrofuran-2-yl]imidazo[5,1-f][1,2,4]triazin-4-yl}-1,2,3,4-tetrahydroisoquinoline |
| 84 | 8.10 | N.D. | 4-(1,3-dimethyl-1,4,6,7-tetrahydro-5H-pyrazolo[4,3-c]pyridin-5-yl)-7-methyl-5-[(3R)-tetrahydrofuran-3-yl]imidazo[5,1-f][1,2,4]triazine |
| 85 | 0.556[b] | 0.182 | 7-methyl-4-{1-methyl-3-(propan-2-yl)-1,4,6,7-tetrahydro-5H-pyrazolo[4,3-c]pyridin-5-yl}-5-[(3R)-tetrahydrofuran-3-yl]imidazo[5,1-f][1,2,4]triazine |
| 86 | 0.132[b] | 0.0444 | 7-methyl-4-[1-methyl-3-(propan-2-yl)-1,4,6,7-tetrahydro-5H-pyrazolo[4,3-c]pyridin-5-yl]-5-[(3S)-tetrahydrofuran-3-yl]imidazo[5,1-f][1,2,4]triazine |

TABLE 8-continued

Biological Activity of Examples 1-175.

| Example Number | Rat PDE10 IC$_{50}$ (nm)$^a$ | Human PDE10A IC$_{50}$ (nm)$^a$ | IUPAC Name |
|---|---|---|---|
| 87 | 1.26$^c$ | N.D. | 6-methoxy-2-{7-methyl-5-[(3R)-tetrahydrofuran-3-yl]imidazo[5,1-f][1,2,4]triazin-4-yl}-1,2,3,4-tetrahydroisoquinoline |
| 88 | 1.56 | 3.64 | 2-methyl-6-{7-methyl-5-[(3S)-tetrahydrofuran-3-yl]imidazo[5,1-f][1,2,4]triazin-4-yl}-4-(trifluoromethyl)-5,6,7,8-tetrahydropyrido[4,3-d]pyrimidine |
| 89 | 0.561 | N.D. | 2-cyclopropyl-6-{7-methyl-5-[(3S)-tetrahydrofuran-3-yl]imidazo[5,1-f][1,2,4]triazin-4-yl}-4-(trifluoromethyl)-5,6,7,8-tetrahydropyrido[4,3-d]pyrimidine |
| 90 | 3.09 | 4.55$^c$ | 2-cyclopropyl-6-[5-(2-fluorophenyl)-7-methylimidazo[5,1-f][1,2,4]triazin-4-yl]-4-(trifluoromethyl)-5,6,7,8-tetrahydropyrido[4,3-d]pyrimidine |
| 91 | 0.793$^c$ | 0.61$^b$ | 7-methyl-441-(propan-2-yl)-1,4,5,7-tetrahydro-6H-pyrazolo[3,4-c]pyridin-6-yl]-5-[(3S)-tetrahydrofuran-3-yl]imidazo[5,1-f][1,2,4]triazine |
| 92 | 0.997$^c$ | 0.664 | 5-(2-fluorophenyl)-7-methyl-4-[1-(propan-2-yl)-1,4,5,7-tetrahydro-6H-pyrazolo[3,4-c]pyridin-6-yl]imidazo[5,1-f][1,2,4]triazine |
| 93 | 0.761$^b$ | N.D. | 4-(1,3-dimethyl-1,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine |
| 94 | 2.89 | N.D. | 4-(3-cyclopropyl-6,7-dihydro[1,2]oxazolo[4,3-c]pyridin-5(4H)-yl)-7-methyl-5-(2-methylpropyl)imidazo[5,1-f][1,2,4]triazine |
| 95 | 10.1 | 8.82 | 6[7-methyl-5-(tetrahydro-2H-pyran-4-yl)imidazo[5,1-f][1,2,4]triazin-4-yl]-5,6,7,8-tetrahydro-1,6-naphthyridine |
| 96 | 5.20 | 4.8 | 6-{7-methyl-5-[(3R)-tetrahydrofuran-3-yl]imidazo[5,1-f][1,2,4]triazin-4-yl]-5,6,7,8-tetrahydro-1,6-naphthyridine |
| 97 | 9.05$^c$ | N.D. | 6-[7-methyl-5-(2-methylpropyl)imidazo[5,1-f][1,2,4]triazin-4-yl]-5,6,7,8-tetrahydro-1,6-naphthyridine |
| 98 | 11.6$^b$ | N.D. | 4-(1-cyclopropyl-1,4,6,7-tetrahydro-5H-pyrazolo[4,3-c]pyridin-5-yl)-7-methyl-5-[(3R)-tetrahydrofuran-3-yl]imidazo[5,1-f][1,2,4]triazine |
| 99 | 6.52 | N.D. | 7-methyl-4-(2-methyl-2,4,6,7-tetrahydro-5H-pyrazolo[4,3-c]pyridin-5-yl)-5-[(3R)-tetrahydrofuran-3-yl]imidazo[5,1-f][1,2,4]triazine |
| 100 | 23.0 | N.D. | 7-methyl-4-[2-(propan-2-yl)-2,4,6,7-tetrahydro-5H-pyrazolo[4,3-c]pyridin-5-yl]-5-[(3R)-tetrahydrofuran-3-yl]imidazo[5,1-f][1,2,4]triazine |
| 101 | 0.283 | N.D. | 4-(2,3-dimethyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine |
| 102 | 3.94 | N.D. | 7-methyl-5-(tetrahydro-2H-pyran-4-yl)-4-[3-(trifluoromethyl)-6,7-dihydropyrazolo[1,5-a]pyrazin-5(4H)-yl]imidazo[5,1-f][1,2,4]triazine |
| 103 | 5.13$^b$ | N.D. | 4-(1,3-dimethyl-1,4,6,7-tetrahydro-5H-pyrazolo[4,3-c]pyridin-5-yl)-7-methyl-5-(tetrahydro-2H-pyran-4-yl)imidazo[5,1-f][1,2,4]triazine |
| 104 | 1.08$^b$ | N.D. | 7-methyl-4[2-methyl-3-(propan-2-yl)-2,4,6,7-tetrahydro-5H-pyrazolo[4,3-c]pyridin-5-yl]-5-(tetrahydro-2H-pyran-4-yl)imidazo[5,1-f][1,2,4]triazine |
| 105 | 1.88$^b$ | N.D. | 4-(3-ethyl-2-methyl-2,4,6,7-tetrahydro-5H-pyrazolo[4,3-c]pyridin-5-yl)-7-methyl-5-(tetrahydro-2H-pyran-4-yl)imidazo[5,1-f][1,2,4]triazine |
| 106 | 1.44$^b$ | N.D. | 4-(3-ethyl-1-methyl-1,4,6,7-tetrahydro-5H-pyrazolo[4,3-c]pyridin-5-yl)-7-methyl-5-(tetrahydro-2H-pyran-4-yl)imidazo[5,1-f][1,2,4]triazine |
| 107 | 0.959$^b$ | N.D. | 4-(3-ethyl-1,4,6,7-tetrahydro-5H-pyrazolo[4,3-c]pyridin-5-yl)-7-methyl-5-(tetrahydro-2H-pyran-4-yl)imidazo[5,1-f][1,2,4]triazine |
| 108 | 0.902 | N.D. | 7-methyl-4-(3-(propan-2-yl)-1,4,6,7-tetrahydro-5H-pyrazolo[4,3-c]pyridin-5-yl)-5-(tetrahydro-2H-pyran-4-yl)imidazo[5,1-f][1,2,4]triazine |

TABLE 8-continued

Biological Activity of Examples 1-175.

| Example Number | Rat PDE10 IC$_{50}$ (nm)$^a$ | Human PDE10A IC$_{50}$ (nm)$^a$ | IUPAC Name |
|---|---|---|---|
| 109 | 1.73 | N.D. | 5-(2-fluorophenyl)-7-methyl-4-[3-(trifluoromethyl)-6,7-dihydropyrazolo[1,5-a]pyrazin-5(4H)-yl]imidazo[5,1-f][1,2,4]triazine |
| 110 | 20.0 | N.D. | 6-[5-(2-fluorophenyl)-7-methylimidazo[5,1-f][1,2,4]triazin-4-yl]-5,6,7,8-tetrahydropyrido[4,3-d]pyrimidine |
| 111 | 6.85$^b$ | 18.6 | 6-[5-(2-fluorophenyl)-7-methylimidazo[5,1-f][1,2,4]triazin-4-yl]-2-methyl-5,6,7,8-tetrahydropyrido[4,3-d]pyrimidine |
| 112 | 0.147 | N.D. | 4-(3-ethyl-2-methyl-2,4,6,7-tetrahydro-5H-pyrazolo[4,3-c]pyridin-5-yl)-5-(2-fluorophenyl)-7-methylimidazo[5,1-f][1,2,4]triazine |
| 113 | 0.638 | N.D. | 4-(2,3-dimethyl-2,4,6,7-tetrahydro-5H-pyrazolo[4,3-c]pyridin-5-yl)-542-fluorophenyl)-7-methylimidazo[5,1-f][1,2,4]triazine |
| 114 | 1.49 | N.D. | 5-(2-fluorophenyl)-7-methyl-4-(2-methyl-6,7-dihydro[1,3]thiazolo[5,4-c]pyridin-5(4H)-yl)imidazo[5,1-f][1,2,4]triazine |
| 115 | 0.834 | N.D. | 4-(1,3-dimethyl-1,4,6,7-tetrahydro-5H-pyrazolo[4,3-c]pyridin-5-yl)-5-(2-fluorophenyl)-7-methylimidazo[5,1-f][1,2,4]triazine |
| 116 | 8.01$^c$ | N.D. | 2-[5-(2-fluorophenyl)-7-methylimidazo[5,1-f][1,2,4]triazin-4-yl]-3-methyl-1,2,3,4-tetrahydroisoquinoline |
| 117 | 0.336 | N.D. | 4-(3-ethyl-1-methyl-1,4,6,7-tetrahydro-5H-pyrazolo[4,3-c]pyridin-5-yl)-542-fluorophenyl)-7-methylimidazo[5,1-f][1,2,4]triazine |
| 118 | 0.943$^b$ | 1.28$^b$ | 5-(2-fluorophenyl)-7-methyl-4-[1-methyl-3-(trifluoromethyl)-1,4,6,7-tetrahydro-5H-pyrazolo[4,3-c]pyridin-5-yl]imidazo[5,1-f][1,2,4]triazine |
| 119 | 0.519 | N.D. | 5-(2-chloro-4-fluorophenyl)-4-(3-ethyl-1-methyl-1,4,6,7-tetrahydro-5H-pyrazolo[4,3-c]pyridin-5-yl)-7-methylimidazo[5,1-f][1,2,4]triazine |
| 120 | 0.233 | N.D. | 5-(2-chloro-4-fluorophenyl)-4-(3-ethyl-2-methyl-2,4,6,7-tetrahydro-5H-pyrazolo[4,3-c]pyridin-5-yl)-7-methylimidazo[5,1-f][1,2,4]triazine |
| 121 | 1.35 | N.D. | 5-(2-chloro-4-fluorophenyl)-4-(1,3-dimethyl-1,4,6,7-tetrahydro-5H-pyrazolo[4,3-c]pyridin-5-yl)-7-methylimidazo[5,1-f][1,2,4]triazine |
| 122 | 2.65 | N.D. | 5-(2-chloro-4-fluorophenyl)-7-methyl-4-(1-methyl-1,4,5,7-tetrahydro-6H-pyrazolo[3,4-c]pyridin-6-yl)imidazo[5,1-f][1,2,4]triazine |
| 123 | 1.43 | N.D. | 4-ethoxy-6-[5-(2-fluorophenyl)-7-methylimidazo[5,1-f][1,2,4]triazin-4-yl]-2-methyl-5,6,7,8-tetrahydropyrido[4,3-d]pyrimidine |
| 124 | 2.71 | N.D. | 6-[5-(2-fluorophenyl)-7-methylimidazo[5,1-f][1,2,4]triazin-4-yl]-2,3-dimethyl-5,6,7,8-tetrahydropyrido[4,3-d]pyrimidin-4(3H)-one |
| 125 | 6.4 | N.D. | 4-(difluoromethoxy)-6-[5-(2-fluorophenyl)-7-methylimidazo[5,1-f][1,2,4]triazin-4-yl]-2-methyl-5,6,7,8-tetrahydropyrido[4,3-d]pyrimidine |
| 126 | 1.19 | N.D. | 3-ethyl-6-[5-(2-fluorophenyl)-7-methylimidazo[5,1-f][1,2,4]triazin-4-yl]-2-methyl-5,6,7,8-tetrahydropyrido[4,3-d]pyrimidin-4(3H)-one |
| 127 | 0.484 | N.D. | 2,3-dimethyl-6-{7-methyl-5-[(3S)-tetrahydrofuran-3-yl]imidazo[5,1-1[1,2,4]triazin-4-yl}-5,6,7,8-tetrahydropyrido[4,3-d]pyrimidin-4(3H)-one |
| 128 | 0.367 | 1.62 | 2-methyl-3-($^2$H$_3$)methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidin-4(3H)-one |
| 129 | 0.0998 | N.D. | 3-ethyl-2-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidin-4(3H)-one |
| 130 | 1.65 | 2.34 | 6-[5-(2-fluorophenyl)-7-methylimidazo[5,1-f][1,2,4]triazin-4-yl]-2,4-dimethyl-5,6,7,8-tetrahydropyrido[4,3-d]pyrimidine |
| 131 | 0.456 | 0.573 | 4-ethyl-6-[5-(2-fluorophenyl)-7-methylimidazo[5,1-f][1,2,4]triazin-4-yl]-2-methyl-5,6,7,8-tetrahydropyrido[4,3-d]pyrimidine |

TABLE 8-continued

Biological Activity of Examples 1-175.

| Example Number | Rat PDE10 IC$_{50}$ (nm)$^a$ | Human PDE10A IC$_{50}$ (nm)$^a$ | IUPAC Name |
|---|---|---|---|
| 132 | 0.174 | 0.346 | 2-methyl-4-[($^2$H$_3$)methyloxy]-6-{7-methyl-5-[(3S)-tetrahydrofuran-3-yl]imidazo[5,1-1[1,2,4]triazin-4-yl}-5,6,7,8-tetrahydropyrido[4,3-d]pyrimidine |
| 133 | 0.370 | 0.625 | 4-ethyl-2-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 134 | 2.44 | 4.51 | 2-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 135 | 1.04 | 1.00$^b$ | 2-cyclopropyl-6-[5-(2-fluorophenyl)-7-methylimidazo[5,1-f][1,2,4]triazin-4-yl]-4-methoxy-5,6,7,8-tetrahydropyrido[4,3-d]pyrimidine |
| 136 | 0.265 | N.D. | 2-cyclopropyl-4-ethyl-6-[5-(2-fluorophenyl)-7-methylimidazo[5,1-f][1,2,4]triazin-4-yl]-5,6,7,8-tetrahydropyrido[4,3-d]pyrimidine |
| 137 | 0.095$^b$ | 0.0777$^b$ | 2-cyclopropyl-4-ethyl-6-{7-methyl-5-[(3S)-tetrahydrofuran-3-yl]imidazo[5,1-1[1,2,4]triazin-4-yl}-5,6,7,8-tetrahydropyrido[4,3-d]pyrimidine |
| 138 | 0.49 | N.D. | 6-[5-(2-fluorophenyl)-7-methylimidazo[5,1-f][1,2,4]triazin-4-yl]-2-methyl-5,6,7,8-tetrahydro-1,6-naphthyridine |
| 139 | 0.270 | 0.279$^b$ | 2-methyl-6-{7-methyl-5-[(3S)-tetrahydrofuran-3-yl]imidazo[5,1-f][1,2,4]triazin-4-yl}-5,6,7,8-tetrahydro-1,6-naphthyridine |
| 140 | 1.50 | N.D. | 2-cyclopropyl-4-(difluoromethoxy)-6-[5-(2-fluorophenyl)-7-methylimidazo[5,1-f][1,2,4]triazin-4-yl]-5,6,7,8-tetrahydropyrido[4,3-d]pyrimidine |
| 141 | 0.142 | N.D. | 2-cyclopropyl-4-(difluoromethoxy)-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 142 | 0.815 | 1.31$^b$ | 2-cyclopropyl-6-[5-(2-fluorophenyl)-7-methylimidazo[5,1-f][1,2,4]triazin-4-yl]-3-methyl-5,6,7,8-tetrahydropyrido[4,3-d]pyrimidin-4(3H)-one |
| 143 | 0.106 | 0.219 | 2-cyclopropyl-3-methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidin-4(3H)-one |
| 144 | 0.0837 | N.D. | 2-cyclopropyl-3-($^2$H$_3$)methyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidin-4(3H)-one |
| 145 | 0.541 | N.D. | 2-cyclopropyl-6-[5-(2-fluorophenyl)-7-methylimidazo[5,1-f][1,2,4]triazin-4-yl]-4-[($^2$H$_3$)methyloxy]-5,6,7,8-tetrahydropyrido[4,3-d]pyrimidine |
| 146 | 1.14 | N.D. | 2-cyclopropyl-6-[5-(2-fluorophenyl)-7-methylimidazo[5,1-f][1,2,4]triazin-4-yl]-3-($^2$H$_3$)methyl-5,6,7,8-tetrahydropyrido[4,3-d]pyrimidin-4(3H)-one |
| 147 | 9.98 | N.D. | 2-cyclopropyl-4-ethoxy-6-[5-(2-fluorophenyl)-7-methylimidazo[5,1-f][1,2,4]triazin-4-yl]-5,6,7,8-tetrahydropyrido[4,3-d]pyrimidine |
| 148 | 0.125 | 0.166 | 2-cyclopropyl-4-ethoxy-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 149 | 0.497 | N.D. | 2-cyclopropyl-3-ethyl-6-[5-(2-fluorophenyl)-7-methylimidazo[5,1-f][1,2,4]triazin-4-yl]-5,6,7,8-tetrahydropyrido[4,3-d]pyrimidin-4(3H)-one |
| 150 | 0.0697 | N.D. | 2-cyclopropyl-3-ethyl-6-{7-methyl-5-[(3S)-tetrahydrofuran-3-yl]imidazo[5,1-f][1,2,4]triazin-4-yl}-5,6,7,8-tetrahydropyrido[4,3-d]pyrimidin-4(3H)-one |
| 151 | 1.01 | N.D. | 6-[5-(2-fluorophenyl)-7-methylimidazo[5,1-f][1,2,4]triazin-4-yl]-5,6,7,8-tetrahydro-1,6-naphthyridine |
| 152 | <0.13$^b$ | 0.333 | N-methyl-6-{7-methyl-5-[(3S)-tetrahydrofuran-3-yl]imidazo[5,1-f][1,2,4]triazin-4-yl}-5,6,7,8-tetrahydro-1,6-naphthyridin-2-amine |

TABLE 8-continued

Biological Activity of Examples 1-175.

| Example Number | Rat PDE10 IC$_{50}$ (nm)$^a$ | Human PDE10A IC$_{50}$ (nm)$^a$ | IUPAC Name |
|---|---|---|---|
| 153 | 0.436 | N.D. | 6-[5-(2-fluorophenyl)-7-methylimidazo[5,1-f][1,2,4]triazin-4-yl]-N-methyl-5,6,7,8-tetrahydro-1,6-naphthyridin-2-amine |
| 154 | 0.144 | N.D. | 2-cyclopropyl-6-{7-methyl-5-[(3S)-tetrahydrofuran-3-yl]imidazo[5,1-f][1,2,4]triazin-4-yl}-5,6,7,8-tetrahydro-1,6-naphthyridine |
| 155 | 0.171 | N.D. | 8-methyl-2-{7-methyl-5-[(3S)-tetrahydrofuran-3-yl]imidazo[5,1-f][1,2,4]triazin-4-yl}-1,2,3,4-tetrahydroisoquinoline |
| 156 | 0.905 | 1.00 | 4-(1-cyclopropyl-1,4,5,7-tetrahydro-6H-pyrazolo[3,4-c]pyridin-6-yl)-5-(2-fluorophenyl)-7-methylimidazo[5,1-f][1,2,4]triazine |
| 157 | 0.196 | 0.295 | 7-{7-methyl-5-[(3S)-tetrahydrofuran-3-yl]imidazo[5,1-f][1,2,4]triazin-4-yl}-2-(trifluoromethyl)-5,6,7,8-tetrahydro-1,7-naphthyridine |
| 158 | 0.227 | N.D. | 2-cyclopentyl-7-{7-methyl-5-[(3S)-tetrahydrofuran-3-yl]imidazo[5,1-f][1,2,4]triazin-4-yl}-5,6,7,8-tetrahydropyrido[3,4-d]pyrimidin-4-ol |
| 159 | 9.70 | 21.2 | 7-[5-(2-fluorophenyl)-7-methylimidazo[5,1-f][1,2,4]triazin-4-yl]-2-(trifluoromethyl)-5,6,7,8-tetrahydro-1,7-naphthyridine |
| 160 | 3.76 | N.D. | 2-cyclopentyl-7-[5-(2-fluorophenyl)-7-methylimidazo[5,1-f][1,2,4]triazin-4-yl]-5,6,7,8-tetrahydropyrido[3,4-d]pyrimidin-4-ol |
| 161 | 0.163 | 0.468 | 6-cyclopropyl-2-{7-methyl-5-[(3S)-tetrahydrofuran-3-yl]imidazo[5,1-f][1,2,4]triazin-4-yl}-1,2,3,4-tetrahydro-2,7-naphthyridine |
| 162 | 2.16 | 5.21 | 6-cyclopropyl-2-[5-(2-fluorophenyl)-7-methylimidazo[5,1-f][1,2,4]triazin-4-yl]-1,2,3,4-tetrahydro-2,7-naphthyridine |
| 163 | 1.19 | 1.78 | 6-methyl-2-{7-methyl-5-[(3S)-tetrahydrofuran-3-yl]imidazo[5,1-f][1,2,4]triazin-4-yl}-1,2,3,4-tetrahydro-2,7-naphthyridine |
| 164 | 3.32 | 5.92 | 2-[5-(2-fluorophenyl)-7-methylimidazo[5,1-f][1,2,4]triazin-4-yl]-6-methyl-1,2,3,4-tetrahydro-2,7-naphthyridine |
| 165 | 0.766 | 1.02 | 4-(1-ethyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine |
| 166 | 0.435 | 0.801 | 4-(1-ethyl-1,4,5,7-tetrahydro-6H-pyrazolo[3,4-c]pyridin-6-yl)-5-(2-fluorophenyl)-7-methylimidazo[5,1-f][1,2,4]triazine |
| 167 | 4.47 | 4.11$^b$ | 4-(1,4-dimethyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine |
| 168 | 6.10 | 3.96 | 4-(1,4-dimethyl-1,4,5,7-tetrahydro-6H-pyrazolo[3,4-c]pyridin-6-yl)-5-(2-fluorophenyl)-7-methylimidazo[5,1-f][1,2,4]triazine |
| 169 | 0.367$^c$ | 0.755$^b$ | 7-methyl-4-[1-(2-methylpropyl)-1,4,5,7-tetrahydro-6H-pyrazolo[3,4-c]pyridin-6-yl]-5-[(3S)-tetrahydrofuran-3-yl]imidazo[5,1-f][1,2,4]triazine |
| 170 | 1.94$^c$ | 2.55$^b$ | 7-methyl-5-[(3S)-tetrahydrofuran-3-yl]-4-[1-(2,2,2-trifluoroethyl)-1,4,5,7-tetrahydro-6H-pyrazolo[3,4-c]pyridin-6-yl]imidazo[5,1-f][1,2,4]triazine |
| 171 | 2.55 | N.D. | 6-{7-methyl-5-[(3S)-tetrahydrofuran-3-yl]imidazo[5,1-f][1,2,4]triazin-4-yl}-5,6,7,8-tetrahydropyrido[3,4-b]pyrazine |
| 172 | 11.3 | N.D. | 6-[5-(2-fluorophenyl)-7-methylimidazo[5,1-f][1,2,4]triazin-4-yl]-5,6,7,8-tetrahydropyrido[4,3-d]pyrimidin-4-ol |
| 173 | 0.136 | N.D. | 2-cyclopropyl-4-[($^2$H$_3$)methyloxy]-6-{7-methyl-5-[(3S)-tetrahydrofuran-3-yl]imidazo[5,1-f][1,2,4]triazin-4-yl}-5,6,7,8-tetrahydropyrido[4,3-d]pyrimidine |
| 174 | 0.359 | 0.345 | 4-[1-(cyclobutylmethyl)-1,4,5,7-tetrahydro-6H-pyrazolo[3,4-c]pyridin-6-yl]-7-methyl-5-[(3S)-tetrahydrofuran-3-yl]imidazo[5,1-f][1,2,4]triazine |

TABLE 8-continued

Biological Activity of Examples 1-175.

| Example Number | Rat PDE10 IC$_{50}$ (nm)[a] | Human PDE10A IC$_{50}$ (nm)[a] | IUPAC Name |
|---|---|---|---|
| 175 | 0.878 | 1.94 | 4-[1-(cyclobutylmethyl)-1,4,5,7-tetrahydro-6H-pyrazolo[3,4-c]pyridin-6-yl]-5-(2-fluorophenyl)-7-methylimidazo[5,1-f][1,2,4]triazine |

[a]Values represent the geometric mean of 2-4 determinations, unless otherwise indicated.
[b]Value represents the geometric mean of ≥5 determinations.
[c]Value represents a single determination.
[d]N.D. means not determined

What is claimed is:

1. A compound of the formula:

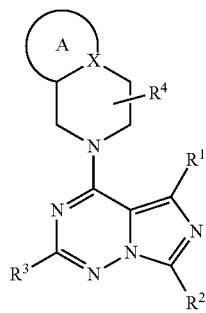

or a pharmaceutically acceptable salt thereof, in which:
A, along with X and the carbon atom to which it is attached, forms a (C$_6$-C$_{10}$)aryl or a 5- to 10-membered heteroaryl moiety, in which said aryl or heteroaryl moiety is optionally substituted with up to 4 substituents, each independently selected from the group consisting of
C$_3$-C$_6$ cycloalkyl, oxo, optionally substituted C$_1$-C$_6$ alkyl, optionally substituted C$_1$-C$_6$ alkoxy, hydroxy, cyano, halo, —NR$^5$R$^6$, —C(O)—NR$^5$R$^6$, —NH—C(O)R$^5$, —C(O)—OR$^5$, —(C$_1$-C$_6$)alkyl-(C$_3$-C$_6$)cycloalkyl, a 4- to 6-membered heterocyclic moiety, phenyl, and benzyl;
X is represented by N or C;
R$^1$ is represented by C$_1$-C$_6$ alkyl, (C$_6$-C$_{10}$)aryl or a 5- to 6-membered heterocyclic moiety, in which said alkyl, aryl or heterocyclic moiety may be optionally substituted with up to 4 substituents, each independently selected from the group consisting of halogen, optionally substituted C$_1$-C$_6$ alkyl, optionally substituted C$_1$-C$_6$ alkoxy, hydroxy, cyano, —NR$^5$R$^6$, —C(O)—NR$^5$R$^6$, —NH—C(O)R$^5$, and —C(O)—OR$^5$;
R$^2$ and R$^3$ are each independently represented by hydrogen, optionally substituted C$_1$-C$_6$ alkyl, or optionally substituted C$_1$-C$_6$ alkoxy;
R$^4$, if present, is optionally represented by up to 2 substituents, each independently selected from the group consisting of fluoro, hydroxy, optionally substituted C$_1$-C$_6$ alkyl, or optionally substituted C$_1$-C$_6$ alkoxy; and
R$^5$ and R$^6$ are each optionally and independently represented by hydrogen or C$_1$-C$_6$ alkyl.

2. A compound, or a pharmaceutically acceptable salt thereof, according to claim 1 in which R$^2$ is methyl.

3. A compound, or a pharmaceutically acceptable salt thereof, according to claim 1 in which R$^3$ is hydrogen.

4. A compound, or a pharmaceutically acceptable salt thereof, according to claim 1 in which R$^1$ is represented by phenyl, which may be optionally substituted.

5. A compound, or a pharmaceutically acceptable salt thereof, according to claim 4, in which said phenyl ring is substituted with one or more substituents selected from the group consisting of methyl, fluoro, methoxy, and chloro.

6. A compound, or a pharmaceutically acceptable salt thereof, according to claim 1 in which R$^1$ is tetrahydrofuran.

7. A compound, or a pharmaceutically acceptable salt thereof, according to claim 6 in which said tetrahydrofuran is unsubstituted.

8. A compound, or a pharmaceutically acceptable salt thereof, according to claim 1 in which R$^1$ is tetrahydropyran.

9. A compound, or a pharmaceutically acceptable salt thereof, according to claim 8 in which said tetrahydropyran is unsubstituted.

10. A compound, or a pharmaceutically acceptable salt thereof, according to claim 1 in which A, along with X and the carbon atom to which it is attached, forms a phenyl ring.

11. A compound, or a pharmaceutically acceptable salt thereof, according to claim 1 in which A, along with X and the carbon atom to which it is attached, forms a heteroaryl moiety.

12. A compound, or a pharmaceutically acceptable salt thereof, according to claim 11 in which said heteroaryl moiety contains at least one nitrogen atom.

13. A compound, or a pharmaceutically acceptable salt thereof, according to claim 11 in which said heteroaryl moiety is selected from the group consisting of pyridine, pyridazine, pyrimidine, and pyrazine.

14. A compound, or a pharmaceutically acceptable salt thereof, according to claim 11 in which said heteroaryl moiety is selected from the group consisting of pyrrole, pyrazole, imidazole, isoxazole, oxazole, isothiazole, and thiazole.

15. A compound, or a pharmaceutically acceptable salt thereof, according to claim 10 in which said phenyl ring is substituted with one or more substituents selected from the group consisting of methyl, methoxy, chloro, fluoro, 2-fluoroethoxy, cyano, —C(O)—OH, —C(O)—NH$_2$, and trifluoromethyl.

16. A compound, or a pharmaceutically acceptable salt thereof, according to claim 11 in which said heteroaryl is substituted with one or more substituents selected from the group consisting of methyl, ethyl, trifluoromethyl, difluoromethyl, difluoromethoxy, methoxy, isopropyl, cyclopropyl, oxo, hydroxy, ethoxy, phenyl, 2-trifluoroethyl, dimethylamino, cyclobutylmethyl, methylamino, and cyclopentyl.

17. A compound, or a pharmaceutically acceptable salt thereof, according to claim 1 in which $R^4$ is absent.

18. A compound selected from the group consisting of:
   i) 4-(3-cyclopropyl-6,7-dihydro[1,2]oxazolo[4,3-c]pyridin-5(4H)-yl)-7-methyl-5-[(3S)-tetrahydrofuran-3-yl]imidazo[5,1-f][1,2,4]triazine,
   ii) 4-(2-cyclopropyl-2,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine,
   iii) 4-(3-cyclopropyl-1-methyl-1,4,6,7-tetrahydro-5H-pyrazolo[4,3-c]pyridin-5-yl)-7-methyl-5-[(3S)-tetrahydrofuran-3-yl]imidazo[5,1-f][1,2,4]triazine,
   iv) 2-cyclopropyl-6-[5-(2-fluorophenyl)-7-methylimidazo[5,1-f][1,2,4]triazin-4-yl]-5,6,7,8-tetrahydropyrido[4,3-d]pyrimidine,
   v) 4-(2-cyclopropyl-6,7-dihydro[1,3]oxazolo[5,4-c]pyridin-5(4H)-yl)-7-methyl-5-[(3S)-tetrahydrofuran-3-yl]imidazo[5,1-f][1,2,4]triazine,
   vi) 8-(2-fluoroethoxy)-7-methoxy-2-{7-methyl-5-[(3S)-tetrahydrofuran-3-yl]imidazo[5,1-f][1,2,4]triazin-4-yl}-1,2,3,4-tetrahydroisoquinoline,
   vii) 5-(2-fluorophenyl)-7-methyl-4-(1-methyl-1,4,5,7-tetrahydro-6H-pyrazolo[3,4-c]pyridin-6-yl)imidazo[5,1-f][1,2,4]triazine,
   viii) 7-methyl-4-(1-methyl-1,4,5,7-tetrahydro-6H-pyrazolo[3,4-c]pyridin-6-yl)-5-[(3S)-tetrahydrofuran-3-yl]imidazo[5,1-f][1,2,4]triazine,
   ix) 4-(1-cyclopropyl-1,4,5,7-tetrahydro-6H-pyrazolo[3,4-c]pyridin-6-yl)-7-methyl-5-[(3S)-tetrahydrofuran-3-yl]imidazo[5,1-f][1,2,4]triazine, and;
   x) 7-methyl-4-(1-methyl-1,4,5,7-tetrahydro-6H-pyrazolo[3,4-c]pyridin-6-yl)-5-[(2R)-tetrahydrofuran-2-yl]imidazo[5,1-f][1,2,4]triazine; or
   a pharmaceutically acceptable salt of any of the compounds listed above.

19. A pharmaceutical composition comprising a compound, or a pharmaceutically acceptable salt thereof, according to claim 1 in association with one, or more, pharmaceutical excipients.

20. 7-{7-Methyl-5-[(3S)-tetrahydrofuran-3-yl]imidazo[5,1-f][1,2,4]triazin-4-yl}-5,6,7,8-tetrahydro-1,7-naphthyridine, or a pharmaceutically acceptable salt thereof.

21. 7-Methyl-4-(1-methyl-1,4,5,7-tetrahydro-6H-pyrazolo[3,4-c]pyridin-6-yl)-5-[(3S)-tetrahydrofuran-3-yl]imidazo[5,1-f][1,2,4]triazine, or a pharmaceutically acceptable salt thereof.

22. 7-Methyl-4-(1-methyl-1,4,5,7-tetrahydro-6H-pyrazolo[3,4-c]pyridin-6-yl)-5-[(2R)-tetrahydrofuran-2-yl]imidazo[5,1-f][1,2,4]triazine, or a pharmaceutically acceptable salt thereof.

23. 8-(2-fluoroethoxy)-7-methoxy-2-{7-methyl-5-[(3S)-tetrahydrofuran-3-yl]imidazo[5,1-f][1,2,4]triazin-4-yl}-1,2,3,4-tetrahydroisoquinoline, or a pharmaceutically acceptable salt thereof.

24. 4-(2-cyclopropyl-6,7-dihydro[1,3]oxazolo[5,4-c]pyridin-5(4H)-yl)-7-methyl-5-[(3S)-tetrahydrofuran-3-yl]imidazo[5,1-f][1,2,4]triazine, or a pharmaceutically acceptable salt thereof.

* * * * *